United States Patent
Culiat

(10) Patent No.: US 11,034,741 B2
(45) Date of Patent: Jun. 15, 2021

(54) METHODS AND COMPOSITIONS FOR REGENERATING TISSUES

(71) Applicant: NELLONE THERAPEUTICS, INC., Oak Ridge, TN (US)

(72) Inventor: Cymbeline T. Culiat, Oak Ridge, TN (US)

(73) Assignee: NellOne Therapeutics, Inc., Oak Ridge, TN (US)

( * ) Notice: Subject to any disclaimer, the term of this patent is extended or adjusted under 35 U.S.C. 154(b) by 0 days.

(21) Appl. No.: 16/813,376

(22) Filed: Mar. 9, 2020

(65) Prior Publication Data

US 2020/0199184 A1 Jun. 25, 2020

Related U.S. Application Data

(62) Division of application No. 15/690,093, filed on Aug. 29, 2017.

(60) Provisional application No. 62/380,920, filed on Aug. 29, 2016.

(51) Int. Cl.
*A61K 38/17* (2006.01)
*C07K 14/47* (2006.01)

(52) U.S. Cl.
CPC ...... *C07K 14/4705* (2013.01); *A61K 38/1709* (2013.01); *C07K 14/47* (2013.01)

(58) Field of Classification Search
CPC . A61K 38/1709; C07K 14/47; C07K 14/4705
See application file for complete search history.

(56) References Cited

U.S. PATENT DOCUMENTS

| | | | |
|---|---|---|---|
| 7,052,856 B2 | 5/2006 | Ting | |
| 7,687,462 B2 * | 3/2010 | Ting | A61F 2/00 514/7.6 |
| 7,884,066 B2 * | 2/2011 | Ting | C07K 14/51 514/1.1 |
| 7,910,542 B2 | 3/2011 | Culiat | |
| 8,722,625 B2 * | 5/2014 | Culiat | A61K 38/18 514/16.4 |
| 8,877,176 B2 | 11/2014 | Culiat | |
| 9,920,104 B2 | 3/2018 | Culiat | |
| 2006/0025367 A1 | 2/2006 | Simari | |
| 2006/0053503 A1 | 3/2006 | Culiat | |
| 2006/0111313 A1 | 3/2006 | Ting et al. | |
| 2006/0228392 A1 | 10/2006 | Ting | |
| 2006/0292670 A1 | 12/2006 | Ting et al. | |
| 2007/0128697 A1 | 6/2007 | Ting et al. | |
| 2007/0134291 A1 | 6/2007 | Ting et al. | |
| 2009/0087415 A1 | 4/2009 | Culiat | |
| 2011/0236325 A1 | 9/2011 | Mitchell et al. | |
| 2014/0205577 A1 | 7/2014 | Culiat | |
| 2015/0037294 A1 * | 2/2015 | Culiat | A61P 17/00 424/93.7 |

FOREIGN PATENT DOCUMENTS

| | | |
|---|---|---|
| WO | WO 2002/100426 | 12/2002 |
| WO | WO 2004/024893 | 3/2004 |
| WO | WO 2004/072100 | 8/2004 |
| WO | WO 2006/089023 | 8/2006 |
| WO | WO 2008/073631 | 6/2008 |
| WO | WO 2008/109274 | 9/2008 |
| WO | WO 2009/042859 | 4/2009 |
| WO | WO 2009/045800 | 4/2009 |
| WO | WO 2011/091244 | 7/2011 |

OTHER PUBLICATIONS

Sethi et al., Kidney Int., 2020, vol. 97(1): 163-174.*
Aghaloo et al., "A Study of the Role of Nell-1 Gene Modified Goat Bone Marrow Stromal Cells in Promoting New Bone Formation," The American Society of Gene Therapy, 2007, 15(10):1872-1880.
Aghaloo et al., "Nell-1-Induced Bone Regeneration in Calvarial Defects," Am J Pathol, 2006, 169(3):903-915.
Bareggi et al., "Protein Kinase C (PKC) Isoenzymes Exhibit Specific Expression in the Vertebral Column of Human Fetuses," J Biol Res, 1995, LXXI:83-91.
Cowan et al., "Nell-1 induced bone formation within the distracted intermaxillary suture," Bone, 2006, 38(1):48-58.
Cowan et al., "Synergistic Effects of Nell-1 and BMP-2 on the Osteogenic Differentiation of Myoblasts," J Bone Mineral Res, Nov. 6, 2007, 22:918-930.
Culiat et al., "Neil1: A Candidate Gene for ENU-Induced Recessive Lethal Mutaitons at the 17R6 Locus and Potential Mouse Models for Human Neonatal Unilateral Coronal Synostosis (UCS)," International Mammalian Genome Society, 15th International Mouse Genome Conference, 2001.
Culiat et al., "Nell1: A Candidate Gene for ENU-Induced Recessive Lethal Mutations at the 17R6 Locus and Potential Mouse Models for Human Neonatal Unilateral Coronal Synostosis (UCS)," Jan. 27-31, 2002, Abstract.
Desai et al., "Nell1, A gene coding for a novel PKC-binding protein is a candidate for late-gestation recessive lethal mutations at the I7R6 locus," 16th International Mouse Genome Conference, San Antonio, TX, 17-21 Nov. 1, 2002, Abstract.
Desai et al., "Nell1-deficient mice have reduced expression of extracellular matrix proteins causing cranial and vertebral defects," Human Molecular Genetics, 2006, 15(8):1329-1341.
Desai et al., "Characterization of Mouse Nell1: A gene coding for a novel PKC-binding protein," Women in Science Meeting, ORNL, Oak Ridge, TN, May 1, 2006, Abstract.

(Continued)

*Primary Examiner* — Xiaozhen Xie
(74) *Attorney, Agent, or Firm* — Womble Bond Dickinson (US) LLP

(57) ABSTRACT

Provided are methods for promoting the healing of injuries to tendons and ligaments by administering a NELL1 protein or a nucleic acid encoding a NELL1 protein to a subject in need thereof. Also provided are NELL1 compositions and methods for promoting tissue regeneration, promoting the healing of wounds, and enhancing fibroblast migration, proliferation, or both migration and proliferation.

20 Claims, 10 Drawing Sheets

Specification includes a Sequence Listing.

(56) References Cited

OTHER PUBLICATIONS

Desai et al., "Nell1-deficient mice have reduced expression of extracellular matrix proteins causing cranial and vertebral defects," Hum Mol Genet, 2006, 15(8):1329-1341.

Diwan et al., "Current Concepts in Interverterbral Disk Restoration," Orthopedic Clinics of North America, Jul. 2000, 31(3):453-464.

Ekser et al., "Clinical xenotransplantation: the next medical revolution?," Lancet, 2012, 379:672-683.

Franke et al., "Systematic Association Mapping Identifies NELL1 as a Novel IBD Disease Gene," PLoS One, Aug 2007, 8:e691, 13 pp.

Haider, "Bone marrow cells for cardiac regeneration and repair: current status and issues," Expert Rev Cardiovasc Ther, 2006, 4(4):557-568.

Hasebe et al., "The C-terminal region of NELL1 mediates osteoblastic cell adhesion through integrin α3β1," FEBS Letters, 2012, 586:2500-2506.

Hasebe et al., "Efficient Production and Characterization of Recombinant Human NELL1 Protein in Human Embryonic Kidney 293-F Cells," Mol Biotechnol, Aug. 5, 2011, 51(1):58-66.

Hentze et al., "Teratoma formation by human embryonic stem cells: Evaluation of essential parameters for future safety studies," Stem Cell Research, 2009, 2:198-210.

James et al., "A New Function of Nell-1 Protein in Repressing Adipogenic Differentiation," Biochem Biophys Res Commun, Jul. 22, 2011, 411(1):126-131.

Kuroda et al., "Biochemical Characterization and Expression Analysis of Neural Thrombospondin-1-like Proteins NELL1 and NELL2," Biochem Biophys Res Commun, 1999, 265:79-86.

Kuroda et al., "Involvement of Epidermal Growth Factor-Like Domain of NELL Proteins in the Novel Protein-Protein Interaction with Protein Kinase C," Biochem Biophys Res Commun, 1999, 265:752-757.

Lecker et al., "Multiple types of skeletal muscle atrophy involve a common program of changes in gene expression," 2004, The FASEB Journal, 18(1):39-51.

Lehto et al., "Skeletal Muscle Injury—Molecular Changes in the Collagen During Healing," 1985, Res Exp Med, 185:95-106.

Li et al., "Effects of administration route on migration and distribution of neural progenitor cells transplanted into rats with focal cerebral ischemia, an MRI Study," J Cereb Blood Flow Metab, Mar. 2010, 30(3):653-662.

Lin et al., "Coagulation Dysregulation as a Barrier to Xenotransplantation in the Primate," Transpl Immunol, Jun. 2009, 21(2):75-80.

Liu, "Characterizing the Role of the Nell1 Gene in Cardiovascular Development," American Association for the Advancement of Science, San Francisco, CA, Presentation on Feb. 15-17, 2007 (Abstract).

Liu et al., "Characterizing the Role of the Nell1 Gene in Cardiovascular Development," U.S. Department of Energy Journal of Undergraduate Research, 2007.

Liu et al., "Characterizing the role of the Nell1 gene in cardiovascular development," Oak Ridge Science Semester Poster Presentation, ORNL, Oak Ridge, TN, Aug. 11, 2006 (Poster).

Lu et al., "The osteoinductive properties of Nell-1 in a rat spinal fusion model," The Spine Journal, 2007, 7:50-60.

Luce et al., "The neuronal EGF-related genes NELL1 and NELL2 are expressed in hemopoietic cells and developmentally regulated in the B lineage," Gene, 1999, 231:121-126.

Maeda et al., "Brain Specific Human Genes, NELL1 and NELL2, Are Predominantly Expressed in Neuroblastoma and Other Embryonal Neuroephithelial Tumors," Neurol Med Chir (Tokyo), 2001, 41(12):582-588.

Martin, "Wound Healing—Aiming for Perfect Skin Regeneration," Science, Apr. 1997, 276:75-81.

Nakamura et al., "Oligomerization-induced Conformational Change in the C-terminal Region of Nel-like Molecule 1 (NELL1) Protein is Necessary for the Efficient mediation of Murine MC3T3-E1 Cell Adhesion and Spreading," Journal of Biological Chemistry, Apr. 4, 2014, 289(14):9781-9794.

Nakamura et al., "Structure-Function Analysis of Nel, a Thrombospondin-1-like Glycoprotein Involved in Neural Development and Functions," J Biol Chem, 2012, 287(5):3282-3291.

Naldini, "Ex vivo gene transfer and correction for cell-based therapies," Nature Reviews, Genetics, May 2011, 12:301-315.

Narang et al., "Biological and Biomaterial Approaches for Improved Islet Transplantation," Pharmacol Rev, 2006, 58(2):194-243.

Ngo et al., "Computational Complexity, Protein Structure Prediction, and the Levinthal Paradox," In Merz and La Grand (Eds), The Protein Folding Problem and Tertiary Structure Prediction, Birkhauser Boston, 1994, pp. 434-506.

Norrman et al., "Quantitative Comparison of Constitutive Promoters in Human ES Cells," PLoS One, 2010, 5(8):1-10.

Orlic et al., "Transplanted Adult Bone Marrow Cells Repair Myocardial Infarcts in Mice," Ann NY Acad Sci, 2001, 938(1):221-230.

Ott et al., "From cardiac repair to cardiac regeneration-ready to translate?," Expert Opin Biol Ther., 2006, 6(9):867-878.

Pettit et al., "The development of site-specific drug-delivery systems for protein and peptide biopharmaceuticals," Tibtech, 1998, 16:343-349.

Prieto et al., "Cells as vehicles for therapeutic genes to treat liver diseases," Gene Therapy, 2008, 15:765-771.

Raymon et al., "Application of ex Vivo Gene Therapy in the Treatment of Parkinson's Disease," Experimental Neurology, 1997, 144:82-91.

Reporter, The, Jun 2006, No. 78, published by Oak Ridge National Laboratory, accessible on line at http://www.oml.gov/info/reporter/no78/June06 dw.htm.

Rich, "Single-Center Study of 83 Horses with Suspensory Injuries Treated with Adipose-Derived Stem and Regenerative Cells," Stem Cell Discovery, 2014, 4:44-53.

Rinchik et al., "Functional annotation of mammalian genomic DNA sequence by chemical mutagenesis: A fine-structure genetic mutation map of a 1- to 2-cM segment of mouse chromosome 7 corresponding to human chromosome 11p14-p15," PNAS, Jan. 22, 2002, 99(2):844-849.

Rosenthal et al., "Growth Factor Enhancement of Cardiac Regeneration," Cell Transplant, 2006, 15(Suppl1):S41-S45.

Rubart et al., "Cell-based Approaches for Cardiac Repair," Ann NY Acad Sci, 2006, 1080:34-38.

Ruszczak, Effect of collagen matrices on dermal wound healing, 2003, Advanced Drug Delivery Reviews, 55:1595-1611.

Santini et al., "Signalling pathways in cardiac rengeneration," Novartis Found Symp, 2006, 274:228-243.

Schmitt et al., "BMP2 initiates chondrogenic lineage development of adult human mesenchymal stem cells in high-density culture," Int Soc Differentiation, 2003, 71:567-577.

Shen et al., "Knock Down of NELL2 in Wilms' Tumor Cell Line," Journal of the William Jarvie Society, 2006, 49:41, Abstract.

Siu et al., "NELL-1 Promotes Cartilage Regeneration in an In Vivo Rabbit Model," Tissue Eng, Part A, 2012, 18(3-4):252-261.

Strauer et al., "Stem Cell Therapy in Perspective," Circulation, 2003, 107:929-934.

Ting et al., "Human NELL-1 Expressed in Unilateral Coronoal Synostosis," J Bone Miner Res, 1999, 14(1):80-89.

Trollet et al., "Gene therapy for muscular dystrophy: current progress and future prospects," Expert Opin Biol Ther, 2009, 9(7):849-866.

Tsutsumi et al., "The Novel Gene Encoding a Putative Transmembrane Protein is Mutated in Gnathodiaphyseal Dysplasia (GDD)," Am J Hum Genet, 2004, 74:1255-1261.

Watanabe et al., "Cloning and Characterization of Two Novel Human cDNAs (NELL1 and NELL2) Encoding Proteins with Six EGF-like Repeats," Genomics, 1996, 38:273-276.

Wells, "Additivity of Mutational Effects in Proteins," Am Chem Soc, Sep. 18, 1990, 29(37):8509-8517.

Yamamoto et al., "Regulation of bone morphogenetic proteins in early embryonic development," Naturwissenschaften, 2004, 91:519-534.

(56) References Cited

OTHER PUBLICATIONS

Yang et al., "In vitro and in vivo induction of bone formation based on ex vivo gene therapy using rat adipose-derived adult stem cells expressing BMP-7," Cytotherapy, 2005, 7(3):273-281.
Zhang et al., "Craniosynostosis in transgenic mice overexpressing Nell-1," J Clin Invest, Sep. 2002, 110(6):861-870.
Zhang et al., "Nell-1 induces acrania-like cranioskeletal deformities during mouse embryonic development," Laborabory Investigation, 2006, 86(7):633-644.
Zhang et al., "Overexpression of Nell1, a Craniosynostosis-Associated Gene, Induces Apoptosis in Osteoblasts During Craniofacial Development," J Bone Miner Res, 2003, 18(12):2126-2134.
Askarinam et al., "Human Perivascular Stem Cells Show Enhanced Osteogenesis and Vasculogenesis with Nel-Like Molecule 1 Protein," 2013, Tissue Engineering: Part A, 19(11-12):1386-1397.
Bassetto et al., "Regenerative Medicine for Tendon Regeneration and Repair: The Role of Bioscaffolds and Mechanical Loading," 2011, Biomaterials Science and Engineering, Ch. 18, Ed. R. Pignatello, InTech, pp. 369-386.
Bi et al., "Identification of tendon stem/progenitor cells and the role of the extracellular matrix in their niche," Nov. 2007, Nature Medicine, 13:1219-1227.
Briggs, "Tackling Tendon and Ligament Injuries," Jun. 3, 2011, The Horse, 7 pp.
Caudill, "Stem Cell Therapy," The American Quarter Horse Racing Journal, www.americashorsedaily.com, Oct. 15, 2015, 6 pp.
Connizzo et al., "Regulatory Role of Collagen V in Establishing Mechanical Properties of Tendons and Ligaments is Tissue Dependent," Jun. 2015, J Orthopaedic Research, 33:882-888.
Davis et al., "MMP inhibition as a potential method to augment the healing of skeletal muscle and tendon extracellular matrix," 2013, J Appl Physiol, 115:884-891.
Endo et al., "High-throughput, genome-scale protein production method based on the wheat germ cell-free expression system," 2003, Biotechnol. Adv. 21(8):695-713.
Estrada et al., "Comparison of healing in forelimb and hindlimb surgically induced core lesions of the equine superficial digital flexor tendon," 2014, Vet Comp Orthop Traumatol, 27(05):358-365.
Fortier et al., "Regenerative Medicine for Tendinous and Ligamentous Injuries of Sport Horses," 2008, Vet Clin Equine, 24:191-201.
Gelfand et al., "Surrogate Endpoints for the Treatment of Venous Leg Ulcers," 2002, J Invest Dermatol, 119:1420-1425.
Gomez et al., "Effects of 3 biologic dressings on healing of cutaneous wounds on the limbs of horse," 2004, The Canadian Journal of Veterinary Research, 68:49-55.
Godwin et al., "Implantation of bone marrow-derived mesenchymal stem cells demonstrates improved outcome in horses with overstain injury of the superficial digital flexor tendon," 2012, Equine Veterinary Journal, 44:25-32.
Hamilton, "Functional role of periostin in development and wound repair: implications for connective tissue disease," 2008, J Cell Commun Signal, 2:9-17.
Ituarte et al., "Anti-inflammatory Properties of Nell-1 on Human Articular Chondrocytes In Vivo," ORS 2014 Annual Meeting, Poster No. 0362.
James et al., "NELL-1 in the treatment of osteoporotic bone loss," 2015, Nature Communications, 6:7362, 14 pp.
Jin et al., "Hypermethylation of the nel-like 1 gene is a common and early event and is associated with poor prognosis in early-stage esophageal adenocarcinoma," 2007, Oncogene, 26:6332-6340.
Juneja et al., "Defects in Tendon, Ligament, and Enthesis in Response to Genetic Alterations in Key Proteoglycans and Glycoproteins: A Review," 2013, Arthritis 2013:1-30.
Lee et al., "Effect of Nell-1 Delivery on Chondrocyte Proliferation and Cartilaginous Extracellular Matrix Deposition," 2010, Tissue Engineering: Part A, 16(5):1791-1800.
Li et al., "Neural EGFL-like 1 is a Downstream Regulator of Runt-Related Transcription Factor 2 in Chondrogenic Differentiation and Maturation," May 2017, Am J Pathol, 187(5):963-972.

Li et al., "Nell-1 Enhances Bone Regeneration in a Rat Critical-Sized Femoral Segmental Defect Model," Feb. 2011, Plast Reconstr Surg, 127(2):580-587.
Lui, "Stem cell technology for tendon regeneration: current status, challenges, and future research directions," 2015, Stem Cells and Cloning: Advances and Applications, 8:163-174.
Madin et al., "A highly efficient and robust cell-free protein synthesis system prepared from wheat embryos: Plants apparently contain a suicide system directed at ribosomes," Jan. 18, 2000, Proc Natl Acad Sci USA, 97(2):559-564.
Matsuhashi et al., "New Gene, nel, Encoding a Mr 93 K Protein With EGF-Like Repeats Is Strongly Expressed in Neural Tissues of Early Stage Chick Embryos," 1995, Developmental Dynamics, 203:212-222.
Mitchell et al., "Nell1 Protein Reduces the Number of Sunburned Cells and Modulates the Inflammatory Response after UV-induced Damage in a 3D Human Skin Model," Mar. 16-20, 2012, 70th Annual Meeting of the American Academy of Dermatology, San Diego, CA.
Morgan et al., "Effects of extracorporeal shock wave therapy on wounds of the distal portion of the limbs in horses," May 1, 2009, J Am Vet Med Assoc, 234(9):1154-1161.
Mori et al., "A Genome-Wide Search Identifies Epigenetic Silencing of Somatostatin, Tachykini-1, and 5 Other Genes in Colon Cancer," 2006, Gastroenterology, 131:797-808.
Nemoto et al., "Tenascin-C Expression in Equine Tendon-derived Cells During Proliferation and Migration," 2013, J Equine Sci, 24(2):17-24.
Nixon et al., "Effect of adipose-derived nucleated cell fractions on tendon repair in horses with collagenase-induced tendinitis," Jul. 2008, Am J Vet Res, 69(7):928-937.
Oke, "Regenerative Therapy Trends and Techniques in Horses," May 18, 2016, Article #37581, pp. 1-4.
Pakvasa et al., "Neural EGF-like protein 1 (NELL1-): Signaling crosstalk in mesenchymal stem cells and applications in regenerative medicine," 2017, Genes & Diseases, 4:127-137.
Pauly et al., "BMP2 and BMP7 affect human rotator cuff tendon cells in vitro," 2011, J Shoulder Elbow Surg, pp. 1-10.
Richardson et al., "Stem cells in veterinary medicine—Attempts at regenerating equine tendon after injury," Oct. 2007, Trends in Biotechnology, pp. 1-10.
Sawasaki et al., "Construction of an efficient expression vector for coupled transcription/translation in a wheat germ cell-free system," 2000, Nucleic Acids Symposium Series, 44:9-10.
Sawasaki et al., "A cell-free protein synthesis system for high-throughput proteomics," Nov. 12, 2002, Proc Natl Acad Sci USA, 99(23):14652-14657.
Schramme et al., "A surgical tendonitis model in horses: Technique, clinical, ultrasonographic and histological characterization," 2010, Vet Comp Orthop Traumatol, 23(04):231-239.
Schumacher et al., "Kinetics of healing of grafted and nongrafted wounds on the distal portion of the forelimbs of horses," 1992, Am J Vet Res 53(9):1568-1571—Abstract only.
Schwarting et al., "Bone Morphogenetic Protein 7 (BMP-7) Influences Tendon-Bone Integration In Vitro," Feb. 2, 2015, PLoS One, 10(2):1-17.
September et al., "Tendon and ligament injuries: the genetic component," 2007, Br J Sports Med, 41:241-246.
Shen et al., "Nell-1 Promotes Cell Adhesion and Differentiation via Integrin β1," 2012, J of Cellular Biochemistry, 113:3620-3628.
Shen et al., "BMP2-Induced Inflammation Can Be Suppressed by the Osteoinductive Growth Factor NELL-1," Nov. 2013, Tissue Eng, Part A, 19(21-22):2390-2401.
Siu et al., "Nell-1 Protein Promotes Bone Formation in a Sheep Spinal Fusion Model," 2011, Tissue Eng, Part A, 17(7-8):1123-1135.
Sun et al., "Targeted Deletion of Collagen V in Tendons and Ligaments Results in a Classic Ehlers-Danlos Syndrome Joint Phenotype," May 2015, Am J Pathol 185(5):1436-1447.
Tan, "A Review and Update on Tendon and Ligament Injuries in Horses," Mar. 30, 2016, The Horse, pp. 1-7.

(56) References Cited

OTHER PUBLICATIONS

Taylor et al., "Gene expression markers of tendon fibroblasts in normal and diseased tissue compared to monolayer and three dimensional culture systems," 2009, BMC Musculoskeletal Disorders, 10:27, 10 pp.

Tempfer et al., "Perivascular cells of the supraspinatus tendon express both tendon- and stem cell-related markers," Histochem Cell Biol, 2009, 131:733-741.

Theoret, "Wound Repair in the Horse: Problems and Proposed Innovative Solutions," 2004, Clin Tech Equine Pract, 3:134-140.

Thomas, A-Cell Therapy Offers Renewed Hope for Horses Incurring Tendon and Ligament Injuries, Sep. 12, 2005, The Chronicle of the Horse, pp. 134-137.

Turner et al., "Human NELL1 Protein Augments Constructive Tissue Remodeling with Biologic Scaffolds," 2013, Cells Tissues Organs, 2013, DOI: 10.1159/000356491.

Watts et al., "A collagenase gel/physical defect model for controlled induction of superficial digial tendonitis," 2012, Equine Veterinary Journal, 44(5):576-586.

Xue et al., "NELL1 promotes high-quality bone regeneration in rat femoral distraction osteogenesis model," 2011, Bone, 48:485-495.

Yang et al., "Tendon and Ligament Regeneration and Repair: Clinical Relevance and Developmental Paradigm," Sep. 2013, Birth Defects Res C Embryo Today, 99(3):203-222.

Zhang et al., "Bioactivity and circulation time of PEGylated NELL-1 in mice and the potential for osteoporosis therapy," 2014, Biomaterials, 35:6614-6621.

Zhu et al., "NEL-like molecule-1-modified bone marrow mesenchymal stem cells/poly lactic-co-glycolic acid composite improves repair of large osteochondral defects in mandibular condyle," 2011, Osteoarthritis and Cartilage, 19:743-750.

James et al., "NELL-1 in the treatment of osteoporotic bone loss," 2015, Nature Communications, 6:7362, 45 pp, including Supplementary Materials.

James et al., "NELL-1 induces Sca-1$^+$ mesenchymal progenitor cell expansion in models of bone maintenance and repair," JCI Insight, 2017, 2(12):e92573, 17 pp.

Lee et al., "Brief Report: Human Perivascular Stem Cells and Nel-Like Protein-1 Synergistically Enhance Spinal Fusion in Osteoporotic Rats," Stem Cells, 2015, 33:3158-3163.

Zhang et al., "The Nell-1 Growth Factor Stimulates Bone Formation by Purified Human Perivascular Cells," Tissue Engineering: Part A, 2011, 17(19-20):2497-2509.

\* cited by examiner

METHODS AND COMPOSITIONS FOR REGENERATING TISSUES

CROSS REFERENCED APPLICATIONS

This application is a divisional of U.S. Patent Application Ser. No. 15/690,093, filed Aug. 29, 2017, which claims the benefit of U.S. Provisional Application No. 62/380,920, filed Aug. 29, 2016, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20171103N885091060US1SEQLIST_ST25.txt, created on Nov. 3, 2017, and having a size of 158,512 bytes. The sequence listing contained in this ASCII formatted document is part of the specification and is herein incorporated by reference in its entirety.

FIELD OF THE INVENTION

This application generally relates to the healing of injuries, including those involving tendons and/or ligaments, with a regenerative protein or a nucleic acid encoding the same.

BACKGROUND OF THE INVENTION

The healing of an injury involves a multistep process whereby injured tissue is repaired, specialized tissue is regenerated, and new tissue is reorganized into a functional unit. Wound healing is generally divided into the inflammatory phase, the proliferative phase, and the maturation and remodeling phase. An impairment in any one of these phases can lead to complications. Particular tissues can be more difficult to heal properly due in part to their cellular makeup, limited vasculature, and/or location in highly mobile parts of the body. Injuries to tendons and ligaments, for example, can be particularly challenging to properly heal.

Tendons are soft connective tissues that connect muscle to bone or cartilage, while ligaments connect bone to bone to hold the skeleton and stabilize the joints. They are composed primarily of packed collagen fibers that impart different mechanical properties based on the shape and how they are organized. There is very little cellularity in these tissues—mostly fibroblasts secreting the extracellular material (ECM). Ligaments have a lower collagen content (~75%) with a random pattern, while tendons have more collagen (80-90%) and are highly organized. The ECM of both tissues are composed of Types I and III collagen, with ligaments having a lesser proportion of Type I (90%) and more of type III (10%) in comparison to tendons which have 95-99% Type 1 and 1-5% Type III. Another key difference between these two types of connective tissue is the presence of elastin in ligaments, which is very minimal in tendons. (Lui (2015) *Stem Cells and Cloning: Advances and Applications* 8:163-174).

Considerable basic studies have been devoted to the understanding of the development, structure, and function of these important tissues, because traumatic tendon/ligament injuries are extremely difficult to heal completely. These injuries often result in permanent disability and chronic pain in human patients, while in veterinary animals such as horses or dogs, damage to key tendon and ligaments can adversely affect the quality of life so severely that euthanasia is necessary. Treating tendon/ligament injuries is clinically challenging in both human and veterinary medicine because of the innate poor tissue healing response, likely due to the primary characteristics of these soft tissues including: a) a low proportion of resident progenitor and stem cells; b) limited vasculature or blood vessel supply; and c) a tendency for persistent inflammation because these are located in highly mobile body parts. The constant motion of the injured sites can hinder healing. Even in cases where healing occurs, a fibrovascular scar is formed which does not possess the biomechanical and biochemical properties of normal/original tendon and/or ligament, thereby resulting in significant loss of function for the individual and increased re-injury rates. (Lui (2015); Ross (2014) *Stem Cell Discovery* 4:44-53)

The three most common tendon injuries in man are tearing of the rotator cuff, injuries to the hand flexor tendon, and injuries to the Achilles tendon. These are often treated by surgical repair, physical therapy/rehabilitation and cryotherapy. In 2004, it was estimated that 45% of 32 million musculoskeletal injuries involved tendons and ligaments, and that the incidence was rapidly rising due to increased sports activities and an aging population. (September et al. (2007) *Br J Sports Med* 41:241-246)

The most common tendon and/or ligament injuries in racehorses and performance horses affect the suspensory ligament running behind the cannon bone, and the superficial and deep digital flexor tendons (SDFT and DDFT) running behind the back of the knee (or hock) all the way down to the navicular bone in each foot, acting as a sling for the fetlock to bear weight. (Briggs (2011) *The Horse* Jun. 3, 2011, pp.1-7). Injuries can be inflammation, sprains, strains, disruptions or tears and lacerations. Tendon/ligament injuries are estimated to be ~46% of all sport horse injuries, and 90% of tendon/ligament injuries are to the SDFT. SDFT damage is confirmed by a veterinarian with a physical exam for lameness and ultrasound. A horse can manifest lameness, heat, sensitivity to touch, tendon swelling or thickening, or a bowed or convex profile. Lameness correlates the degree of inflammation. (Tan (2016) *The Horse* Mar. 30, 2016, pp.1-7). DDFT injuries are common in the hoof capsule and tendon sheath and are classified as tendon enlargements, changes in shape, focal core lesions, mineralization and marginal tears. Tears are best detected with ultrasound, MRI or tenoscopy.

Ligament injuries in horses are often proximal suspensory desmitis (PSD) in the limbs that result in acute lameness. Hind limb PSD occurs frequently in high-level dressage horses and is not very responsive to conservative therapy which consists of repeated bandaging, administration of anti-inflammatories and analgesics (only 14% return without lameness for less than one year).

The repair or regeneration of tendon/ligament injuries have been a consistent target of the increasing number of regenerative medicine technologies, such as stem cells, platelet rich plasma (PRP), bone marrow aspirate concentrate, growth factors, and bioengineered scaffolds. Techniques such as extracorporeal shock wave therapy, low level laser therapy and mechanical stimulation have also been employed. (Thomas (2005) *The Chronicle of the Horse* 134-137; Fortier and Smith (2008) *Vet. Clin. Equine* 24:191-201; Briggs (2011); Yang et al. (2013) *Birth Defects Res. C. Embryo Today* 99(3):203-222; Lui (2015); Tan (2016); Basetto et al. (2011) Biomaterials Science and Engineering, Ch. 18, Ed. R. Pignatello, InTech, 2011, pp.369-386) More effective treatments to restore or regenerate tendon/ligament tissues after injury are needed.

SUMMARY OF THE INVENTION

Compositions comprising a variant NELL1 peptide or a nucleic acid encoding the same are provided. The variant NELL1 peptide lacks at least one of the carboxy-terminal von Willebrand factor, type C (VWC) domains of a NELL1 protein. In some embodiments of the invention, the variant NELL1 peptide lacks both carboxy-terminal VWC domains. In some of these embodiments, the variant NELL1 peptide lacks the carboxy-terminal 179 amino acid residues. In particular aspects of the invention, the variant NELL1 peptide has at least 75% sequence identity to the disclosed SEQ ID NO: 17 or 18 and one of the following properties: enhanced efficacy in tissue regeneration, promotion of wound healing, easier purification, higher yield, and less aggregate formation, when compared to a full-length NELL1 protein. In some of these embodiments, the variant NELL1 peptide comprises or consists essentially of SEQ ID NO: 17 or 18. Also provided herein are pharmaceutical compositions and kits comprising the variant NELL1 peptide or a nucleic acid encoding the same.

The variant NELL1 peptides or nucleic acids encoding the same find use in regenerating injured tissues, promoting the maturation of a progenitor cell, enhancing the migration and/or proliferation of fibroblast cells, and promoting the healing of a wound, such as an injury to a tendon or a ligament. In particular aspects of the invention, the wound is an open wound. In certain embodiments, the wound comprises an injury to skeletal muscle, cartilage, bone, skin, tendon, ligament or a combination thereof. In some aspects, the variant NELL1 peptide or nucleic acid encoding the same is administered locally to the wound. In particular embodiments, the subject in need of promotion of healing of a wound is a mammal, such as a human or a horse. The variant NELL1 peptide or nucleic acid encoding the same can be administered to the wound about two days after the injury.

Methods for promoting the healing of an injury to a tendon or ligament in a subject in need thereof are provided herein. These presently disclosed methods involve the administration of an effective amount of a NELL1 peptide or a nucleic acid encoding a NELL1 peptide to the subject. The subject can be a mammal, such as a human or a horse. The methods find use in treating various injuries in humans, including injuries to Achilles tendons. Horses, especially racehorses, are particularly prone to tendon and ligament injuries, such as the superficial digital flexor tendon or deep digital flexor tendon, and the presently disclosed methods are useful in promoting the healing of these injuries. The NELL1 peptide or nucleic acid encoding the same can be administered via local injection to the area surrounding the injured tendon or ligament or can be incorporated into a matrix, such as a wound dressing and applied directly to the injured tissue. The NELL1 peptide or nucleic acid encoding the same can be administered to the tendon or ligament injury about seven days after the injury.

Methods for enhancing the migration and/or proliferation of fibroblast cells with a NELL1 peptide or a nucleic acid encoding the same are also provided herein. In particular aspects of the invention, the fibroblast cell is a dermal fibroblast or a ligament fibroblast. In some embodiments, the migration of the fibroblasts towards a wound area is enhanced with a NELL1 peptide or a nucleic acid encoding the same.

The foregoing is a summary and thus contains, by necessity, simplifications, generalizations, and omissions of detail; consequently, those skilled in the art will appreciate that the summary is illustrative and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 2A and 2B) and horse NEL1 variant protein aa3-612 (FIGS. 2C and 2D). FIGS. 2A and 2C depict sodium dodecyl sulfate polyacrylamide gel electrophoresis (SDS-PAGE), whereas FIGS. 2B and 2D depict Western Blots using mouse anti-GST antibody (1 µg/ml) to the GST tag attached to the NELL1 protein, followed by Jackson anti-mouse IgG-HRP (1500X). The lanes in FIG. 2A are as follows: M=molecular markers (kilodaltons or kDa) 10 µl/lane; lane 1=NELL1 protein aa3-791 (5 µl/lane); and lanes 2-5 are loading control proteins at 0.1 µg/lane, 0.2 µg/lane, 0.5 µg/lane, and 1.0 µg/lane, respectively. The lanes in FIG. 2B are as follows: M=molecular markers (kDa); lane 1 is NELL1 aa3-791 protein (5 µl); and lane 2 is GST protein. The lanes in FIG. 2C are as follows: M=molecular markers 10 µl/lane (kDa); lane 1=NELL1 protein aa3-612 (5 µl/lane); and lanes 2-5 are loading control proteins at 0.1 µg/lane, 0.2 µg/lane, 0.5 µg/lane, and 1.0 µg/lane, respectively. The lanes in FIG. 2D are as follows: M=molecular markers (kDa); lane 1 is NELL1 aa3-612 protein (5 µl); and lane 2 is GST protein.

FIG. 3A demonstrates a dose-dependent increase in wound healing on Type 1 diabetic human dermal fibroblasts in an in vitro wound scratch assay with Nell1 variant protein (aa3-612). There is increased migration of the diabetic dermal fibroblasts into the wound area when treated with 100 ng/ml (line b), 200 ng/ml (line c), and 300 ng/ml (line d) of the protein, compared to the untreated controls (line a). FIGS. 3B, 3C, and 3D demonstrates an increased wound healing effect on Type 1 diabetic human dermal fibroblasts, normal human dermal fibroblasts, and normal human ligament fibroblasts, respectively, in an in vitro wound scratch assay by 300 ng/ml of NELL1 variant protein (aa3-612; line C), compared to the full-length NELL1 protein at the same dose (line B) and the untreated control (line A).

DETAILED DESCRIPTION OF THE INVENTION

I. Introduction

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes and are not to be construed as limiting the subject matter described. Finally, for the purposes of the instant disclosure all identifying sequence Accession numbers may be found in the NCBI Reference Sequence (RefSeq) database and/or the NCBI GenBank archival sequence database unless otherwise noted.

II. NELL1

The neural epidermal growth-factor-like (nel) gene was first detected in neural tissue from an embryonic chicken cDNA library, and its human ortholog neural epidermal growth-factor-like 1 (NEL-like 1, NELL1) was discovered later in B-cells. Studies have reported the presence of NELL1 in various fetal and adult organs, including, but not limited to, skeletal and cardiac muscle, skin, the brain, kidneys, colon, thymus, lung, and small intestine.

The human NELL1 gene encodes an 810-amino acid polypeptide. Generally, the arrangement of the functional domains of the NELL1 protein bears resemblance to thrombospondin-1 (THBS1) and consists of a thrombospondin N-terminal domain (TSPN) and several von Willebrand factor, type C (VWC), and epidermal growth-factor (EGF) domains. A domain is a region of a protein with a characteristic primary structure and function.

Additional studies have shown that there are at least two human NELL1 transcript variants encoding different isoforms. In humans, the nel-like 1 isoform 1 precursor transcript variant (set forth in SEQ ID NO: 1) represents the longer transcript (set forth in GenBank Acc. No. NM_006157) and encodes the longer isoform 1 (set forth in SEQ ID NO: 2).

Figure 1:
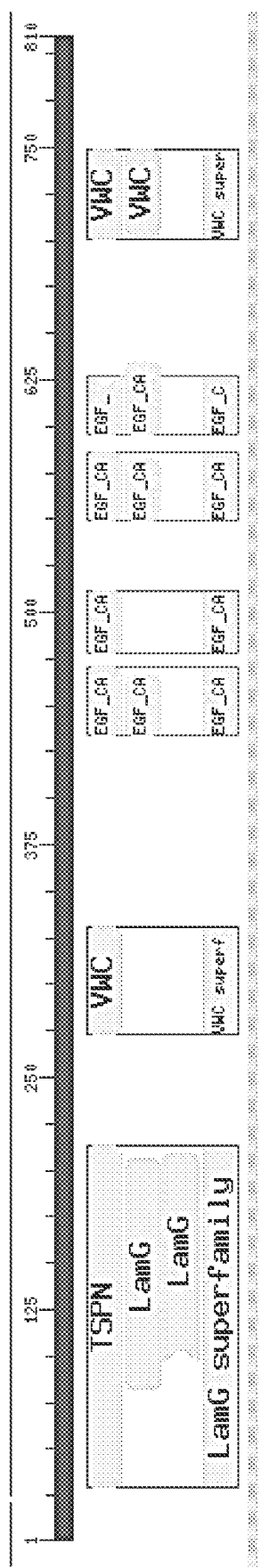
FIG. 1 shows the general structure of the human nel-like 1 isoform 1 (SEQ ID NO: 2).
Figure 2B:
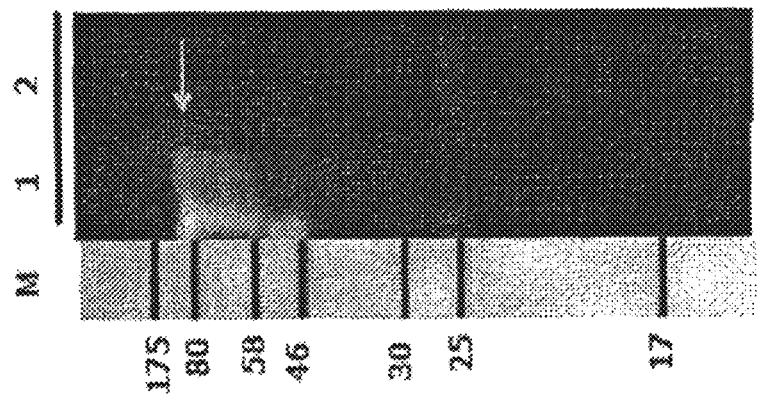
FIGS. 2A-2D depict purified recombinant horse NELL1 protein aa3-791 (full-length.
Figure 2A:
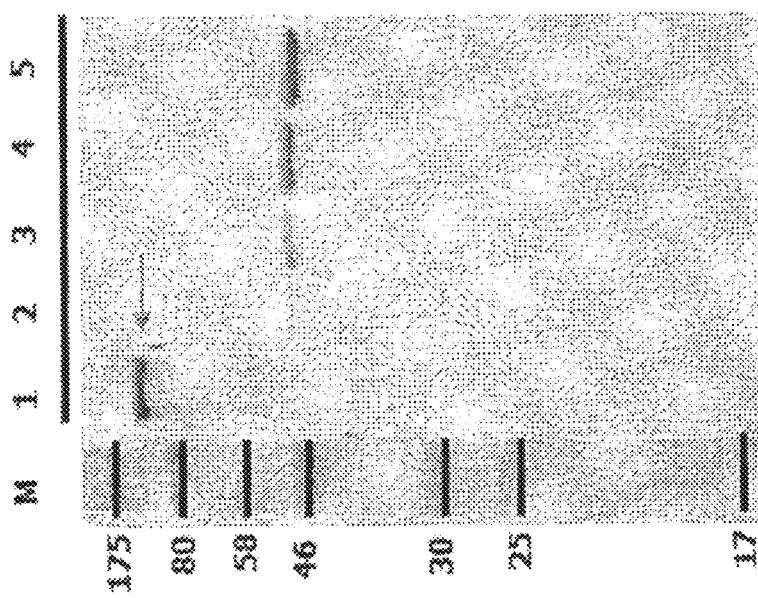
Figure 2C:
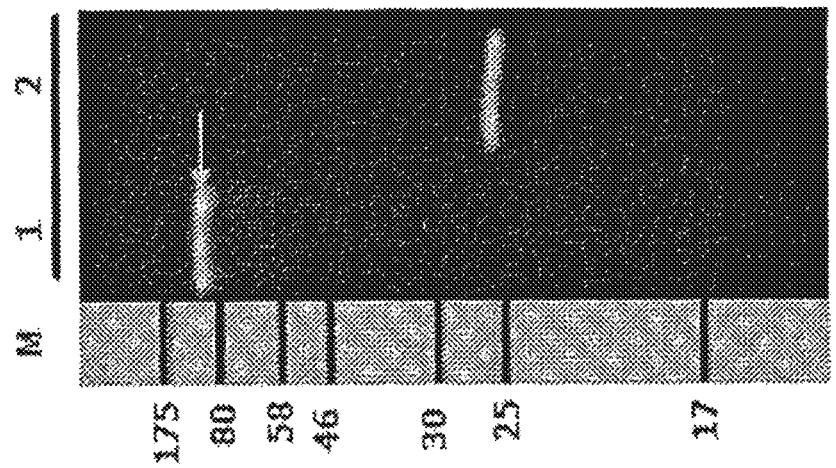
Figure 2D:
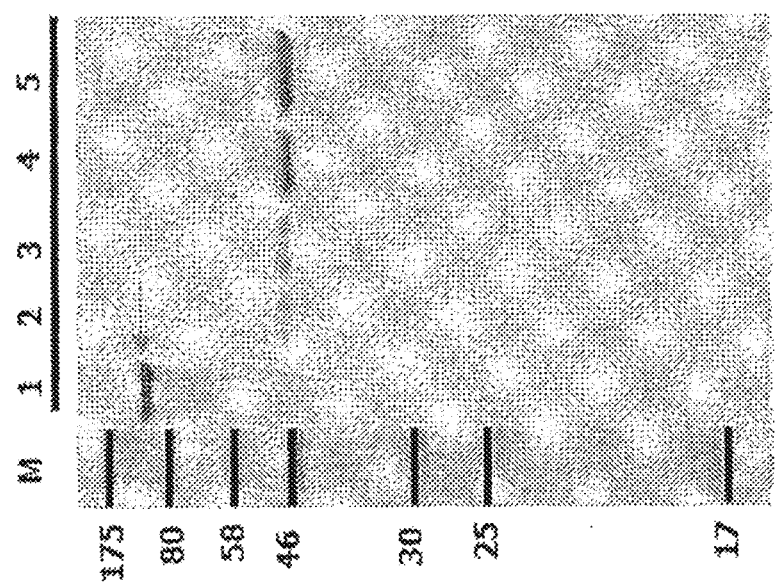

FIG. 1 shows the general structure of human nel-like 1 isoform 1 (SEQ ID NO: 2). The conserved domains reside in seven regions of the isoform 1 peptide and include: (1) a TSPN domain/Laminin G superfamily domain; (2) a VWC domain; (3) four EGF-like domains; and (4) a VWC domain. NELL1 also comprises a secretion signal peptide domain (amino acid residues 1-16 of SEQ ID NO: 2) that is generally involved in transport of the protein to cell organelles where it is processed for secretion outside the cell.

The first conserved domain region comprises amino acids (amino acids 29 to 213 of SEQ ID NO: 2) that are most similar to a thrombospondin N-terminal-like domain. Thrombospondins are a family of related, adhesive glycoproteins, which are synthesized, secreted and incorporated into the (ECM) of a variety of cells, including alpha granules of platelets following thrombin activation and endothelial cells. They interact with a number of blood coagulation factors and anticoagulant factors, and are involved in cell adhesion, platelet aggregation, cell proliferation, angiogenesis, tumor metastasis, vascular smooth muscle growth and tissue repair. The first conserved domain also comprises amino acids (amino acids 82 to 206; amino acids 98 to 209 of SEQ ID NO: 2) that are similar to a Laminin G-like domain. Laminin G-like (LamG) domains usually are $Ca^{2+}$ mediated receptors that can have binding sites for steroids, β1-integrins, heparin, sulfatides, fibulin-1, and α-dystroglycans. Proteins that contain LamG domains serve a variety of purposes, including signal transduction via cell-surface steroid receptors, adhesion, migration and differentiation through mediation of cell adhesion molecules.

Studies show that NELL1 signaling involves an integrin-related molecule and tyrosine kinases that are triggered by NELL1 binding to a NELL1 specific receptor and a subsequent formation of an extracellular complex. As thus far understood, in human NELL1 (hNELL1), the laminin G domain comprises about 128 amino acid residues that show a high degree of similarity to the laminin G domain of extracellular matrix (ECM) proteins; such as human laminin α3 chain (hLAMA3), mouse laminin α3 chain (mLAMA3), human collagen 11 α3 chain (hCOLA1), and human thrombospondin-1 (hTSP1). This complex facilitates either activation of tyrosine kinases, inactivation of tyrosine phosphatases, or intracellular recruitment of tyrosine-phosphorylated proteins. The ligand bound integrin (cell surface receptors that interact with ECM proteins such as, for example, laminin 5, fibronectin, vitronectin, TSP1/2) transduces the signals through activation of the focal adhesion kinase (FAK) followed by indirect activation of the Ras-MAPK cascade, and then leads to osteogenic differentiation through Runx2; the laminin G domain is believed to play a role in the interaction between integrins and a 67 kDa laminin receptor (Shen et al. (2012) *J. Cell Biochem* 113: 3620-3628).

The second conserved domain (amino acids 273 to 331 of SEQ ID NO: 2) and seventh conserved domain (amino acids 701 to 749 of SEQ ID NO: 2) are similar to von Willebrand factor type C (VWC) domains, also known as chordin-like repeats. An additional VWC domain is also found from amino acid residues 634 to 686 of SEQ ID NO: 2. VWC domains occur in numerous proteins of diverse functions and have been associated with facilitating protein oligomerization.

The third conserved domain (amino acids 434 to 466 of SEQ ID NO: 2), fourth conserved domain (amino acids 478 to 512 of SEQ ID NO: 2), fifth conserved domain (amino acids 549 to 586 of SEQ ID NO: 2), and sixth conserved domain (amino acids 596 to 627 of SEQ ID NO: 2) are similar to a calcium-binding EGF-like domain. Calcium-binding EGF-like domains are present in a large number of membrane-bound and extracellular (mostly animal) proteins. Many of these proteins require calcium for their biological function. Calcium-binding sites have been found to be located at the N-terminus of particular EGF-like domains, suggesting calcium-binding may be crucial for numerous protein-protein interactions. Six conserved core cysteines form three disulfide bridges as in non-calcium-binding EGF domains whose structures are very similar. The calcium-binding EGF-like domains of NELL1 bind protein kinase C beta, which is typically involved in cell signaling pathways in growth and differentiation.

The nel-like 1 isoform 2 precursor transcript variant (set forth in GenBank Acc. No. NM_201551 and SEQ ID NO: 3) lacks an alternate in-frame exon compared to variant 1. The resulting isoform 2 (set forth in SEQ ID NO: 4), which has the same N- and C-termini as isoform 1 but is shorter compared to isoform 1, has six conserved regions including a TSPN domain/LamG superfamily domain (amino acids 29 to 213 of SEQ ID NO: 4); VWC domains (amino acids 273 of SEQ ID NO: 4; amino acids 654 to 702 of SEQ ID NO: 4); and calcium-binding EGF-like domains (amino acids 478 to 512 of SEQ ID NO: 4; amino acids 434 to 466 of SEQ ID NO: 4; amino acids 549 to 580 of SEQ ID NO: 4).

NELL1 and its orthologs are found across several species including *Homo sapiens* (man), *Bos taurus* (cow; the nucleic acid sequence of which is set forth in GenBank Acc. No. XM_002699102 and the amino acid sequence is set forth in SEQ ID NO: 19), *Equus caballus* (horse; the nucleic acid sequence of isoforms 1 and 2 are set forth in GenBank Acc. Nos. XM_001504986 and XM_001504987, respectively, and in SEQ ID NO: 5 and 7, respectively; the amino acid sequences are set forth in SEQ ID NO: 6 and 8, respectively), *Macaca mulatta* (rhesus monkey; the nucleic acid sequence of isoforms 1, 2, 3, and 4 are set forth in GenBank Acc. Nos. XM_002799606, XM_001092428, XM_001092540, and XM_001092655, respectively), *Mus musculus* (mouse; the nucleic acid sequence of which is set forth in GenBank Acc. No. NM_001037906 and in SEQ ID NO: 9; the amino acid sequence of which is set forth in SEQ ID NO: 10), *Rattus norvegicus* (rat; the nucleic acid sequence of which is set forth in GenBank Acc. No. NM_031069 and in SEQ ID NO: 11; the amino acid sequence of which is set forth in SEQ ID NO: 12), *Pan troglodytes* (chimpanzee; the nucleic acid sequence of which is set forth in GenBank Acc. No. XM_508331.2), *Felis catus* (cat; the amino acid sequences of isoform 1 and 2 are set forth in GenBank Acc. Nos. XP_003993117.1 and XP_003993118.1, and SEQ ID NOs: 13 and 14, respectively, *Canis lupis familiaris* (dog; the amino acid sequence is set forth in GenBank Acc. No. XP_534090 and SEQ ID NO: 15), and *Ovis aries* (sheep; the amino acid sequence is set forth in GenBank Acc. No. XP_004019490 and SEQ ID NO: 16).

NELL1 is a signaling protein that mediates tissue growth and maturation in a variety of tissues such as bone, cartilage, heart and skeletal muscle—during fetal development and the healing of acute injuries in adult tissues (Desai et al. (2006) *Hum. Mol. Genet.* 15(8):1329-1341; Siu et al. (2011) *Tissue Eng Part A* 17(7-8):1123-1135; Siu et al. (2012) *Tissue Eng Part A* 18(3-4):252-261; Xue et al. (2011) *Bone* 48(3):485-495; Li et al. (2011) *Plast. Reconstr. Surg.* 127(2):580-587; Turner et al. (2013) *Cells Tissues and Organs* 198(4):249-265). During early development, NELL1 regulates the production of many components of the extracellular matrix (ECM) which collectively serve as an architectural framework and communication highway to mediate new tissue formation.

In vitro studies on three-dimensional human skin models exposed to UV radiation demonstrated that NELL1 reduces levels of key pro-inflammatory molecules (e.g. IL1-β, IL8) after adult tissue injury (Mitchell et al. (2012) Abstract, 70th Annual Meeting of the American Academy of Dermatology, San Diego, Calif., March 16-20). Human genome-wide association studies have also suggested that in certain genetic populations NELL1 plays a role in controlling severe inflammatory conditions (Franke et al. (2007) *PLoS ONE* 2(8):e691).

Multiple effects of NELL1 are believed to contribute to its ability to heal injuries to tendons and/or ligaments. Such effects include its pro-angiogenic activity, which stimulates blood vessel formation in areas having poor blood supply. NELL1 accomplishes this via effects on VEGF and perivascular stem cells (Askarinam et al. (2013) *Tissue Eng. A* 19(11-12):1386-1397). The effect of NELL1 in perivascular cells is particularly important in tendon regeneration because the capillaries of tendons contain perivascular stem cells that express tendon- and stem/precursor cell-like characteristics which could be the source of the formation/regeneration of new tendon tissue (Tempfer et al. (2009) *Histochem. Cell Biol.* 131(6):733-741). While not being held by any theory or mechanism of action, it is believed that NELL1 can also stimulate the proliferation and migration of tendon precursor stem cells, fibroblasts or perivascular stem cells, contributing to the healing of tendons (Nemoto et al. (2013) *J. Equine Sci.* 24(2):17-24).

NELL1 induces the production of molecules in the extracellular matrix that are key structural components of tendons and ligaments or molecules that regulate the production of components and their assembly/organization into the correct functional architecture. Some of the known genes in the NELL1 pathway directly impact tendon or ligament development, structure, function, repair and regeneration after injuries. This list includes tenascin C, collagen V, Bmp7, periostin or osteoblast specific factor 2, and Prg4 (lubricin). Tenascin C is a glycoprotein abundant in tissues with high tensile strength and subject to compression stress. It is believed to be a key factor in tendon healing due to its ability to promote fibroblast/tendon cell proliferation and migration. Tenascin C is a genetic determinant of Achilles heel tendinopathies and ruptures and is linked to tissue response to mechanical loading, probably by regulating cell-ECM interactions (September et al. (2007); Taylor et al. (2009) *BMC Musculoskeletal Disorders* 10(27):1-10; Juneja & Veillette (2013) *Arthritis* 2013:1-30; Nemoto et al. (2013)). Collagen V, specifically Col5a1 and Col5a3, is a component of fibrillary collagen that regulates collagen fiber assembly and diameter in tendons and ligaments (September et al. (2007); Connizzo et al. (2015) *J. Orthopaedic. Research* 33:882-888; Sun et al. (2015) *Am. J. Pathol.* 185:1436-1447). Bmp7 is a bone morphogenetic protein that serves as a growth factor promoting cell growth and differentiation. It facilitates tendon-bone integration. Other studies show it increases collagen type 1 production and cell activity (Pauly et al. (2012) *J. Shoulder Elbow Surg.* 21(4):464-473; Schwarting et al. (2015) *PLoS One* 10(2):1-17). Periostin or osteoblast specific factor 2 is a matricellular protein that is abundant in collagen rich connective tissue, where it is essential for proper ECM synthesis, collagen 1 fibrillogenesis, and tendon crosslinking. (Hamilton et al. (2008) *J. Cell Commun. Signal* 2:9-17; Juneja & Veilette (2013)). Prg4 (lubricin) is a proteoglycan that plays a role in boundary lubrication in articulating joints and tendon gliding. Its absence leads to decreased lubrication, which causes tissue damage, matrix remodeling and dystrophic calcification. (Juneja & Veillete (2013)).NELL1 modulates the inflammatory response via the downregulation of cytokines such as IL-1 beta and IL8 (Mitchell et al. (2012)). Tendon and ligament injuries are prone to prolonged inflammation because the injured sites are often subjected to constant motion. NELL1 downregulates matrix metalloproteinases (e.g. MMPI), which degrade the collagen in tendon ECM. MMPs are needed to maintain ECM homeostasis, but tendon injury can lead to an imbalance or dysregulation so that high levels can further degrade tendon architecture and function. (Mitchell et al. (2012); Davis et al. (2013) *J. Applied Physiol.* 115(6):884-891).

Disclosed herein is the discovery that NELL1 also enhances the migration and/or the proliferation of fibroblast cells (e.g., ligament fibroblasts, dermal fibroblasts from normal individuals and type 1 diabetic patients). This effect can serve to promote wound healing by increasing the numbers of fibroblasts within a wound area, thus enhancing the contraction and closure of the wound. The proliferation and migration of fibroblasts into the provisional wound matrix/fibrin clot are critical processes that are triggered early in wound healing (e.g., few days after injury in human skin) and have significant roles in supporting other biological processes throughout normal wound healing, including the degradation of the fibrin clot, secretion of new extracellular matrix and collagen-rich structures to support the activities of other cells, and wound contraction. The presently disclosed methods and compositions utilize a NELL1 peptide or a nucleic acid molecule encoding the same to promote the healing of injuries to tendons or ligaments or to enhance the migration and/or proliferation of fibroblasts. Certain NELL1 variants also find broader use in regenerating tissues, promoting healing of wounds, and promoting the maturation of progenitor cells.

A peptide, polypeptide, or protein is a sequence of subunit amino acids, amino acid analogs, or peptidomimetics. A peptidomimetic is a small protein-like chain designed to mimic a peptide. A peptidomimetic typically arises from modification of an existing peptide in order to alter the molecule's properties.

A peptide, polypeptide or protein can also be amino acid polymers in which one or more amino acid residue is an artificial chemical analogue of a corresponding naturally occurring amino acid, as well as to naturally-occurring amino acid polymers. A polypeptide, peptide or protein is inclusive of modifications including, but not limited to, glycosylation, lipid attachment, sulfation, gamma-carboxylation of glutamic acid residues, hydroxylation, phosphorylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translation natural processes and by entirely synthetic methods, as well.

A NELL1 peptide, NELL1 polypeptide, or NELL1 protein is a naturally-occurring NELL1 protein, or a variant or fragment thereof that retains the ability to promote the healing of injuries to tendons and/or ligaments. In some embodiments, the NELL1 peptide exhibits any one of the activities selected from the group consisting of: stimulation of ECM production (e.g., through the upregulation of at least one of tenascins, proteoglycans, elastin, glycosaminoglycans, including epidermal hyaluronic acid, and collagens), reduction in the levels of inflammatory mediators (e.g., IL-1β and IL-8), reduction in the levels of matrix metalloproteinases (e.g., MMP1), and enhancing the migration and/or proliferation of fibroblasts. In other embodiments, the NELL1 peptide can also exhibit at least one of the activities selected from the group consisting of binding to PKC-beta, stimulation of differentiation of a precursor cell (e.g., skeletal satellite cell, osteoblast precursor, perivascular stem cell, or tendon precursor stem cell) to maturity, and stimulation of angiogenesis. To determine whether a peptide exhibits any one of these activities, any method known in the art useful for measuring these activities can be used.

Suitable assays for determining if a given peptide can stimulate ECM production and reduce the levels of inflammatory mediators or MMPs include assays that measure transcript levels (e.g., quantitative polymerase chain reaction) or levels of the protein (e.g., enzyme-linked immunoassay) directly or indirectly (by measuring the activity of the protein), including those that are described elsewhere herein.

Suitable assays for assessing the binding of NELL1 to PKC beta is described in e.g., Kuroda et al. (1999) *Biochem. Biophys. Res. Comm.* 265:752-757. For example, protein-protein interactions can be analyzed by using the yeast two-hybrid system. Briefly, a NELL1 protein can be fused with GAL4 activating domain and the regulatory domain of PKC can be fused with the GAL4 DNA-binding domain.

In other embodiments, the NELL1 peptide stimulates the differentiation of precursor cells, such as skeletal satellite cells, osteoblast precursors, perivascular stem cells, and tendon precursor stem cells, to maturity. The maturity of cells can be assessed cellularly (histology) and molecularly (expression of cell-specific proteins or extracellular matrix materials).

Suitable assays for determining if a peptide is capable of promoting the healing of tendon and/or ligament injuries include those known in the art (Nemoto et al. (2013); Taylor et al. (2009); Yanming et al. (2007) *Nature Medicine* 13:1219-1227; Tempfer et al. (2009)) and disclosed elsewhere herein.

Suitable assays for determining if a NELL1 peptide can promote the migration and/or proliferation of fibroblasts include wound scratch assays known in the art and described elsewhere herein.

The NELL1 peptide may be a naturally-occurring (i.e., wild-type) NELL1 protein or an active variant or fragment thereof. Naturally refers to as found in nature; wild-type; innately or inherently. A naturally-occurring NELL1 peptide may be purified from a natural source or may be a peptide that has been recombinantly or synthetically produced that has the same amino acid sequence as a NELL1 peptide found in nature.

A polynucleotide can be a singular nucleic acid, as well as plural nucleic acids, and refers to a nucleic acid molecule or construct, e.g., messenger RNA (mRNA), complementary DNA (cDNA), plasmid DNA (pDNA), or short interfering RNA (siRNA). A polynucleotide can be single-stranded or double-stranded, linear or circular and can be comprised of DNA, RNA, or a combination thereof. A polynucleotide can comprise a conventional phosphodiester bond or a non-conventional bond (e.g., an amide bond, such as found in peptide nucleic acids (PNA)). A nucleic acid can be any one or more nucleic acid segments, e.g., DNA or RNA fragments, present in a polynucleotide. The polynucleotide can contain modified nucleic acids, such as phosphorothioate, phosphate, ring atom modified derivatives, and the like. The polynucleotide can be a naturally occurring polynucleotide (i.e., one existing in nature without human intervention), a recombinant polynucleotide (i.e., one existing with human intervention), or a synthetically derived polynucleotide.

An isolated material can refer to a nucleic acid, peptide, polypeptide, or protein, which is: (1) substantially or essentially free from components that normally accompany or interact with it as found in its naturally occurring environment. Substantially free or essentially free refer to considerably or significantly free of, or more than about 95% free of, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868, each of which is incorporated by reference herein. Likewise, a naturally occurring nucleic acid (for example, a promoter) becomes isolated if it is introduced by non-naturally occurring means to a locus of the genome not native to that nucleic acid.

Fragments and variants of native (i.e., naturally-occurring) NELL polypeptides can be employed in the various methods and compositions of the invention. A fragment is intended a portion of a polynucleotide or a portion of a polypeptide. Fragments of a polynucleotide may encode polypeptide fragments that retain the biological activity of the native polypeptide. A fragment of a polynucleotide that encodes a biologically active portion of a NELL1 polypeptide will encode at least 15, 25, 30, 50, 100, 150, 200, 250, 300, 350, 400, 450, 500, 550, 600, 650, 700, 750, or 800 contiguous amino acids, or up to the total number of amino acids present in a full-length NELL1 polypeptide. In certain embodiments, the NELL1 fragment is 610 amino acids in length.

A fragment of a native NELL1 polypeptide can be prepared by isolating a portion of a polynucleotide encoding the portion of the NELL1 polypeptide and expressing the encoded portion of the polypeptide (e.g., by recombinant expression in vitro). Polynucleotides that encode fragments of a NELL1 polypeptide can comprise nucleotide sequences comprising at least 15, 20, 50, 75, 100, 150, 200, 250, 300, 350, 400, 450, 500, 550, 600, 650, 700, 800, 900, 1000, 1100, 1200, 1300, 1400, 1500, 1600, 1700, 1800, 1900, 2000, 2100, 2200, 2300, or 2400 contiguous nucleotides, or up to the number of nucleotides present in a full-length NELL1 nucleotide sequence. In some embodiments, the fragment lacks the first amino acid residue, or the first 2, 3, 4, 5, 6, 7, 8, 9, 10, 20, 21, 22, 23, 24, 25, 26, 27, 28, 29, 30, 35, 40, or 45 amino acid residues from the amino terminal end of the NELL1 protein. In some embodiments, the fragment lacks the last 5, 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 205, 210, 220, 230, 240, 250, 260 or more amino acid residues. In certain embodiments, the fragment of a NELL1 protein lacks the most carboxy-terminal 179 amino acid residues from the end of the protein. In other embodiments, the NELL1 protein fragment lacks the first two amino acid residues from the amino terminal end and the last 179 amino acid residues from the carboxy terminal end of the protein. In some embodiments, the NELL1 protein fragment has 610 amino acid residues.

The inventors determined that removal of 179 amino acid residues from the carboxy-terminus of the *Equus caballus* NELL1 isoform 1 protein unexpectedly provided a higher yield and easier purification during manufacture of the protein. Without being bound by any theory or mechanism of action, it is believed that the removal of the carboxy-terminal domains led to decreased formation of aggregates of the protein. Although NELL1 protein naturally oligomerizes into trimers, which are functional, aggregates of NELL1 protein refer to large, higher-ordered macromolecular complexes that prevent or reduce the function of the protein or make the protein products difficult to extract and purify. The NELL1 protein lacking the C-terminal 179 amino acid residues is also unexpectedly more efficacious than full-length NELL1 protein in horse body wound healing studies and fibroblast wound scratch assays. Thus, in specific embodiments, the NELL1 protein fragment lacks the last 179 amino acid residues from the carboxy terminus. In some of these embodiments, the NELL1 protein fragment also lacks the first two amino acid residues from the amino terminus. The sequence of this horse NELL1 fragment is set forth in SEQ ID NO: 18. In other embodiments, the NELL1 protein fragment lacks the first 21 amino acid residues from the amino terminus and the last 179 amino acid residues from the carboxy terminus. The sequence of this human NELL1 fragment is set forth in SEQ ID NO: 17. In certain embodiments, the NELL1 protein fragment lacks at least one of the two carboxy-terminal VWC domains (located at amino acid residues 634-686 and 701-749 of SEQ ID NO: 2). In some of these embodiments, the NELL1 protein fragment lacks both of these carboxy-terminal VWC domains. Compositions comprising these NELL1 fragments are contemplated herein and methods for using these NELL1 fragments for regenerating tissues (e.g., bone, cartilage, heart, vasculature, skeletal muscle), promoting the maturation of progenitor cells for various tissues (e.g., bone, cartilage, heart, vasculature, skeletal muscle, tendons, ligaments), and promoting the migration and/or proliferation of fibroblasts are also contemplated herein.

In those embodiments wherein a variant NELL1 protein lacks at least one C-terminal VWC domain, the variant NELL1 protein exhibits at least one of the following characteristics: enhanced efficacy in tissue regeneration and/or promotion of wound healing, easier purification, higher yield, less aggregate formation, and enhanced efficacy in fibroblast migration and/or proliferation, when compared to a full-length NELL1 protein. An easier purification includes a purification process whereby a single polypeptide species is substantially separated from other polypeptide species or a natural or synthetic milieu comprising the single polypeptide species and other polypeptide species that comprises fewer steps required for substantial separation or wherein the time required for at least one of the steps in the separation is reduced. An easier purification also refers to a purification process which results in a higher yield of the substantially purified or separated polypeptide species. The terms "substantially purified" or "substantially separated" when used in reference to a single polypeptide species refers to a level of purification whereby the single polypeptide species represents at least about 70% of a total population of polypeptide species within a sample, including but not limited to at least about 75%, 80%, 85%, 86%, 87%, 88%, 89%, 90%, 91%, 92%, 93%, 94%, 95%, 96%, 97%, 98%, 99%, or greater of a total population of polypeptide species within a sample. A yield of a protein product from a purification process refers to the overall concentration of the polypeptide within a solution. The higher the concentration of the polypeptide within the solution, the more yield is obtained. If a polypeptide is present within a solution at <0.1 µg/µl, the protein is considered difficult to produce and purify. Thus, in some embodiments, a variant NELL1 protein that lacks at least one C-terminal VWC domain exhibits the ability to be purified using conventional purification means known in the art, such as those methods described elsewhere herein, to a concentration greater than 0.1 µg/µl. In some of these embodiments, a variant NELL1 protein has the ability to be purified using conventional purification means known in the art to a concentration of about 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30 µg/µl, or greater. In certain embodiments, a variant NELL1 protein lacking at least one C-terminal VWC domain exhibits both a higher yield and a greater purity as compared to a full-length NELL1 protein following a purification process.

Variant sequences have a high degree of sequence similarity. For polynucleotides, conservative variants include those sequences that, because of the degeneracy of the genetic code, encode the amino acid sequence of a NELL1 polypeptide. Variants such as these can be identified with the use of well-known molecular biology techniques, such as, for example, polymerase chain reaction (PCR) and hybridization techniques. Variant polynucleotides also include synthetically derived nucleotide sequences, such as those generated, for example, by using site-directed mutagenesis. In some embodiments, the variant polynucleotide still encodes a NELL1 polypeptide or a fragment thereof. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide can also be evaluated by comparison of the percent sequence identity between the polypeptide encoded by a variant polynucleotide and the polypeptide encoded by the reference polynucleotide. Thus, variants include, for example, polynucleotides that encode a polypeptide with a given percent sequence identity to a native NELL1 polypeptide.

Percent sequence identity between any two polypeptides can be calculated using sequence alignment programs and parameters described herein. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

A variant polypeptide is a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. The activity of variant NELL1 polypeptides can be assessed using the methods disclosed herein to determine if the variant is biologically active. Such variants may result from, for example, genetic polymorphism or from human manipulation. Biologically active variants of a native NELL1 polypeptide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native polypeptide as determined by sequence alignment programs and parameters described elsewhere herein. A biologically active variant of a polypeptide may differ from that polypeptide by as few as 1-15 amino acid residues, as few as 1-10, such as 6-10, as few as 5, as few as 4, 3, 2, or even 1 amino acid residue.

Biologically active variants of the NELL1 fragments disclosed herein (i.e., those lacking at least one of the two VWC domains at the carboxy terminus of NELL1) are also contemplated herein and may have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the active NELL1 fragment (e.g., SEQ ID NO: 17 or 18).

Polypeptides may be altered in various ways including amino acid substitutions, deletions, truncations, and insertions. Methods for such manipulations are generally known in the art. For example, amino acid sequence variants of native NELL1 polypeptides can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.). Conservative substitutions, such as exchanging one amino acid with another having similar properties, may be preferable.

Generally, the mutations made in the polynucleotide encoding the variant NELL1 polypeptide should not place the sequence out of reading frame, and/or create complementary regions that could produce secondary mRNA structure. See, EP Patent Application Publication No. 75,444.

Variant NELL1 polynucleotides and polypeptides also encompass sequences and polypeptides derived from a mutagenic and recombinogenic procedure such as DNA shuffling. With such a procedure, one or more different NELL1 coding sequences can be manipulated to create peptides that can be evaluated to determine if it retains NELL1 activity. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) Nature 391:288-291; and U.S. Pat. Nos. 5,605,793 and 5,837,458.

Variant NELL1 polynucleotides and polypeptides also encompass sequences and polypeptides derived from gene editing systems, such as CRISPR/Cas system.

Sequence identity in the context of two polynucleotides or polypeptide sequences makes reference to the residues in the two sequences that are the same when aligned for maximum correspondence over a specified comparison window. When percentage of sequence identity is used in reference to polypeptides it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have sequence similarity or similarity. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Percentage of sequence identity is the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3; % identity and % similarity for an amino acid sequence using GAP Weight of 8 and Length Weight of 2, and the BLOSUM62 scoring matrix; or any equivalent program thereof. An equivalent program is any sequence comparison program that, for any two sequences in question, generates an alignment having identical nucleotide or amino acid residue matches and an identical percent sequence identity when compared to the corresponding alignment generated by GAP Version 10.

The NELL1 peptide may be made synthetically, i.e. from individual amino acids, or semi-synthetically, i.e. from oligopeptide units or a combination of oligopeptide units and individual amino acids. Suitable methods for synthesizing proteins are described by Stuart and Young in "*Solid Phase Peptide Synthesis,*" Second Edition, Pierce Chemical Company (1984), *Solid Phase Peptide Synthesis, Methods Enzymol.*, 289, Academic Press, Inc, New York (1997).

The NELL1 peptide may also be prepared by methods that are well known in the art. One such method includes isolating or synthesizing DNA encoding the NELL1 peptide, and producing the recombinant protein by expressing the DNA, optionally in a recombinant vector, in a suitable host cell. Suitable methods for synthesizing DNA are described by Caruthers et al. (1985) *Science* 230:281-285; and *DNA Structure, Part A: Synthesis and Physical Analysis of DNA,* Lilley, D. M. J. and Dahlberg, J. E. (Eds.), *Methods Enzymol.*, 211, Academic Press, Inc., New York (1992).

In some embodiments of the presently disclosed methods, a nucleic acid molecule encoding a NELL1 peptide is administered to a subject in need thereof in order to regenerate tissue, promote the healing of an injury (e.g., tendon or ligament injury), or to enhance migration and/or proliferation of fibroblasts. As used herein, the terms "encoding" or "encoded" when used in the context of a specified nucleic acid mean that the nucleic acid comprises the requisite information to direct translation of the nucleotide sequence into a specified polypeptide.

In some embodiments of the presently disclosed methods, the NELL1 nucleic acid molecule is operably linked to at least one regulatory element. A regulatory element is a nucleic acid sequence(s) capable of effecting the expression of nucleic acid(s), or the peptide or protein product thereof. Non-limiting examples of regulatory elements include promoters, enhancers, polyadenylation signals, transcription or translation termination signals, ribosome binding sites, or other segments of DNA where regulatory proteins, such as, but not limited to, transcription factors, bind preferentially to control gene expression and thus protein expression.

Regulatory elements may be operably linked to the nucleic acids, peptides, or proteins of the described invention. When two or more elements are operably linked, there exists a a functional linkage between the elements. For example, when a promoter and a protein coding sequence are operably linked, the promoter sequence initiates and mediates transcription of the protein coding sequence. The regulatory elements need not be contiguous with the nucleic acids, peptides, or proteins whose expression they control as long as they function to direct the expression thereof. Thus, for example, intervening untranslated yet transcribed sequences may be present between a promoter sequence and a nucleic acid of the described invention and the promoter sequence may still be considered operably linked to the coding sequence.

In certain embodiments, the NELL1 nucleic acid molecule is a recombinant expression cassette or is part of an expression system. The term "recombinant expression cassette" refers to a nucleic acid construct, generated recombinantly or synthetically, with a series of specified nucleic acid elements which permit transcription of a particular nucleic acid (e.g., protein coding sequence) in a host cell. The recombinant expression cassette can be incorporated into a plasmid, chromosome, mitochondrial DNA, virus, or nucleic acid fragment. Typically, the recombinant expression cassette portion of an expression vector includes, among other sequences, a nucleic acid to be transcribed, a promoter, and a transcription termination signal such as a poly-A signal.

The expression cassette or cloning vector can be generated using molecular biology techniques known in the art and utilizing restriction enzymes, ligases, recombinases, and nucleic acid amplification techniques such as polymerase chain reaction that can be coupled with reverse transcription.

In some embodiments, the NELL1 protein is produced using a cell-free expression system such as the wheat germ in vitro translation system.

In some embodiments, the NELL1 nucleic acid molecule is in a host cell that can be used for propagation of the nucleic acid molecule or for expression of the NELL1 peptide and subsequent isolation and/or purification. A host cell is any cell that contains a heterologous nucleic acid molecule. A heterologous polypeptide or nucleotide sequence is a polypeptide or a sequence that originates from a different species, or if from the same species, is substantially modified from its native form in composition and/or genomic locus by deliberate human intervention. The host cell typically supports the replication and/or expression of the vector. Host cells may be prokaryotic cells such as, but not limited to, *Escherichia coli,* or eukaryotic cells such as, but not limited to, yeast, insect, amphibian, plant (e.g., *Nicotiana tabacum* (tobacco), *Oryza sativa* (rice), *Arabidopsis thaliana* (cress)), or mammalian cells. The term as used herein means any cell which may exist in culture or in vivo as part of a unicellular organism, part of a multicellular organism, or a fused or engineered cell culture. A cloning host cell is a host cell that contains a cloning vector.

A recombinant cell or vector is one that has been modified by the introduction of a heterologous nucleic acid or the cell that is derived from a cell so modified. Recombinant cells express genes that are not found in identical form within the native (non-recombinant) form of the cell or express native genes that are otherwise abnormally expressed, under-expressed or not expressed at all as a result of deliberate human intervention. The alteration of a cell or vector by naturally occurring events (e.g., spontaneous mutation, natural transformation transduction/transposition), such as those occurring without deliberate human intervention, does not result in a recombinant cell or vector.

The NELL1 nucleic acid molecule can be introduced into a host cell for propagation of production of NELL1 using any method known in the art, including transfection, transformation, or transduction, so long as the nucleic acid molecule gains access to the interior of the cell. The insertion or introduction of a nucleic acid into a cell refers to transfection or transformation or transduction and includes the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The NELL1 nucleic acid molecule can be introduced to allow for stable transformation or transient transformation. Stable transformation is intended to mean that the nucleotide construct introduced into a cell integrates into a genome of the cell. Transient transformation is intended to mean that a polynucleotide is introduced into the cell and does not integrate into a genome of the cell.

The NELL1 protein can be administered by a cell based gene therapy. For example, autologous, allogeneic or xenogeneic donor cells are genetically modified in vitro to express and secrete NELL1 protein. The genetically modified donor cells are then subsequently implanted into the subject in need of delivery of NELL1 protein in vivo. Examples of suitable cells include, but are not limited to, tenocytes, endothelial cells, fibroblasts (including tendon-derived fibroblasts), or stem/precursor cells, such as adult stem cells, embryonic stem cells, cord blood stem cells, perivascular stem cells, or tendon/stem progenitor cells (TSPCs).

III. Methods

The presently disclosed methods involve the regeneration of tissue, promotion of healing of an injury (e.g., tendon or ligament injury), or the enhancement of fibroblast migration and/or proliferation in a subject in need thereof. NELL1 peptides also find use in enhancing fibroblast migration and/or proliferation in an in vitro or ex vivo setting, for example in a wound scratch assay.

The regeneration of tissue refers to the process of renewal and growth of cells and extracellular matrix components within a particular tissue that results in the production of tissue that has a cellular component and architecture that allows for the normal functions of the particular tissue type. As described elsewhere herein, NELL1 has been demonstrated to stimulate the regeneration of tissues such as bone, cartilage, and skeletal muscle, which is believed to be attributed to at least one of the following effects of NELL1 protein: stimulation of the differentiation of precursor cells to maturity, pro-angiogenic activity, stimulation of ECM production, and reduction in levels of MMPs and inflammatory mediators. As disclosed herein, NELL1 also enhances the migration and/or proliferation of fibroblast cells, which can also contribute to tissue regeneration, particularly in response to a wound or within an area of injury.

As disclosed herein, the administration of NELL1 to fibroblast cells results in an increased migration rate and greater cell numbers within an area of tissue injury. The greater cell numbers can be a result of an enhanced migration rate and/or an increase in proliferation of the fibroblasts. Thus, a NELL1 protein can enhance the migration and/or proliferation of fibroblast cells. An enhancement of fibroblast migration refers to an increase in the rate of movement of fibroblasts from one region to another, for example, chemotactic movement towards a chemical signal or movement towards an area of injury (i.e., a wound). Thus, NELL1 proteins find use in methods of enhancing the migration and/or proliferation of fibroblast cells, in vivo or in vitro. In vitro settings in which NELL1 proteins can enhance the migration and/or proliferation of fibroblast cells include wound scratch assays whereby a confluent or substantially confluent layer of fibroblast cells grown in culture are disturbed through the introduction of a "scratch" or removal of a portion of the fibroblast monolayer, followed by a period of culturing the cells such that the fibroblasts begin to repopulate the "wounded" area either through migration of the fibroblasts into the wounded area or proliferation of the fibroblasts, or a combination of the two.

The promotion of the healing of a wound refers to an increase in the speed with which an injury (i.e., wound) heals or an improved outcome. Healing of an injury is considered to be promoted, for example, if the time of healing of an injury treated with NELL1 compared to an injury not treated with NELL1 is decreased by about 10%, about 25%, about 50%, or about 75%. Alternatively, healing of an injury is considered to be promoted if the extent of re-acquisition of tendon and/or ligament function of an injury treated with NELL1 compared to an injury not treated with NELL1 is improved by about 10%, about 25%, about 50%, or about 75%. Conversely, healing of an injury is considered to be promoted if the degree and/or amount of scar tissue resulting from an injury treated with NELL1 as compared to an injury not treated with NELL1 is reduced by about 10%, about 25%, about 50%, or about 75%. Promotion of healing of an injury to a tendon or ligament can also be considered if there is an improvement in the composition (e.g., proportion and amount of collagen types) and/or architecture (e.g., correct alignment of collagen fibrils/fibers/bundles) of at least about 10%, about 25%, about 50%, or about 75% of an injury treated with NELL1 compared to an injury not treated with NELL1.

The NELL1 peptide or nucleic acid molecule encoding the same is administered to a subject in need thereof to regenerate tissue, particularly to promote healing of an injury (e.g., a tendon and/or ligament injury), or to enhance the migration and/or proliferation of fibroblasts (e.g., dermal fibroblasts, ligament fibroblasts). The terms "subject", "individual", and "patient" are used interchangeably to refer to a member of a species that comprises tendons and ligaments. In certain embodiments, the subject is a mammal, including but not limited to, mouse, rat, cat, goat, sheep, horse, hamster, ferret, pig, dog, platypus, guinea pig, rabbit and a primate, such as, for example, a monkey, ape, or human. In some of these embodiments, the subject is a human or a horse, such as a racehorse. Subjects in need of treatment with a NELL1 peptide or nucleic acid molecule include those having an injury or those that are prone to injuries or an impaired healing process. Subjects that are prone to the development of injuries to a ligament and/or tendon include racehorses and athletes. Subjects in need of treatment with a NELL1 peptide or nucleic acid molecular encoding the same include those that have or are prone to impaired wound healing, impaired neovascularization, or impaired angiogenesis, including but not limited to those subjects with diabetes (type 1 or type 2), vascular diseases, hypercholesterolemia, and aging.

An injury or wound refers to damage or harm to a structure or function of the body caused by intrinsic and/or extrinsic factors. Non-limiting intrinsic or extrinsic factors that can cause an injury or wound include those of chemical, mechanical, thermal, bacterial, or physical means and encompass those that occur as the result of surgical procedures, overuse, or environmental conditions. The wound can be an open wound in which the skin is broken (e.g., lacerations, abrasions, puncture wound) or a closed wound. Particular wounds that can be healed with NELL1 include, but are not limited to, bone injuries (e.g., complete or partial fractures), skin wounds, and skeletal muscle injuries.

Intrinsic factors that can contribute to the development of injuries to tendons and/or ligaments include genetic susceptibility, overuse, poor biomechanics, poor nutrition, and obesity.

The extrinsic factors are often related to sports and include excessive forces or loading, poor training techniques, environmental conditions, and surgical procedures. The injury to the tendon and/or ligament can be a closed wound or an open wound, where the skin is lacerated, cut or punctured. The injury can include inflammation, a sprain, strain, tearing, stretching, or laceration of the tendon or ligament.

A tendon is a band of connective tissue that connects muscles to bones or cartilage. A ligament is a band of connective tissue that connects bones to other bones to form joints.

Injuries to tendons include tendinitis (acute tendon injury accompanied by inflammation), tendinosis (chronic tendon injury with degeneration at the cellular level and no inflammation), and other tendinopathies exhibiting chronic tendon injury with no etiological implications. With tendinosis, damage to collagen, cells, and the vascular components of the tendon can occur, such as irregularities of collagen fibrils (e.g., disorientation, degeneration, thinning, non-uniformity in length or diameter, increase in the amount of glycosaminoglycans between the fibrils), rounded tenocytes or other cell abnormalities, and the ingrowth of blood vessels.

The healing of an injury to any type of tendon can be promoted with NELL1, including a hand flexor tendon, a tendon within the rotator cuff, and an Achilles tendon, and within horses, a superficial digital flexor tendon (SDFT) and a deep digital flexor tendon (DDFT) of either the hindlimb(s) or forelimb(s).

Likewise, the healing of an injury to any type of ligament can be promoted with NELL1, including an anterior cruciate ligament (ACL), posterior cruciate ligament (PCL), lateral collateral ligament (LCL), medial collateral ligament (MCL), and in horses, a suspensory ligament of either the hindlimb(s) or forelimb(s). A common ligament injury in horses that can be healed according to the presently disclosed methods is proximal suspensory desmitis, an inflammation of the suspensory ligament just below the hock.

The NELL1 peptide or nucleic acid encoding the same can be administered to subjects in need thereof in the form of a composition further comprising a carrier. The term "carrier" as used herein describes a material that does not cause significant irritation to an organism and does not abrogate the biological activity and properties of the composition of the described invention. Carriers must be of sufficiently high purity and of sufficiently low toxicity to render them suitable for administration to a subject being treated. The carrier can be inert, or it can possess pharmaceutical benefits.

A pharmaceutical composition is a composition that is employed to prevent, reduce in intensity, cure or otherwise treat a target condition or disease.

A pharmaceutically acceptable carrier refers to one or more compatible solid or liquid filler, diluents or encapsulating substances which are suitable for administration to a human or other vertebrate animal.

The formulations may be presented conveniently in unit dosage form and may be prepared by any of the methods well known in the art of pharmacy. All methods include the step of bringing into association the NELL1 peptide or nucleic acid encoding the same ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The NELL1 peptide or nucleic acid encoding the same may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions, may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring the addition of the sterile liquid carrier, for example, saline, water-for-injection, a semi-liquid foam, or gel, immediately prior to use. Extemporaneous injection solutions and suspensions may be prepared from sterile powders, granules and tablets of the kind previously described. Alternatively, a NELL1 peptide or nucleic acid encoding the same is dissolved in a buffered liquid solution that is frozen in a unit-dose or multi-dose container and later thawed for injection or kept/stabilized under refrigeration until use. Any label on, or associated with, the container(s) indicates that the enclosed composition is used for promoting the healing of injuries to tendons and/or ligaments.

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. In some embodiments, the use of a long-term sustained release implant may be particularly suitable for treatment of chronic conditions. Long-term sustained release implants are well-known to those of ordinary skill in the art and include some of the release systems described above.

In some embodiments wherein the pharmaceutical composition is in the form of an implant, the NELL1 peptide or a nucleic acid encoding the same is impregnated into drug eluting devices, scaffolds or matrices that are implanted into an injured area to deliver NELL1 in a controlled release fashion. The protein can also be linked to sutures that are used for tendon and/or ligament surgeries. In those instances wherein the NELL1 peptide is delivered by genetically modified donor cells, the cells can be incorporated into a matrix containing an appropriate microenvironment to maintain, for a given time, the viability and growth of the genetically modified donor cells.

Non-limiting examples of suitable matrices include, but are not limited to, wound dressings, collagen matrix, patches, and hydrogels. The matrix can be applied to the injured tendon and/or ligament that has been exposed post-surgically, for example. After the injured tendon and/or ligament is healed, the matrix can be removed or the matrix incorporating the NELL1 peptide or nucleic acid encoding the same can be replaced intermittently throughout the healing process. In some embodiments, a rapidly degradable (e.g., 3-5 days in horses and 1-2 weeks in rats) scaffold or dressing is used to deliver NELL1 (e.g., calcium alginate). Rapidly degradable scaffolds or dressings allow for the release of a burst of NELL1 in the first phase of healing and activates tissue regeneration instead of scarring pathways. In certain embodiments, the scaffold or dressing is simpler (e.g., consisting essentially of collagen type A), rather than a complex biological carrier, such as those made from urinary bladder or intestinal linings that may comprise various growth factors and collagens. In some embodiments, the wound dressing or matrix used to deliver NELL1 comprises or consists essentially of calcium alginate.

The NELL1 peptide or nucleic acid encoding the same can be administered to a subject by dispensing, supplying, applying, or giving the NELL1 peptide or nucleic acid encoding the same to the subject. Administration may be in vivo or administration directly to tissue ex vivo. Generally, NELL1 peptides, nucleic acid molecules encoding the same, or compositions comprising the NELL1 peptide or nucleic acid may be administered systemically either orally, buccally, parenterally, topically, by inhalation or insufflation (i.e., through the mouth or through the nose), or rectally in dosage unit formulations, optionally containing the conventional nontoxic pharmaceutically acceptable carriers, adjuvants, and vehicles as desired, or may be locally administered by means such as, but not limited to, injection, implantation, grafting, or topical application. Additional administration may be performed, for example, intravenously, transmucosally, transdermally, intramuscularly, subcutaneously, intraperitoneally, intrathecally, intralymphatically, intralesionally, or epidurally.

Any suitable route of administration may be used to deliver the NELL1 peptide or nucleic acid molecule encoding the same for the purposes of tissue regeneration, such as promoting the healing of an injury to a tendon and/or ligament. In certain embodiments, the NELL1 peptide or nucleic acid encoding the same is administered locally to the site of injury or of desired tissue regeneration or fibroblast migration and/or proliferation. In some of these embodiments, the NELL1 peptide, NELL1 nucleic acid molecule, or a composition comprising the NELL1 peptide or NELL1 nucleic acid molecule are administered parenterally. The term "parenteral" as used herein refers to introduction into the body by way of an injection (i.e., administration by injection), including, for example, subcutaneously (i.e., an injection beneath the skin beneath the dermis into the subcutaneous tissue or "superficial fascia"), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. Injectable preparations, such as sterile injectable aqueous or oleaginous suspensions, may be formulated according to the known art using suitable dispersing or wetting agents and suspending agents. According to some such embodiments, the NELL1 peptide or nucleic acid molecule encoding the same is administered by injection.

In certain embodiments, the NELL1 peptide or nucleic acid molecule is administered as a spray onto a tissue, such as a tendon or ligament that has been exposed surgically (e.g., tendon splitting procedures to ease strain). The NELL1 peptide or nucleic acid molecule can also be administered via adhesion to novel materials such as nanoparticles. Lyophilized NELL protein, which may or not be reconstituted as a liquid or a gel, can be placed directly onto an injured tendon or ligament.

Administering can be performed, for example, once, a plurality of times, and/or over one or more extended periods. Generally, an effective dose of the NELL1 peptide or nucleic acid encoding the same is administered to a subject one or more times. In certain preferred embodiments, the course of treatment will comprise multiple doses of the NELL1 peptide or nucleic acid encoding the same over a period of weeks or months. More specifically, the NELL1 peptide or nucleic acid encoding the same may be administered once every day, every two days, every three days, every four days, every five days, every six days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

An effective amount of a pharmaceutical composition of the invention is any amount that is effective to achieve its purpose. The effective amount, usually expressed in mg/kg can be determined by routine methods during pre-clinical and clinical trials by those of skill in the art.

The NELL1 peptide or nucleic acid encoding the same can be administered immediately after the injury to a tissue (e.g., the tendon and/or ligament) occurred or the administration can be delayed post-injury for about three hours, 12 hours, one day, two days, three days, four days, five days, six days, seven days, eight days, nine days, ten days, two weeks, three weeks, or longer.

The NELL1 peptide or nucleic acid encoding the same can be administered prior to, along with, or subsequent to another treatment for healing the injury (e.g., tendon and/or ligament injury). Non-limiting examples of other treatments include surgery, rehabilitation, cryotherapy, administration of precursor cells, extracellular matrix materials (synthetic or purified), anti-inflammatory agents, and analgesics.

NELL1 can be combined with cells that are important in the formation of new tissues. For example, for tendons and ligaments tenocytes, tendon-derived fibroblasts, tendon stem/progenitor cells (TSPCs) and perivascular stem cells, as well as adult stem cells, such as mesenchymal stem cells, adipose derived stem cells, and bone marrow aspirate, can be used. The combination of NELL1 with cells can be delivered as an injectable mixture or in a complex scaffold (synthetic or natural scaffold) that degrades in the injured site and acts both as a starting architectural guide for new tissue to form and also for releasing correct signals that draw into the injured site growth factors and cells needed for healing. This can be either novel scaffolds or existing commercial products (e.g. mesenchymal stem cells) that have already demonstrated activity in healing injuries, such as those to tendons and/or ligaments but whose activity can be boosted by the addition of NELL1 for more severe or challenging traumatic tissue damage. (Yanming et al. 2007; Tempfer et al. 2009; Nemoto et al. 2013)

NELL1 can be added to formulations or products that are acellular extracellular matrix materials either extracted from natural sources (e.g. linings of urinary bladder, small intestinal submucosa etc.) or manufactured as a synthetic. Acellular products for regenerative medicine that contain extracellular matrix material may not have all the needed signals for tissue regeneration and the addition of NELL1 can enhance the ability of some of these materials to effect cell differentiation and tissue maturation.

In practicing combination therapy, the NELL1 peptide or nucleic acid encoding the same and the additional treatment or therapeutic agent may be administered to the subject simultaneously, either in a single composition, or as two or more distinct compositions using the same or different administration routes. Alternatively, the NELL1 peptide or nucleic acid encoding the same may precede, or follow, the additional treatment or therapeutic agent by, e.g., intervals ranging from minutes to weeks. In at least one embodiment, the NELL1 peptide or nucleic acid encoding the same and the additional treatment or therapeutic agent are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the NELL1 peptide or nucleic acid encoding the same and the additional treatment or therapeutic agent. In some of these embodiments, the NELL1 peptide or nucleic acid is administered along with platelet derived plasma (PRP).

IV. Articles of Manfacture

The invention includes kits comprising a NELL1 peptide or nucleic acid encoding the same comprising one or more containers. The kit can contain a unit dosage of a NELL1 peptide or nucleic acid encoding the same, and may also contain one or more additional agents, such as those agents that promote wound healing, stimulate the regeneration of a tissue, or promote the migration or proliferation of fibroblast cells.

The components of the kit may be provided in one or more liquid solutions, such as a sterile aqueous solution. Alternatively, the components of the kit may be provided in a lyophilized form that is suitable for reconstitution with an aqueous or non-aqueous liquid. Such a liquid may be provided in a separate container.

The kit can further comprise a label or package insert associated with the container(s) providing information regarding the use of the kit, such as for regenerating tissues, promoting the healing of wounds, or promoting the migration or proliferation of fibroblast cells.

IV. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference, regardless of whether the phrase "incorporated by reference" is or is not used in relation to the particular reference. The foregoing detailed description and the examples that follow have been given for clarity of understanding. No unnecessary limitations are to be understood therefrom. The invention is not limited to the exact details shown and described. Variations obvious to one skilled in the art are included in the invention defined by the claims. Any section headings used herein are for organizational purposes and are not to be construed as limiting the subject matter described.

V. Sequence Summary and Sequences

The following Table 1 provides a summary of the included sequences.

TABLE 1

Nucleotide and amino acid sequences disclosed herein.

| SEQ ID NO. | Description |
| --- | --- |
| 1 | Homo sapiens NELL1 isoform 1 transcript variant (nucleotide) |
| 2 | Homo sapiens NELL1 isoform 1 (amino acid) |
| 3 | Homo sapiens NELL1 isoform 2 transcript variant (nucleotide) |
| 4 | Homo sapiens NELL1 isoform 2 (amino acid) |
| 5 | Equus caballus NELL1 isoform 1 (nucleotide) |
| 6 | Equus caballus NELL1 isoform 1 (amino acid) |
| 7 | Equus caballus NELL1 isoform 2 (nucleotide) |
| 8 | Equus caballus NELL1 isoform 2 (amino acid) |
| 9 | Mus musculus NELL1 (nucleotide) |
| 10 | Mus musculus NELL1 (amino acid) |
| 11 | Rattus norvegicus NELL1 (nucleotide) |
| 12 | Rattus norvegicus NELL1 (amino acid) |
| 13 | Felis catus NELL1 isoform 1 (amino acid) |
| 14 | Felis catus NELL1 isoform 2 (amino acid) |
| 15 | Canis lupis familiaris NELL1 (amino acid) |
| 16 | Ovis aries NELL1 (amino acid) |
| 17 | Homo sapiens NELL1 fragment (amino acid) |
| 18 | Equus caballus NELL1 fragment (amino acid) |
| 19 | Bos taurus NELL1 (amino acid) |

Homo sapiens NELL1 isoform 1 nucleotide sequence (SEQ ID NO: 1) and translated amino acid sequence (SEQ ID NO: 2)

```
atatgcgagc gcagcacccg gcgctgccga gccacctccc ccgccgcccg ctagcaagtt     60
tggcggctcc aagccaggcg cgcctcagga tccaggctca tttgcttcca cctagcttcg    120
gtgccccctg ctaggcgggg accctcgaga gcg atg ccg atg gat ttg att tta    174
                                    Met Pro Met Asp Leu Ile Leu gtt gtg tgg ttc tgt gtg tgc act gcc agg aca gtg gtg ggc ttt ggg    222
Val Val Trp Phe Cys Val Cys Thr Ala Arg Thr Val Val Gly Phe Gly atg gac cct gac ctt cag atg gat atc gtc acc gag ctt gac ctt gtg    270
Met Asp Pro Asp Leu Gln Met Asp Ile Val Thr Glu Leu Asp Leu Val aac acc acc ctt gga gtt gct cag gtg tct gga atg cac aat gcc agc    318
Asn Thr Thr Leu Gly Val Ala Gln Val Ser Gly Met His Asn Ala Ser aaa gca ttt tta ttt caa gac ata gaa aga gag atc cat gca gct cct    366
Lys Ala Phe Leu Phe Gln Asp Ile Glu Arg Glu Ile His Ala Ala Pro cat gtg agt gag aaa tta att cag ctg ttc cgg aac aag agt gaa ttc    414
His Val Ser Glu Lys Leu Ile Gln Leu Phe Arg Asn Lys Ser Glu Phe
```

```
acc att ttg gcc act gta cag cag aag cca tcc act tca gga gtg ata      462
Thr Ile Leu Ala Thr Val Gln Gln Lys Pro Ser Thr Ser Gly Val Ile ctg tcc att cga gaa ctg gag cac agc tat ttt gaa ctg gag agc agt      510
Leu Ser Ile Arg Glu Leu Glu His Ser Tyr Phe Glu Leu Glu Ser Ser ggc ctg agg gat gag att cgg tat cac tac ata cac aat ggg aag cca      558
Gly Leu Arg Asp Glu Ile Arg Tyr His Tyr Ile His Asn Gly Lys Pro agg aca gag gca ctt cct tac cgc atg gca gat gga caa tgg cac aag      606
Arg Thr Glu Ala Leu Pro Tyr Arg Met Ala Asp Gly Gln Trp His Lys gtt gca ctg tca gtt agc gcc tct cat ctc ctg ctc cat gtc gac tgt      654
Val Ala Leu Ser Val Ser Ala Ser His Leu Leu Leu His Val Asp Cys aac agg att tat gag cgt gtg ata gac cct cca gat acc aac ctt ccc      702
Asn Arg Ile Tyr Glu Arg Val Ile Asp Pro Pro Asp Thr Asn Leu Pro cca gga atc aat tta tgg ctt ggc cag cgc aac caa aag cat ggc tta      750
Pro Gly Ile Asn Leu Trp Leu Gly Gln Arg Asn Gln Lys His Gly Leu ttc aaa ggg atc atc caa gat ggg aag atc atc ttt atg ccg aat gga      798
Phe Lys Gly Ile Ile Gln Asp Gly Lys Ile Ile Phe Met Pro Asn Gly tat ata aca cag tgt cca aat cta aat cac act tgc cca acc tgc agt      846
Tyr Ile Thr Gln Cys Pro Asn Leu Asn His Thr Cys Pro Thr Cys Ser gat ttc tta agc ctg gtg caa gga ata atg gat tta caa gag ctt ttg      894
Asp Phe Leu Ser Leu Val Gln Gly Ile Met Asp Leu Gln Glu Leu Leu gcc aag atg act gca aaa cta aat tat gca gag aca aga ctt agt caa      942
Ala Lys Met Thr Ala Lys Leu Asn Tyr Ala Glu Thr Arg Leu Ser Gln ttg gaa aac tgt cat tgt gag aag act tgt caa gtg agt gga ctg ctc      990
Leu Glu Asn Cys His Cys Glu Lys Thr Cys Gln Val Ser Gly Leu Leu tat cga gat caa gac tct tgg gta gat ggt gac cat tgc agg aac tgc     1038
Tyr Arg Asp Gln Asp Ser Trp Val Asp Gly Asp His Cys Arg Asn Cys act tgc aaa agt ggt gcc gtg gaa tgc cga agg atg tcc tgt ccc cct     1086
Thr Cys Lys Ser Gly Ala Val Glu Cys Arg Arg Met Ser Cys Pro Pro ctc aat tgc tcc cca gac tcc ctc cca gtg cac att gct ggc cag tgc     1134
Leu Asn Cys Ser Pro Asp Ser Leu Pro Val His Ile Ala Gly Gln Cys tgt aag gtc tgc cga cca aaa tgt atc tat gga gga aaa gtt ctt gca     1182
Cys Lys Val Cys Arg Pro Lys Cys Ile Tyr Gly Gly Lys Val Leu Ala gaa ggc cag cgg att tta acc aag agc tgt cgg gaa tgc cga ggt gga     1230
Glu Gly Gln Arg Ile Leu Thr Lys Ser Cys Arg Glu Cys Arg Gly Gly gtt tta gta aaa att aca gaa atg tgt cct cct ttg aac tgc tca gaa     1278
Val Leu Val Lys Ile Thr Glu Met Cys Pro Pro Leu Asn Cys Ser Glu aag gat cac att ctt cct gag aat cag tgc tgc cgt gtc tgt aga ggt     1326
Lys Asp His Ile Leu Pro Glu Asn Gln Cys Cys Arg Val Cys Arg Gly cat aac ttt tgt gca gaa gga cct aaa tgt ggt gaa aac tca gag tgc     1374
His Asn Phe Cys Ala Glu Gly Pro Lys Cys Gly Glu Asn Ser Glu Cys aaa aac tgg aat aca aaa gct act tgt gag tgc aag agt ggt tac atc     1422
Lys Asn Trp Asn Thr Lys Ala Thr Cys Glu Cys Lys Ser Gly Tyr Ile tct gtc cag gga gac tct gcc tac tgt gaa gat att gat gag tgt gca     1470
Ser Val Gln Gly Asp Ser Ala Tyr Cys Glu Asp Ile Asp Glu Cys Ala gct aag atg cat tac tgt cat gcc aat act gtg tgt gtc aac ctt cct     1518
Ala Lys Met His Tyr Cys His Ala Asn Thr Val Cys Val Asn Leu Pro ggg tta tat cgc tgt gac tgt gtc cca gga tac att cgt gtg gat gac     1566
Gly Leu Tyr Arg Cys Asp Cys Val Pro Gly Tyr Ile Arg Val Asp Asp ttc tct tgt aca gaa cac gat gaa tgt ggc agc ggc cag cac aac tgt     1614
Phe Ser Cys Thr Glu His Asp Glu Cys Gly Ser Gly Gln His Asn Cys gat gag aat gcc atc tgc acc aac act gtc cag gga cac agc tgc acc     1662
Asp Glu Asn Ala Ile Cys Thr Asn Thr Val Gln Gly His Ser Cys Thr tgc aaa ccg ggc tac gtg ggg aac ggg acc atc tgc aga gct ttc tgt     1710
Cys Lys Pro Gly Tyr Val Gly Asn Gly Thr Ile Cys Arg Ala Phe Cys
```

```
gaa gag ggc tgc aga tac ggt gga acg tgt gtg gct ccc aac aaa tgt    1758
Glu Glu Gly Cys Arg Tyr Gly Gly Thr Cys Val Ala Pro Asn Lys Cys gtc tgt cca tct gga ttc aca gga agc cac tgc gag aaa gat att gat    1806
Val Cys Pro Ser Gly Phe Thr Gly Ser His Cys Glu Lys Asp Ile Asp gaa tgt tca gag gga atc att gag tgc cac aac cat tcc cgc tgc gtt    1854
Glu Cys Ser Glu Gly Ile Ile Glu Cys His Asn His Ser Arg Cys Val aac ctg cca ggg tgg tac cac tgt gag tgc aga agc ggt ttc cat gac    1902
Asn Leu Pro Gly Trp Tyr His Cys Glu Cys Arg Ser Gly Phe His Asp gat ggg acc tat tca ctg tcc ggg gag tcc tgt att gac att gat gaa    1950
Asp Gly Thr Tyr Ser Leu Ser Gly Glu Ser Cys Ile Asp Ile Asp Glu tgt gcc tta aga act cac acc tgt tgg aac gat tct gcc tgc atc aac    1998
Cys Ala Leu Arg Thr His Thr Cys Trp Asn Asp Ser Ala Cys Ile Asn ctg gca ggg ggc ttt gac tgt ctc tgc ccc tct ggg ccc tcc tgc tct    2046
Leu Ala Gly Gly Phe Asp Cys Leu Cys Pro Ser Gly Pro Ser Cys Ser ggt gac tgt cct cat gaa ggg ggg ctg aag cac aat ggc cag gtg tgg    2094
Gly Asp Cys Pro His Glu Gly Gly Leu Lys His Asn Gly Gln Val Trp acc ttg aaa gaa gac agg tgt tct gtc tgc tcc tgc aag gat ggc aag    2142
Thr Leu Lys Glu Asp Arg Cys Ser Val Cys Ser Cys Lys Asp Gly Lys ata ttc tgc cga cgg aca gct tgt gat tgc cag aat cca agt gct gac    2190
Ile Phe Cys Arg Arg Thr Ala Cys Asp Cys Gln Asn Pro Ser Ala Asp cta ttc tgt tgc cca gaa tgt gac acc aga gtc aca agt caa tgt tta    2238
Leu Phe Cys Cys Pro Glu Cys Asp Thr Arg Val Thr Ser Gln Cys Leu gac caa aat ggt cac aag ctg tat cga agt gga gac aat tgg acc cat    2286
Asp Gln Asn Gly His Lys Leu Tyr Arg Ser Gly Asp Asn Trp Thr His agc tgt cag cag tgt cgg tgt ctg gaa gga gag gta gat tgc tgg cca    2334
Ser Cys Gln Gln Cys Arg Cys Leu Glu Gly Glu Val Asp Cys Trp Pro ctc act tgc ccc aac ttg agc tgt gag tat aca gct atc tta gaa ggg    2382
Leu Thr Cys Pro Asn Leu Ser Cys Glu Tyr Thr Ala Ile Leu Glu Gly gaa tgt tgt ccc cgc tgt gtc agt gac ccc tgc cta gct gat aac atc    2430
Glu Cys Cys Pro Arg Cys Val Ser Asp Pro Cys Leu Ala Asp Asn Ile acc tat gac atc aga aaa act tgc ctg gac agc tat ggt gtt tca cgg    2478
Thr Tyr Asp Ile Arg Lys Thr Cys Leu Asp Ser Tyr Gly Val Ser Arg ctt agt ggc tca gtg tgg acg atg gct gga tct ccc tgc aca acc tgt    2526
Leu Ser Gly Ser Val Trp Thr Met Ala Gly Ser Pro Cys Thr Thr Cys aaa tgc aag aat gga aga gtc tgt tgt tct gtg gat ttt gag tgt ctt    2574
Lys Cys Lys Asn Gly Arg Val Cys Cys Ser Val Asp Phe Glu Cys Leu caa aat aat tga agtatttaca gtggactcaa cgcagaagaa tggacgaaat        2626
Gln Asn Asn * gaccatccaa cgtgattaag gataggaatc ggtagtttgg tttttttgtt tgttttgttt  2686
ttttaaccac agataattgc caaagtttcc acctgaggac ggtgtttgga ggttgccttt  2746
tggacctacc actttgctca ttcttgctaa cctagtctag gtgacctaca gtgccgtgca  2806
tttaagtcaa tggttgttaa agaagtttc ccgtgttgta aatcatgttt cccttatcag   2866
atcatttgca aatacattta aatgatctca tggtaaatgt tgatgtattt tttggtttat  2926
tttgtgtact aacataatag agagagactc agctccttt attttattttg ttgatttatg  2986 gatcaaattc taaaataaag ttgcctgttg tgacttttgt cccatctact gcatacttag  3046
tgctgagatc cctgtaaaat gttttgatga aaatatgtat gtagagtcca gtcgcattat  3106
acatacattt catagtgctg aaccttctta aatgcctact cattcagctt aaacaggctg  3166
aagccaagta tgacaaagag gggaagggcc aaaaacataa tcaaagaata atttttaaga  3226 gaattccttgt ctctcttgca aaaaaaaaa                                   3255
```

*Homo sapiens* NELL1 isoform 1 amino acid sequence
(SEQ ID NO: 2)

Met Pro Met Asp Leu Ile Leu Val Val Trp Phe Cys Val
Cys Thr Ala Arg Thr Val Val Gly Phe Gly Met Asp Pro
Asp Leu Gln Met Asp Ile Val Thr Glu Leu Asp Leu Val
Asn Thr Thr Leu Gly Val Ala Gln Val Ser Gly Met His
Asn Ala Ser Lys Ala Phe Leu Phe Gln Asp Ile Glu Arg
Glu Ile His Ala Ala Pro His Val Ser Glu Lys Leu Ile
Gln Leu Phe Arg Asn Lys Ser Glu Phe Thr Ile Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Leu Arg Asp Glu Ile Arg Tyr His Tyr Ile
His Asn Gly Lys Pro Arg Thr Glu Ala Leu Pro Tyr Arg
Met Ala Asp Gly Gln Trp His Lys Val Ala Leu Ser Val
Ser Ala Ser His Leu Leu Leu His Val Asp Cys Asn Arg
Ile Tyr Glu Arg Val Ile Asp Pro Pro Asp Thr Asn Leu
Pro Pro Gly Ile Asn Leu Trp Leu Gly Gln Arg Asn Gln
Lys His Gly Leu Phe Lys Gly Ile Ile Gln Asp Gly Lys
Ile Ile Phe Met Pro Asn Gly Tyr Ile Thr Gln Cys Pro
Asn Leu Asn His Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Ser Gln Leu Glu Asn Cys His Cys Glu Lys Thr Cys
Gln Val Ser Gly Leu Leu Tyr Arg Asp Gln Asp Ser Trp
Val Asp Gly Asp His Cys Arg Asn Cys Thr Cys Lys Ser
Gly Ala Val Glu Cys Arg Arg Met Ser Cys Pro Pro Leu
Asn Cys Ser Pro Asp Ser Leu Pro Val His Ile Ala Gly
Gln Cys Cys Lys Val Cys Arg Pro Lys Cys Ile Tyr Gly
Gly Lys Val Leu Ala Glu Gly Gln Arg Ile Leu Thr Lys
Ser Cys Arg Glu Cys Arg Gly Gly Val Leu Val Lys Ile
Thr Glu Met Cys Pro Pro Leu Asn Cys Ser Glu Lys Asp
His Ile Leu Pro Glu Asn Gln Cys Cys Arg Val Cys Arg
Gly His Asn Phe Cys Ala Glu Gly Pro Lys Cys Gly Glu
Asn Ser Glu Cys Lys Asn Trp Asn Thr Lys Ala Thr Cys
Glu Cys Lys Ser Gly Tyr Ile Ser Val Gln Gly Asp Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Val Pro Gly Tyr Ile Arg
Val Asp Asp Phe Ser Cys Thr Glu His Asp Glu Cys Gly
Ser Gly Gln His Asn Cys Asp Glu Asn Ala Ile Cys Thr
Asn Thr Val Gln Gly His Ser Cys Thr Cys Lys Pro Gly
Tyr Val Gly Asn Gly Thr Ile Cys Arg Ala Phe Cys Glu
Glu Gly Cys Arg Tyr Gly Gly Thr Cys Val Ala Pro Asn
Lys Cys Val Cys Pro Ser Gly Phe Thr Gly Ser His Cys
Glu Lys Asp Ile Asp Glu Cys Ser Gly Ile Ile Glu
Cys His Asn His Ser Arg Cys Val Asn Leu Pro Gly Trp
Tyr His Cys Glu Cys Arg Ser Gly Phe His Asp Asp Gly
Thr Tyr Ser Leu Ser Gly Glu Ser Cys Ile Asp Ile Asp
Glu Cys Ala Leu Arg Thr His Thr Cys Trp Asn Asp Ser
Ala Cys Ile Asn Leu Ala Gly Gly Phe Asp Cys Leu Cys
Pro Ser Gly Pro Ser Cys Ser Gly Asp Cys Pro His Glu
Gly Gly Leu Lys His Asn Gly Gln Val Trp Thr Leu Lys
Glu Asp Arg Cys Ser Val Cys Ser Cys Lys Asp Gly Lys
Ile Phe Cys Arg Arg Thr Ala Cys Asp Cys Gln Asn Pro
Ser Ala Asp Leu Phe Cys Cys Pro Glu Cys Asp Thr Arg
Val Thr Ser Gln Cys Leu Asp Gln Asn Gly His Lys Leu
Tyr Arg Ser Gly Asp Asn Trp Thr His Ser Cys Gln Gln
Cys Arg Cys Leu Glu Gly Glu Val Asp Cys Trp Pro Leu
Thr Cys Pro Asn Leu Ser Cys Glu Tyr Thr Ala Ile Leu
Glu Gly Glu Cys Cys Pro Arg Cys Val Ser Asp Pro Cys
Leu Ala Asp Asn Ile Thr Tyr Asp Ile Arg Lys Thr Cys
Leu Asp Ser Tyr Gly Val Ser Arg Leu Ser Gly Ser Val
Trp Thr Met Ala Gly Ser Pro Cys Thr Thr Cys Lys Cys
Lys Asn Gly Arg Val Cys Cys Ser Val Asp Phe Glu Cys
Leu Gln Asn Asn

*Homo sapiens* NELL1 isoform 2 nucleotide sequence
(SEQ ID NO: 3) and translated amino acid sequence (SEQ
ID NO: 4)

```
atatgcgagc gcagcacccg gcgctgccga gccacctccc ccgccgcccg ctagcaagtt    60
tggcggctcc aagccaggcg cgcctcagga tccaggctca tttgcttcca cctagcttcg   120
gtgccccctg ctaggcgggg accctcgaga gcg atg ccg atg gat ttg att tta   174
                                   Met Pro Met Asp Leu Ile Leu
gtt gtg tgg ttc tgt gtg tgc act gcc agg aca gtg gtg ggc ttt ggg    222
Val Val Trp Phe Cys Val Cys Thr Ala Arg Thr Val Val Gly Phe Gly
```

```
atg gac cct gac ctt cag atg gat atc gtc acc gag ctt gac ctt gtg      270
Met Asp Pro Asp Leu Gln Met Asp Ile Val Thr Glu Leu Asp Leu Val aac acc acc ctt gga gtt gct cag gtg tct gga atg cac aat gcc agc      318
Asn Thr Thr Leu Gly Val Ala Gln Val Ser Gly Met His Asn Ala Ser aaa gca ttt tta ttt caa gac ata gaa aga gag atc cat gca gct cct      366
Lys Ala Phe Leu Phe Gln Asp Ile Glu Arg Glu Ile His Ala Ala Pro cat gtg agt gag aaa tta att cag ctg ttc cgg aac aag agt gaa ttc      414
His Val Ser Glu Lys Leu Ile Gln Leu Phe Arg Asn Lys Ser Glu Phe acc att ttg gcc act gta cag cag aag cca tcc act tca gga gtg ata      462
Thr Ile Leu Ala Thr Val Gln Gln Lys Pro Ser Thr Ser Gly Val Ile ctg tcc att cga gaa ctg gag cac agc tat ttt gaa ctg gag agc agt      510
Leu Ser Ile Arg Glu Leu Glu His Ser Tyr Phe Glu Leu Glu Ser Ser ggc ctg agg gat gag att cgg tat cac tac ata cac aat ggg aag cca      558
Gly Leu Arg Asp Glu Ile Arg Tyr His Tyr Ile His Asn Gly Lys Pro agg aca gag gca ctt cct tac cgc atg gca gat gga caa tgg cac aag      606
Arg Thr Glu Ala Leu Pro Tyr Arg Met Ala Asp Gly Gln Trp His Lys gtt gca ctg tca gtt agc gcc tct cat ctc ctg ctc cat gtc gac tgt      654
Val Ala Leu Ser Val Ser Ala Ser His Leu Leu Leu His Val Asp Cys aac agg att tat gag cgt gtg ata gac cct cca gat acc aac ctt ccc      702
Asn Arg Ile Tyr Glu Arg Val Ile Asp Pro Pro Asp Thr Asn Leu Pro cca gga atc aat tta tgg ctt ggc cag cgc aac caa aag cat ggc tta      750
Pro Gly Ile Asn Leu Trp Leu Gly Gln Arg Asn Gln Lys His Gly Leu ttc aaa ggg atc atc caa gat ggg aag atc atc ttt atg ccg aat gga      798
Phe Lys Gly Ile Ile Gln Asp Gly Lys Ile Ile Phe Met Pro Asn Gly tat ata aca cag tgt cca aat cta aat cac act tgc cca acc tgc agt      846
Tyr Ile Thr Gln Cys Pro Asn Leu Asn His Thr Cys Pro Thr Cys Ser gat ttc tta agc ctg gtg caa gga ata atg gat tta caa gag ctt ttg      894
Asp Phe Leu Ser Leu Val Gln Gly Ile Met Asp Leu Gln Glu Leu Leu gcc aag atg act gca aaa cta aat tat gca gag aca aga ctt agt caa      942
Ala Lys Met Thr Ala Lys Leu Asn Tyr Ala Glu Thr Arg Leu Ser Gln ttg gaa aac tgt cat tgt gag aag act tgt caa gtg agt gga ctg ctc      990
Leu Glu Asn Cys His Cys Glu Lys Thr Cys Gln Val Ser Gly Leu Leu tat cga gat caa gac tct tgg gta gat ggt gac cat tgc agg aac tgc     1038
Tyr Arg Asp Gln Asp Ser Trp Val Asp Gly Asp His Cys Arg Asn Cys act tgc aaa agt ggt gcc gtg gaa tgc cga agg atg tcc tgt ccc cct     1086
Thr Cys Lys Ser Gly Ala Val Glu Cys Arg Arg Met Ser Cys Pro Pro ctc aat tgc tcc cca gac tcc ctc cca gtg cac att gct ggc cag tgc     1134
Leu Asn Cys Ser Pro Asp Ser Leu Pro Val His Ile Ala Gly Gln Cys tgt aag gtc tgc cga cca aaa tgt atc tat gga gga aaa gtt ctt gca     1182
Cys Lys Val Cys Arg Pro Lys Cys Ile Tyr Gly Gly Lys Val Leu Ala gaa ggc cag cgg att tta acc aag agc tgt cgg gaa tgc cga ggt gga     1230
Glu Gly Gln Arg Ile Leu Thr Lys Ser Cys Arg Glu Cys Arg Gly Gly gtt tta gta aaa att aca gaa atg tgt cct cct ttg aac tgc tca gaa     1278
Val Leu Val Lys Ile Thr Glu Met Cys Pro Pro Leu Asn Cys Ser Glu aag gat cac att ctt cct gag aat cag tgc tgc cgt gtc tgt aga ggt     1326
Lys Asp His Ile Leu Pro Glu Asn Gln Cys Cys Arg Val Cys Arg Gly cat aac ttt tgt gca gaa gga cct aaa tgt ggt gaa aac tca gag tgc     1374
His Asn Phe Cys Ala Glu Gly Pro Lys Cys Gly Glu Asn Ser Glu Cys aaa aac tgg aat aca aaa gct act tgt gag tgc aag agt ggt tac atc     1422
Lys Asn Trp Asn Thr Lys Ala Thr Cys Glu Cys Lys Ser Gly Tyr Ile tct gtc cag gga gac tct gcc tac tgt gaa gat att gat gag tgt gca     1470
Ser Val Gln Gly Asp Ser Ala Tyr Cys Glu Asp Ile Asp Glu Cys Ala gct aag atg cat tac tgt cat gcc aat act gtg tgt gtc aac ctt cct     1518
Ala Lys Met His Tyr Cys His Ala Asn Thr Val Cys Val Asn Leu Pro
```

-continued

| | |
|---|---|
| ggg tta tat cgc tgt gac tgt gtc cca gga tac att cgt gtg gat gac<br>Gly Leu Tyr Arg Cys Asp Cys Val Pro Gly Tyr Ile Arg Val Asp Asp | 1566 |
| ttc tct tgt aca gaa cac gat gaa tgt ggc agc ggc cag cac aac tgt<br>Phe Ser Cys Thr Glu His Asp Glu Cys Gly Ser Gly Gln His Asn Cys | 1614 |
| gat gag aat gcc atc tgc acc aac act gtc cag gga cac agc tgc acc<br>Asp Glu Asn Ala Ile Cys Thr Asn Thr Val Gln Gly His Ser Cys Thr | 1662 |
| tgc aaa ccg ggc tac gtg ggg aac ggg acc atc tgc aga gct ttc tgt<br>Cys Lys Pro Gly Tyr Val Gly Asn Gly Thr Ile Cys Arg Ala Phe Cys | 1710 |
| gaa gag ggc tgc aga tac ggt gga acg tgt gtg gct ccc aac aaa tgt<br>Glu Glu Gly Cys Arg Tyr Gly Gly Thr Cys Val Ala Pro Asn Lys Cys | 1758 |
| gtc tgt cca tct gga ttc aca gga agc cac tgc gag aaa gac att gat<br>Val Cys Pro Ser Gly Phe Thr Gly Ser His Cys Glu Lys Asp Ile Asp | 1806 |
| gaa tgt gcc tta aga act cac acc tgt tgg aac gat tct gcc tgc atc<br>Glu Cys Ala Leu Arg Thr His Thr Cys Trp Asn Asp Ser Ala Cys Ile | 1854 |
| aac ctg gca ggg ggc ttt gac tgt ctc tgc ccc tct ggg ccc tcc tgc<br>Asn Leu Ala Gly Gly Phe Asp Cys Leu Cys Pro Ser Gly Pro Ser Cys | 1902 |
| tct ggt gac tgt cct cat gaa ggg ggg ctg aag cac aat ggc cag gtg<br>Ser Gly Asp Cys Pro His Glu Gly Gly Leu Lys His Asn Gly Gln Val | 1950 |
| tgg acc ttg aaa gaa gac agg tgt tct gtc tgc tcc tgc aag gat ggc<br>Trp Thr Leu Lys Glu Asp Arg Cys Ser Val Cys Ser Cys Lys Asp Gly | 1998 |
| aag ata ttc tgc cga cgg aca gct tgt gat tgc cag aat cca agt gct<br>Lys Ile Phe Cys Arg Arg Thr Ala Cys Asp Cys Gln Asn Pro Ser Ala | 2046 |
| gac cta ttc tgt tgc cca gaa tgt gac acc aga gtc aca agt caa tgt<br>Asp Leu Phe Cys Cys Pro Glu Cys Asp Thr Arg Val Thr Ser Gln Cys | 2094 |
| tta gac caa aat ggt cac aag ctg tat cga agt gga gac aat tgg acc<br>Leu Asp Gln Asn Gly His Lys Leu Tyr Arg Ser Gly Asp Asn Trp Thr | 2142 |
| cat agc tgt cag cag tgt cgg tgt ctg gaa gga gag gta gat tgc tgg<br>His Ser Cys Gln Gln Cys Arg Cys Leu Glu Gly Glu Val Asp Cys Trp | 2190 |
| cca ctc act tgc ccc aac ttg agc tgt gag tat aca gct atc tta gaa<br>Pro Leu Thr Cys Pro Asn Leu Ser Cys Glu Tyr Thr Ala Ile Leu Glu | 2238 |
| ggg gaa tgt tgt ccc cgc tgt gtc agt gac ccc tgc cta gct gat aac<br>Gly Glu Cys Cys Pro Arg Cys Val Ser Asp Pro Cys Leu Ala Asp Asn | 2286 |
| atc acc tat gac atc aga aaa act tgc ctg gac agc tat ggt gtt tca<br>Ile Thr Tyr Asp Ile Arg Lys Thr Cys Leu Asp Ser Tyr Gly Val Ser | 2334 |
| cgg ctt agt ggc tca gtg tgg acg atg gct gga tct ccc tgc aca acc<br>Arg Leu Ser Gly Ser Val Trp Thr Met Ala Gly Ser Pro Cys Thr Thr | 2382 |
| tgt aaa tgc aag aat gga aga gtc tgt tgt tct gtg gat ttt gag tgt<br>Cys Lys Cys Lys Asn Gly Arg Val Cys Cys Ser Val Asp Phe Glu Cys | 2430 |
| ctt caa aat aat tga agtatttaca gtggactcaa cgcagaagaa tggacgaaat<br>Leu Gln Asn Asn * | 2485 |
| gaccatccaa cgtgattaag gataggaatc ggtagtttgg tttttttgtt tgttttgttt | 2545 |
| ttttaaccac agataattgc caaagtttcc acctgaggac ggtgtttgga ggttgccttt | 2605 |
| tggacctacc actttgctca ttcttgctaa cctagtctag gtgacctaca gtgccgtgca | 2665 |
| tttaagtcaa tggttgttaa aagaagtttc ccgtgttgta aatcatgttt cccttatcag | 2725 |
| atcatttgca aatacattta aatgatctca tggtaaatgt tgatgtattt tttggtttat | 2785 |
| tttgtgtact aacataatag agagagactc agctcctttt atttattttg ttgatttatg | 2845 |
| gatcaaattc taaataaag ttgcctgttg tgacttttgt cccatctact gcatacttag | 2905 |
| tgctgagatc cctgtaaaat gttttgatga aaatatgtat gtagagtcca gtcgcattat | 2965 |
| acatacattt catagtgctg aaccttctta aatgcctact cattcagctt aaacaggctg | 3025 |
| aagccaagta tgacaaagag gggaagggcc aaaaacataa tcaaagaata attttaaaga | 3085 |
| gaattcttgt ctctcttgca aaaaaaaaa | 3114 |

*Homo sapiens* NELL1 isoform 2 amino acid sequence (SEQ ID NO: 4)

Met Pro Met Asp Leu Ile Leu Val Val Trp Phe Cys Val
Cys Thr Ala Arg Thr Val Val Gly Phe Gly Met Asp Pro
Asp Leu Gln Met Asp Ile Val Thr Glu Leu Asp Leu Val
Asn Thr Thr Leu Gly Val Ala Gln Val Ser Gly Met His
Asn Ala Ser Lys Ala Phe Leu Phe Gln Asp Ile Glu Arg
Glu Ile His Ala Ala Pro His Val Ser Glu Lys Leu Ile
Gln Leu Phe Arg Asn Lys Ser Glu Phe Thr Ile Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Leu Arg Asp Glu Ile Arg Tyr His Tyr Ile
His Asn Gly Lys Pro Arg Thr Glu Ala Leu Pro Tyr Arg
Met Ala Asp Gly Gln Trp His Lys Val Ala Leu Ser Val
Ser Ala Ser His Leu Leu Leu His Val Asp Cys Asn Arg
Ile Tyr Glu Arg Val Ile Asp Pro Pro Asp Thr Asn Leu
Pro Pro Gly Ile Asn Leu Trp Leu Gly Gln Arg Asn Gln
Lys His Gly Leu Phe Lys Gly Ile Ile Gln Asp Gly Lys
Ile Ile Phe Met Pro Asn Gly Tyr Ile Thr Gln Cys Pro
Asn Leu Asn His Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Ser Gln Leu Glu Asn Cys His Cys Glu Lys Thr Cys
Gln Val Ser Gly Leu Leu Tyr Arg Asp Gln Asp Ser Trp
Val Asp Gly Asp His Cys Arg Asn Cys Thr Cys Lys Ser
Gly Ala Val Glu Cys Arg Arg Met Ser Cys Pro Pro Leu
Asn Cys Ser Pro Asp Ser Leu Pro Val His Ile Ala Gly
Gln Cys Cys Lys Val Cys Arg Pro Lys Cys Ile Tyr Gly
Gly Lys Val Leu Ala Glu Gly Gln Arg Ile Leu Thr Lys
Ser Cys Arg Glu Cys Arg Gly Gly Val Leu Val Lys Ile
Thr Glu Met Cys Pro Pro Leu Asn Cys Ser Glu Lys Asp
His Ile Leu Pro Glu Asn Gln Cys Cys Arg Val Cys Arg
Gly His Asn Phe Cys Ala Glu Gly Pro Lys Cys Gly Glu
Asn Ser Glu Cys Lys Asn Trp Asn Thr Lys Ala Thr Cys
Glu Cys Lys Ser Gly Tyr Ile Ser Val Gln Gly Asp Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Val Pro Gly Tyr Ile Arg
Val Asp Asp Phe Ser Cys Thr Glu His Asp Glu Cys Gly
Ser Gly Gln His Asn Cys Asp Glu Asn Ala Ile Cys Thr
Asn Thr Val Gln Gly His Ser Cys Thr Cys Lys Pro Gly
Tyr Val Gly Asn Gly Thr Ile Cys Arg Ala Phe Cys Glu
Glu Gly Cys Arg Tyr Gly Gly Thr Cys Val Ala Pro Asn
Lys Cys Val Cys Pro Ser Gly Phe Thr Gly Ser His Cys
Glu Lys Asp Ile Asp Glu Cys Ala Leu Arg Thr His Thr
Cys Trp Asn Asp Ser Ala Cys Ile Asn Leu Ala Gly Gly
Phe Asp Cys Leu Cys Pro Ser Gly Pro Ser Cys Ser Gly
Asp Cys Pro His Glu Gly Gly Leu Lys His Asn Gly Gln
Val Trp Thr Leu Lys Glu Asp Arg Cys Ser Val Cys Ser
Cys Lys Asp Gly Lys Ile Phe Cys Arg Arg Thr Ala Cys
Asp Cys Gln Asn Pro Ser Ala Asp Leu Phe Cys Cys Pro
Glu Cys Asp Thr Arg Val Thr Ser Gln Cys Leu Asp Gln
Asn Gly His Lys Leu Tyr Arg Ser Gly Asp Asn Trp Thr
His Ser Cys Gln Gln Cys Arg Cys Leu Glu Gly Glu Val
Asp Cys Trp Pro Leu Thr Cys Pro Asn Leu Ser Cys Glu
Tyr Thr Ala Ile Leu Glu Gly Glu Cys Cys Pro Arg Cys
Val Ser Asp Pro Cys Leu Ala Asp Asn Ile Thr Tyr Asp
Ile Arg Lys Thr Cys Leu Asp Ser Tyr Gly Val Ser Arg
Leu Ser Gly Ser Val Trp Thr Met Ala Gly Ser Pro Cys
Thr Thr Cys Lys Cys Lys Asn Gly Arg Val Cys Cys Ser
Val Asp Phe Glu Cys Leu Gln Asn Asn

*Equus caballus* NELL1 isoform 1 nucleotide sequence (SEQ ID NO: 5) and translated amino acid sequence (SEQ ID NO: 6)

```
atg ggc ttt ggg atg gac ccc gac ctt caa atg gat att atc acc gag    48
Met Gly Phe Gly Met Asp Pro Asp Leu Gln Met Asp Ile Ile Thr Glu ctc gac ctc gtg aac acc acc ctt gga gtc act cag gtg tcc gga ctg    96
Leu Asp Leu Val Asn Thr Thr Leu Gly Val Thr Gln Val Ser Gly Leu cac aat gcc agc aaa gca ttt tta ttt caa gat gta gag aga gag atc   144
His Asn Ala Ser Lys Ala Phe Leu Phe Gln Asp Val Glu Arg Glu Ile cat gca gcc cca cac gtg agt gag aaa tta att cag ctg ttc cgg aat   192
His Ala Ala Pro His Val Ser Glu Lys Leu Ile Gln Leu Phe Arg Asn aag agt gaa ttc acc ttt ttg gcc act gtg cag cag aag ccg tca act   240
Lys Ser Glu Phe Thr Phe Leu Ala Thr Val Gln Gln Lys Pro Ser Thr
```

```
tca gga gtg ata ctg tcc att cga gaa ctg gaa aac agt tat ttt gaa      288
Ser Gly Val Ile Leu Ser Ile Arg Glu Leu Glu Asn Ser Tyr Phe Glu ctg gag agc agt ggc ctg aga gat gag att cga tat cac tac aca cac      336
Leu Glu Ser Ser Gly Leu Arg Asp Glu Ile Arg Tyr His Tyr Thr His aag ggg aag ccc agg aca gag gca ctt ccc tac cgg atg gcg gac gga      384
Lys Gly Lys Pro Arg Thr Glu Ala Leu Pro Tyr Arg Met Ala Asp Gly cgg tgg cac aag gtg gcg ctg tca gtt agc gcc tct cat ctc ctg ctc      432
Arg Trp His Lys Val Ala Leu Ser Val Ser Ala Ser His Leu Leu Leu cac atc gac tgc aac agg att tat gaa cgt gtg ata gac act cct gag      480
His Ile Asp Cys Asn Arg Ile Tyr Glu Arg Val Ile Asp Thr Pro Glu acc aac ctc ccc cca gga agc aat ttg tgg ctg ggt cag cga aac caa      528
Thr Asn Leu Pro Pro Gly Ser Asn Leu Trp Leu Gly Gln Arg Asn Gln aag cac ggc tta ttc aaa gga atc atc caa gat gga aaa atc atc ttc      576
Lys His Gly Leu Phe Lys Gly Ile Ile Gln Asp Gly Lys Ile Ile Phe atg ccg aat gga tac ata aca cag tgt ccg aac ctg aat cgc act tgc      624
Met Pro Asn Gly Tyr Ile Thr Gln Cys Pro Asn Leu Asn Arg Thr Cys cca acg tgc agt gat ttc tta agc ctg gtg caa gga atc atg gat tta      672
Pro Thr Cys Ser Asp Phe Leu Ser Leu Val Gln Gly Ile Met Asp Leu caa gag ctt ctg gcc aag atg act gcg aaa cta aat tat gca gag aca      720
Gln Glu Leu Leu Ala Lys Met Thr Ala Lys Leu Asn Tyr Ala Glu Thr cga ctt agt caa ttg gaa aac tgc cac tgc gag aag acc tgt caa gtg      768
Arg Leu Ser Gln Leu Glu Asn Cys His Cys Glu Lys Thr Cys Gln Val agt gga ctg ctc tat aga gac cag gac tcc tgg gtt gat ggc gat cac      816
Ser Gly Leu Leu Tyr Arg Asp Gln Asp Ser Trp Val Asp Gly Asp His tgt agg aac tgc acg tgc aaa agc ggc gct gtg gaa tgt cgg agg atg      864
Cys Arg Asn Cys Thr Cys Lys Ser Gly Ala Val Glu Cys Arg Arg Met tct tgt ccc cct ctc aat tgc tcc cca gac tcc ctc cct gtg cac gtt      912
Ser Cys Pro Pro Leu Asn Cys Ser Pro Asp Ser Leu Pro Val His Val gcc ggc cag tgc tgt aag gtc tgc cga cca aaa tgt atc tac gga ggg      960
Ala Gly Gln Cys Cys Lys Val Cys Arg Pro Lys Cys Ile Tyr Gly Gly aaa gtc ctt gca gaa ggc cag cgg att tta acc aag agc tgt cgg gaa     1008
Lys Val Leu Ala Glu Gly Gln Arg Ile Leu Thr Lys Ser Cys Arg Glu tgc cga ggt gga gtt tta gtg aaa att aca gaa gcg tgc cct cct ttg     1056
Cys Arg Gly Gly Val Leu Val Lys Ile Thr Glu Ala Cys Pro Pro Leu aac tgc tca gac aag gat cac att ctc cca gag aat cag tgc tgc agc     1104
Asn Cys Ser Asp Lys Asp His Ile Leu Pro Glu Asn Gln Cys Cys Ser gtc tgc aga ggt cat aac ttt tgt gcg gaa gga cct aaa tgt ggt gaa     1152
Val Cys Arg Gly His Asn Phe Cys Ala Glu Gly Pro Lys Cys Gly Glu aat tca gag tgc aaa aac tgg aat aca aaa gct act tgc gag tgc aag     1200
Asn Ser Glu Cys Lys Asn Trp Asn Thr Lys Ala Thr Cys Glu Cys Lys aat ggt tat atc tct gtc cag ggg gac tcc gcc tac tgt gaa gat atc     1248
Asn Gly Tyr Ile Ser Val Gln Gly Asp Ser Ala Tyr Cys Glu Asp Ile gat gag tgt gct gct aag atg cat tac tgt cgt gcc aat act gtg tgt     1296
Asp Glu Cys Ala Ala Lys Met His Tyr Cys Arg Ala Asn Thr Val Cys gtc aac ctg cct ggg tta tat cgg tgt gac tgt gtc ccg gga tac att     1344
Val Asn Leu Pro Gly Leu Tyr Arg Cys Asp Cys Val Pro Gly Tyr Ile cgc gtg gat gat ttc tct tgt aca gaa cat gac gaa tgt ggc agc ggg     1392
Arg Val Asp Asp Phe Ser Cys Thr Glu His Asp Glu Cys Gly Ser Gly cag cac aac tgt gat gag aat gcc atc tgc acc aac act gtc cag gga     1440
Gln His Asn Cys Asp Glu Asn Ala Ile Cys Thr Asn Thr Val Gln Gly cac agc tgc acc tgc aaa ccg ggc tac gtg ggg aat ggg acc agc tgc     1488
His Ser Cys Thr Cys Lys Pro Gly Tyr Val Gly Asn Gly Thr Ser Cys aga gcg ttc tgc gaa gag ggc tgc aga tat ggc ggg aca tgc gtg gct     1536
Arg Ala Phe Cys Glu Glu Gly Cys Arg Tyr Gly Gly Thr Cys Val Ala
```

-continued

```
cct aac aaa tgt gtc tgt cct tct gga ttc aca gga agc cac tgt gag    1584
Pro Asn Lys Cys Val Cys Pro Ser Gly Phe Thr Gly Ser His Cys Glu aaa gat att gat gaa tgt aca gag gga atc att gag tgc cac aac cat    1632
Lys Asp Ile Asp Glu Cys Thr Glu Gly Ile Ile Glu Cys His Asn His tcc cgc tgc gtt aac ctg cca ggg tgg tac cac tgt gag tgc aga agc    1680
Ser Arg Cys Val Asn Leu Pro Gly Trp Tyr His Cys Glu Cys Arg Ser ggt ttc cat gac gat ggg acc tat tca ctg tcc ggg gag tcc tgt att    1728
Gly Phe His Asp Asp Gly Thr Tyr Ser Leu Ser Gly Glu Ser Cys Ile gac att gat gaa tgt gcc tta aga act cac acc tgt tgg aat gat tct    1776
Asp Ile Asp Glu Cys Ala Leu Arg Thr His Thr Cys Trp Asn Asp Ser gcc tgc atc aac ttg gca ggg ggc ttc gac tgc ctg tgt ccc tca ggg    1824
Ala Cys Ile Asn Leu Ala Gly Gly Phe Asp Cys Leu Cys Pro Ser Gly cca tcc tgc tct ggt gac tgc ccc cac gaa gga gga ctg aag cgc aac    1872
Pro Ser Cys Ser Gly Asp Cys Pro His Glu Gly Gly Leu Lys Arg Asn ggg cag gtg tgg acc ctg aaa gaa gac agg tgt tct gtg tgt tcc tgc    1920
Gly Gln Val Trp Thr Leu Lys Glu Asp Arg Cys Ser Val Cys Ser Cys aag gat ggg aag ata ttc tgc cga cgg aca gct tgt gat tgc cag aat    1968
Lys Asp Gly Lys Ile Phe Cys Arg Arg Thr Ala Cys Asp Cys Gln Asn cca agc gtt gac ctt ttc tgt tgc cca gag tgt gac acc agg gtc aca    2016
Pro Ser Val Asp Leu Phe Cys Cys Pro Glu Cys Asp Thr Arg Val Thr agt caa tgt tta gac caa aat gga cac aag ctc tat cga agt gga gac    2064
Ser Gln Cys Leu Asp Gln Asn Gly His Lys Leu Tyr Arg Ser Gly Asp aat tgg act cac agc tgt cag cag tgc cgg tgt ctg gaa gga gag gta    2112
Asn Trp Thr His Ser Cys Gln Gln Cys Arg Cys Leu Glu Gly Glu Val gat tgc tgg cca ctc act tgc ccc aga ttg agc tgt gag tac aca gcc    2160
Asp Cys Trp Pro Leu Thr Cys Pro Arg Leu Ser Cys Glu Tyr Thr Ala atc ttg gaa ggg gag tgt tgt cca cgc tgt gtc agc gac ccc tgc ctg    2208
Ile Leu Glu Gly Glu Cys Cys Pro Arg Cys Val Ser Asp Pro Cys Leu gcg gat aac atc gtc tat gac atc aga gaa act tgc ctg gac agc tat    2256
Ala Asp Asn Ile Val Tyr Asp Ile Arg Glu Thr Cys Leu Asp Ser Tyr gga gtt tca agg ctt agt ggc tca gtg tgg aca ttg gct gga tct ccc    2304
Gly Val Ser Arg Leu Ser Gly Ser Val Trp Thr Leu Ala Gly Ser Pro tgc acg acc tgc aaa tgc aag aat gga agt gtc tgc tgt tct gtg gat    2352
Cys Thr Thr Cys Lys Cys Lys Asn Gly Ser Val Cys Cys Ser Val Asp ttg gag tgt ctt cat aat aat tga aggatttaaa atggactcat gatcgccaga   2406
Leu Glu Cys Leu His Asn Asn  * gaaaaatgga caaatgacca tccatgatga tgaaagaaca ggagttggtg ttttttttac   2466
cacagacaat taccaaagtc tccgtctgag gaaggtgttt gcaggttgcc ttttggacct   2526
cccactctgc tcattcttgc taacctagtc taggtgacct acagtgcatt tcagtctatg   2586
gttgttaaaa gaagttttcc gtgttgtaaa tcacgtttcc cttaccaggt cattgcaaat   2646
acatttaaat gatttcatgg taaatgttga tgtatttttt gggtttattt tgtgtactaa   2706
cataatagag attcagctgc ttttatttat ttttttcttg acttttggat caaattcaac   2766
aaataaagtt gcctgttgtg atttt                                        2791
```

*Equus caballus* NELL1 isoform 1 amino acid sequence (SEQ ID NO: 6)

Met Gly Phe Gly Met Asp Pro Asp Leu Gln Met Asp Ile

Ile Thr Glu Leu Asp Leu Val Asn Thr Thr Leu Gly Val

Thr Gln Val Ser Gly Leu His Asn Ala Ser Lys Ala Phe

Leu Phe Gln Asp Val Glu Arg Glu Ile His Ala Ala Pro

His Val Ser Glu Lys Leu Ile Gln Leu Phe Arg Asn Lys

Ser Glu Phe Thr Phe Leu Ala Thr Val Gln Gln Lys Pro

Ser Thr Ser Gly Val Ile Leu Ser Ile Arg Glu Leu Glu

Asn Ser Tyr Phe Glu Leu Glu Ser Ser Gly Leu Arg Asp

Glu Ile Arg Tyr His Tyr Thr His Lys Gly Lys Pro Arg

Thr Glu Ala Leu Pro Tyr Arg Met Ala Asp Gly Arg Trp
His Lys Val Ala Leu Ser Val Ser Ala Ser His Leu Leu
Leu His Ile Asp Cys Asn Arg Ile Tyr Glu Arg Val Ile
Asp Thr Pro Glu Thr Asn Leu Pro Pro Gly Ser Asn Leu
Trp Leu Gly Gln Arg Asn Gln Lys His Gly Leu Phe Lys
Gly Ile Ile Gln Asp Gly Lys Ile Ile Phe Met Pro Asn
Gly Tyr Ile Thr Gln Cys Pro Asn Leu Asn Arg Thr Cys
Pro Thr Cys Ser Asp Phe Leu Ser Leu Val Gln Gly Ile
Met Asp Leu Gln Glu Leu Leu Ala Lys Met Thr Ala Lys
Leu Asn Tyr Ala Glu Thr Arg Leu Ser Gln Leu Glu Asn
Cys His Cys Glu Lys Thr Cys Gln Val Ser Gly Leu Leu
Tyr Arg Asp Gln Asp Ser Trp Val Asp Gly Asp His Cys
Arg Asn Cys Thr Cys Lys Ser Gly Ala Val Glu Cys Arg
Arg Met Ser Cys Pro Pro Leu Asn Cys Ser Pro Asp Ser
Leu Pro Val His Val Ala Gly Gln Cys Cys Lys Val Cys
Arg Pro Lys Cys Ile Tyr Gly Gly Lys Val Leu Ala Glu
Gly Gln Arg Ile Leu Thr Lys Ser Cys Arg Glu Cys Arg
Gly Gly Val Leu Val Lys Ile Thr Glu Ala Cys Pro Pro
Leu Asn Cys Ser Asp Lys Asp His Ile Leu Pro Glu Asn
Gln Cys Cys Ser Val Cys Arg Gly His Asn Phe Cys Ala
Glu Gly Pro Lys Cys Gly Glu Asn Ser Glu Cys Lys Asn
Trp Asn Thr Lys Ala Thr Cys Glu Cys Lys Asn Gly Tyr
Ile Ser Val Gln Gly Asp Ser Ala Tyr Cys Glu Asp Ile
Asp Glu Cys Ala Ala Lys Met His Tyr Cys Arg Ala Asn
Thr Val Cys Val Asn Leu Pro Gly Leu Tyr Arg Cys Asp
Cys Val Pro Gly Tyr Ile Arg Val Asp Asp Phe Ser Cys
Thr Glu His Asp Glu Cys Gly Ser Gly Gln His Asn Cys

Asp Glu Asn Ala Ile Cys Thr Asn Thr Val Gln Gly His
Ser Cys Thr Cys Lys Pro Gly Tyr Val Gly Asn Gly Thr
Ser Cys Arg Ala Phe Cys Glu Glu Gly Cys Arg Tyr Gly
Gly Thr Cys Val Ala Pro Asn Lys Cys Val Cys Pro Ser
Gly Phe Thr Gly Ser His Cys Glu Lys Asp Ile Asp Glu
Cys Thr Glu Gly Ile Ile Glu Cys His Asn His Ser Arg
Cys Val Asn Leu Pro Gly Trp Tyr His Cys Glu Cys Arg
Ser Gly Phe His Asp Asp Gly Thr Tyr Ser Leu Ser Gly
Glu Ser Cys Ile Asp Ile Asp Glu Cys Ala Leu Arg Thr
His Thr Cys Trp Asn Asp Ser Ala Cys Ile Asn Leu Ala
Gly Gly Phe Asp Cys Leu Cys Pro Ser Gly Pro Ser Cys
Ser Gly Asp Cys Pro His Glu Gly Gly Leu Lys Arg Asn
Gly Gln Val Trp Thr Leu Lys Glu Asp Arg Cys Ser Val
Cys Ser Cys Lys Asp Gly Lys Ile Phe Cys Arg Arg Thr
Ala Cys Asp Cys Gln Asn Pro Ser Val Asp Leu Phe Cys
Cys Pro Glu Cys Asp Thr Arg Val Thr Ser Gln Cys Leu
Asp Gln Asn Gly His Lys Leu Tyr Arg Ser Gly Asp Asn
Trp Thr His Ser Cys Gln Gln Cys Arg Cys Leu Glu Gly
Glu Val Asp Cys Trp Pro Leu Thr Cys Pro Arg Leu Ser
Cys Glu Tyr Thr Ala Ile Leu Glu Gly Glu Cys Cys Pro
Arg Cys Val Ser Asp Pro Cys Leu Ala Asp Asn Ile Val
Tyr Asp Ile Arg Glu Thr Cys Leu Asp Ser Tyr Gly Val
Ser Arg Leu Ser Gly Ser Val Trp Thr Leu Ala Gly Ser
Pro Cys Thr Thr Cys Lys Cys Lys Asn Gly Ser Val Cys
Cys Ser Val Asp Leu Glu Cys Leu His Asn Asn

*Equus caballus* NELL1 isoform 2 nucleotide sequence (SEQ ID NO: 7) and translated amino acid sequence (SEQ ID NO: 8)

```
atg ggc ttt ggg atg gac ccc gac ctt caa atg gat att atc acc gag    48
Met Gly Phe Gly Met Asp Pro Asp Leu Gln Met Asp Ile Ile Thr Glu ctc gac ctc gtg aac acc acc ctt gga gtc act cag gtg tcc gga ctg    96
Leu Asp Leu Val Asn Thr Thr Leu Gly Val Thr Gln Val Ser Gly Leu cac aat gcc agc aaa gca ttt tta ttt caa gat gta gag aga gag atc   144
His Asn Ala Ser Lys Ala Phe Leu Phe Gln Asp Val Glu Arg Glu Ile cat gca gcc cca cac gtg agt gag aaa tta att cag ctg ttc cgg aat   192
His Ala Ala Pro His Val Ser Glu Lys Leu Ile Gln Leu Phe Arg Asn aag agt gaa ttc acc ttt ttg gcc act gtg cag cag aag ccg tca act   240
Lys Ser Glu Phe Thr Phe Leu Ala Thr Val Gln Gln Lys Pro Ser Thr tca gga gtg ata ctg tcc att cga gaa ctg gaa aac agt tat ttt gaa   288
Ser Gly Val Ile Leu Ser Ile Arg Glu Leu Glu Asn Ser Tyr Phe Glu ctg gag agc agt ggc ctg aga gat gag att cga tat cac tac aca cac   336
Leu Glu Ser Ser Gly Leu Arg Asp Glu Ile Arg Tyr His Tyr Thr His aag ggg aag ccc agg aca gag gca ctt ccc tac cgg atg gcg gac gga   384
Lys Gly Lys Pro Arg Thr Glu Ala Leu Pro Tyr Arg Met Ala Asp Gly
```

-continued

```
cgg tgg cac aag gtg gcg ctg tca gtt agc gcc tct cat ctc ctg ctc    432
Arg Trp His Lys Val Ala Leu Ser Val Ser Ala Ser His Leu Leu Leu cac atc gac tgc aac agg att tat gaa cgt gtg ata gac act cct gag    480
His Ile Asp Cys Asn Arg Ile Tyr Glu Arg Val Ile Asp Thr Pro Glu acc aac ctc ccc cca gga agc aat ttg tgg ctg ggt cag cga aac caa    528
Thr Asn Leu Pro Pro Gly Ser Asn Leu Trp Leu Gly Gln Arg Asn Gln aag cac ggc tta ttc aaa gga atc atc caa gat gga aaa atc atc ttc    576
Lys His Gly Leu Phe Lys Gly Ile Ile Gln Asp Gly Lys Ile Ile Phe atg ccg aat gga tac ata aca cag tgt ccg aac ctg aat cgc act tgc    624
Met Pro Asn Gly Tyr Ile Thr Gln Cys Pro Asn Leu Asn Arg Thr Cys cca acg tgc agt gat ttc tta agc ctg gtg caa gga atc atg gat tta    672
Pro Thr Cys Ser Asp Phe Leu Ser Leu Val Gln Gly Ile Met Asp Leu caa gag ctt ctg gcc aag atg act gcg aaa cta aat tat gca gag aca    720
Gln Glu Leu Leu Ala Lys Met Thr Ala Lys Leu Asn Tyr Ala Glu Thr cga ctt agt caa ttg gaa aac tgc cac tgc gag aag acc tgt caa gtg    768
Arg Leu Ser Gln Leu Glu Asn Cys His Cys Glu Lys Thr Cys Gln Val agt gga ctg ctc tat aga gac cag gac tcc tgg gtt gat ggc gat cac    816
Ser Gly Leu Leu Tyr Arg Asp Gln Asp Ser Trp Val Asp Gly Asp His tgt agg aac tgc acg tgc aaa agc ggc gct gtg aat tgt cgg agg atg    864
Cys Arg Asn Cys Thr Cys Lys Ser Gly Ala Val Glu Cys Arg Arg Met tct tgt ccc cct ctc aat tgc tcc cca gac tcc ctc cct gtg cac gtt    912
Ser Cys Pro Pro Leu Asn Cys Ser Pro Asp Ser Leu Pro Val His Val gcc ggc cag tgc tgt aag gtc tgc cga cca aaa tgt atc tac gga ggg    960
Ala Gly Gln Cys Cys Lys Val Cys Arg Pro Lys Cys Ile Tyr Gly Gly aaa gtc ctt gca gaa ggc cag cgg att tta acc aag agc tgt cgg gaa   1008
Lys Val Leu Ala Glu Gly Gln Arg Ile Leu Thr Lys Ser Cys Arg Glu tgc cga ggt gga gtt tta gtg aaa att aca gaa gcg tgc cot cct ttg   1056
Cys Arg Gly Gly Val Leu Val Lys Ile Thr Glu Ala Cys Pro Pro Leu aac tgc tca gac aag gat cac att ctc cca gag aat cag tgc tgc agc   1104
Asn Cys Ser Asp Lys Asp His Ile Leu Pro Glu Asn Gln Cys Cys Ser gtc tgc aga ggt cat aac ttt tgt gcg gaa gga cct aaa tgt ggt gaa   1152
Val Cys Arg Gly His Asn Phe Cys Ala Glu Gly Pro Lys Cys Gly Glu aat tca gag tgc aaa aac tgg aat aca aaa gct act tgc gag tgc aag   1200
Asn Ser Glu Cys Lys Asn Trp Asn Thr Lys Ala Thr Cys Glu Cys Lys aat ggt tat atc tct gtc cag ggg gac tcc gcc tac tgt gaa gat atc   1248
Asn Gly Tyr Ile Ser Val Gln Gly Asp Ser Ala Tyr Cys Glu Asp Ile gat gag tgt gct gct aag atg cat tac tgt cgt gcc aat act gtg tgt   1296
Asp Glu Cys Ala Ala Lys Met His Tyr Cys Arg Ala Asn Thr Val Cys gtc aac ctg cct ggg tta tat cgg tgt gac tgt gtc ccg gga tac att   1344
Val Asn Leu Pro Gly Leu Tyr Arg Cys Asp Cys Val Pro Gly Tyr Ile cgc gtg gat gat ttc tct tgt aca gaa cat gac gaa tgt ggc agc ggg   1392
Arg Val Asp Asp Phe Ser Cys Thr Glu His Asp Glu Cys Gly Ser Gly cag cac aac tgt gat gag aat gcc atc tgc acc aac act gtc cag gga   1440
Gln His Asn Cys Asp Glu Asn Ala Ile Cys Thr Asn Thr Val Gln Gly cac agc tgc acc tgc aaa ccg ggc tac gtg ggg aat ggg acc agc tgc   1488
His Ser Cys Thr Cys Lys Pro Gly Tyr Val Gly Asn Gly Thr Ser Cys aga gcg ttc tgc gaa gag ggc tgc aga tat ggc ggg aca tgc gtg gct   1536
Arg Ala Phe Cys Glu Glu Gly Cys Arg Tyr Gly Gly Thr Cys Val Ala cct aac aaa tgt gtc tgt cct tct gga ttc aca gga agc cac tgt gag   1584
Pro Asn Lys Cys Val Cys Pro Ser Gly Phe Thr Gly Ser His Cys Glu aaa gac att gat gaa tgt gcc tta aga act cac acc tgt tgg aat gat   1632
Lys Asp Ile Asp Glu Cys Ala Leu Arg Thr His Thr Cys Trp Asn Asp tct gcc tgc atc aac ttg gca ggg ggc ttc gac tgc ctg tgt ccc tca   1680
Ser Ala Cys Ile Asn Leu Ala Gly Gly Phe Asp Cys Leu Cys Pro Ser
```

-continued

```
ggg cca tcc tgc tct ggt gac tgc ccc cac gaa gga gga ctg aag cgc   1728
Gly Pro Ser Cys Ser Gly Asp Cys Pro His Glu Gly Gly Leu Lys Arg aac ggg cag gtg tgg acc ctg aaa gaa gac agg tgt tct gtg tgt tcc   1776
Asn Gly Gln Val Trp Thr Leu Lys Glu Asp Arg Cys Ser Val Cys Ser tgc aag gat ggg aag ata ttc tgc cga cgg aca gct tgt gat tgc cag   1824
Cys Lys Asp Gly Lys Ile Phe Cys Arg Arg Thr Ala Cys Asp Cys Gln aat cca agc gtt gac ctt ttc tgt tgc cca gag tgt gac acc agg gtc   1872
Asn Pro Ser Val Asp Leu Phe Cys Cys Pro Glu Cys Asp Thr Arg Val aca agt caa tgt tta gac caa aat gga cac aag ctc tat cga agt gga   1920
Thr Ser Gln Cys Leu Asp Gln Asn Gly His Lys Leu Tyr Arg Ser Gly gac aat tgg act cac agc tgt cag cag tgc cgg tgt ctg gaa gga gag   1968
Asp Asn Trp Thr His Ser Cys Gln Gln Cys Arg Cys Leu Glu Gly Glu gta gat tgc tgg cca ctc act tgc ccc aga ttg agc tgt gag tac aca   2016
Val Asp Cys Trp Pro Leu Thr Cys Pro Arg Leu Ser Cys Glu Tyr Thr gcc atc ttg gaa ggg gag tgt tgt cca cgc tgt gtc agc gac ccc tgc   2064
Ala Ile Leu Glu Gly Glu Cys Cys Pro Arg Cys Val Ser Asp Pro Cys ctg gcg gat aac atc gtc tat gac atc aga gaa act tgc ctg gac agc   2112
Leu Ala Asp Asn Ile Val Tyr Asp Ile Arg Glu Thr Cys Leu Asp Ser tat gga gtt tca agg ctt agt ggc tca gtg tgg aca ttg gct gga tct   2160
Tyr Gly Val Ser Arg Leu Ser Gly Ser Val Trp Thr Leu Ala Gly Ser ccc tgc acg acc tgc aaa tgc aag aat gga agt gtc tgc tgt tct gtg   2208
Pro Cys Thr Thr Cys Lys Cys Lys Asn Gly Ser Val Cys Cys Ser Val gat ttg gag tgt ctt cat aat aat tga aggatttaaa atggactcat          2255
Asp Leu Glu Cys Leu His Asn Asn  * gatcgccaga gaaaaatgga caaatgacca                                    2285
```

*Equus caballus* NELL1 isoform 2 amino acid sequence (SEQ ID NO: 8)

Met Gly Phe Gly Met Asp Pro Asp Leu Gln Met Asp Ile
Ile Thr Glu Leu Asp Leu Val Asn Thr Thr Leu Gly Val
Thr Gln Val Ser Gly Leu His Asn Ala Ser Lys Ala Phe
Leu Phe Gln Asp Val Glu Arg Glu Ile His Ala Ala Pro
His Val Ser Glu Lys Leu Ile Gln Leu Phe Arg Asn Lys
Ser Glu Phe Thr Phe Leu Ala Thr Val Gln Gln Lys Pro
Ser Thr Ser Gly Val Ile Leu Ser Ile Arg Glu Leu Glu
Asn Ser Tyr Phe Glu Leu Glu Ser Ser Gly Leu Arg Asp
Glu Ile Arg Tyr His Tyr Thr His Lys Gly Lys Pro Arg
Thr Glu Ala Leu Pro Tyr Arg Met Ala Asp Gly Arg Trp
His Lys Val Ala Leu Ser Val Ser Ala Ser His Leu Leu
Leu His Ile Asp Cys Asn Arg Ile Tyr Glu Arg Val Ile
Asp Thr Pro Glu Thr Asn Leu Pro Pro Gly Ser Asn Leu
Trp Leu Gly Gln Arg Asn Gln Lys His Gly Leu Phe Lys
Gly Ile Ile Gln Asp Gly Lys Ile Ile Phe Met Pro Asn
Gly Tyr Ile Thr Gln Cys Pro Asn Leu Asn Arg Thr Cys
Pro Thr Cys Ser Asp Phe Leu Ser Leu Val Gln Gly Ile
Met Asp Leu Gln Glu Leu Leu Ala Lys Met Thr Ala Lys
Leu Asn Tyr Ala Glu Thr Arg Leu Ser Gln Leu Glu Asn
Cys His Cys Glu Lys Thr Cys Gln Val Ser Gly Leu Leu
Tyr Arg Asp Gln Asp Ser Trp Val Asp Gly Asp His Cys
Arg Asn Cys Thr Cys Lys Ser Gly Ala Val Glu Cys Arg
Arg Met Ser Cys Pro Pro Leu Asn Cys Ser Pro Asp Ser
Leu Pro Val His Val Ala Gly Gln Cys Cys Lys Val Cys
Arg Pro Lys Cys Ile Tyr Gly Gly Lys Val Leu Ala Glu
Gly Gln Arg Ile Leu Thr Lys Ser Cys Arg Glu Cys Arg
Gly Gly Val Leu Val Lys Ile Thr Glu Ala Cys Pro Pro
Leu Asn Cys Ser Asp Lys Asp His Ile Leu Pro Glu Asn
Gln Cys Cys Ser Val Cys Arg Gly His Asn Phe Cys Ala
Glu Gly Pro Lys Cys Gly Glu Asn Ser Glu Cys Lys Asn
Trp Asn Thr Lys Ala Thr Cys Glu Cys Lys Asn Gly Tyr
Ile Ser Val Gln Gly Asp Ser Ala Tyr Cys Glu Asp Ile
Asp Glu Cys Ala Ala Lys Met His Tyr Cys Arg Ala Asn
Thr Val Cys Val Asn Leu Pro Gly Leu Tyr Arg Cys Asp
Cys Val Pro Gly Tyr Ile Arg Val Asp Asp Phe Ser Cys
Thr Glu His Asp Glu Cys Gly Ser Gly Gln His Asn Cys
Asp Glu Asn Ala Ile Cys Thr Asn Thr Val Gln Gly His
Ser Cys Thr Cys Lys Pro Gly Tyr Val Gly Asn Gly Thr

-continued

Ser Cys Arg Ala Phe Cys Glu Glu Gly Cys Arg Tyr Gly

Gly Thr Cys Val Ala Pro Asn Lys Cys Val Cys Pro Ser

Gly Phe Thr Gly Ser His Cys Glu Lys Asp Ile Asp Glu

Cys Ala Leu Arg Thr His Thr Cys Trp Asn Asp Ser Ala

Cys Ile Asn Leu Ala Gly Gly Phe Asp Cys Leu Cys Pro

Ser Gly Pro Ser Cys Ser Gly Asp Cys Pro His Glu Gly

Gly Leu Lys Arg Asn Gly Gln Val Trp Thr Leu Lys Glu

Asp Arg Cys Ser Val Cys Ser Cys Lys Asp Gly Lys Ile

Phe Cys Arg Arg Thr Ala Cys Asp Cys Gln Asn Pro Ser

Val Asp Leu Phe Cys Cys Pro Glu Cys Asp Thr Arg Val

Thr Ser Gln Cys Leu Asp Gln Asn Gly His Lys Leu Tyr

Arg Ser Gly Asp Asn Trp Thr His Ser Cys Gln Gln Cys

Arg Cys Leu Glu Gly Glu Val Asp Cys Trp Pro Leu Thr

Cys Pro Arg Leu Ser Cys Glu Tyr Thr Ala Ile Leu Glu

Gly Glu Cys Cys Pro Arg Cys Val Ser Asp Pro Cys Leu

Ala Asp Asn Ile Val Tyr Asp Ile Arg Glu Thr Cys Leu

Asp Ser Tyr Gly Val Ser Arg Leu Ser Gly Ser Val Trp

Thr Leu Ala Gly Ser Pro Cys Thr Thr Cys Lys Cys Lys

Asn Gly Ser Val Cys Cys Ser Val Asp Leu Glu Cys Leu

His Asn Asn

*Mus musculus* NELL1 nucleotide sequence (SEQ ID NO: 9) and translated amino acid sequence (SEQ ID NO: 10)

```
gcgttggtgc gccctgcttg gcgggggggcc tccggagcg atg ccg atg gat gtg       54
                                            Met Pro Met Asp Val att tta gtt ttg tgg ttc tgt gtg tgc acc gcc agg aca gtg ctg ggc      102
Ile Leu Val Leu Trp Phe Cys Val Cys Thr Ala Arg Thr Val Leu Gly ttt ggg atg gac cct gac ctt cag atg gac atc atc act gaa ctt gac      150
Phe Gly Met Asp Pro Asp Leu Gln Met Asp Ile Ile Thr Glu Leu Asp ctt gtg aac acc acc ctg ggc gtc act cag gtg gct gga cta cac aat      198
Leu Val Asn Thr Thr Leu Gly Val Thr Gln Val Ala Gly Leu His Asn gcc agt aag gca ttt ctg ttt caa gat gta cag aga gag atc cac tca      246
Ala Ser Lys Ala Phe Leu Phe Gln Asp Val Gln Arg Glu Ile His Ser gcc cct cat gtg agt gag aag ctg atc cag cta ttc cgg aat aag agt      294
Ala Pro His Val Ser Glu Lys Leu Ile Gln Leu Phe Arg Asn Lys Ser gag ttt acc ttt ttg gct aca gtg cag cag aag ccg tcc acc tca ggg      342
Glu Phe Thr Phe Leu Ala Thr Val Gln Gln Lys Pro Ser Thr Ser Gly gtg ata ctg tcg atc cgg gag ctg gaa cac agc tat ttt gaa ctg gag      390
Val Ile Leu Ser Ile Arg Glu Leu Glu His Ser Tyr Phe Glu Leu Glu agc agt ggc cca aga gaa gag ata cgc tat cat tac atc cat ggc ggc      438
Ser Ser Gly Pro Arg Glu Glu Ile Arg Tyr His Tyr Ile His Gly Gly aag ccc agg act gag gcc ctt ccc tac cgc atg gcc gat gga cag tgg      486
Lys Pro Arg Thr Glu Ala Leu Pro Tyr Arg Met Ala Asp Gly Gln Trp cac aag gtc gcg ctg tct gtg agc gcc tct cac ctc cta ctc cat gtc      534
His Lys Val Ala Leu Ser Val Ser Ala Ser His Leu Leu Leu His Val gac tgc aat agg att tat gag cgt gtg ata gat cct ccg gag acc aac      582
Asp Cys Asn Arg Ile Tyr Glu Arg Val Ile Asp Pro Pro Glu Thr Asn ctt cct cca gga agc aat cta tgg ctt ggg caa cgt aat caa aag cat      630
Leu Pro Pro Gly Ser Asn Leu Trp Leu Gly Gln Arg Asn Gln Lys His ggc ttt ttc aaa gga atc atc caa gat ggc aag atc atc ttc atg ccg      678
Gly Phe Phe Lys Gly Ile Ile Gln Asp Gly Lys Ile Ile Phe Met Pro aac ggc ttc atc aca cag tgc ccc aac cta aat cgc act tgc cca aca      726
Asn Gly Phe Ile Thr Gln Cys Pro Asn Leu Asn Arg Thr Cys Pro Thr tgc agt gat ttc ctg agc ctg gtt caa gga ata atg gat ttg caa gag      774
Cys Ser Asp Phe Leu Ser Leu Val Gln Gly Ile Met Asp Leu Gln Glu ctt ttg gcc aag atg act gca aaa ctg aat tat gca gag acg aga ctt      822
Leu Leu Ala Lys Met Thr Ala Lys Leu Asn Tyr Ala Glu Thr Arg Leu ggt caa ctg gaa aat tgc cac tgt gag aag acc tgc caa gtg agt ggg      870
Gly Gln Leu Glu Asn Cys His Cys Glu Lys Thr Cys Gln Val Ser Gly ctg ctc tac agg gac caa gac tcc tgg gta gat ggt gac aac tgc agg      918
Leu Leu Tyr Arg Asp Gln Asp Ser Trp Val Asp Gly Asp Asn Cys Arg
```

```
aac tgc aca tgc aaa agt ggt gct gtg gag tgc cga agg atg tcc tgt      966
Asn Cys Thr Cys Lys Ser Gly Ala Val Glu Cys Arg Arg Met Ser Cys ccc cca ctc aac tgt tcc cca gac tca ctt cct gtg cat att tct ggc     1014
Pro Pro Leu Asn Cys Ser Pro Asp Ser Leu Pro Val His Ile Ser Gly caa tgt tgt aaa gtt tgc aga cca aaa tgt atc tat gga gga aaa gtt     1062
Gln Cys Cys Lys Val Cys Arg Pro Lys Cys Ile Tyr Gly Gly Lys Val ctt gct gag ggc cag cgg att tta acc aag acc tgc cgg gaa tgt cga     1110
Leu Ala Glu Gly Gln Arg Ile Leu Thr Lys Thr Cys Arg Glu Cys Arg ggt gga gtc ttg gta aaa atc aca gaa gct tgc cct cct ttg aac tgc     1158
Gly Gly Val Leu Val Lys Ile Thr Glu Ala Cys Pro Pro Leu Asn Cys tca gag aag gat cat att ctt ccg gag aac cag tgc tgc agg gtc tgc     1206
Ser Glu Lys Asp His Ile Leu Pro Glu Asn Gln Cys Cys Arg Val Cys cga ggt cat aac ttc tgt gca gaa gca cct aag tgt gga gaa aac tcg     1254
Arg Gly His Asn Phe Cys Ala Glu Ala Pro Lys Cys Gly Glu Asn Ser gaa tgc aaa aat tgg aat aca aaa gcg act tgt gag tgc aag aat gga     1302
Glu Cys Lys Asn Trp Asn Thr Lys Ala Thr Cys Glu Cys Lys Asn Gly tac atc tct gtc cag ggc aac tct gca tac tgt gaa gat atc gat gag     1350
Tyr Ile Ser Val Gln Gly Asn Ser Ala Tyr Cys Glu Asp Ile Asp Glu tgt gca gca aag atg cac tac tgt cat gcc aac acg gtg tgt gtc aac     1398
Cys Ala Ala Lys Met His Tyr Cys His Ala Asn Thr Val Cys Val Asn ttg ccg ggg tta tat cgc tgt gac tgc atc cca gga tac atc cgt gtg     1446
Leu Pro Gly Leu Tyr Arg Cys Asp Cys Ile Pro Gly Tyr Ile Arg Val gat gac ttc tct tgt acg gag cat gat gat tgt ggc agc gga caa cac     1494
Asp Asp Phe Ser Cys Thr Glu His Asp Asp Cys Gly Ser Gly Gln His aac tgt gac aaa aat gcc atc tgt acc aac aca gtc cag gga cac agc     1542
Asn Cys Asp Lys Asn Ala Ile Cys Thr Asn Thr Val Gln Gly His Ser tgt acc tgc cag cca ggc tac gtg gga aat ggt act gtc tgc aaa gca     1590
Cys Thr Cys Gln Pro Gly Tyr Val Gly Asn Gly Thr Val Cys Lys Ala ttc tgt gaa gag ggt tgc aga tac gga ggt acc tgt gtg gcc cct aac     1638
Phe Cys Glu Glu Gly Cys Arg Tyr Gly Gly Thr Cys Val Ala Pro Asn aaa tgt gtc tgt cct tct gga ttc aca gga agc cac tgt gag aaa gat     1686
Lys Cys Val Cys Pro Ser Gly Phe Thr Gly Ser His Cys Glu Lys Asp att gat gaa tgt gca gag gga ttc gtt gag tgc cac aac cac tcc cgc     1734
Ile Asp Glu Cys Ala Glu Gly Phe Val Glu Cys His Asn His Ser Arg tgc gtt aac ctt cca ggg tgg tac cac tgt gag tgc aga agc ggt ttc     1782
Cys Val Asn Leu Pro Gly Trp Tyr His Cys Glu Cys Arg Ser Gly Phe cat gac gat ggg acc tat tca ctg tcc ggg gag tcc tgc att gat att     1830
His Asp Asp Gly Thr Tyr Ser Leu Ser Gly Glu Ser Cys Ile Asp Ile gat gaa tgt gcc tta aga act cac act tgt tgg aat gac tct gcc tgc     1878
Asp Glu Cys Ala Leu Arg Thr His Thr Cys Trp Asn Asp Ser Ala Cys atc aac tta gca gga gga ttt gac tgc ctg tgt ccc tct ggg ccc tcc     1926
Ile Asn Leu Ala Gly Gly Phe Asp Cys Leu Cys Pro Ser Gly Pro Ser tgc tct ggt gac tgt ccc cac gaa ggg ggg ctg aag cat aat ggg cag     1974
Cys Ser Gly Asp Cys Pro His Glu Gly Gly Leu Lys His Asn Gly Gln gtg tgg att ctg aga gaa gac agg tgt tca gtc tgt tcc tgt aag gat     2022
Val Trp Ile Leu Arg Glu Asp Arg Cys Ser Val Cys Ser Cys Lys Asp ggg aag ata ttc tgc cgg cgg aca gct tgt gat tgc cag aat cca aat     2070
Gly Lys Ile Phe Cys Arg Arg Thr Ala Cys Asp Cys Gln Asn Pro Asn gtt gac ctt ttc tgc tgc cca gag tgt gac acc agg gtc act agc caa     2118
Val Asp Leu Phe Cys Cys Pro Glu Cys Asp Thr Arg Val Thr Ser Gln tgt tta gat caa agc gga cag aag ctc tat cga agt gga gac aac tgg     2166
Cys Leu Asp Gln Ser Gly Gln Lys Leu Tyr Arg Ser Gly Asp Asn Trp acc cac agc tgc cag cag tgc cga tgt ctg gaa gga gag gca gac tgc     2214
Thr His Ser Cys Gln Gln Cys Arg Cys Leu Glu Gly Glu Ala Asp Cys
```

-continued

```
tgg cct cta gct tgc cct agt ttg agc tgt gaa tac aca gcc atc ttt    2262
Trp Pro Leu Ala Cys Pro Ser Leu Ser Cys Glu Tyr Thr Ala Ile Phe gaa gga gag tgt tgt ccc cgc tgt gtc agt gac ccc tgc ctg gct gat    2310
Glu Gly Glu Cys Cys Pro Arg Cys Val Ser Asp Pro Cys Leu Ala Asp aat att gcc tat gac atc aga aaa act tgc ctg gac agc tct ggt att    2358
Asn Ile Ala Tyr Asp Ile Arg Lys Thr Cys Leu Asp Ser Ser Gly Ile tcg agg ctg agc ggc gca gtg tgg aca atg gct gga tct ccc tgt aca    2406
Ser Arg Leu Ser Gly Ala Val Trp Thr Met Ala Gly Ser Pro Cys Thr acc tgt caa tgc aag aat ggg aga gtc tgc tgc tct gtg gat ctg gtg    2454
Thr Cys Gln Cys Lys Asn Gly Arg Val Cys Cys Ser Val Asp Leu Val tgt ctt gag aat aac tga agattttaaa tggactcatc acatgagaaa           2502
Cys Leu Glu Asn Asn * atggacaaaa tgaccatcca acctgaggaa gaggaggggc tgatttcttt ttcttttttaa 2562 ccacagtcaa ttaccaaagt ctccatcaga ggaaggcgtt tgggttgcct ttaccacttt  2622
gctcatcctt gctgacctag tctagatgcc tgcagtaccg tgtatttcgg tcgatggttg  2682
ttgagtctcc gtgctgtaaa tcacatttcc cttgtcagat catttacaga tacatttaaa  2742
ggattccatg ataaatgtta aagtaccttt tgtttatttt gtgtaccaac ataatagaga  2802
cttggcacca                                                        2812
```

*Mus musculus* NELL1 amino acid sequence (SEQ ID NO: 10)

Met Pro Met Asp Val Ile Leu Val Leu Trp Phe Cys Val
Cys Thr Ala Arg Thr Val Leu Gly Phe Gly Met Asp Pro
Asp Leu Gln Met Asp Ile Ile Thr Glu Leu Asp Leu Val
Asn Thr Thr Leu Gly Val Thr Gln Val Ala Gly Leu His
Asn Ala Ser Lys Ala Phe Leu Phe Gln Asp Val Gln Arg
Glu Ile His Ser Ala Pro His Val Ser Glu Lys Leu Ile
Gln Leu Phe Arg Asn Lys Ser Glu Phe Thr Phe Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Pro Arg Glu Glu Ile Arg Tyr His Tyr Ile
His Gly Gly Lys Pro Arg Thr Glu Ala Leu Pro Tyr Arg
Met Ala Asp Gly Gln Trp His Lys Val Ala Leu Ser Val
Ser Ala Ser His Leu Leu Leu His Val Asp Cys Asn Arg
Ile Tyr Glu Arg Val Ile Asp Pro Pro Glu Thr Asn Leu
Pro Pro Gly Ser Asn Leu Trp Leu Gly Gln Arg Asn Gln
Lys His Gly Phe Phe Lys Gly Ile Ile Gln Asp Gly Lys
Ile Ile Phe Met Pro Asn Gly Phe Ile Thr Gln Cys Pro
Asn Leu Asn Arg Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Gly Gln Leu Glu Asn Cys His Cys Glu Lys Thr Cys
Gln Val Ser Gly Leu Leu Tyr Arg Asp Gln Asp Ser Trp
Val Asp Gly Asp Asn Cys Arg Asn Cys Thr Cys Lys Ser
Gly Ala Val Glu Cys Arg Arg Met Ser Cys Pro Pro Leu
Asn Cys Ser Pro Asp Ser Leu Pro Val His Ile Ser Gly
Gln Cys Cys Lys Val Cys Arg Pro Lys Cys Ile Tyr Gly
Gly Lys Val Leu Ala Glu Gly Gln Arg Ile Leu Thr Lys
Thr Cys Arg Glu Cys Arg Gly Gly Val Leu Val Lys Ile
Thr Glu Ala Cys Pro Pro Leu Asn Cys Ser Glu Lys Asp
His Ile Leu Pro Glu Asn Gln Cys Cys Arg Val Cys Arg
Gly His Asn Phe Cys Ala Glu Ala Pro Lys Cys Gly Glu
Asn Ser Glu Cys Lys Asn Trp Asn Thr Lys Ala Thr Cys
Glu Cys Lys Asn Gly Tyr Ile Ser Val Gln Gly Asn Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Ile Pro Gly Tyr Ile Arg
Val Asp Asp Phe Ser Cys Thr Glu His Asp Asp Cys Gly
Ser Gly Gln His Asn Cys Asp Lys Asn Ala Ile Cys Thr
Asn Thr Val Gln Gly His Ser Cys Thr Cys Gln Pro Gly
Tyr Val Gly Asn Gly Thr Val Cys Lys Ala Phe Cys Glu
Glu Gly Cys Arg Tyr Gly Gly Thr Cys Val Ala Pro Asn
Lys Cys Val Cys Pro Ser Gly Phe Thr Gly Ser His Cys
Glu Lys Asp Ile Asp Glu Cys Ala Glu Gly Phe Val Glu
Cys His Asn His Ser Arg Cys Val Asn Leu Pro Gly Trp
Tyr His Cys Glu Cys Arg Ser Gly Phe His Asp Asp Gly
Thr Tyr Ser Leu Ser Gly Glu Ser Cys Ile Asp Ile Asp

-continued

Glu Cys Ala Leu Arg Thr His Thr Cys Trp Asn Asp Ser

Ala Cys Ile Asn Leu Ala Gly Gly Phe Asp Cys Leu Cys

Pro Ser Gly Pro Ser Cys Ser Gly Asp Cys Pro His Glu

Gly Gly Leu Lys His Asn Gly Gln Val Trp Ile Leu Arg

Glu Asp Arg Cys Ser Val Cys Ser Cys Lys Asp Gly Lys

Ile Phe Cys Arg Arg Thr Ala Cys Asp Cys Gln Asn Pro

Asn Val Asp Leu Phe Cys Cys Pro Glu Cys Asp Thr Arg

Val Thr Ser Gln Cys Leu Asp Gln Ser Gly Gln Lys Leu

Tyr Arg Ser Gly Asp Asn Trp Thr His Ser Cys Gln Gln

-continued

Cys Arg Cys Leu Glu Gly Glu Ala Asp Cys Trp Pro Leu

Ala Cys Pro Ser Leu Ser Cys Glu Tyr Thr Ala Ile Phe

Glu Gly Glu Cys Cys Pro Arg Cys Val Ser Asp Pro Cys

Leu Ala Asp Asn Ile Ala Tyr Asp Ile Arg Lys Thr Cys

Leu Asp Ser Ser Gly Ile Ser Arg Leu Ser Gly Ala Val

Trp Thr Met Ala Gly Ser Pro Cys Thr Thr Cys Gln Cys

Lys Asn Gly Arg Val Cys Cys Ser Val Asp Leu Val Cys

Leu Glu Asn Asn

*Rattus norvegicus* NELL1 nucleotide sequence (SEQ ID NO: 11) and translated amino acid sequence (SEQ ID NO: 12)

| | | |
|---|---|---|
| aagcactggt ttcttgttag cgttggtgcg ccctgcttgg cggggggttct ccggagcg | | 58 |
| atg ccg atg gat gtg att tta gtt ttg tgg ttc tgt gta tgc acc gcc<br>Met Pro Met Asp Val Ile Leu Val Leu Trp Phe Cys Val Cys Thr Ala | | 106 |
| agg aca gtg ttg ggc ttt ggg atg gac cct gac ctt cag ctg gac atc<br>Arg Thr Val Leu Gly Phe Gly Met Asp Pro Asp Leu Gln Leu Asp Ile | | 154 |
| atc tca gag ctc gac ctg gtg aac acc acc ctg gga gtc acg cag gtg<br>Ile Ser Glu Leu Asp Leu Val Asn Thr Thr Leu Gly Val Thr Gln Val | | 202 |
| gct gga ctg cac aac gcc agt aaa gca ttt cta ttt caa gat gta cag<br>Ala Gly Leu His Asn Ala Ser Lys Ala Phe Leu Phe Gln Asp Val Gln | | 250 |
| aga gag atc cat tcg gcc cct cac gtg agt gag aag ctg atc cag cta<br>Arg Glu Ile His Ser Ala Pro His Val Ser Glu Lys Leu Ile Gln Leu | | 298 |
| ttc cgg aat aag agc gag ttc acc ttt ttg gct aca gtg cag cag aaa<br>Phe Arg Asn Lys Ser Glu Phe Thr Phe Leu Ala Thr Val Gln Gln Lys | | 346 |
| cca tcc acc tca ggg gtg ata ctg tcc atc cgg gag ctg gag cac agc<br>Pro Ser Thr Ser Gly Val Ile Leu Ser Ile Arg Glu Leu Glu His Ser | | 394 |
| tat ttt gaa ctg gag agc agt ggc cca aga gaa gag ata cgc tac cat<br>Tyr Phe Glu Leu Glu Ser Ser Gly Pro Arg Glu Glu Ile Arg Tyr His | | 442 |
| tac ata cat ggt gga aag ccc agg act gag gcc ctt ccc tac cgc atg<br>Tyr Ile His Gly Gly Lys Pro Arg Thr Glu Ala Leu Pro Tyr Arg Met | | 490 |
| gca gac gga caa tgg cac aag gtc gcg ctg tca gtg agc gcc tct cac<br>Ala Asp Gly Gln Trp His Lys Val Ala Leu Ser Val Ser Ala Ser His | | 538 |
| ctc ctg ctc cac atc gac tgc aat agg att tac gag cgt gtg ata gac<br>Leu Leu Leu His Ile Asp Cys Asn Arg Ile Tyr Glu Arg Val Ile Asp | | 586 |
| cct ccg gag acc aac ctt cct cca gga agc aat ctg tgg ctt ggg caa<br>Pro Pro Glu Thr Asn Leu Pro Pro Gly Ser Asn Leu Trp Leu Gly Gln | | 634 |
| cgt aac caa aag cat ggc ttt ttc aaa gga atc atc caa gat ggt aag<br>Arg Asn Gln Lys His Gly Phe Phe Lys Gly Ile Ile Gln Asp Gly Lys | | 682 |
| atc atc ttc atg ccg aat ggt ttc atc aca cag tgt ccc aac ctc aat<br>Ile Ile Phe Met Pro Asn Gly Phe Ile Thr Gln Cys Pro Asn Leu Asn | | 730 |
| cgc act tgc cca aca tgc agt gac ttc ctg agc ctg gtt caa gga ata<br>Arg Thr Cys Pro Thr Cys Ser Asp Phe Leu Ser Leu Val Gln Gly Ile | | 778 |
| atg gat ttg caa gag ctt ttg gcc aag atg act gca aaa ctg aat tat<br>Met Asp Leu Gln Glu Leu Leu Ala Lys Met Thr Ala Lys Leu Asn Tyr | | 826 |
| gca gag acg aga ctt ggt caa ctg gaa aat tgc cac tgt gag aag acc<br>Ala Glu Thr Arg Leu Gly Gln Leu Glu Asn Cys His Cys Glu Lys Thr | | 874 |
| tgc caa gtg agt ggg ctg ctc tac agg gac caa gac tcc tgg gtg gat<br>Cys Gln Val Ser Gly Leu Leu Tyr Arg Asp Gln Asp Ser Trp Val Asp | | 922 |
| ggt gac aac tgt ggg aac tgc acg tgc aaa agt ggt gcc gtg gag tgc<br>Gly Asp Asn Cys Gly Asn Cys Thr Cys Lys Ser Gly Ala Val Glu Cys | | 970 |

-continued

```
cgc agg atg tcc tgt ccc ccg ctc aac tgt tcc ccg gac tca ctt cct    1018
Arg Arg Met Ser Cys Pro Pro Leu Asn Cys Ser Pro Asp Ser Leu Pro gtg cac att tcc ggc cag tgt tgt aaa gtt tgc aga cca aaa tgt atc    1066
Val His Ile Ser Gly Gln Cys Cys Lys Val Cys Arg Pro Lys Cys Ile tat gga gga aaa gtt ctt gct gag ggc cag cgg att tta acc aag acc    1114
Tyr Gly Gly Lys Val Leu Ala Glu Gly Gln Arg Ile Leu Thr Lys Thr tgc cgg gaa tgt cga ggt gga gtc ttg gta aaa atc aca gaa gct tgc    1162
Cys Arg Glu Cys Arg Gly Gly Val Leu Val Lys Ile Thr Glu Ala Cys cct cct ttg aac tgc tca gca aag gat cat att ctt cca gag aat cag    1210
Pro Pro Leu Asn Cys Ser Ala Lys Asp His Ile Leu Pro Glu Asn Gln tgc tgc agg gtc tgc cca ggt cat aac ttc tgt gca gaa gca cct aag    1258
Cys Cys Arg Val Cys Pro Gly His Asn Phe Cys Ala Glu Ala Pro Lys tgc gga gaa aac tcg gaa tgc aaa aat tgg aat aca aaa gca acc tgt    1306
Cys Gly Glu Asn Ser Glu Cys Lys Asn Trp Asn Thr Lys Ala Thr Cys gag tgc aag aat gga tac atc tct gtc cag ggc aac tct gca tac tgt    1354
Glu Cys Lys Asn Gly Tyr Ile Ser Val Gln Gly Asn Ser Ala Tyr Cys gaa gat att gat gag tgt gca gct aaa atg cac tat tgt cat gcc aac    1402
Glu Asp Ile Asp Glu Cys Ala Ala Lys Met His Tyr Cys His Ala Asn acc gtg tgt gtc aac ttg ccg ggg ttg tat cgc tgt gac tgc gtc cca    1450
Thr Val Cys Val Asn Leu Pro Gly Leu Tyr Arg Cys Asp Cys Val Pro ggg tac atc cgt gtg gat gac ttc tct tgt acg gag cat gat gat tgt    1498
Gly Tyr Ile Arg Val Asp Asp Phe Ser Cys Thr Glu His Asp Asp Cys ggc agc gga caa cac aac tgc gac aaa aat gcc atc tgt acc aac aca    1546
Gly Ser Gly Gln His Asn Cys Asp Lys Asn Ala Ile Cys Thr Asn Thr gtc cag gga cac agc tgc acc tgc cag ccg ggt tac gtg gga aat ggc    1594
Val Gln Gly His Ser Cys Thr Cys Gln Pro Gly Tyr Val Gly Asn Gly acc atc tgc aaa gca ttc tgt gaa gag ggt tgc aga tac gga ggt acc    1642
Thr Ile Cys Lys Ala Phe Cys Glu Glu Gly Cys Arg Tyr Gly Gly Thr tgt gtg gct cct aac aag tgt gtc tgt cct tct gga ttc acg gga agc    1690
Cys Val Ala Pro Asn Lys Cys Val Cys Pro Ser Gly Phe Thr Gly Ser cac tgt gag aaa gat att gat gaa tgc gca gag gga ttc gtt gaa tgc    1738
His Cys Glu Lys Asp Ile Asp Glu Cys Ala Glu Gly Phe Val Glu Cys cac aac tac tcc cgc tgt gtt aac ctg cca ggg tgg tac cac tgt gag    1786
His Asn Tyr Ser Arg Cys Val Asn Leu Pro Gly Trp Tyr His Cys Glu tgc aga agc ggt ttc cat gac gat ggg acc tac tca ctg tcc ggg gag    1834
Cys Arg Ser Gly Phe His Asp Asp Gly Thr Tyr Ser Leu Ser Gly Glu tcc tgc att gat atc gat gaa tgt gcc tta aga act cac act tgt tgg    1882
Ser Cys Ile Asp Ile Asp Glu Cys Ala Leu Arg Thr His Thr Cys Trp aat gac tct gcc tgc atc aac tta gca gga gga ttt gac tgc ctg tgt    1930
Asn Asp Ser Ala Cys Ile Asn Leu Ala Gly Gly Phe Asp Cys Leu Cys ccc tct ggg ccc tcc tgc tct ggt gac tgt ccc cac gaa gga ggg ctg    1978
Pro Ser Gly Pro Ser Cys Ser Gly Asp Cys Pro His Glu Gly Gly Leu aag cat aat ggg cag gtg tgg att ctg aga gaa gac agg tgt tca gtc    2026
Lys His Asn Gly Gln Val Trp Ile Leu Arg Glu Asp Arg Cys Ser Val tgt tcc tgc aag gat ggg aag ata ttc tgc cgg cgg aca gct tgt gat    2074
Cys Ser Cys Lys Asp Gly Lys Ile Phe Cys Arg Arg Thr Ala Cys Asp tgc cag aat cca aat gtt gac ctt ttt tgc tgc cca gag tgc gat acc    2122
Cys Gln Asn Pro Asn Val Asp Leu Phe Cys Cys Pro Glu Cys Asp Thr agg gtc acc agc caa tgt tta gat caa agt gga cag aag ctc tat cga    2170
Arg Val Thr Ser Gln Cys Leu Asp Gln Ser Gly Gln Lys Leu Tyr Arg agt gga gac aac tgg acc cac agc tgc cag cag tgc cga tgt ctg gaa    2218
Ser Gly Asp Asn Trp Thr His Ser Cys Gln Gln Cys Arg Cys Leu Glu gga gag gca gac tgc tgg cct ctg gct tgc cct agt ttg ggc tgt gaa    2266
Gly Glu Ala Asp Cys Trp Pro Leu Ala Cys Pro Ser Leu Gly Cys Glu
```

```
tac aca gcc atg ttt gaa ggg gag tgt tgt ccc cga tgt gtc agt gac    2314
Tyr Thr Ala Met Phe Glu Gly Glu Cys Cys Pro Arg Cys Val Ser Asp ccc tgc ctg gct ggt aat att gcc tat gac atc aga aaa act tgc ctg    2362
Pro Cys Leu Ala Gly Asn Ile Ala Tyr Asp Ile Arg Lys Thr Cys Leu gac agc ttt ggt gtt tcg agg ctg agc gga gcc gtg tgg aca atg gct    2410
Asp Ser Phe Gly Val Ser Arg Leu Ser Gly Ala Val Trp Thr Met Ala gga tct cct tgt aca acc tgc aaa tgc aag aat ggg aga gtc tgc tgc    2458
Gly Ser Pro Cys Thr Thr Cys Lys Cys Lys Asn Gly Arg Val Cys Cys tct gtg gat ctg gag tgt att gag aat aac tga agattttaaa tggactcgtc  2511
Ser Val Asp Leu Glu Cys Ile Glu Asn Asn * acgtgagaaa atgggcaaaa tgatcatccc acctgaggaa gaagaggggc tgatttcttt  2571
ttcttttaa ccacagtcaa ttaccaaagt ctccatctga ggaaggcgtt tggattgcct   2631
ttgccacttt gctcatcctt gctgacctag tctagatgcc tgcagtaccg tgcatttcgg  2691
tcgatggttg ttgagtctca gtgttgtaaa tcgcatttcc ctcgtcagat catttacaga  2751
tacatttaaa ggggttccat gataaatgtt aatgtaactt tgtttatttt tgtgtactga  2811
cataatagag acttggcacc atttatttat ttttcttgat ttttggatca aattctaaaa  2871
ataaagttgc ctgttgcgaa aaaaaaaaaa aaaaaaaaaa aaaa                   2915
```

*Rattus norvegicus* NELL1 amino acid sequence (SEQ ID NO: 12)

Met Pro Met Asp Val Ile Leu Val Leu Trp Phe Cys Val
Cys Thr Ala Arg Thr Val Leu Gly Phe Gly Met Asp Pro
Asp Leu Gln Leu Asp Ile Ile Ser Glu Leu Asp Leu Val
Asn Thr Thr Leu Gly Val Thr Gln Val Ala Gly Leu His
Asn Ala Ser Lys Ala Phe Leu Phe Gln Asp Val Gln Arg
Glu Ile His Ser Ala Pro His Val Ser Glu Lys Leu Ile
Gln Leu Phe Arg Asn Lys Ser Glu Phe Thr Phe Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Pro Arg Glu Glu Ile Arg Tyr His Tyr Ile
His Gly Gly Lys Pro Arg Thr Glu Ala Leu Pro Tyr Arg
Met Ala Asp Gly Gln Trp His Lys Val Ala Leu Ser Val
Ser Ala Ser His Leu Leu Leu His Ile Asp Cys Asn Arg
Ile Tyr Glu Arg Val Ile Asp Pro Pro Glu Thr Asn Leu
Pro Pro Gly Ser Asn Leu Trp Leu Gly Gln Arg Asn Gln
Lys His Gly Phe Phe Lys Gly Ile Ile Gln Asp Gly Lys
Ile Ile Phe Met Pro Asn Gly Phe Ile Thr Gln Cys Pro
Asn Leu Asn Arg Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Gly Gln Leu Glu Asn Cys His Cys Glu Lys Thr Cys
Gln Val Ser Gly Leu Leu Tyr Arg Asp Gln Asp Ser Trp
Val Asp Gly Asp Asn Cys Gly Asn Cys Thr Cys Lys Ser
Gly Ala Val Glu Cys Arg Arg Met Ser Cys Pro Pro Leu
Asn Cys Ser Pro Asp Ser Leu Pro Val His Ile Ser Gly
Gln Cys Cys Lys Val Cys Arg Pro Lys Cys Ile Tyr Gly
Gly Lys Val Leu Ala Glu Gly Gln Arg Ile Leu Thr Lys
Thr Cys Arg Glu Cys Arg Gly Gly Val Leu Val Lys Ile
Thr Glu Ala Cys Pro Pro Leu Asn Cys Ser Ala Lys Asp
His Ile Leu Pro Glu Asn Gln Cys Cys Arg Val Cys Pro
Gly His Asn Phe Cys Ala Glu Ala Pro Lys Cys Gly Glu
Asn Ser Glu Cys Lys Asn Trp Asn Thr Lys Ala Thr Cys
Glu Cys Lys Asn Gly Tyr Ile Ser Val Gln Gly Asn Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Val Pro Gly Tyr Ile Arg
Val Asp Asp Phe Ser Cys Thr Glu His Asp Asp Cys Gly
Ser Gly Gln His Asn Cys Asp Lys Asn Ala Ile Cys Thr
Asn Thr Val Gln Gly His Ser Cys Thr Cys Gln Pro Gly
Tyr Val Gly Asn Gly Thr Ile Cys Lys Ala Phe Cys Glu
Glu Gly Cys Arg Tyr Gly Gly Thr Cys Val Ala Pro Asn
Lys Cys Val Cys Pro Ser Gly Phe Thr Gly Ser His Cys
Glu Lys Asp Ile Asp Glu Cys Ala Glu Gly Phe Val Glu
Cys His Asn Tyr Ser Arg Cys Val Asn Leu Pro Gly Trp
Tyr His Cys Glu Cys Arg Ser Gly Phe His Asp Asp Gly
Thr Tyr Ser Leu Ser Gly Glu Ser Cys Ile Asp Ile Asp
Glu Cys Ala Leu Arg Thr His Thr Cys Trp Asn Asp Ser

Ala Cys Ile Asn Leu Ala Gly Gly Phe Asp Cys Leu Cys
Pro Ser Gly Pro Ser Cys Ser Gly Asp Cys Pro His Glu
Gly Gly Leu Lys His Asn Gly Gln Val Trp Ile Leu Arg
Glu Asp Arg Cys Ser Val Cys Ser Cys Lys Asp Gly Lys
Ile Phe Cys Arg Arg Thr Ala Cys Asp Cys Gln Asn Pro
Asn Val Asp Leu Phe Cys Cys Pro Glu Cys Asp Thr Arg
Val Thr Ser Gln Cys Leu Asp Gln Ser Gly Gln Lys Leu
Tyr Arg Ser Gly Asp Asn Trp Thr His Ser Cys Gln Gln
Cys Arg Cys Leu Glu Gly Glu Ala Asp Cys Trp Pro Leu
Ala Cys Pro Ser Leu Gly Cys Glu Tyr Thr Ala Met Phe
Glu Gly Glu Cys Cys Pro Arg Cys Val Ser Asp Pro Cys
Leu Ala Gly Asn Ile Ala Tyr Asp Ile Arg Lys Thr Cys
Leu Asp Ser Phe Gly Val Ser Arg Leu Ser Gly Ala Val
Trp Thr Met Ala Gly Ser Pro Cys Thr Thr Cys Lys Cys
Lys Asn Gly Arg Val Cys Cys Ser Val Asp Leu Glu Cys
Ile Glu Asn Asn

*Felis catus* NELL1 isoform 1 amino acid sequence (SEQ ID NO: 13)

Met Pro Arg Asp Val Ile Leu Val Val Trp Phe Cys Val
Cys Thr Ala Arg Thr Val Val Gly Phe Gly Thr Asp Pro
Asp Leu Gln Val Asp Ile Ile Ala Glu Leu Asp Leu Val
Asn Thr Thr Ala Gly Val Thr Gln Val Ser Gly Leu His
Asn Ala Ser Lys Ala Tyr Leu Phe Gln Glu Thr Glu Arg
Glu Ile His Ala Ala Pro His Val Ser Glu Lys Leu Ile
Gln Leu Phe Arg Asn Lys Ser Glu Phe Ser Phe Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Leu Arg Asp Glu Ile Arg Tyr His Tyr Ile
His Asn Gly Lys Pro Arg Thr Glu Ala Leu Pro Tyr Arg
Met Ala Asp Gly Gln Trp His Lys Val Ala Leu Ser Ile
Ser Ala Ser His Leu Leu Leu His Val Asp Cys Asn Arg
Ile Tyr Glu Arg Val Ile Asp Pro Pro Glu Thr Asn Leu
Pro Pro Gly Ser Asn Val Trp Leu Gly Gln Arg Asn Gln
Lys His Gly Leu Phe Lys Gly Ile Ile Gln Asp Gly Lys
Ile Ile Phe Met Pro Asn Gly Tyr Ile Thr Gln Cys Pro
Asn Leu Asn Arg Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Asn Gln Leu Glu Asn Cys His Cys Glu Lys Thr Cys
Gln Val Ser Gly Leu Leu Tyr Arg Asp Gln Asp Ser Trp

Val Asp Gly Asp His Cys Arg Asn Cys Thr Cys Lys Ser
Gly Ala Val Glu Cys Arg Arg Met Ser Cys Pro Pro Leu
Asn Cys Ser Pro Asp Ser Leu Pro Val His Ile Ala Gly
Gln Cys Cys Lys Val Cys Arg Pro Lys Cys Ile Tyr Gly
Gly Lys Val Leu Ala Glu Gly Gln Arg Ile Leu Thr Lys
Ser Cys Arg Glu Cys Arg Gly Gly Val Leu Val Lys Ile
Thr Asp Ala Cys Pro Pro Leu Asn Cys Ser Glu Lys Asp
His Ile Leu Pro Glu Asn Gln Cys Cys Ser Val Cys Arg
Gly His Asn Phe Cys Ala Glu Gly Pro Thr Cys Gly Glu
Asn Ser Glu Cys Lys Asn Trp Asn Thr Lys Ala Thr Cys
Glu Cys Lys Asn Gly Tyr Ile Ser Val Gln Gly Asp Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Val Pro Gly Tyr Ile Arg
Val Asp Asp Phe Ser Cys Thr Glu His Asp Glu Cys Gly
Ser Gly Gln His Asn Cys Asp Glu Asn Ala Ile Cys Thr
Asn Thr Val Gln Gly His Ser Cys Thr Cys Lys Pro Gly
Tyr Val Gly Asn Gly Thr Ile Cys Arg Ala Phe Cys Gln
Glu Gly Cys Arg Tyr Gly Gly Thr Cys Val Ser Pro Asn
Lys Cys Val Cys Pro Ser Gly Phe Thr Gly Ser His Cys
Glu Lys Asp Ile Asp Glu Cys Thr Glu Gly Ile Ile Glu
Cys His Asn His Ser Arg Cys Val Asn Leu Pro Gly Trp
Tyr His Cys Glu Cys Arg Ser Gly Phe His Asp Asp Gly
Thr Tyr Ser Leu Ser Gly Glu Ser Cys Ile Asp Ile Asp
Glu Cys Ala Leu Arg Thr His Thr Cys Trp Asn Asp Ser
Ala Cys Ile Asn Leu Ala Gly Gly Phe Asp Cys Leu Cys
Pro Ser Gly Pro Ser Cys Ser Gly Asp Cys Pro His Glu
Gly Gly Leu Lys Arg Asn Gly Gln Val Trp Thr Leu Lys
Glu Asp Arg Cys Ser Val Cys Ser Cys Lys Asp Gly Lys
Ile Phe Cys Arg Arg Thr Ala Cys Asp Cys Gln Asn Pro
Ser Val Asp Leu Phe Cys Cys Pro Glu Cys Asp Thr Arg
Val Thr Ser Gln Cys Leu Asp Gln Asn Gly His Lys Leu
Tyr Arg Ser Gly Asp Asn Trp Thr His Ser Cys Gln Gln
Cys Arg Cys Leu Glu Gly Glu Val Asp Cys Trp Pro Leu
Thr Cys Pro Asn Leu Ser Cys Glu Tyr Thr Ala Met Leu
Glu Gly Glu Cys Cys Pro Arg Cys Val Ser Asp Pro Cys
Leu Ala Asp Asn Ile Ala Tyr Asp Ile Arg Lys Thr Cys
Leu Asp Ser Tyr Gly Ile Set Arg Leu Ser Gly Ala Val

*Felis catus* NELL1 isoform 2 amino acid sequence (SEQ ID NO: 14)

Met Pro Arg Asp Val Ile Leu Val Val Trp Phe Cys Val
Cys Thr Ala Arg Thr Val Val Gly Phe Gly Thr Asp Pro
Asp Leu Gln Val Asp Ile Ile Ala Glu Leu Asp Leu Val
Asn Thr Thr Ala Gly Val Thr Gln Val Ser Gly Leu His
Asn Ala Ser Lys Ala Tyr Leu Phe Gln Glu Thr Glu Arg
Glu Ile His Ala Ala Pro His Val Ser Glu Lys Leu Ile
Gln Leu Phe Arg Asn Lys Ser Glu Phe Ser Phe Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Leu Arg Asp Glu Ile Arg Tyr His Tyr Ile
His Asn Gly Lys Pro Arg Thr Glu Ala Leu Pro Tyr Arg
Met Ala Asp Gly Gln Trp His Lys Val Ala Leu Ser Ile
Ser Ala Ser His Leu Leu Leu His Val Asp Cys Asn Arg
Ile Tyr Glu Arg Val Ile Asp Pro Pro Glu Thr Asn Leu
Pro Pro Gly Ser Asn Val Trp Leu Gly Gln Arg Asn Gln
Lys His Gly Leu Phe Lys Gly Ile Ile Gln Asp Gly Lys
Ile Ile Phe Met Pro Asn Gly Tyr Ile Thr Gln Cys Pro
Asn Leu Asn Arg Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Asn Gln Leu Glu Asn Cys His Cys Glu Lys Thr Cys
Gln Val Ser Gly Leu Leu Tyr Arg Asp Gln Asp Ser Trp
Val Asp Gly Asp His Cys Arg Asn Cys Thr Cys Lys Ser
Gly Ala Val Glu Cys Arg Arg Met Ser Cys Pro Pro Leu
Asn Cys Ser Pro Asp Ser Leu Pro Val His Ile Ala Gly
Gln Cys Cys Lys Val Cys Arg Pro Lys Cys Ile Tyr Gly
Gly Lys Val Leu Ala Glu Gly Gln Arg Ile Leu Thr Lys
Ser Cys Arg Glu Cys Arg Gly Gly Val Leu Val Lys Ile
Thr Asp Ala Cys Pro Pro Leu Asn Cys Ser Glu Lys Asp
His Ile Leu Pro Glu Asn Gln Cys Cys Ser Val Cys Arg
Gly His Asn Phe Cys Ala Glu Gly Pro Thr Cys Gly Glu
Asn Ser Glu Cys Lys Asn Trp Asn Thr Lys Ala Thr Cys
Glu Cys Lys Asn Gly Tyr Ile Ser Val Gln Gly Asp Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Val Pro Gly Tyr Ile Arg
Val Asp Asp Phe Ser Cys Thr Glu His Asp Glu Cys Gly
Ser Gly Gln His Asn Cys Asp Glu Asn Ala Ile Cys Thr
Asn Thr Val Gln Gly His Ser Cys Thr Cys Lys Pro Gly
Tyr Val Gly Asn Gly Thr Ile Cys Arg Ala Phe Cys Gln
Glu Gly Cys Arg Tyr Gly Gly Thr Cys Val Ser Pro Asn
Lys Cys Val Cys Pro Ser Gly Phe Thr Gly Ser His Cys
Glu Lys Asp Ile Asp Glu Cys Ala Leu Arg Thr His Thr
Cys Trp Asn Asp Ser Ala Cys Ile Asn Leu Ala Gly Gly
Phe Asp Cys Leu Cys Pro Ser Gly Pro Ser Cys Ser Gly
Asp Cys Pro His Glu Gly Gly Leu Lys Arg Asn Gly Gln
Val Trp Thr Leu Lys Glu Asp Arg Cys Ser Val Cys Ser
Cys Lys Asp Gly Lys Ile Phe Cys Arg Arg Thr Ala Cys
Asp Cys Gln Asn Pro Ser Val Asp Leu Phe Cys Cys Pro
Glu Cys Asp Thr Arg Val Thr Ser Gln Cys Leu Asp Gln
Asn Gly His Lys Leu Tyr Arg Ser Gly Asp Asn Trp Thr
His Ser Cys Gln Gln Cys Arg Cys Leu Glu Gly Glu Val
Asp Cys Trp Pro Leu Thr Cys Pro Asn Leu Ser Cys Glu
Tyr Thr Ala Met Leu Glu Gly Glu Cys Cys Pro Arg Cys
Val Ser Asp Pro Cys Leu Ala Asp Asn Ile Ala Tyr Asp
Ile Arg Lys Thr Cys Leu Asp Ser Tyr Gly Ile Ser Arg
Leu Ser Gly Ala Val Trp Thr Met Ala Gly Ser Pro Cys
Thr Thr Cys Lys Cys Lys Asn Gly Ser Val Cys Cys Ser
Val Asp Leu Glu Cys Leu His Asn Asn

*Canis lupis familiaris* NELL1 amino acid sequence (SEQ ID NO: 15)

Met Thr Ser Thr Ser Phe Leu Leu Trp Leu Gly Cys Val
His Asn Thr Lys Phe Pro Phe Pro Leu Val Leu Val Thr
Arg Ala Ile Val Val Val Val Glu Val Val Gly Val
Gly Ser Pro Gly Val Arg Ile Arg Ser Thr Gly Cys Asp
Ile Leu Leu Leu Tyr Glu Val Leu Glu His Leu Leu Gly
Ile Arg Phe Leu Cys Val Asp Gln Gly Glu Asn Ser Cys
His His Gly Gln Cys Ala Cys Arg Leu Gln Val Ile Val
Pro Lys Ala Leu Met Ser Val Phe Glu Ala Lys Thr Ala
Val Cys Phe Phe Pro Val Val Gly Phe Gly Thr Asp Pro
Asp Leu Gln Met Asp Ile Ile Thr Glu Leu Asp Leu Val
Asn Ile Ser Leu Gly Val Thr Gln Val Ser Gly Leu His
Asn Ala Ser Lys Ala Tyr Val Phe Gln Asp Thr Ala Arg
Glu Ile His Ala Ala Pro His Val Ser Glu Lys Leu Ile
Gln Leu Phe Arg Asn Lys Ser Asp Phe Thr Phe Leu Ala

-continued

Thr Val Gln Gln Lys Pro Ser Thr Ser Gly Val Ile Leu
Ser Ile Arg Glu Leu Glu His Ser Tyr Phe Glu Leu Glu
Ser Ser Gly Leu Arg Asp Glu Ile Arg Tyr His Tyr Met
His Asn Gly Lys Pro Arg Thr Glu Ala Leu Pro Tyr Arg
Leu Ala Asp Gly Gln Trp His Lys Val Ala Leu Ser Val
Ser Ala Ser His Leu Leu Leu His Ile Asp Cys Asn Arg
Ile Tyr Glu Arg Val Ile Asp Pro Pro Glu Thr Asn Leu
Pro Pro Gly Ser Asn Leu Trp Leu Gly Gln Arg Asn Gln
Lys His Gly Phe Phe Lys Gly Ile Ile Gln Asp Gly Lys
Ile Ile Phe Met Pro Asn Gly Tyr Ile Thr Gln Cys Pro
Asn Leu Asn Arg Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Ser Gln Leu Glu Asn Cys His Cys Glu Lys Thr Cys
Gln Val Ser Gly Leu Leu Tyr Arg Asp Gln Asp Ser Trp
Val Asp Gly Asp His Cys Arg Asn Cys Thr Cys Lys Gly
Gly Ala Val Glu Cys Arg Arg Met Ser Cys Pro Pro Leu
Asn Cys Ser Pro Asp Ser Leu Pro Val His Ile Ala Gly
Gln Cys Cys Lys Val Cys Arg Pro Lys Cys Ile Tyr Gly
Gly Arg Val Leu Ala Glu Gly Gln Arg Ile Leu Thr Lys
Ser Cys Arg Glu Cys Arg Gly Gly Val Leu Val Lys Ile
Thr Asp Ala Cys Pro Pro Leu Asn Cys Ser Glu Lys Asp
His Ile Leu Pro Glu Asn Gln Cys Cys Ser Val Cys Arg
Gly His Asn Phe Cys Ala Glu Gly Pro Lys Cys Gly Glu
Asn Ser Glu Cys Lys Asn Trp Asn Thr Lys Ala Thr Cys
Glu Cys Lys Asn Gly Tyr Ile Ser Val Gln Gly Asp Ser
Ala Tyr Cys Glu Asp Ile Asp Glu Cys Ala Ala Lys Met
His Tyr Cys His Ala Asn Thr Val Cys Val Asn Leu Pro
Gly Leu Tyr Arg Cys Asp Cys Val Pro Gly Tyr Ile Arg
Val Asp Asp Phe Ser Cys Thr Glu His Asp Glu Cys Gly
Ser Gly Gln His Asn Cys Asp Glu Asn Ala Ile Cys Thr
Asn Thr Val Arg Gly His Ser Cys Thr Cys Lys Pro Gly
Tyr Val Gly Asn Gly Thr Ile Cys Arg Ala Phe Cys Gln
Glu Gly Cys Arg Tyr Gly Gly Ser Cys Val Ser Pro Asn
Lys Cys Val Cys Pro Ser Gly Phe Thr Gly Ser His Cys
Glu Lys Asp Ile Asp Glu Cys Thr Glu Gly Ile Ile Glu
Cys His Asn His Ser Arg Cys Val Asn Leu Pro Gly Trp
Tyr His Cys Glu Cys Arg Ser Gly Phe His Asp Asp Gly
Thr Tyr Ser Leu Ser Gly Glu Ser Cys Ile Asp Ile Asp
Glu Cys Ala Leu Arg Thr His Thr Cys Trp Asn Asp Ser

Ala Cys Ile Asn Leu Ala Gly Gly Phe Asp Cys Leu Cys
Pro Ser Gly Pro Ser Cys Ser Gly Asp Cys Pro His Glu
Gly Gly Leu Lys Arg Asn Gly Gln Val Trp Thr Leu Lys
Glu Asp Arg Cys Ser Val Cys Ser Cys Lys Asp Gly Lys
Ile Leu Cys Arg Arg Thr Ala Cys Asp Cys Gln Asn Pro
Ser Val Asp Leu Phe Cys Cys Pro Glu Cys Asp Thr Arg
Val Thr Ser Gln Cys Leu Asp Gln Asn Gly His Lys Leu
Tyr Arg Ser Gly Asp Asn Trp Thr His Ser Cys Gln Gln
Cys Arg Cys Leu Glu Gly Glu Val Asp Cys Trp Pro Leu
Thr Cys Pro Asn Leu Ser Cys Glu Tyr Thr Ala Ile Leu
Glu Gly Glu Cys Cys Pro Arg Cys Val Ser Asp Pro Cys
Leu Ala Asp Asn Ile Ala Tyr Asp Ile Arg Lys Thr Cys
Leu Asp Ser Tyr Gly Ile Ser Arg Leu Ser Gly Ser Val
Trp Thr Met Ala Gly Ser Pro Cys Thr Thr Cys Lys Cys
Lys Asn Gly Ser Val Cys Cys Ser Val Asp Leu Glu Cys
Leu His Asn Asn

*Ovis aries* NELL1 amino acid sequence (SEQ ID NO: 16)

Met Pro Arg Gly Val Ile Leu Val Val Cys Phe Cys Val
Cys Ala Ala Arg Thr Val Val Gly Phe Gly Met Asp Pro
Asp Leu Gln Leu Asp Ile Ile Thr Glu Leu Asp Leu Val
Asn Thr Thr Leu Gly Val Thr Gln Val Ser Gly Leu His
Asn Thr Ser Lys Ala Phe Leu Phe Gln Asp Ala Glu Arg
Glu Ile His Ala Ala Pro His Val Ser Glu Lys Leu Ile
Gln Leu Phe Arg Asn Lys Ser Glu Phe Thr Phe Leu Ala
Thr Val Gln Gln Lys Pro Ser Thr Ser Gly Val Ile Leu
Ser Ile Arg Glu Leu Glu His Ser Tyr Phe Glu Leu Glu
Ser Ser Gly Leu Arg Asp Glu Ile Arg Tyr His Tyr Met
His Ser Gly Arg Pro Arg Thr Glu Ala Leu Pro Tyr Arg
Leu Ala Asp Gly Gln Trp His Arg Val Ala Leu Ser Val
Ser Ala Ser His Leu Leu Leu His Ile Asp Cys Asn Arg
Ile Tyr Glu Arg Val Ile Asp Pro Pro Glu Thr Asn Leu
Pro Pro Gly Ser Asn Leu Trp Leu Gly Gln Arg Asn Gln
Lys His Gly Leu Phe Lys Gly Ile Ile Gln Asp Gly Lys
Ile Ile Phe Met Pro Asn Gly Tyr Ile Thr Gln Cys Pro
Asn Leu Asn Arg Thr Cys Pro Thr Cys Ser Asp Phe Leu
Ser Leu Val Gln Gly Ile Met Asp Leu Gln Glu Leu Leu
Ala Lys Met Thr Ala Lys Leu Asn Tyr Ala Glu Thr Arg
Leu Ser Gln Leu Glu Asn Cys His Cys Glu Lys Thr Cys
Gln Val Ser Gly Leu Leu Tyr Arg Asp Gln Asp Ser Trp
Val Asp Gly Asp His Cys Arg Asn Cys Thr Cys Lys Ser

Gly Ala Val Glu Cys Arg Arg Met Ser Cys Pro Pro Leu

Asn Cys Ser Pro Asp Ser Leu Pro Val His Ile Ala Gly

Gln Cys Cys Lys Val Cys Arg Pro Lys Cys Ile Tyr Gly

Gly Lys Val Leu Ala Glu Gly Gln Arg Ile Leu Ser Lys

Asn Cys Gln Glu Cys Arg Gly Gly Val Leu Val Lys Ile

Thr Glu Ala Cys Pro Leu Leu Asn Cys Ser Glu Lys Asp

His Ile Leu Pro Glu Asn Gln Cys Cys Ser Val Cys Arg

Gly His Asn Phe Cys Ala Glu Gly Pro Lys Cys Gly Glu

Asn Ser Glu Cys Lys Asn Trp Asn Thr Lys Ala Thr Cys

Glu Cys Lys Asn Gly Tyr Ile Ser Val Gln Gly Asp Ser

Ala Tyr Cys Glu Asp Ile Asp Glu Cys Ala Ala Lys Met

His Tyr Cys His Ala Asn Thr Val Cys Val Asn Leu Pro

Gly Leu Tyr Arg Cys Asp Cys Val Pro Gly Tyr Ile Arg

Val Asp Asp Phe Ser Cys Thr Glu His Asp Asp Cys Gly

Ser Gly Gln His Asn Cys Asp Glu Asn Ala Ile Cys Thr

Asn Thr Val Gln Gly His Ser Cys Thr Cys Lys Pro Gly

Tyr Val Gly Asn Gly Thr Ile Cys Arg Ala Phe Cys Glu

Glu Gly Cys Arg Tyr Gly Gly Thr Cys Met Ala Pro Asn

Lys Cys Val Cys Pro Ser Gly Phe Thr Gly Ser His Cys

Glu Lys Asp Ile Asp Glu Cys Ala Glu Gly Ile Ile Glu

Cys His Ser His Ser Arg Cys Val Asn Leu Pro Gly Trp

Tyr His Cys Glu Cys Arg Ser Gly Phe His Asp Asp Gly

Thr Tyr Ser Leu Ser Gly Glu Ser Cys Val Asp Ile Asp

Glu Cys Ala Leu Arg Thr His Thr Cys Trp Asn Asp Ser

Ala Cys Ile Asn Leu Ala Gly Gly Phe Asp Cys Leu Cys

Pro Ser Gly Pro Ser Cys Ser Gly Asp Cys Pro His Glu

Gly Gly Leu Lys Arg Asn Gly Gln Val Trp Thr Leu Lys

Glu Asp Arg Cys Ser Val Cys Ser Cys Lys Asp Gly Lys

Ile Phe Cys Arg Arg Thr Ala Cys Asp Cys Gln Asn Pro

Ser Val Asp Leu Phe Cys Cys Pro Glu Cys Asp Thr Arg

Val Thr Ser Gln Cys Leu Asp Gln Asn Gly Asn Lys Leu

Tyr Arg Ser Gly Asp Asn Trp Thr His Ser Cys Gln Gln

Cys Arg Cys Leu Glu Gly Glu Val Asp Cys Trp Pro Leu

Thr Cys Pro Ser Leu Ser Cys Glu Tyr Thr Thr Ile Leu

Glu Gly Glu Cys Cys Pro Arg Cys Val Ser Asp Pro Cys

Leu Ala Asp Asn Ile Ala Tyr Asp Ile Arg Lys Thr Cys

Leu Asp Ser Tyr Gly Leu Ser Arg Leu Ser Gly Ser Val

Trp Thr Met Ala Gly Ser Pro Cys Thr Thr Cys Lys Cys

Lys Asn Gly Ser Val Cys Cys Ser Val Asp Leu Glu Cys

Leu His Asn Asn

*Homo sapiens* NELL1 fragment amino acid sequence (SEQ ID NO: 17)

Phe Gly Met Asp Pro Asp Leu Gln Met Asp Ile Val Thr

Glu Leu Asp Leu Val Asn Thr Thr Leu Gly Val Ala Gln

Val Ser Gly Met His Asn Ala Ser Lys Ala Phe Leu Phe

Gln Asp Ile Glu Arg Glu Ile His Ala Ala Pro His Val

Ser Glu Lys Leu Ile Gln Leu Phe Arg Asn Lys Ser Glu

Phe Thr Ile Leu Ala Thr Val Gln Gln Lys Pro Ser Thr

Ser Gly Val Ile Leu Ser Ile Arg Glu Leu Glu His Ser

Tyr Phe Glu Leu Glu Ser Ser Gly Leu Arg Asp Glu Ile

Arg Tyr His Tyr Ile His Asn Gly Lys Pro Arg Thr Glu

Ala Leu Pro Tyr Arg Met Ala Asp Gly Gln Trp His Lys

Val Ala Leu Ser Val Ser Ala Ser His Leu Leu Leu His

Val Asp Cys Asn Arg Ile Tyr Glu Arg Val Ile Asp Pro

Pro Asp Thr Asn Leu Pro Pro Gly Ile Asn Leu Trp Leu

Gly Gln Arg Asn Gln Lys His Gly Leu Phe Lys Gly Ile

Ile Gln Asp Gly Lys Ile Ile Phe Met Pro Asn Gly Tyr

Ile Thr Gln Cys Pro Asn Leu Asn His Thr Cys Pro Thr

Cys Ser Asp Phe Leu Ser Leu Val Gln Gly Ile Met Asp

Leu Gln Glu Leu Leu Ala Lys Met Thr Ala Lys Leu Asn

Tyr Ala Glu Thr Arg Leu Ser Gln Leu Glu Asn Cys His

Cys Glu Lys Thr Cys Gln Val Ser Gly Leu Leu Tyr Arg

Asp Gln Asp Ser Trp Val Asp Gly Asp His Cys Arg Asn

Cys Thr Cys Lys Ser Gly Ala Val Glu Cys Arg Arg Met

Ser Cys Pro Pro Leu Asn Cys Ser Pro Asp Ser Leu Pro

Val His Ile Ala Gly Gln Cys Cys Lys Val Cys Arg Pro

Lys Cys Ile Tyr Gly Gly Lys Val Leu Ala Glu Gly Gln

Arg Ile Leu Thr Lys Ser Cys Arg Glu Cys Arg Gly Gly

Val Leu Val Lys Ile Thr Glu Met Cys Pro Pro Leu Asn

Cys Ser Glu Lys Asp His Ile Leu Pro Glu Asn Gln Cys

Cys Arg Val Cys Arg Gly His Asn Phe Cys Ala Glu Gly

Pro Lys Cys Gly Glu Asn Ser Glu Cys Lys Asn Trp Asn

Thr Lys Ala Thr Cys Glu Cys Lys Ser Gly Tyr Ile Ser

Val Gln Gly Asp Ser Ala Tyr Cys Glu Asp Ile Asp Glu

Cys Ala Ala Lys Met His Tyr Cys His Ala Asn Thr Val

Cys Val Asn Leu Pro Gly Leu Tyr Arg Cys Asp Cys Val

Pro Gly Tyr Ile Arg Val Asp Asp Phe Ser Cys Thr Glu

His Asp Glu Cys Gly Ser Gly Gln His Asn Cys Asp Glu

Asn Ala Ile Cys Thr Asn Thr Val Gln Gly His Ser Cys

Thr Cys Lys Pro Gly Tyr Val Gly Asn Gly Thr Ile Cys

Arg Ala Phe Cys Glu Glu Gly Cys Arg Tyr Gly Gly Thr

-continued

Cys Val Ala Pro Asn Lys Cys Val Cys Pro Ser Gly Phe
Thr Gly Ser His Cys Glu Lys Asp Ile Asp Glu Cys Ser
Glu Gly Ile Ile Glu Cys His Asn His Ser Arg Cys Val
Asn Leu Pro Gly Trp Tyr His Cys Glu Cys Arg Ser Gly
Phe His Asp Asp Gly Thr Tyr Ser Leu Ser Gly Glu Ser
Cys Ile Asp Ile Asp Glu Cys Ala Leu Arg Thr His Thr
Cys Trp Asn Asp Ser Ala Cys Ile Asn Leu Ala Gly Gly
Phe Asp Cys Leu Cys Pro Ser Gly Pro Ser Cys Ser

*Equus caballus* NELL1 fragment amino acid sequence (SEQ ID NO: 18)

Phe Gly Met Asp Pro Asp Leu Gln Met Asp Ile Ile Thr
Glu Leu Asp Leu Val Asn Thr Thr Leu Gly Val Thr Gln
Val Ser Gly Leu His Asn Ala Ser Lys Ala Phe Leu Phe
Gln Asp Val Glu Arg Glu Ile His Ala Ala Pro His Val
Ser Glu Lys Leu Ile Gln Leu Phe Arg Asn Lys Ser Glu
Phe Thr Phe Leu Ala Thr Val Gln Gln Lys Pro Ser Thr
Ser Gly Val Ile Leu Ser Ile Arg Glu Leu Glu Asn Ser
Tyr Phe Glu Leu Glu Ser Ser Gly Leu Arg Asp Glu Ile
Arg Tyr His Tyr Thr His Lys Gly Lys Pro Arg Thr Glu
Ala Leu Pro Tyr Arg Met Ala Asp Gly Arg Trp His Lys
Val Ala Leu Ser Val Ser Ala Ser His Leu Leu Leu His
Ile Asp Cys Asn Arg Ile Tyr Glu Arg Val Ile Asp Thr
Pro Glu Thr Asn Leu Pro Pro Gly Ser Asn Leu Trp Leu
Gly Gln Arg Asn Gln Lys His Gly Leu Phe Lys Gly Ile
Ile Gln Asp Gly Lys Ile Ile Phe Met Pro Asn Gly Tyr
Ile Thr Gln Cys Pro Asn Leu Asn Arg Thr Cys Pro Thr
Cys Ser Asp Phe Leu Ser Leu Val Gln Gly Ile Met Asp
Leu Gln Glu Leu Leu Ala Lys Met Thr Ala Lys Leu Asn
Tyr Ala Glu Thr Arg Leu Ser Gln Leu Glu Asn Cys His
Cys Glu Lys Thr Cys Gln Val Ser Gly Leu Leu Tyr Arg
Asp Gln Asp Ser Trp Val Asp Gly Asp His Cys Arg Asn
Cys Thr Cys Lys Ser Gly Ala Val Glu Cys Arg Arg Met
Ser Cys Pro Pro Leu Asn Cys Ser Pro Asp Ser Leu Pro
Val His Val Ala Gly Gln Cys Cys Lys Val Cys Arg Pro
Lys Cys Ile Tyr Gly Gly Lys Val Leu Ala Glu Gly Gln
Arg Ile Leu Thr Lys Ser Cys Arg Glu Cys Arg Gly Gly
Val Leu Val Lys Ile Thr Glu Ala Cys Pro Pro Leu Asn
Cys Ser Asp Lys Asp His Ile Leu Pro Glu Asn Gln Cys
Cys Ser Val Cys Arg Gly His Asn Phe Cys Ala Glu Gly
Pro Lys Cys Gly Glu Asn Ser Glu Cys Lys Asn Trp Asn

Thr Lys Ala Thr Cys Glu Cys Lys Asn Gly Tyr Ile Ser
Val Gln Gly Asp Ser Ala Tyr Cys Glu Asp Ile Asp Glu
Cys Ala Ala Lys Met His Tyr Cys Arg Ala Asn Thr Val
Cys Val Asn Leu Pro Gly Leu Tyr Arg Cys Asp Cys Val
Pro Gly Tyr Ile Arg Val Asp Asp Phe Ser Cys Thr Glu
His Asp Glu Cys Gly Ser Gly Gln His Asn Cys Asp Glu
Asn Ala Ile Cys Thr Asn Thr Val Gln Gly His Ser Cys
Thr Cys Lys Pro Gly Tyr Val Gly Asn Gly Thr Ser Cys
Arg Ala Phe Cys Glu Glu Gly Cys Arg Tyr Gly Gly Thr
Cys Val Ala Pro Asn Lys Cys Val Cys Pro Ser Gly Phe
Thr Gly Ser His Cys Glu Lys Asp Ile Asp Glu Cys Thr
Glu Gly Ile Ile Glu Cys His Asn His Ser Arg Cys Val
Asn Leu Pro Gly Trp Tyr His Cys Glu Cys Arg Ser Gly
Phe His Asp Asp Gly Thr Tyr Ser Leu Ser Gly Glu Ser
Cys Ile Asp Ile Asp Glu Cys Ala Leu Arg Thr His Thr
Cys Trp Asn Asp Ser Ala Cys Ile Asn Leu Ala Gly Gly
Phe Asp Cys Leu Cys Pro Ser Gly Pro Ser Cys Ser

*Bos taurus* NELL1 amino acid sequence (SEQ ID NO: 19)

Met Ala Leu Cys Ser Phe Ser Val Val Gly Phe Gly Leu
Asp Pro Asp Leu Gln Leu Asp Ile Ile Thr Glu Leu Asp
Leu Val Asn Thr Thr Leu Gly Val Thr Gln Val Ser Gly
Leu His Asn Thr Ser Lys Ala Phe Leu Phe Gln Asp Ala
Glu Arg Glu Ile His Ala Ala Pro His Val Ser Glu Lys
Leu Ile Gln Leu Phe Arg Asn Lys Ser Glu Phe Thr Phe
Leu Ala Thr Val Gln Gln Lys Pro Ser Thr Ser Gly Val
Ile Leu Ser Ile Arg Glu Leu Glu His Ser Tyr Phe Glu
Leu Glu Ser Ser Gly Leu Arg Asp Glu Ile Arg Tyr His
Tyr Val His Ser Gly Arg Pro Arg Thr Glu Ala Leu Pro
Tyr Arg Leu Ala Asp Gly Gln Trp His Arg Val Ala Leu
Ser Val Ser Ala Ser His Leu Leu Leu His Ile Asp Cys
Asn Arg Ile Tyr Glu Arg Val Ile Asp Pro Pro Glu Thr
Asn Leu Pro Pro Gly Ser Asn Leu Trp Leu Gly Gln Arg
Asn Gln Lys His Gly Leu Phe Lys Gly Ile Ile Gln Asp
Gly Lys Ile Ile Phe Met Pro Asn Gly Tyr Ile Thr Gln
Cys Pro Asn Leu Asn Arg Thr Cys Pro Thr Cys Ser Asp
Phe Leu Ser Leu Val Gln Gly Ile Met Asp Leu Gln Glu
Leu Leu Ala Lys Met Thr Ala Lys Leu Asn Tyr Ala Glu
Thr Arg Leu Ser Gln Leu Glu Asn Cys His Cys Glu Lys
Thr Cys Gln Val Ser Gly Leu Leu Tyr Arg Asp Gln Asp

-continued

Ser Trp Val Asp Gly Asp His Cys Arg Asn Cys Thr Cys

Lys Ser Gly Ala Val Glu Cys Arg Arg Met Ser Cys Pro

Pro Leu Asn Cys Ser Pro Asp Ser Leu Pro Val His Ile

Ala Gly Glu Cys Cys Lys Val Cys Arg Pro Lys Cys Ile

Tyr Gly Gly Lys Val Leu Ala Glu Gly Gln Arg Ile Leu

Ser Lys Ser Cys Gln Glu Cys Arg Gly Gly Val Leu Val

Lys Ile Thr Glu Ala Cys Pro Leu Leu Asn Cys Ser Glu

Lys Asp His Ile Leu Pro Glu Asn Gln Cys Cys Ser Val

Cys Arg Gly His Asn Phe Cys Ala Glu Gly Pro Lys Cys

Gly Glu Asn Ser Glu Cys Lys Asn Trp Asn Thr Lys Ala

Thr Cys Glu Cys Lys Asn Gly Tyr Ile Ser Val Gln Gly

Asp Ser Ala Tyr Cys Glu Asp Ile Asp Glu Cys Ala Ala

Lys Met His Tyr Cys His Ala Asn Thr Val Cys Val Asn

Leu Pro Gly Leu Tyr Arg Cys Asp Cys Val Pro Gly Tyr

Ile Arg Val Asp Asp Phe Ser Cys Thr Glu His Asp Asp

Cys Gly Ser Gly Gln His Asn Cys Asp Glu Asn Ala Ile

Cys Thr Asn Thr Val Gln Gly His Ser Cys Thr Cys Lys

Pro Gly Tyr Val Gly Asn Gly Thr Ile Cys Arg Gly Met

Pro Glu Val Gly Pro Pro Arg Ala Leu Leu Asn Ser Leu

Asp Leu Gly Phe Leu Ser Phe Ser Lys Glu Ala Leu Ala

Val Gly Met Ile Thr Leu Glu Gly Asn Ile Val Ala Lys

Ser Phe Thr Asp Asp Glu Thr Leu Val Glu Arg Gly Arg

Glu Lys Val Ile Ala Leu Leu Phe Ser Trp Leu His Lys

Glu Lys Leu Ser Leu Glu Asn Leu Arg Asp Ile Tyr Cys

Lys Ala Asn Ser Leu Val Gly Leu Asp His Leu Pro Gln

Arg

EXAMPLES

The present invention, thus generally described, will be understood more readily by reference to the following Examples, which are provided by way of illustration and are not intended to be limiting of the instant invention. The Examples are not intended to represent that the experiments below are all experiments performed.

Example 1

Cloning and Expression of Recombinant Horse NELL1 Peptides

Various Nell 1 polypeptides were designed based on the horse (Equus caballus) reference sequence: XP_001505306.1 GI: 149719523 (Aug. 14, 2013). The horse protein sequence has recently been updated in the NCBI database as XP_014597419 (Nov. 20, 2015).

The "full-length" version coding sequence begins at amino acid (aa) #3 which is the start of the signaling sequence till the last amino acid (#791) and contains all predicted conserved protein domains. Three variant NELL1 proteins were designed such that certain specific N- or C-terminal domain(s) was/were missing and the alternative form was shorter in size than the full-length version (Table 2). These four different recombinant NELL1 proteins were manufactured using a high-throughput wheat germ cell-free translation system (commercial Cell-Free System (CFS) In Vitro Wheat Germ System developed by Abnova Corporation, Taipei, Taiwan). The gene sequence was cloned in a plasmid vector that was transcribed and then translated in vitro in a wheat germ extract containing all 20 different amino acids. This protein expression system was pioneered by Yaeta Endo and later developed into a high throughput format (Madin et al. (2000) Proc. Natl. Acad. Sci. U.S.A. 97(2):559-564; Sawasaki et al. (2000) Nucleic Acids Symp. Ser. 44:9-10; Sawasaki et al. (2002) Proc. Natl. Acad. Sci. U.S.A. 99(23):14652-14657; and Endo and Sawasaki (2003) Biotechnol. Adv. 21(8):695-713). Purification of the products was accomplished by binding of the NELL1 protein tagged with glutathione S-transferase (GST) to an anti-GST resin. The products were eluted in 50 mM Tris-HCl, 10 mM reduced glutathione, pH 8.0.

TABLE 2

Description of recombinant horse NELL1 peptides.

| NELL1 Protein Description | Deleted Domains | MW (kDa)* | Concentration (µg/µl) | Purity (%) |
|---|---|---|---|---|
| NELL1 aa 3-791 (full-length) | None | 112.42 | 0.09 | 87.22 |
| NELL1 aa 252-791 | Entire N-terminal thrombospondin domain | 85.03 | 0.05 | 56.27 |
| NELL1 aa 3-612 | Two C-terminal von Willebrand factor C (VWC) domains | 92.73 | 0.13 | 89.44 |
| NELL1 aa 34-612 | Initial part of N-terminal thrombospondin domain and 2 C-terminal VWC domains | 89.32 | 0.17 | 65.82 |

*includes GST-tag of 26 kDa

To determine purity, 0.5 microgram protein was loaded in a lane on a 12.5% SDS-PAGE gel and stained with Coomassie Blue. BioSpectrum AC® Imaging System with software-VisionWorksLS V6.8 was employed to determine the purities by calculating the ratio of the major expected band for each protein variant relative to other minor bands. The value of concentration is the index of yield. The higher the concentration, the more yield is obtained. If a polypeptide has <0.1 µg/µl, the protein is considered difficult to produce and purify.

The full-length horse NELL1 protein (aa 3-791) has both lower concentration/yield and purity (0.09 µg/µl; 87.22%), compared to the NELL1 variant with 3-612 amino acid sequence (0.13 µg/µl; 89.44%). The other NELL1 variants (MW=85.03 kDa and MW=89.32) have very low concentration/yield and/or purity and were not deemed optimal for testing further for biological activity in vivo.

Additional independent preparations of variant and full-length NELL1 proteins were produced and utilized to check biological activity using in vitro (e.g. elution of protein from two scaffolds and wound healing scratch assays) and in vivo experiments (e.g. horse body wound healing study). Several preparations of amounts ranging from 20 micrograms-2.5 milligrams consistently yielded levels of concentration and purities similar to those obtained in the first experiment—>90% for the NELL1 variant #3-612 and 85-87% for the full-length (FIGS. 2A-2D).

Example 2

Effects of NELL1 Peptide on an In Vitro Model of Tendon Injury and Repair

There are several in vitro systems that can be utilized to demonstrate the efficacy of NELL1 in tendon repair and regeneration. These strategies make use of precursor or stem cells that give rise to tendons and can show that addition of NELL1 protein stimulates proliferation, differentiation, gene expression of key genes in tendon formation and/or migration of these cells.

The effects of NELL1 in the in vitro model of tendon injury and repair as described in Nemoto et al. (2013) *J. Equine Sci.* 24(2):17-24 are determined as follows. Fibroblasts are obtained from tendon explants dissected and minced into pieces from the superficial digital flexor tendon of healthy adult horses at the time of slaughter. Treatment with 0.1% type I collagenase (37 degrees, 20 minutes) will degrade the collagen holding cells in the tendon ECM, thereby releasing cells. Cells are cultured on Dulbecco's Modified Eagle Medium [with 10% fetal bovine serum, 100U/ml penicillin G, 100 microgram/ml streptomycin] at 5% $CO_2$, 37° C. to sub-confluence. Cell cultures are dispersed with 0.1% trypsin in PBS and sub-cultured close to confluence (~4 days in 12-well plates), then used for the classic scratch assay. Five parallel 0.1 mm "scratches" are made (1000 microliter blue pipette tip) in each cell culture plate, simulating a "wound gap" or injury in the cell sheet.

NELL1 protein, at varying doses, is added to three cultures per dose (15 gaps or wounds per dose measured). Three cultures are designated as negative controls. Initial doses for testing based on other in vitro studies with NELL1 are (ng/mL): 10, 31.6, 100, 316, 1000, and 3160.

The gaps are examined and measured every other day until they are closed. Data is analyzed to determined rates of closure and which treatment(s) exhibited the best and fastest healing.

The experiment described above is repeated and instead of quantitative measurements of gap closure, samples are cultured and harvested at various time points (after 0, 12, 24, 28 and 78 hrs post NELL1 treatment) for RNA extraction, cDNA synthesis and gene expression analysis. Genes that are biomarkers for tendon proliferation and migration are assessed. Examples of such genes are: Collagen 1, Collagen III, Tenascin C, and COMP.

Example 3

NELL1 Peptide Promotes Cell Migration and Wound Healing in Human Fibroblasts In Vitro The effects of two NELL1 proteins (full-length and variant 3-612aa) on cell migration and wound healing were tested and compared using in vitro models of primary human fibroblasts: adult dermal fibroblasts, type 1 diabetes dermal fibroblasts, and ligament fibroblasts. Three doses of both NELL1 proteins (full-length and variant 3-612aa) were tested on wound healings assays for each cell type using 4-6 replicates per dose: 100 ng/ml, 200 ng/ml, 300 ng/ml. Human fibroblasts were cultured in typical fibroblast growth media (FGM) supplemented with fetal bovine serum (FBS) and various growth factors. Cells in the logarithmic growing phase were cultured overnight in 96-well plates to make cell monolayers. Wound areas (750-micron wide) were generated in the middle of the cell monolayers in a consistent manner using an IncuCyte WoundMaker® 96 (Essen Bioscience, Michigan, U.S.A.). After treatment, cells were incubated and observed in an IncuCyte® Live-Cell Analysis System (Essen Bioscience, Michigan, U.S.A.). Images of cell migration and wound closure were captured using phase contrast microscopy each hour over a 24-hour period. Wound areas, cell confluence and healing rates (average velocity of cells moving into gap) were measured and data was analyzed using GraphPad Prism 7.0.

Figure 3A:
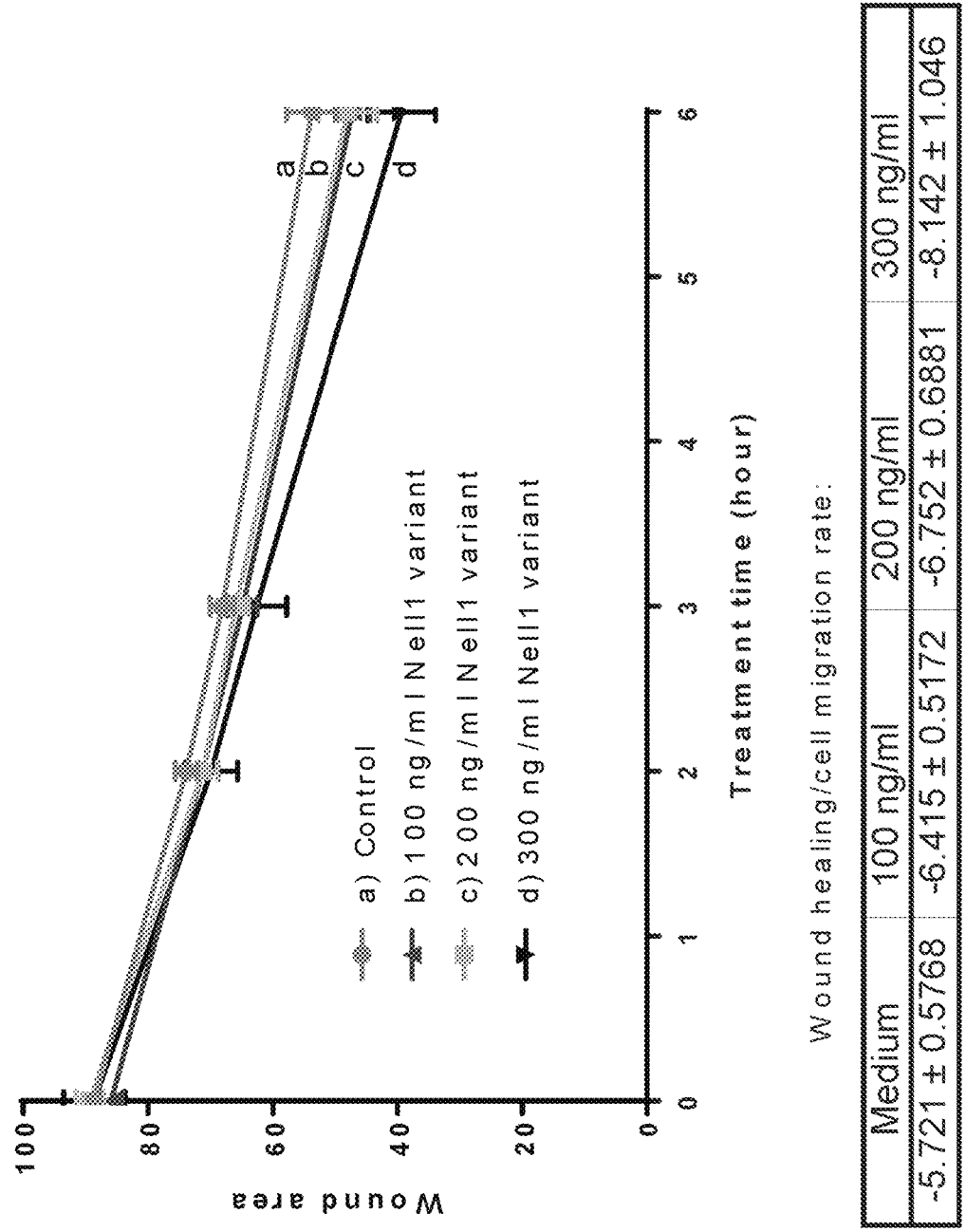
FIGS. 3A-3D depict effects of full-length NELL1 protein (aa3-791) or a NELL1 protein variant (aa3-612) on wound healing assays using diabetic dermal fibroblasts (FIGS. 3A and 3B), normal dermal fibroblasts (FIG. 3C), and normal ligament fibroblasts (FIG. 3D).
Figure 3B:
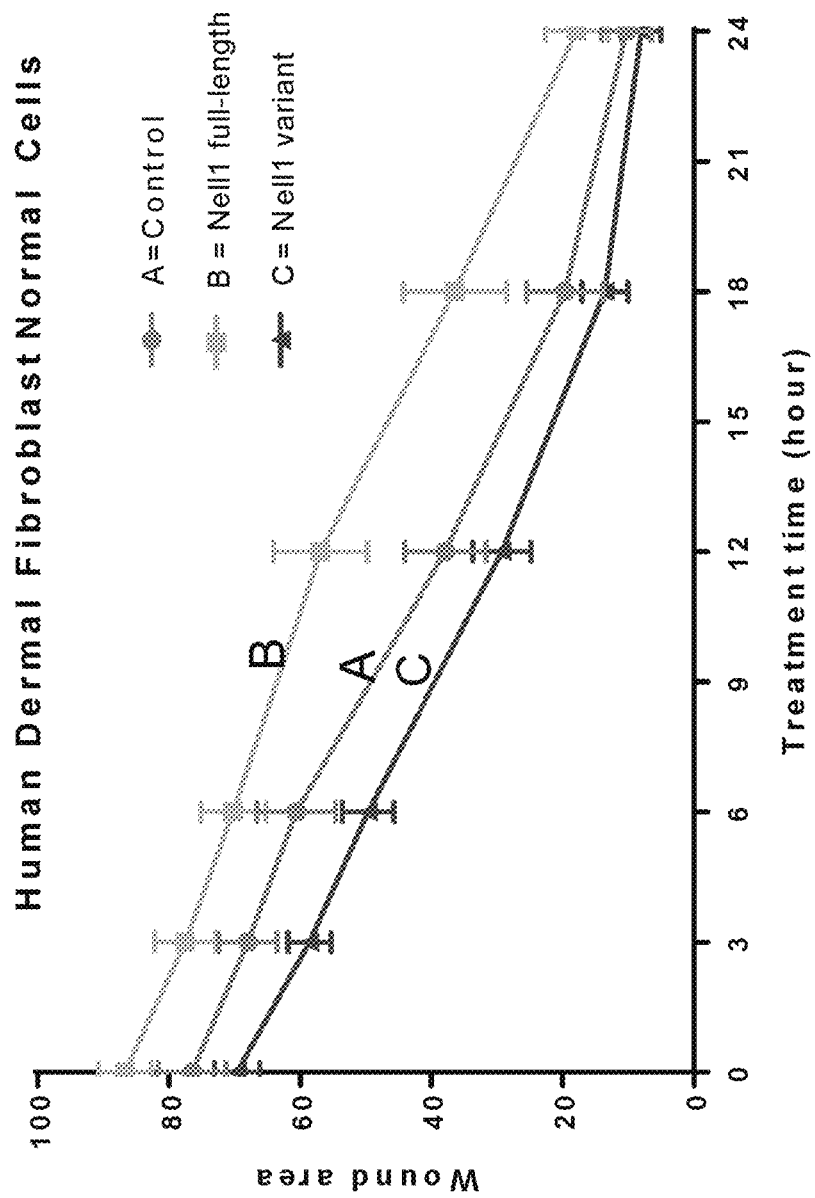
Figure 3C:
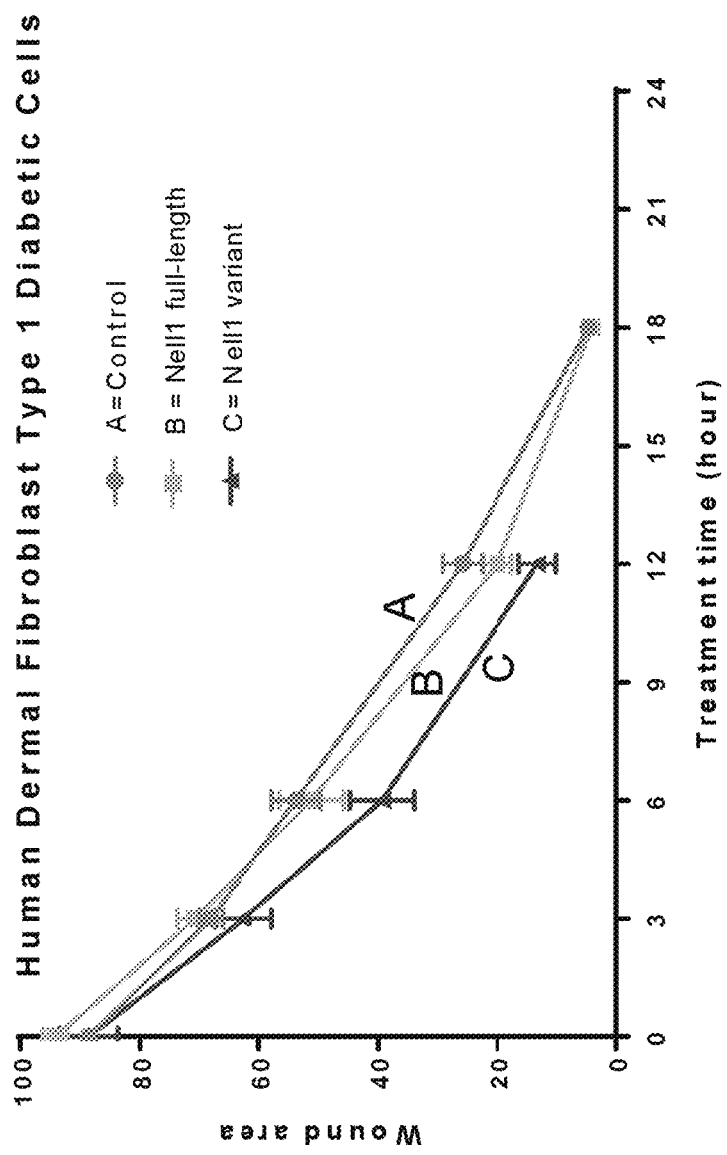
Figure 3D:
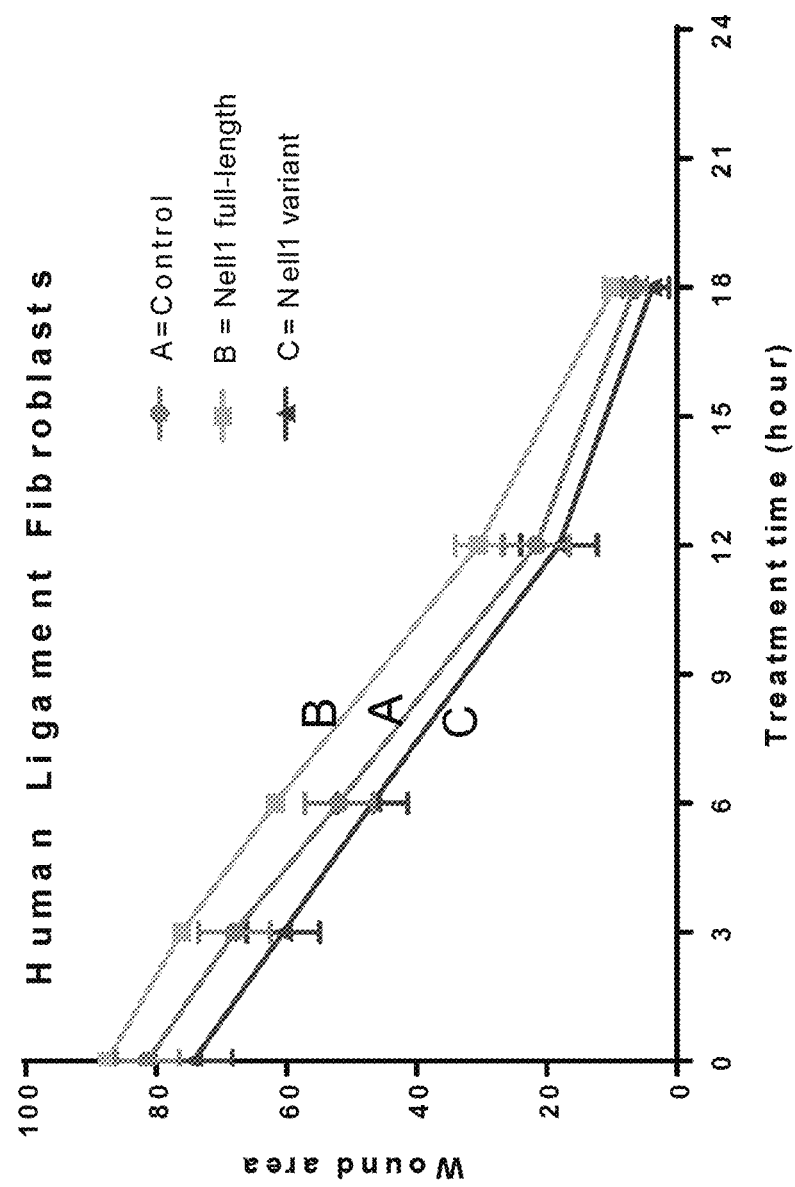

Not only did the NELL1 variant protein increase the rate of normal human dermal fibroblast cell migration, but also the migration of type 1 diabetes dermal fibroblast cells and in a dose dependent manner compared to the full-length NELL1 protein and control untreated cells, with the highest dose tested showing the highest increase in wound closure (FIGS. 3A-3C). The mean migration rates were: 5.7, 6.4, 6.8, and 8.1 for medium control, 100, 200, and 300 ng/ml of NELL1 variant, respectively. Treatment with the NELL1 variant at the highest dose tested (300 ng/ml) also showed increased wound healing in ligament-derived fibroblasts compared to untreated controls (FIG. 3D).

Although full-length NELL1 protein did not promote closure of the wound areas in these initial studies, an alternative dosage of full-length NELL1 protein or alternative culture conditions, for example, growth of the fibroblasts in serum-free medium, might be necessary in order to exhibit such an effect.

Methods

Cells. The following primary cells were purchased: normal human dermal fibroblasts (ixcells Biotech, Cat.#10HU-014), type 1 diabetes human dermal fibroblasts (ixcells Biotech, Cat.#10HU-014), and normal human ligament fibroblasts (ScienCell Research Lab, Inc., Cat. #2630).

Primary cultures of these human fibroblasts were established in complete Fibroblast Growth Medium (FGM; ScienCell Research Laboratories; Cat. #2301) and incubated in a humidified 37° C., 5% $CO_2$ incubator. The FGM was supplemented with 10% heat-inactivated fetal bovine serum (FBS), penicillin (100 units/ml), streptomycin (100 µg/ml), and other growth factors, according to the protocol of the cell suppliers.

Human fibroblast monolayer scratch (wound healing) assay. 96-well plates were coated with a thin layer of biomatrix according to cell types. The cell numbers were optimized/titrated per well in the plate for each type of cells. Cells were seeded in the log growing phase into each well (maximum of 100 µL per well) on 96-well microplates and cells were incubated overnight in a humidified 37° C., $CO_2$ incubator to form 100% confluent cell monolayers.

An IncuCyte® WoundMaker device/platform was used to create homogeneous, 750-micron wide scratch wounds in the middle of the cell monolayers on 96-well microplates, by strictly following the IncuCyte® WoundMaker protocol. The medium with cell debris was removed immediately after wounding /scratching by gentle aspiration on the side of each well. Each well was carefully replenished with 100 µL per well of fresh pre-warmed medium and any cell debris removed by gentle aspiration on the side of each well. Each well (free of debris) was replenished with 50 µL per well of fresh pre-warmed medium, or 50 µL per well of fresh medium with NELL1 protein (full-length or NELL1 3-612aa variant) with the appropriate concentration to achieve the required dose in each well. Four dosages were tested in at least 4 replicates per treatment: untreated Control (0), 100 ng/mL, 200 ng/mL and 300 ng/mL for each of the NELL1 full-length protein and the NELL1 variant protein. Plates were gently tapped to mix.

The plate with cells was incubated in an IncuCyte® Live-Cell Analysis System. Phase contrast images of cell migration towards the empty space in the wounded area were captured/recorded (10× magnification, digitally zoomed) at time of 0 (start), and then every other hour post wounding and treatments. The time courses of migration of cells in an IncuCyte® Live-Cell Analysis System were recorded. The total pixel of cells in the wounded area before and after treatments was measured using the IncuCyte™ Software. The following calculations were made from the data:

Wound area at timepoints (Tn)–the area between wound boundaries over time

Cell confluence area=Wound area (T0)–Wound area (Tn)

Relative cell confluence in the wound=Cell confluence in the wound/total wound area *100

Wound healing rate=the average velocity at which the cells collectively move into the wound gap; is the absolute value of the slope of curve fitting of cell confluence areas over the times (dA/dt) before 50% cell confluency.

Data were analyzed and plotted out using GraphPad Prism 7.0 (San Diego, Calif.).

Example 4

Effects of NELL1 Peptide on an In Vivo Model of Equine Tendon/Ligament Injury

Tendon injury animal models are well established in horses because of the great demand for treatments of tendon damage, especially in valuable racehorses and show/dressage horses (Schramme et al. (2010) *Vet Comp. Orthop. Traumatol.* 358-365; Estrada et al. (2014) *Vet Comp Orthop Traumatol* 358-365; Nixon et al. (2008) *Am. J. Vet Res.* 69:928-937; Watts et al. (2012) *EVJ* 44(5):576-586). The most common model of damage to the Superficial Digital Flexor Tendon (SDFT) is a good model for the human Achilles tendon, a significant and common injury in human patients. Equine SDFT tendonitis can be created chemically using collagenase or via surgical means.

The following study is performed on a surgically induced SDFT tendonitis equine model.

Twenty-four healthy adult horses are selected and randomly assigned into four groups with six horses per group. The dosing of NELL1 is extrapolated from wound healing studies in horses based on the amount of protein per area of injury. Group 1 is administered saline solution as a control. Group 2 is administered dose 1 (400 micrograms of NELL1). Group 3 is administered dose 2 (800 micrograms of NELL1) and Group 4 is administered dose 3 (1600 micrograms of NELL1).

After general anesthesia, a core lesion of 8 cm in the SDFT of a randomized forelimb is generated with a 3.5 mm synovial resector under ultrasound imaging. Operated limbs are bandaged for two weeks post-operation until sutures are removed. Horses are confined to a stall during this two week period.

NELL1 treatment is administered under sedation via intralesional injection guided by ultrasound imaging, once at seven days post-injury.

Rehabilitation is performed on a treadmill after two weeks with the length of time walking steadily increasing (10 mins/day during weeks 3-6, 20 mins/day during weeks 7-10, 30 mins/day during weeks 11-14, 40 mins/day during weeks 15-20). During weeks 21-22, rehabilitation will be 35 mins/day walking and 5 mins/day trotting. Rehab during weeks 23-24 will consist of 30 mins/day walking and 10 mins/day trotting.

Healing is assessed by a variety of techniques: a) regular ultrasound evaluation at 2-weeks, 4-weeks, 6-weeks, 8-weeks, 12-weeks, 16-weeks, 20-weeks and 24-weeks; b) histological examination of tendons at the end of study; and c) gene expression via quantitative RTPCR techniques of tendon-specific genes (collagen types I, III, decorin, cartilage oligomeric protein (COMP) and Tenascin C.

Example 5

NELL1 Peptide Promotes Healing of Body Wounds in Horse

In order to test the efficacy of the NELL1 protein in healing soft tissue injuries in a large animal model with economic/commercial veterinary significance, purified, recombinant, horse NELL1, full-length protein (NFL) and a variant domain-specific form (NV1) were administered to body wounds of horses. NFL spans amino acids 3-791 of the horse NELL1 protein and contains all the known/predicted domains of the horse NELL1 protein, while NV1 contains amino acids 3-612 and does not contain the last two von willebrand factor domains at the C-terminus of the protein.

Six circular 4-cm diameter wounds (3/side) were created surgically on the thorax of 8 adult female horses to evaluate wound healing. Two days after wounding, during the first dressing change, wounds were treated with one of the following: control—volume equal to that of sterile saline that was used to dilute the stock NELL1 protein; dose 1 (95.2 µg/4-cm wound) of NFL or NV1; or dose 2 (190.4 µg/4-cm wound) of NFL or NV1. NELL1 was delivered by directly infusing a biodegradable, commercially available calcium alginate dressing. Wound healing was assessed over a period of 42 days using a 3-D imaging system (Eykona camera; Bowling et al. (2008) The Eykona Wound Measurement System: Modernizing Wound Measurement for the 21$^{st}$ Century. 12$^{th}$ *Malvern Diabetic Foot Conference*, UK8, May 14-16; and Bowling et al. (2009) *Diabetic Medicine* 26(1):93-96). Researchers administering the treatment and performing the regular wound healing measurements were blinded to the treatment and dosage given to a wound.

Statistical analyses indicated significant healing effects for the variant NELL1 protein that enhanced healing based on the remaining inner unhealed wound area at the end of the study (Day 42 post-treatment). In contrast, there were no statistically significant differences observed between untreated control wounds and those treated with the full-length NELL1 protein (NFL). Interestingly, from days 3-14 post-treatment, wounds treated with NFL had consistently lower unhealed areas compared to controls, but these effects were not increased or sustained until the end of the study.

Six general health parameters were monitored daily throughout the study to evaluate safety: body temperature, pulse rate, respiratory rates, defecation, appetite and behavior/attitude (irritability, aggressiveness or unusual behavior). Results indicated that both NFL and NV1 NELL1 proteins did not elicit adverse effects in the test subjects and therefore, is a safe product to use for wound healing in horses.

This initial equine study suggested that healing effects might be boosted with a second application of the NELL1 protein within the second week. There were strong trends of increased wound healing observed from days 3-14 with both NELL1 proteins, but these trends were not sustained for the full-length NELL1. Future wide range dose optimization studies might provide a statistically significant effect with full-length NELL1 and also enhance the observed effects of the variant NELL1 protein.

Methods

Horses. Eight mixed-breed, female adult horses, 8 to 15 years old, weighing 453-589 kgs, free of any clinically detectable medical disorder, were housed in individual stalls and were kept under constant conditions (i.e., temperature, feeding, cleaning) throughout the study. They were examined daily for signs of discomfort, lameness, and illness. Horses were randomly assigned numbers (referred to as treatment identification numbers) 1 through 8, and based on their number, received pre-determined grid pattern of wounds, outlined in FIG. 4, and treatments, listed in Table 3.

Figure 4:
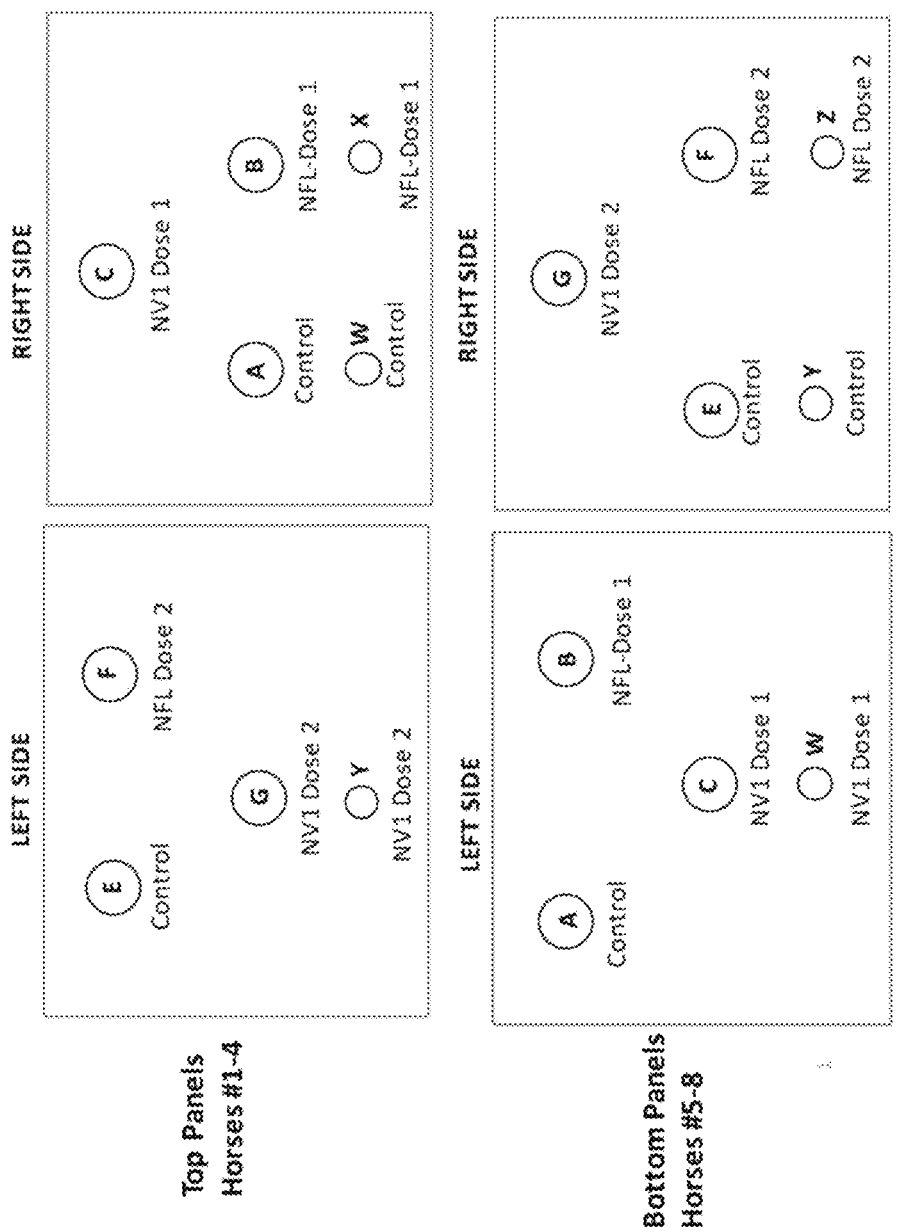
FIG. 4 provides an illustration of the wound grid on each side of the horses indicating the three 4-cm diameter (A, B, C or E, F, G) and the 2-cm diameter cutaneous wounds (W, Y, W and X, or Y and Z) and treatments with control, full-length NELL1 (NFL), or NELL1 variant (NV1). Top grids were for horses 1-4 and the bottom grids were for horses 5-8.
Figure 5:
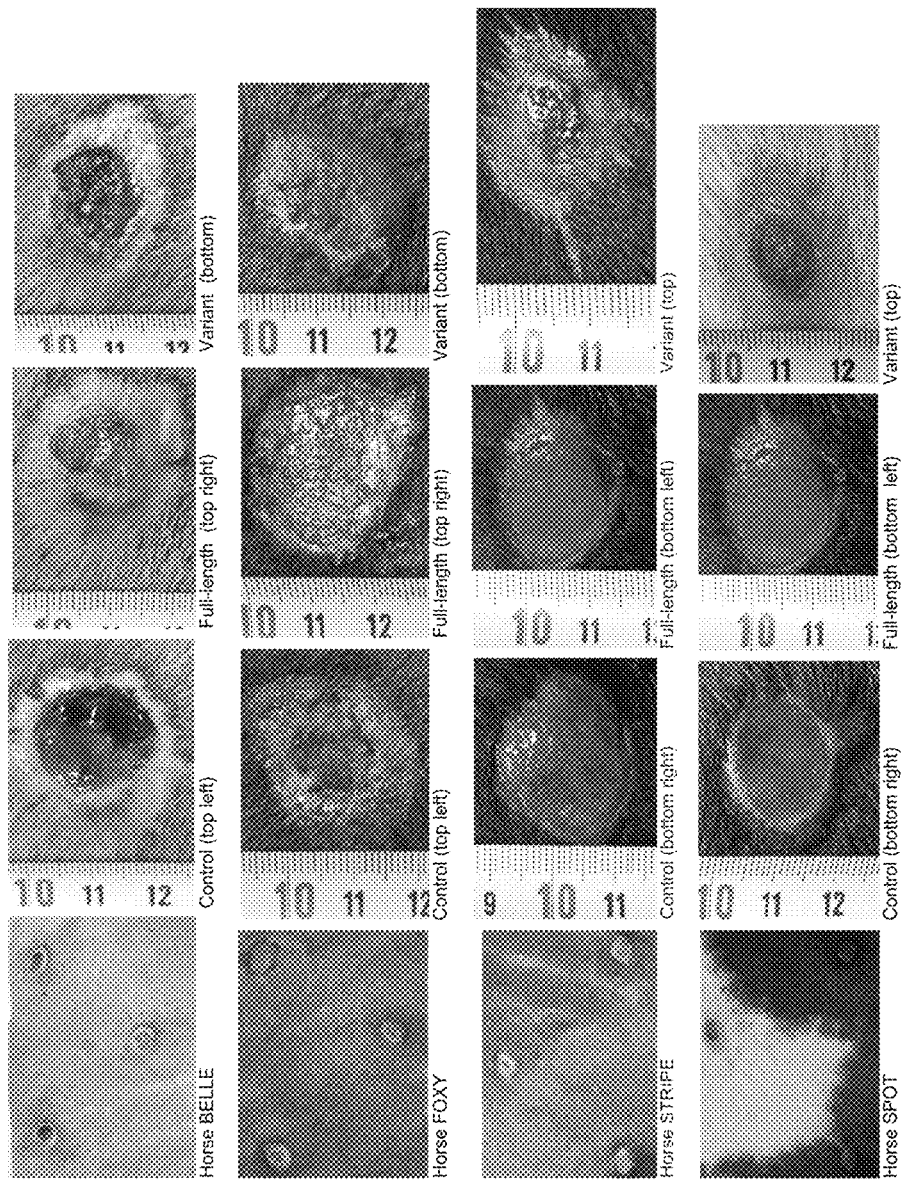
FIG. 5 shows horse body wounds at day 42 post-treatment showing improved healing with NELL1 variant (NV1) compared to full-length NELL1 (NFL) and controls.

Wounding Protocol and Treatment Groups. All procedures were carried out according to approved IACUC protocol (UTK-IACUC No. 2247-0314). The wound model used was a modification of an established equine model (Schumacher et al. (1992) *Am. J. Vet Res.* 53(9):1568-1571; Gomez et al. (2004) *The Canadian Journal of Veterinary Research* 68:49-55; and Morgan et al. (2009) *J. Am. Vet Med. Assoc.* 234(9):1-8). On day 0, each horse was sedated with detomidine HCl (0.006-.012 mg/kg) and butorphanol (0.006-0.012 mg/kg). Hair on the right and left sides of the thorax was removed with clippers, and the sides of the thorax were prepared for aseptic surgery. Sites of wounds were desensitized with a local anesthetic (2% mepivacaine HCl) subcutaneously. Three, 4-cm diameter and one or two, 2-cm diameter, circular, full-thickness, cutaneous defects were created on the dorsal aspect of the right and left sides of the thorax (FIG. 4). The 4-cm diameter wounds were created at least 8 cm apart from each other, and 2-cm diameter biopsy wounds were created at least 4 cm ventral to the most ventral 4-cm diameter wound(s). All wounds were created using sterilized, 4-cm and 2-cm diameter, stainless steel, custom-made, biopsy punches. 4-cm diameter wounds were allowed to heal over 42 days and were assessed qualitatively and by quantitative measurements (FIG. 5). The large wounds were arranged in a triangular pattern, as illustrated in FIG. 4, designed to prevent solutions applied to the dorsally located wounds from migrating by gravity to the ventral wounds. The smaller wounds generated for biopsy were located directly ventral to the ventral large wounds and were treated identically to the large wounds. Biopsy tissues were collected for future molecular analyses.

Wounds were covered with a sterile, alginate dressing cut to the size of the wound. The dressings were held in place with a sterile, non-adhesive dressing (Telfa Pad, Johnson & Johnson, New Brunswick, N.J.), which was stapled to the skin beneath it. Each side of the thorax was covered with a large, sterile combine to compress the wound and to absorb exudate, if any, from the wound. The dressings and the combines were held in place with a custom-made, belly bandage (Boa Abdominal Bandage; Wire 2 Wire Vet Products, LLC, Lexington, K.Y.) positioned over the right and left sides over the thorax, directly over the wounds. Horses received phenylbutazone (2.2 mg/kg, IV) before surgery and for 1 day after surgery (2.2 mg/kg, orally, q12h).

On day 2 after wounding, the alginate dressings were carefully removed. NELL1 protein of the appropriate dose (FIG. 4, Table 3) or sterile isotonic saline solution (control) was loaded into the alginate dressing cut to the size of the wound. The NELL1-soaked dressing or the isotonic saline solution-soaked dressing was laid directly on the wound and covered with a fresh, sterile, non-absorbent non-adhesive dressing, which was stapled to the skin beneath it. The dressings were removed 2 days later, and thereafter, the wounds were dressed twice weekly with a sterile combine pad applied to each side of the thorax and held in place with the belly bandage. FIG. 4 illustrates the position and designations of the wounds, and Table 3 indicates the treatment applied to each wound.

TABLE 3

NELL1 form and dosage for treatment of horse wounds.

| Horse # | 4-cm diameter wound | 2-cm diameter wound for biopsy | Treatment | Dose |
|---|---|---|---|---|
| 1-4 | A-right side | | Control | NA |
| | B-right side | | NELL1, full-length (NFL) | 1 = 95.2 µg |
| | C-right side | | NELL1, Variant 1 (NV1) | 1 = 95.2 µg |
| | | W-right side | Control | NA |
| | | X-right side | NFL | 1 = 23.7 µg |
| | E-left side | | Control | NA |
| | F-left side | | NFL | 2 = 190.4 µg |
| | G-left side | | NV1 | 2 = 190.4 µg |
| | | Y-left side | NV1 | 2 = 47.4 µg |
| 5-8 | A-left side | | control | |
| | B-left side | | NFL | 1 = 95.2 µg |
| | C-left side | | NV1 | 1 = 95.2 µg |
| | | W-left side | NV1 | 1 = 23.7 µg |
| | E-right side | | Control | NA |
| | F-right side | | NFL | 2 = 190.4 µg |
| | G-right side | | NV1 | 2 = 190.4 µg |
| | | Y-right side | Control | NA |
| | | Z-right side | NFL | 2 = 47.4 µg |

Following the treatment groups shown in Table 3, the total samples per group were:

Control=16 big (4-cm) wounds
NFL Dose 1=8 big wounds
NV1 Dose 1=8 big wounds
NFL Dose 2=8 big wounds
NV1 Dose 2=8 big wounds Horse NELL1 protein and variants. Purified recombinant horse NELL1 proteins were manufactured as described in Example 1. The efficacy of two forms of NELL1 protein in treating equine wounds was tested. These two forms were the full-length protein (aa3-791), designated as NFL, and one shorter domain-specific variant (aa3-612), designated as NV1. The NELL1 proteins were stored in buffered solution and shipped frozen in dry ice from Abnova Corp. for storage at −80° C. until ready for use. These proteins were used within 4 weeks of delivery.

Dosage and Delivery. Wounds were treated with a control (isotonic saline solution), NELL1 full-length protein, or the NELL1 variant protein two days after wounding, during the first dressing change. Control treatment was phosphate buffered saline (PBS). Dose 1 (i.e., NELL1 full-length protein) was 95.2 micrograms per 4-cm diameter circular wound, and Dose 2 (i.e., NELL1 variant protein) was 190.4 micrograms per 4-cm diameter wound.

NELL1 proteins were thawed on ice, proper concentrations were prepared, and the buffered NELL1 proteins were loaded/pipetted directly into the selected dressing. The NELL1 protein was loaded in a volume of 2400 μL for application to each of all of the 4-cm diameter wounds, and in a volume of 600 μL for application to each of the 2-cm diameter wounds. These volumes were determined by loading the dressings cut to the sizes of the wounds and by testing various volumes of phosphate-buffered isotonic saline solution to determine maximum loading volume without the solution dripping from the dressing. A 100-mm diameter sterile plastic Petri dish was used for each dressing, and all protein-soaked dressings were prepared under sterile conditions in a tissue culture hood. Each Petri dish was labelled with the horse treatment identification number and the type and dose of the protein applied.

Evaluation of Wound Healing 3-D Imaging. Wound measurements were taken from images obtained from a digital, 3-D wound imaging device that enables rapid, secure, repeatable collection of wound data (TOMI 3D, Eykona Medical, USA). Images were acquired at the following time points: time of wounding, initial treatment, each dressing change (i.e., twice weekly), and at the termination of study.

Data Analyses. All images were downloaded onto a computer with image analysis software developed by Eykona. The images were then analyzed individually using a trace-area function in the software. The outer most margin of the wound was measured first and the area recorded in mm$^2$. These values were recorded over the various time points to determine the rate of wound contraction. The inner area, or non-epithelialized area, was then measured in similar fashion by tracing the area outlined by the epithelial margin. These values were recorded over time and used to calculate the rate of epithelialization.

Because there was some degree of variation in the initial size of the wounds, all measurements were normalized on a percent scale so that the initial wound measurement reflected 100% of the size of the wound. Changes in the overall area of the wound and of the epithelialized area were then subsequently expressed as a percentage. Rates of contraction and epithelialization were expressed as mm$^2$/day.

Rate of contraction was calculated by subtracting the area of the wound at one time-point from the determined area of the wound at the previous time-point and then dividing the difference in area by the number of days between those two time-points. An overall rate of contraction was calculated by subtracting the final area of the wound from the initial area of the wound and dividing the difference by the total number of days between those two time-points. The area of epithelialization for each 4-cm diameter wound was calculated by subtracting the area of the wound from the area of granulation tissue, and the rate of epithelialization was then calculated in similar fashion by subtracting the area of epithelialization at one time-point from the area of epithelialization at the previous time-point and then dividing the difference in area by the number of days between those two time-points.

Results and Discussion

Overall Health Effects of NELL1 Protein. All horses were monitored daily throughout the study period. No adverse effects on the health and behavior of the horses were observed. The temperature, pulse and respiratory rates, defecation, appetite, and attitude of the horses were monitored daily and were within normal limits throughout the 42-day study.

Delivery of NELL1 protein via calcium alginate dressing. This study is the first in which NELL1 protein was administered into soft tissue injuries in horses using a calcium alginate dressing. The selection of this dressing was based upon a previous in vitro study comparing the release of NELL1 protein from a collagen and a calcium alginate commercial dressing. The elution profiles suggested that in a calcium alginate carrier, the NELL1 protein is released within 2-3 days. In this in vivo study, at day 3 post-treatment there was no visual evidence of the dressing and no abnormal acute inflammatory reactions were observed.

Effects of NELL1 on Wound Healing (Days 3-42, rates of wound healing, epithelialization and contraction). For all data analyses, at a given time point, the total area of the wound, the inner area (i.e. the area filled with granulation tissue) and the epithelialized area (i.e., the difference between the total area and the inner area) were calculated for each 4-cm diameter wound of each horse from images obtained at the time of each bandage change. Each measurement was represented as a change in mm$^2$ relative to the previous measurement.

Data was also normalized to account for variation in wound sizes at day 0 and considers that all wounds are at 100% value (all unhealed areas) before treatment.

Figure 6:
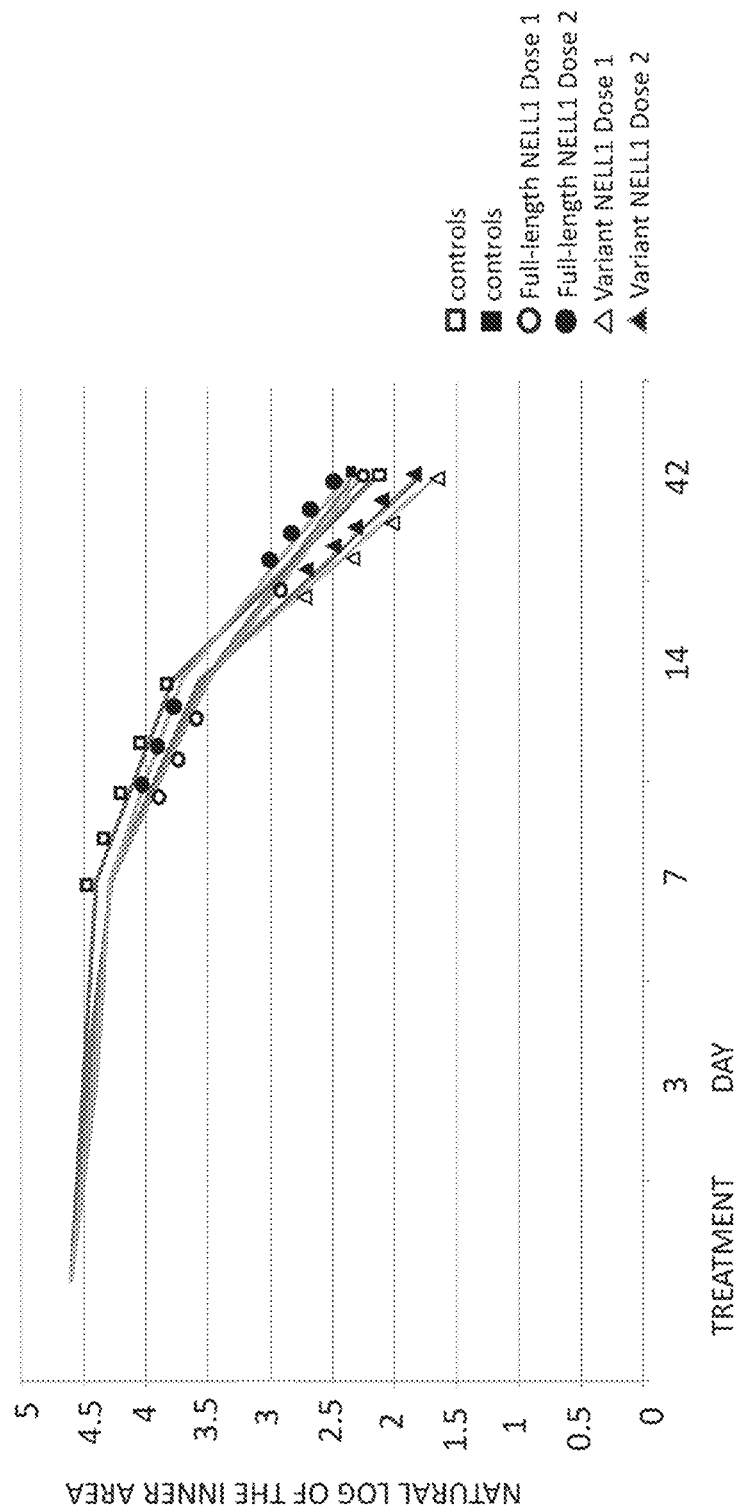
FIG. 6 shows a graph of the natural log values of the inner area in horse wounds that remain unhealed on days post-treatment with full-length (lines 3 and 4) or variant NELL1 protein (lines 5 and 6) and untreated control wounds (lines 1 and 2).

For statistical analyses, cumulative data from each treatment group were analyzed. Initially, standard T-TEST using Microsoft Excel (Windows 7) was used to compare these changes, and the p values were calculated. At day 42 (last day of observation/end of experimental part), analyses of normalized data of inner area (unhealed) indicated strong trends in the wounds treated with the variant NELL1 form (p=0.08 for both Dose 1 and Dose 2; p=0.04 for all wounds treated with the variant regardless of dose). Data shows that horse wounds at Day 42 treated with NELL1 variant showed faster healing (smaller unhealed inner area) compared to control. The wounds have smaller areas that remain unhealed and the variation/standard deviation was consistently lower in wounds treated with the smaller NELL1 variant compared to controls and those treated with the full-length form (FIGS. 5 and 6 and Table 4).

TABLE 4

Healing of 4-cm horse body wounds based on the remaining unhealed inner area at various days post-treatment with a degradable calcium alginate dressing infused with saline solution (untreated controls), full-length (amino acids #3-791) or variant (amino acids #3-612) horse NELL1 protein.

| | OBSERVATIONS (N) | MEAN (mm$^2$) | STANDARD DEVIATION |
|---|---|---|---|
| CONTROL (UNTREATED) | | | |
| Day 3 (T3) | 16 | 90.1 | 5.9 |
| Day 7 (T7) | 16 | 76.7 | 10.5 |
| Day 14 (T14) | 16 | 39.2 | 9.5 |
| Day 42 (T42) | 16 | 9.8 | 5.4 |

TABLE 4-continued

Healing of 4-cm horse body wounds based on the remaining unhealed inner area at various days post-treatment with a degradable calcium alginate dressing infused with saline solution (untreated controls), full-length (amino acids #3-791) or variant (amino acids #3-612) horse NELL1 protein.

|  | OBSERVATIONS (N) | MEAN (mm$^2$) | STANDARD DEVIATION |
|---|---|---|---|
| FULL-LENGTH NELL1: DOSE 1 | | | |
| T3 | 8 | 85.8 | 4.9 |
| T7 | 8 | 71.1 | 9.7 |
| T14 | 8 | 32.1 | 6.2 |
| T42 | 8 | 10.3 | 7.9 |
| FULL-LENGTH NELL1: DOSE 2 | | | |
| T3 | 8 | 81.7 | 7.5 |
| T7 | 8 | 72.3 | 10.9 |
| T14 | 8 | 41.0 | 6.5 |
| T42 | 8 | 11.0 | 9.9 |
| VARIANT NELL1 (aa #3-612): DOSE 1 | | | |
| T3 | 8 | 85.3 | 8.6 |
| T7 | 8 | 72.3 | 8.4 |
| T14 | 8 | 31.2 | 14.6 |
| T42 | 8 | 5.5 | 3.9 |
| VARIANT NELL1 (aa #3-612): DOSE 2 | | | |
| T3 | 8 | 86.8 | 5.7 |
| T7 | 8 | 72.2 | 4.3 |
| T14 | 8 | 35.5 | 4.0 |
| T42 | 8 | 6.2 | 2.8 |

Wounds treated with full-length NELL1 did not show significant differences or trend towards better healing at day 42. Interestingly, wounds treated with full-length NELL1 showed significant differences in having a smaller inner unhealed area with Dose 2 at 3 days post-treatment (p=0.03)

Because wound healing is not a linear process and previous reports suggested plotting log-transformed values, data was converted into log values and plotted (Gelfand et al. (2002) *The Society for Investigative Dermatology* 119: 1420-1425). These log values were then used for graphical representation of the data (FIG. 6). Consistent with the initial analyses, the graphs for wounds treated with the smaller variant showed a trend for better healing from the controls and at and after day 14, these wounds start to heal faster than the other treatment groups.

In addition to the standard T-test, additional statistical tools and approaches were used to analyze the data. A mixed-model ANOVA was used to analyze the data to factor in fixed and random effects and the study design where a single horse was given several different treatments (2 NELL1 protein forms and 2 doses per form).

When treatments were analyzed individually, there are significant differences by the mean rate of healing through time and these time patterns differ by treatment. This was also observed for the other parameters such as rate of contraction, rate of epithelialization, and overall healing rate. The mixed model ANOVA analyses confirmed the earlier results where treatment with NELL1 variant showed faster healing (smaller unhealed inner area) compared to control.

Summary and Conclusions

NELL1 horse proteins did not elicit any adverse effects on the wounds, over-all health and behavior of the horses. Horse NELL1 protein is deemed to be a safe product in the manner delivered and dosages tested in this study. This is the first known application of the horse NELL1 protein into an animal model.

NELL1 protein can be effectively and efficiently delivered into horse body wounds via a calcium alginate biodegradable dressing. The dressing enables delivery into the soft tissue injury within three days, wherein the entire dressing was completely absorbed into the wounds (by visual/macroscopic examination). This study represents the first known test in vivo of a calcium alginate dressing to administer NELL1 protein into soft tissue injuries.

NELL1 variant protein exhibited effects that promoted wound healing as measured by the remaining inner unhealed area assessed at day 42 post-treatment. The standard deviation for treatment at both doses was very low compared to either control or full-length NELL. There was no statistically significant difference between the two tested doses.

There were no statistically significant effects nor strong trends for control wounds or those treated with full-length NELL1 (except for day 3 post-treatment for NFL Dose 2, p=0.03) and the variations were large for both of these groups compared to the NELL1 variant form.

The mixed model analysis indicated that the pattern of healing over time was significantly different between the various treatment groups. The log graphs of inner unhealed area size for the different groups showed that the NELL1 variant treated wounds started differentiation or separation from the other treatments after day 14. These data suggested that perhaps a re-application of the NELL1 protein (before the end of 14 days) might sustain the effects beyond the initial weeks and yield more dramatic effects than initially observed in this study.

Those skilled in the art will further appreciate that the present invention may be embodied in other specific forms without departing from the spirit or central attributes thereof. In that the foregoing description of the present invention discloses exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A method of regenerating injured tissue in a subject comprising administering an effective amount of a NELL1 peptide fragment or variant thereof to a subject in need thereof, wherein said NELL1 peptide fragment or variant thereof has at least 95% sequence identity to SEQ ID NO: 17 or 18, and wherein said NELL1 peptide fragment or variant thereof lacks the carboxy-terminal 179 amino acid residues of the fragment's respective full-length NELL1 protein, wherein said injured tissue comprises at least one tissue type selected from the group consisting of heart muscle, skeletal muscle, cartilage, bone, and skin.

2. The method of claim 1, wherein said NELL1 peptide fragment or variant thereof is the amino acid sequence set forth in SEQ ID NO: 17 or 18.

3. The method of claim 1, wherein said subject is a mammal.

4. The method of claim 3, wherein said mammal is a human.

5. The method of claim 1, wherein said NELL1 peptide fragment or variant thereof is incorporated into a drug eluting device, scaffold, matrix, or sutures.

6. The method of claim 1, wherein said NELL1 peptide fragment or variant thereof is incorporated into a wound dressing, collagen matrix, calcium alginate matrix, patch, or hydrogel.

7. The method of claim 1, wherein said administering comprises intramuscular, intravenous, subcutaneous, or intraperitoneal administering.

8. The method of claim 1, wherein said administering comprises locally administering said effective amount of said NELL1 peptide fragment or variant thereof to a site of injured tissue in said subject.

9. A method of promoting the healing of an injury to a tissue comprising administering an effective amount of a NELL1 peptide fragment or variant thereof to a subject in need thereof, wherein said NELL1 peptide fragment or variant thereof has at least 95% sequence identity to SEQ ID NO: 17 or 18, and wherein said NELL1 peptide fragment or variant thereof lacks the carboxy-terminal 179 amino acid residues of the fragment's respective full-length NELL1 protein, wherein said tissue comprises at least one tissue type selected from the group consisting of heart muscle, skeletal muscle, cartilage, bone, and skin.

10. The method of claim 9, wherein said NELL1 peptide fragment or variant thereof is the amino acid sequence set forth in SEQ ID NO: 17 or 18.

11. The method of claim 9, wherein said subject is a mammal.

12. The method of claim 11, wherein said mammal is a human.

13. The method of claim 9, wherein said NELL1 peptide fragment or variant thereof is incorporated into a drug eluting device, scaffold, matrix, or sutures.

14. The method of claim 9, wherein said NELL1 peptide fragment or variant thereof is incorporated into a wound dressing, collagen matrix, calcium alginate matrix, patch, or hydrogel.

15. The method of claim 9, wherein said administering comprises intramuscular, intravenous, subcutaneous, or intraperitoneal administering.

16. The method of claim 9, wherein said administering comprises locally administering said effective amount of said NELL1 peptide fragment or variant thereof to said injury.

17. A method of promoting the maturation of a progenitor cell in an injured tissue in a subject comprising contacting said progenitor cell with an effective amount of a NELL1 peptide fragment or variant thereof having at least 95% sequence identity to SEQ ID NO: 17 or 18, wherein said NELL1 peptide fragment or variant thereof lacks the carboxy-terminal 179 amino acid residues of the fragment's respective full-length NELL1 protein, and wherein said injured tissue comprises at least one tissue type selected from the group consisting of heart muscle, skeletal muscle, cartilage, bone, and skin.

18. The method of claim 17, wherein said NELL1 peptide fragment or variant thereof is the amino acid sequence set forth in SEQ ID NO: 17 or 18.

19. The method of claim 17, wherein said subject is a mammal.

20. The method of claim 19, wherein said mammal is a human.

* * * * *

SEQUENCE LISTING

<160> NUMBER OF SEQ ID NOS: 19

<210> SEQ ID NO 1
<211> LENGTH: 3255
<212> TYPE: DNA
<213> ORGANISM: Homo sapiens
<220> FEATURE:
<221> NAME/KEY: CDS
<222> LOCATION: (154)..(2586)

<400> SEQUENCE: 1

```
atatgcgagc gcagcacccg gcgctgccga gccacctccc ccgccgcccg ctagcaagtt        60
tggcggctcc aagccaggcg cgcctcagga tccaggctca tttgcttcca cctagcttcg       120 gtgcccctg ctaggcgggg accctcgaga gcg atg ccg atg gat ttg att tta        174
                                     Met Pro Met Asp Leu Ile Leu
                                       1               5 gtt gtg tgg ttc tgt gtg tgc act gcc agg aca gtg gtg ggc ttt ggg        222
Val Val Trp Phe Cys Val Cys Thr Ala Arg Thr Val Val Gly Phe Gly
          10                  15                  20 atg gac cct gac ctt cag atg gat atc gtc acc gag ctt gac ctt gtg        270
Met Asp Pro Asp Leu Gln Met Asp Ile Val Thr Glu Leu Asp Leu Val
 25                  30                  35 aac acc acc ctt gga gtt gct cag gtg tct gga atg cac aat gcc agc        318
Asn Thr Thr Leu Gly Val Ala Gln Val Ser Gly Met His Asn Ala Ser
 40                  45                  50                  55 aaa gca ttt tta ttt caa gac ata gaa aga gag atc cat gca gct cct        366
Lys Ala Phe Leu Phe Gln Asp Ile Glu Arg Glu Ile His Ala Ala Pro
                 60                  65                  70 cat gtg agt gag aaa tta att cag ctg ttc cgg aac aag agt gaa ttc        414
His Val Ser Glu Lys Leu Ile Gln Leu Phe Arg Asn Lys Ser Glu Phe
             75                  80                  85 acc att ttg gcc act gta cag cag aag cca tcc act tca gga gtg ata        462
Thr Ile Leu Ala Thr Val Gln Gln Lys Pro Ser Thr Ser Gly Val Ile
         90                  95                 100 ctg tcc att cga gaa ctg gag cac agc tat ttt gaa ctg gag agc agt        510
Leu Ser Ile Arg Glu Leu Glu His Ser Tyr Phe Glu Leu Glu Ser Ser
105                 110                 115 ggc ctg agg gat gag att cgg tat cac tac ata cac aat ggg aag cca        558
Gly Leu Arg Asp Glu Ile Arg Tyr His Tyr Ile His Asn Gly Lys Pro
120                 125                 130                 135 agg aca gag gca ctt cct tac cgc atg gca gat gga caa tgg cac aag        606
Arg Thr Glu Ala Leu Pro Tyr Arg Met Ala Asp Gly Gln Trp His Lys
                140                 145                 150 gtt gca ctg tca gtt agc gcc tct cat ctc ctg ctc cat gtc gac tgt        654
Val Ala Leu Ser Val Ser Ala Ser His Leu Leu Leu His Val Asp Cys
            155                 160                 165 aac agg att tat gag cgt gtg ata gac cct cca gat acc aac ctt ccc        702
Asn Arg Ile Tyr Glu Arg Val Ile Asp Pro Pro Asp Thr Asn Leu Pro
        170                 175                 180 cca gga atc aat tta tgg ctt ggc cag cgc aac caa aag cat ggc tta        750
Pro Gly Ile Asn Leu Trp Leu Gly Gln Arg Asn Gln Lys His Gly Leu
    185                 190                 195 ttc aaa ggg atc atc caa gat ggg aag atc atc ttt atg ccg aat gga        798
Phe Lys Gly Ile Ile Gln Asp Gly Lys Ile Ile Phe Met Pro Asn Gly
200                 205                 210                 215 tat ata aca cag tgt cca aat cta aat cac act tgc cca acc tgc agt        846
Tyr Ile Thr Gln Cys Pro Asn Leu Asn His Thr Cys Pro Thr Cys Ser
                220                 225                 230 gat ttc tta agc ctg gtg caa gga ata atg gat tta cag gag ctt ttg        894
Asp Phe Leu Ser Leu Val Gln Gly Ile Met Asp Leu Gln Glu Leu Leu
```

```
                        235                 240                 245
gcc aag atg act gca aaa cta aat tat gca gag aca aga ctt agt caa        942
Ala Lys Met Thr Ala Lys Leu Asn Tyr Ala Glu Thr Arg Leu Ser Gln
            250                 255                 260 ttg gaa aac tgt cat tgt gag aag act tgt caa gtg agt gga ctg ctc        990
Leu Glu Asn Cys His Cys Glu Lys Thr Cys Gln Val Ser Gly Leu Leu
265                 270                 275 tat cga gat caa gac tct tgg gta gat ggt gac cat tgc agg aac tgc       1038
Tyr Arg Asp Gln Asp Ser Trp Val Asp Gly Asp His Cys Arg Asn Cys
280                 285                 290                 295 act tgc aaa agt ggt gcc gtg gaa tgc cga agg atg tcc tgt ccc cct       1086
Thr Cys Lys Ser Gly Ala Val Glu Cys Arg Arg Met Ser Cys Pro Pro
                300                 305                 310 ctc aat tgc tcc cca gac tcc ctc cca gtg cac att gct ggc cag tgc       1134
Leu Asn Cys Ser Pro Asp Ser Leu Pro Val His Ile Ala Gly Gln Cys
            315                 320                 325 tgt aag gtc tgc cga cca aaa tgt atc tat gga gga aaa gtt ctt gca       1182
Cys Lys Val Cys Arg Pro Lys Cys Ile Tyr Gly Gly Lys Val Leu Ala
        330                 335                 340 gaa ggc cag cgg att tta acc aag agc tgt cgg gaa tgc cga ggt gga       1230
Glu Gly Gln Arg Ile Leu Thr Lys Ser Cys Arg Glu Cys Arg Gly Gly
345                 350                 355 gtt tta gta aaa att aca gaa atg tgt cct cct ttg aac tgc tca gaa       1278
Val Leu Val Lys Ile Thr Glu Met Cys Pro Pro Leu Asn Cys Ser Glu
360                 365                 370                 375 aag gat cac att ctt cct gag aat cag tgc tgc cgt gtc tgt aga ggt       1326
Lys Asp His Ile Leu Pro Glu Asn Gln Cys Cys Arg Val Cys Arg Gly
                380                 385                 390 cat aac ttt tgt gca gaa gga cct aaa tgt ggt gaa aac tca gag tgc       1374
His Asn Phe Cys Ala Glu Gly Pro Lys Cys Gly Glu Asn Ser Glu Cys
            395                 400                 405 aaa aac tgg aat aca aaa gct act tgt gag tgc aag agt ggt tac atc       1422
Lys Asn Trp Asn Thr Lys Ala Thr Cys Glu Cys Lys Ser Gly Tyr Ile
        410                 415                 420 tct gtc cag gga gac tct gcc tac tgt gaa gat att gat gag tgt gca       1470
Ser Val Gln Gly Asp Ser Ala Tyr Cys Glu Asp Ile Asp Glu Cys Ala
425                 430                 435 gct aag atg cat tac tgt cat gcc aat act gtg tgt gtc aac ctt cct       1518
Ala Lys Met His Tyr Cys His Ala Asn Thr Val Cys Val Asn Leu Pro
440                 445                 450                 455 ggg tta tat cgc tgt gac tgt gtc cca gga tac att cgt gtg gat gac       1566
Gly Leu Tyr Arg Cys Asp Cys Val Pro Gly Tyr Ile Arg Val Asp Asp
                460                 465                 470 ttc tct tgt aca gaa cac gat gaa tgt ggc agc ggc cag cac aac tgt       1614
Phe Ser Cys Thr Glu His Asp Glu Cys Gly Ser Gly Gln His Asn Cys
            475                 480                 485 gat gag aat gcc atc tgc acc aac act gtc cag gga cac agc tgc acc       1662
Asp Glu Asn Ala Ile Cys Thr Asn Thr Val Gln Gly His Ser Cys Thr
        490                 495                 500 tgc aaa ccg ggc tac gtg ggg aac ggg acc atc tgc aga gct ttc tgt       1710
Cys Lys Pro Gly Tyr Val Gly Asn Gly Thr Ile Cys Arg Ala Phe Cys
505                 510                 515 gaa gag ggc tgc aga tac ggt gga acg tgt gtg gct ccc aac aaa tgt       1758
Glu Glu Gly Cys Arg Tyr Gly Gly Thr Cys Val Ala Pro Asn Lys Cys
520                 525                 530                 535 gtc tgt cca tct gga ttc aca gga agc cac tgc gag aaa gat att gat       1806
Val Cys Pro Ser Gly Phe Thr Gly Ser His Cys Glu Lys Asp Ile Asp
                540                 545                 550 gaa tgt tca gag gga atc att gag tgc cac aac cat tcc cgc tgc gtt       1854
Glu Cys Ser Glu Gly Ile Ile Glu Cys His Asn His Ser Arg Cys Val
```

|  |  |  |  |  |  |  |  |  |  |  |  |  |  |
|---|---|---|---|---|---|---|---|---|---|---|---|---|---|
| Glu | Cys | Ser | Glu | Gly | Ile | Ile | Glu | Cys | His | Asn | His | Ser | Arg | Cys | Val |
|  |  | 555 |  |  |  | 560 |  |  |  | 565 |  |  |  |

```
aac ctg cca ggg tgg tac cac tgt gag tgc aga agc ggt ttc cat gac        1902
Asn Leu Pro Gly Trp Tyr His Cys Glu Cys Arg Ser Gly Phe His Asp
        570                 575                 580 gat ggg acc tat tca ctg tcc ggg gag tcc tgt att gac att gat gaa        1950
Asp Gly Thr Tyr Ser Leu Ser Gly Glu Ser Cys Ile Asp Ile Asp Glu
    585                 590                 595 tgt gcc tta aga act cac acc tgt tgg aac gat tct gcc tgc atc aac        1998
Cys Ala Leu Arg Thr His Thr Cys Trp Asn Asp Ser Ala Cys Ile Asn
600                 605                 610                 615 ctg gca ggg ggc ttt gac tgt ctc tgc ccc tct ggg ccc tcc tgc tct        2046
Leu Ala Gly Gly Phe Asp Cys Leu Cys Pro Ser Gly Pro Ser Cys Ser
                620                 625                 630 ggt gac tgt cct cat gaa ggg ggg ctg aag cac aat ggc cag gtg tgg        2094
Gly Asp Cys Pro His Glu Gly Gly Leu Lys His Asn Gly Gln Val Trp
            635                 640                 645 acc ttg aaa gaa gac agg tgt tct gtc tgc tcc tgc aag gat ggc aag        2142
Thr Leu Lys Glu Asp Arg Cys Ser Val Cys Ser Cys Lys Asp Gly Lys
        650                 655                 660 ata ttc tgc cga cgg aca gct tgt gat gca cag aat cca agt gct gac        2190
Ile Phe Cys Arg Arg Thr Ala Cys Asp Ala Gln Asn Pro Ser Ala Asp
665                 670                 675 cta ttc tgt tgc cca gaa tgt gac acc aga gtc aca agt caa tgt tta        2238
Leu Phe Cys Cys Pro Glu Cys Asp Thr Arg Val Thr Ser Gln Cys Leu
680                 685                 690                 695 gac caa aat ggt cac aag ctg tat cga agt gga gac aat tgg acc cat        2286
Asp Gln Asn Gly His Lys Leu Tyr Arg Ser Gly Asp Asn Trp Thr His
                700                 705                 710 agc tgt cag cag tgt cgg tgt ctg gaa gga gag gta gat tgc tgg cca        2334
Ser Cys Gln Gln Cys Arg Cys Leu Glu Gly Glu Val Asp Cys Trp Pro
            715                 720                 725 ctc act tgc ccc aac ttg agc tgt gag tat aca gct atc tta gaa ggg        2382
Leu Thr Cys Pro Asn Leu Ser Cys Glu Tyr Thr Ala Ile Leu Glu Gly
        730                 735                 740 gaa tgt tgt ccc cgc tgt gtc agt gac ccc tgc cta gct gat aac atc        2430
Glu Cys Cys Pro Arg Cys Val Ser Asp Pro Cys Leu Ala Asp Asn Ile
745                 750                 755 acc tat gac atc aga aaa act tgc ctg gac agc tat ggt gtt tca cgg        2478
Thr Tyr Asp Ile Arg Lys Thr Cys Leu Asp Ser Tyr Gly Val Ser Arg
760                 765                 770                 775 ctt agt ggc tca gtg tgg acg atg gct gga tct ccc tgc aca acc tgt        2526
Leu Ser Gly Ser Val Trp Thr Met Ala Gly Ser Pro Cys Thr Thr Cys
                780                 785                 790 aaa tgc aag aat gga aga gtc tgt tgt tct gtg gat ttt gag tgt ctt        2574
Lys Cys Lys Asn Gly Arg Val Cys Cys Ser Val Asp Phe Glu Cys Leu
            795                 800                 805 caa aat aat tga agtatttaca gtggactcaa cgcagaagaa tggacgaaat           2626
Gln Asn Asn
        810 gaccatccaa cgtgattaag gataggaatc ggtagtttgg ttttttttgtt tgttttgttt    2686 ttttaaccac agataattgc caaagtttcc acctgaggac ggtgtttgga ggttgccttt     2746 tggacctacc actttgctca ttcttgctaa cctagtctag gtgacctaca gtgccgtgca     2806 tttaagtcaa tggttgttaa aagaagtttc ccgtgttgta aatcatgttt cccttatcag     2866 atcatttgca aatacattta aatgatctca tggtaaatgt tgatgtattt tttggtttat     2926 tttgtgtact aacataatag agagagactc agctcctttt atttatttg ttgatttatg     2986
```

```
gatcaaattc taaaataaag ttgcctgttg tgacttttgt cccatctact gcatacttag   3046
tgctgagatc cctgtaaaat gttttgatga aaatatgtat gtagagtcca gtcgcattat   3106
acatacattt catagtgctg aaccttctta aatgcctact cattcagctt aaacaggctg   3166
aagccaagta tgacaaagag gggaagggcc aaaaacataa tcaaagaata attttaaaga   3226
gaattcttgt ctctcttgca aaaaaaaaa                                     3255
```

<210> SEQ ID NO 2
<211> LENGTH: 810
<212> TYPE: PRT
<213> ORGANISM: Homo sapiens

<400> SEQUENCE: 2

```
Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
                20                  25                  30

Val Thr Glu Leu Asp Leu Val Asn Thr Thr Leu Gly Val Ala Gln Val
            35                  40                  45

Ser Gly Met His Asn Ala Ser Lys Ala Phe Leu Phe Gln Asp Ile Glu
        50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
```

```
                325                 330                 335
Tyr Gly Gly Lys Val Leu Ala Glu Gly Gln Arg Ile Leu Thr Lys Ser
                340                 345                 350
Cys Arg Glu Cys Arg Gly Gly Val Leu Val Lys Ile Thr Glu Met Cys
                355                 360                 365
Pro Pro Leu Asn Cys Ser Glu Lys Asp His Ile Leu Pro Glu Asn Gln
                370                 375                 380
Cys Cys Arg Val Cys Arg Gly His Asn Phe Cys Ala Glu Gly Pro Lys
385                 390                 395                 400
Cys Gly Glu Asn Ser Glu Cys Lys Asn Trp Asn Thr Lys Ala Thr Cys
                405                 410                 415
Glu Cys Lys Ser Gly Tyr Ile Ser Val Gln Gly Asp Ser Ala Tyr Cys
                420                 425                 430
Glu Asp Ile Asp Glu Cys Ala Ala Lys Met His Tyr Cys His Ala Asn
                435                 440                 445
Thr Val Cys Val Asn Leu Pro Gly Leu Tyr Arg Cys Asp Cys Val Pro
                450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
                500                 505                 510
Thr Ile Cys Arg Ala Phe Cys Glu Glu Gly Cys Arg Tyr Gly Gly Thr
                515                 520                 525
Cys Val Ala Pro Asn Lys Cys Val Cys Pro Ser Gly Phe Thr Gly Ser
                530                 535                 540
His Cys Glu Lys Asp Ile Asp Glu Cys Ser Gly Ile Ile Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
                580                 585                 590
Ser Cys Ile Asp Ile Asp Glu Cys Ala Leu Arg Thr His Thr Cys Trp
                595                 600                 605
Asn Asp Ser Ala Cys Ile Asn Leu Ala Gly Gly Phe Asp Cys Leu Cys
                610                 615                 620
Pro Ser Gly Pro Ser Cys Ser Gly Asp Cys Pro His Glu Gly Gly Leu
625                 630                 635                 640
Lys His Asn Gly Gln Val Trp Thr Leu Lys Glu Asp Arg Cys Ser Val
                645                 650                 655
Cys Ser Cys Lys Asp Gly Lys Ile Phe Cys Arg Arg Thr Ala Cys Asp
                660                 665                 670
Cys Gln Asn Pro Ser Ala Asp Leu Phe Cys Pro Glu Cys Asp Thr
                675                 680                 685
Arg Val Thr Ser Gln Cys Leu Asp Gln Asn Gly His Lys Leu Tyr Arg
                690                 695                 700
Ser Gly Asp Asn Trp Thr His Ser Cys Gln Gln Cys Arg Cys Leu Glu
705                 710                 715                 720
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
                740                 745                 750
```

```
Pro Cys Leu Ala Asp Asn Ile Thr Tyr Asp Ile Arg Lys Thr Cys Leu
        755                 760                 765

Asp Ser Tyr Gly Val Ser Arg Leu Ser Gly Ser Val Trp Thr Met Ala
770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810

<210> SEQ ID NO 3
<211> LENGTH: 3114
<212> TYPE: DNA
<213> ORGANISM: Homo sapiens
<220> FEATURE:
<221> NAME/KEY: CDS
<222> LOCATION: (154)..(2445)

<400> SEQUENCE: 3
atatgcgagc gcagcacccg gcgctgccga gccacctccc ccgccgcccg ctagcaagtt     60
tggcggctcc aagccaggcg cgcctcagga tccaggctca tttgcttcca cctagcttcg    120
gtgccccctg ctaggcgggg accctcgaga gcg atg ccg atg gat ttg att tta    174
                                    Met Pro Met Asp Leu Ile Leu
                                      1               5 gtt gtg tgg ttc tgt gtg tgc act gcc agg aca gtg gtg ggc ttt ggg     222
Val Val Trp Phe Cys Val Cys Thr Ala Arg Thr Val Val Gly Phe Gly
         10                  15                  20 atg gac cct gac ctt cag atg gat atc gtc acc gag ctt gac ctt gtg     270
Met Asp Pro Asp Leu Gln Met Asp Ile Val Thr Glu Leu Asp Leu Val
     25                  30                  35 aac acc acc ctt gga gtt gct cag gtg tct gga atg cac aat gcc agc     318
Asn Thr Thr Leu Gly Val Ala Gln Val Ser Gly Met His Asn Ala Ser
 40                  45                  50                  55 aaa gca ttt tta ttt caa gac ata gaa aga gag atc cat gca gct cct     366
Lys Ala Phe Leu Phe Gln Asp Ile Glu Arg Glu Ile His Ala Ala Pro
                 60                  65                  70 cat gtg agt gag aaa tta att cag ctg ttc cgg aac aag agt gaa ttc     414
His Val Ser Glu Lys Leu Ile Gln Leu Phe Arg Asn Lys Ser Glu Phe
             75                  80                  85 acc att ttg gcc act gta cag cag aag cca tcc act tca gga gtg ata     462
Thr Ile Leu Ala Thr Val Gln Gln Lys Pro Ser Thr Ser Gly Val Ile
         90                  95                 100 ctg tcc att cga gaa ctg gag cac agc tat ttt gaa ctg gag agc agt     510
Leu Ser Ile Arg Glu Leu Glu His Ser Tyr Phe Glu Leu Glu Ser Ser
    105                 110                 115 ggc ctg agg gat gag att cgg tat cac tac ata cac aat ggg aag cca     558
Gly Leu Arg Asp Glu Ile Arg Tyr His Tyr Ile His Asn Gly Lys Pro
120                 125                 130                 135 agg aca gag gca ctt cct tac cgc atg gca gat gga caa tgg cac aag     606
Arg Thr Glu Ala Leu Pro Tyr Arg Met Ala Asp Gly Gln Trp His Lys
                140                 145                 150 gtt gca ctg tca gtt agc gcc tct cat ctc ctg ctc cat gtc gac tgt     654
Val Ala Leu Ser Val Ser Ala Ser His Leu Leu Leu His Val Asp Cys
            155                 160                 165 aac agg att tat gag cgt gtg ata gac cct cca gat acc aac ctt ccc     702
Asn Arg Ile Tyr Glu Arg Val Ile Asp Pro Pro Asp Thr Asn Leu Pro
        170                 175                 180 cca gga atc aat tta tgg ctt ggc cag cgc aac caa aag cat ggc tta    750
Pro Gly Ile Asn Leu Trp Leu Gly Gln Arg Asn Gln Lys His Gly Leu
    185                 190                 195
```

```
ttc aaa ggg atc atc caa gat ggg aag atc atc ttt atg ccg aat gga      798
Phe Lys Gly Ile Ile Gln Asp Gly Lys Ile Ile Phe Met Pro Asn Gly
200                 205                 210                 215 tat ata aca cag tgt cca aat cta aat cac act tgc cca acc tgc agt      846
Tyr Ile Thr Gln Cys Pro Asn Leu Asn His Thr Cys Pro Thr Cys Ser
            220                 225                 230 gat ttc tta agc ctg gtg caa gga ata atg gat tta caa gag ctt ttg      894
Asp Phe Leu Ser Leu Val Gln Gly Ile Met Asp Leu Gln Glu Leu Leu
                235                 240                 245 gcc aag atg act gca aaa cta aat tat gca gag aca aga ctt agt caa      942
Ala Lys Met Thr Ala Lys Leu Asn Tyr Ala Glu Thr Arg Leu Ser Gln
            250                 255                 260 ttg gaa aac tgt cat tgt gag aag act tgt caa gtg agt gga ctg ctc      990
Leu Glu Asn Cys His Cys Glu Lys Thr Cys Gln Val Ser Gly Leu Leu
265                 270                 275 tat cga gat caa gac tct tgg gta gat ggt gac cat tgc agg aac tgc     1038
Tyr Arg Asp Gln Asp Ser Trp Val Asp Gly Asp His Cys Arg Asn Cys
280                 285                 290                 295 act tgc aaa agt ggt gcc gtg gaa tgc cga agg atg tcc tgt ccc cct     1086
Thr Cys Lys Ser Gly Ala Val Glu Cys Arg Arg Met Ser Cys Pro Pro
                300                 305                 310 ctc aat tgc tcc cca gac tcc ctc cca gtg cac att gct ggc cag tgc     1134
Leu Asn Cys Ser Pro Asp Ser Leu Pro Val His Ile Ala Gly Gln Cys
                315                 320                 325 tgt aag gtc tgc cga cca aaa tgt atc tat gga gga aaa gtt ctt gca     1182
Cys Lys Val Cys Arg Pro Lys Cys Ile Tyr Gly Gly Lys Val Leu Ala
            330                 335                 340 gaa ggc cag cgg att tta acc aag agc tgt cgg gaa tgc cga ggt gga     1230
Glu Gly Gln Arg Ile Leu Thr Lys Ser Cys Arg Glu Cys Arg Gly Gly
345                 350                 355 gtt tta gta aaa att aca gaa atg tgt cct cct ttg aac tgc tca gaa     1278
Val Leu Val Lys Ile Thr Glu Met Cys Pro Pro Leu Asn Cys Ser Glu
360                 365                 370                 375 aag gat cac att ctt cct gag aat cag tgc tgc cgt gtc tgt aga ggt     1326
Lys Asp His Ile Leu Pro Glu Asn Gln Cys Cys Arg Val Cys Arg Gly
                380                 385                 390 cat aac ttt tgt gca gaa gga cct aaa tgt ggt gaa aac tca gag tgc     1374
His Asn Phe Cys Ala Glu Gly Pro Lys Cys Gly Glu Asn Ser Glu Cys
                395                 400                 405 aaa aac tgg aat aca aaa gct act tgt gag tgc aag agt ggt tac atc     1422
Lys Asn Trp Asn Thr Lys Ala Thr Cys Glu Cys Lys Ser Gly Tyr Ile
            410                 415                 420 tct gtc cag gga gac tct gcc tac tgt gaa gat att gat gag tgt gca     1470
Ser Val Gln Gly Asp Ser Ala Tyr Cys Glu Asp Ile Asp Glu Cys Ala
            425                 430                 435 gct aag atg cat tac tgt cat gcc aat act gtg tgt gtc aac ctt cct     1518
Ala Lys Met His Tyr Cys His Ala Asn Thr Val Cys Val Asn Leu Pro
440                 445                 450                 455 ggg tta tat cgc tgt gac tgt gtc cca gga tac att cgt gtg gat gac     1566
Gly Leu Tyr Arg Cys Asp Cys Val Pro Gly Tyr Ile Arg Val Asp Asp
                460                 465                 470 ttc tct tgt aca gaa cac gat gaa tgt ggc agc ggc cag cac aac tgt     1614
Phe Ser Cys Thr Glu His Asp Glu Cys Gly Ser Gly Gln His Asn Cys
                475                 480                 485 gat gag aat gcc atc tgc acc aac act gtc cag gga cac agc tgc acc     1662
Asp Glu Asn Ala Ile Cys Thr Asn Thr Val Gln Gly His Ser Cys Thr
                490                 495                 500 tgc aaa ccg ggc tac gtg ggg aac ggg acc atc tgc aga gct ttc tgt     1710
Cys Lys Pro Gly Tyr Val Gly Asn Gly Thr Ile Cys Arg Ala Phe Cys
```

```
                    505                 510                 515
gaa gag ggc tgc aga tac ggt gga acg tgt gtg gct ccc aac aaa tgt      1758
Glu Glu Gly Cys Arg Tyr Gly Gly Thr Cys Val Ala Pro Asn Lys Cys
520                 525                 530                 535 gtc tgt cca tct gga ttc aca gga agc cac tgc gag aaa gac att gat      1806
Val Cys Pro Ser Gly Phe Thr Gly Ser His Cys Glu Lys Asp Ile Asp
                540                 545                 550 gaa tgt gcc tta aga act cac acc tgt tgg aac gat tct gcc tgc atc      1854
Glu Cys Ala Leu Arg Thr His Thr Cys Trp Asn Asp Ser Ala Cys Ile
                555                 560                 565 aac ctg gca ggg ggc ttt gac tgt ctc tgc ccc tct ggg ccc tcc tgc      1902
Asn Leu Ala Gly Gly Phe Asp Cys Leu Cys Pro Ser Gly Pro Ser Cys
570                 575                 580 tct ggt gac tgt cct cat gaa ggg ggg ctg aag cac aat ggc cag gtg      1950
Ser Gly Asp Cys Pro His Glu Gly Gly Leu Lys His Asn Gly Gln Val
                585                 590                 595 tgg acc ttg aaa gaa gac agg tgt tct gtc tgc tcc tgc aag gat ggc      1998
Trp Thr Leu Lys Glu Asp Arg Cys Ser Val Cys Ser Cys Lys Asp Gly
600                 605                 610                 615 aag ata ttc tgc cga cgg aca gct tgt gat tgc cag aat cca agt gct      2046
Lys Ile Phe Cys Arg Arg Thr Ala Cys Asp Cys Gln Asn Pro Ser Ala
                620                 625                 630 gac cta ttc tgt tgc cca gaa tgt gac acc aga gtc aca agt caa tgt      2094
Asp Leu Phe Cys Cys Pro Glu Cys Asp Thr Arg Val Thr Ser Gln Cys
                635                 640                 645 tta gac caa aat ggt cac aag ctg tat cga agt gga gac aat tgg acc      2142
Leu Asp Gln Asn Gly His Lys Leu Tyr Arg Ser Gly Asp Asn Trp Thr
                650                 655                 660 cat agc tgt cag cag tgt cgg tgt ctg gaa gga gag gta gat tgc tgg      2190
His Ser Cys Gln Gln Cys Arg Cys Leu Glu Gly Glu Val Asp Cys Trp
665                 670                 675 cca ctc act tgc ccc aac ttg agc tgt gag tat aca gct atc tta gaa      2238
Pro Leu Thr Cys Pro Asn Leu Ser Cys Glu Tyr Thr Ala Ile Leu Glu
680                 685                 690                 695 ggg gaa tgt tgt ccc cgc tgt gtc agt gac ccc tgc cta gct gat aac      2286
Gly Glu Cys Cys Pro Arg Cys Val Ser Asp Pro Cys Leu Ala Asp Asn
                700                 705                 710 atc acc tat gac atc aga aaa act tgc ctg gac agc tat ggt gtt tca      2334
Ile Thr Tyr Asp Ile Arg Lys Thr Cys Leu Asp Ser Tyr Gly Val Ser
                715                 720                 725 cgg ctt agt ggc tca gtg tgg acg atg gct gga tct ccc tgc aca acc      2382
Arg Leu Ser Gly Ser Val Trp Thr Met Ala Gly Ser Pro Cys Thr Thr
                730                 735                 740 tgt aaa tgc aag aat gga aga gtc tgt tgt tct gtg gat ttt gag tgt      2430
Cys Lys Cys Lys Asn Gly Arg Val Cys Cys Ser Val Asp Phe Glu Cys
745                 750                 755 ctt caa aat aat tga agtatttaca gtggactcaa cgcagaagaa tggacgaaat      2485
Leu Gln Asn Asn
760 gaccatccaa cgtgattaag gataggaatc ggtagtttgg ttttttttgtt tgttttgttt    2545 ttttaaccac agataattgc caaagtttcc acctgaggac ggtgtttgga ggttgccttt    2605 tggacctacc actttgctca ttcttgctaa cctagtctag gtgacctaca gtgccgtgca    2665 tttaagtcaa tggttgttaa aagaagtttc ccgtgttgta aatcatgttt cccttatcag    2725 atcatttgca aatacattta aatgatctca tggtaaatgt tgatgtattt tttggtttat    2785 tttgtgtact aacataatag agagagactc agctccttt atttattttg ttgatttatg     2845 gatcaaattc taaaataaag ttgcctgttg tgactttgt cccatctact gcatacttag     2905
```

```
tgctgagatc cctgtaaaat gttttgatga aaatatgtat gtagagtcca gtcgcattat    2965
acatacattt catagtgctg aaccttctta aatgcctact cattcagctt aaacaggctg    3025
aagccaagta tgacaaagag gggaagggcc aaaaacataa tcaaagaata attttaaaga    3085
gaattcttgt ctctcttgca aaaaaaaaa                                      3114
```

<210> SEQ ID NO 4
<211> LENGTH: 763
<212> TYPE: PRT
<213> ORGANISM: Homo sapiens

<400> SEQUENCE: 4

```
Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Gln Asp Gly Lys
        195                 200                 205

Ile Ile Phe Met Pro Asn Gly Tyr Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335
```

```
Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Glu Met Cys
            355                 360             365

Pro Pro Leu Asn Cys Ser Glu Lys Asp His Ile Leu Pro Glu Asn Gln
        370                 375             380

Cys Cys Arg Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
                405                 410                 415

Glu Cys Lys Ser Gly Tyr Ile Ser Val Gln Gly Asp Ser Ala Tyr Cys
            420                 425                 430

Glu Asp Ile Asp Glu Cys Ala Ala Lys Met His Tyr Cys His Ala Asn
            435                 440                 445

Thr Val Cys Val Asn Leu Pro Gly Leu Tyr Arg Cys Asp Cys Val Pro
        450                 455                 460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
            500                 505                 510

Thr Ile Cys Arg Ala Phe Cys Glu Glu Gly Cys Arg Tyr Gly Gly Thr
            515                 520                 525

Cys Val Ala Pro Asn Lys Cys Val Cys Pro Ser Gly Phe Thr Gly Ser
        530                 535                 540

His Cys Glu Lys Asp Ile Asp Glu Cys Ala Leu Arg Thr His Thr Cys
545                 550                 555                 560

Trp Asn Asp Ser Ala Cys Ile Asn Leu Ala Gly Gly Phe Asp Cys Leu
                565                 570                 575

Cys Pro Ser Gly Pro Ser Cys Ser Gly Asp Cys Pro His Glu Gly Gly
            580                 585                 590

Leu Lys His Asn Gly Gln Val Trp Thr Leu Lys Glu Asp Arg Cys Ser
            595                 600                 605

Val Cys Ser Cys Lys Asp Gly Lys Ile Phe Cys Arg Arg Thr Ala Cys
        610                 615                 620

Asp Cys Gln Asn Pro Ser Ala Asp Leu Phe Cys Cys Pro Glu Cys Asp
625                 630                 635                 640

Thr Arg Val Thr Ser Gln Cys Leu Asp Gln Asn Gly His Lys Leu Tyr
                645                 650                 655

Arg Ser Gly Asp Asn Trp Thr His Ser Cys Gln Gln Cys Arg Cys Leu
            660                 665                 670

Glu Gly Glu Val Asp Cys Trp Pro Leu Thr Cys Pro Asn Leu Ser Cys
            675                 680                 685

Glu Tyr Thr Ala Ile Leu Glu Gly Glu Cys Cys Pro Arg Cys Val Ser
        690                 695                 700

Asp Pro Cys Leu Ala Asp Asn Ile Thr Tyr Asp Ile Arg Lys Thr Cys
705                 710                 715                 720

Leu Asp Ser Tyr Gly Val Ser Arg Leu Ser Gly Ser Val Trp Thr Met
                725                 730                 735

Ala Gly Ser Pro Cys Thr Thr Cys Lys Cys Lys Asn Gly Arg Val Cys
            740                 745                 750
```

```
                    Cys Ser Val Asp Phe Glu Cys Leu Gln Asn Asn
                            755                 760

<210> SEQ ID NO 5
<211> LENGTH: 2791
<212> TYPE: DNA
<213> ORGANISM: Equus caballus
<220> FEATURE:
<221> NAME/KEY: CDS
<222> LOCATION: (1)..(2376)

<400> SEQUENCE: 5 atg ggc ttt ggg atg gac ccc gac ctt caa atg gat att atc acc gag      48
Met Gly Phe Gly Met Asp Pro Asp Leu Gln Met Asp Ile Ile Thr Glu
1               5                   10                  15 ctc gac ctc gtg aac acc acc ctt gga gtc act cag gtg tcc gga ctg      96
Leu Asp Leu Val Asn Thr Thr Leu Gly Val Thr Gln Val Ser Gly Leu
                20                  25                  30 cac aat gcc agc aaa gca ttt tta ttt caa gat gta gag aga gag atc     144
His Asn Ala Ser Lys Ala Phe Leu Phe Gln Asp Val Glu Arg Glu Ile
            35                  40                  45 cat gca gcc cca cac gtg agt gag aaa tta att cag ctg ttc cgg aat     192
His Ala Ala Pro His Val Ser Glu Lys Leu Ile Gln Leu Phe Arg Asn
        50                  55                  60 aag agt gaa ttc acc ttt ttg gcc act gtg cag cag aag ccg tca act     240
Lys Ser Glu Phe Thr Phe Leu Ala Thr Val Gln Gln Lys Pro Ser Thr
65                  70                  75                  80 tca gga gtg ata ctg tcc att cga gaa ctg gaa aac agt tat ttt gaa     288
Ser Gly Val Ile Leu Ser Ile Arg Glu Leu Glu Asn Ser Tyr Phe Glu
                85                  90                  95 ctg gag agc agt ggc ctg aga gat gag att cga tat cac tac aca cac     336
Leu Glu Ser Ser Gly Leu Arg Asp Glu Ile Arg Tyr His Tyr Thr His
                100                 105                 110 aag ggg aag ccc agg aca gag gca ctt ccc tac cgg atg gcg gac gga     384
Lys Gly Lys Pro Arg Thr Glu Ala Leu Pro Tyr Arg Met Ala Asp Gly
            115                 120                 125 cgg tgg cac aag gtg gcg ctg tca gtt agc gcc tct cat ctc ctg ctc     432
Arg Trp His Lys Val Ala Leu Ser Val Ser Ala Ser His Leu Leu Leu
        130                 135                 140 cac atc gac tgc aac agg att tat gaa cgt gtg ata gac act cct gag     480
His Ile Asp Cys Asn Arg Ile Tyr Glu Arg Val Ile Asp Thr Pro Glu
145                 150                 155                 160 acc aac ctc ccc cca gga agc aat ttg tgg ctg ggt cag cga aac caa     528
Thr Asn Leu Pro Pro Gly Ser Asn Leu Trp Leu Gly Gln Arg Asn Gln
                165                 170                 175 aag cac ggc tta ttc aaa gga atc atc caa gat gga aaa atc atc ttc     576
Lys His Gly Leu Phe Lys Gly Ile Ile Gln Asp Gly Lys Ile Ile Phe
                180                 185                 190 atg ccg aat gga tac ata aca cag tgt ccg aac ctg aat cgc act tgc     624
Met Pro Asn Gly Tyr Ile Thr Gln Cys Pro Asn Leu Asn Arg Thr Cys
            195                 200                 205 cca acg tgc agt gat ttc tta agc ctg gtg caa gga atc atg gat tta     672
Pro Thr Cys Ser Asp Phe Leu Ser Leu Val Gln Gly Ile Met Asp Leu
        210                 215                 220 caa gag ctt ctg gcc aag atg act gcg aaa cta aat tat gca gag aca     720
Gln Glu Leu Leu Ala Lys Met Thr Ala Lys Leu Asn Tyr Ala Glu Thr
225                 230                 235                 240 cga ctt agt caa ttg gaa aac tgc cac tgc gag aag acc tgt caa gtg     768
Arg Leu Ser Gln Leu Glu Asn Cys His Cys Glu Lys Thr Cys Gln Val
                245                 250                 255 agt gga ctg ctc tat aga gac cag gac tcc tgg gtt gat ggc gat cac     816
Ser Gly Leu Leu Tyr Arg Asp Gln Asp Ser Trp Val Asp Gly Asp His
```

```
                Ser Gly Leu Leu Tyr Arg Asp Gln Asp Ser Trp Val Asp Gly Asp His
                            260                 265                 270 tgt agg aac tgc acg tgc aaa agc ggc gct gtg gaa tgt cgg agg atg        864
Cys Arg Asn Cys Thr Cys Lys Ser Gly Ala Val Glu Cys Arg Arg Met
            275                 280                 285 tct tgt ccc cct ctc aat tgc tcc cca gac tcc ctc cct gtg cac gtt        912
Ser Cys Pro Pro Leu Asn Cys Ser Pro Asp Ser Leu Pro Val His Val
290                 295                 300 gcc ggc cag tgc tgt aag gtc tgc cga cca aaa tgt atc tac gga ggg        960
Ala Gly Gln Cys Cys Lys Val Cys Arg Pro Lys Cys Ile Tyr Gly Gly
305                 310                 315                 320 aaa gtc ctt gca gaa ggc cag cgg att tta acc aag agc tgt cgg gaa       1008
Lys Val Leu Ala Glu Gly Gln Arg Ile Leu Thr Lys Ser Cys Arg Glu
            325                 330                 335 tgc cga ggt gga gtt tta gtg aaa att aca gaa gcg tgc cct cct ttg       1056
Cys Arg Gly Gly Val Leu Val Lys Ile Thr Glu Ala Cys Pro Pro Leu
            340                 345                 350 aac tgc tca gac aag gat cac att ctc cca gag aat cag tgc tgc agc       1104
Asn Cys Ser Asp Lys Asp His Ile Leu Pro Glu Asn Gln Cys Cys Ser
            355                 360                 365 gtc tgc aga ggt cat aac ttt tgt gcg gaa gga cct aaa tgt ggt gaa       1152
Val Cys Arg Gly His Asn Phe Cys Ala Glu Gly Pro Lys Cys Gly Glu
370                 375                 380 aat tca gag tgc aaa aac tgg aat aca aaa gct act tgc gag tgc aag       1200
Asn Ser Glu Cys Lys Asn Trp Asn Thr Lys Ala Thr Cys Glu Cys Lys
385                 390                 395                 400 aat ggt tat atc tct gtc cag ggg gac tcc gcc tac tgt gaa gat atc       1248
Asn Gly Tyr Ile Ser Val Gln Gly Asp Ser Ala Tyr Cys Glu Asp Ile
                405                 410                 415 gat gag tgt gct gct aag atg cat tac tgt cgt gcc aat act gtg tgt       1296
Asp Glu Cys Ala Ala Lys Met His Tyr Cys Arg Ala Asn Thr Val Cys
            420                 425                 430 gtc aac ctg cct ggg tta tat cgg tgt gac tgt gtc ccg gga tac att       1344
Val Asn Leu Pro Gly Leu Tyr Arg Cys Asp Cys Val Pro Gly Tyr Ile
            435                 440                 445 cgc gtg gat gat ttc tct tgt aca gaa cat gac gaa tgt ggc agc ggg       1392
Arg Val Asp Asp Phe Ser Cys Thr Glu His Asp Glu Cys Gly Ser Gly
450                 455                 460 cag cac aac tgt gat gag aat gcc atc tgc acc aac act gtc cag gga       1440
Gln His Asn Cys Asp Glu Asn Ala Ile Cys Thr Asn Thr Val Gln Gly
465                 470                 475                 480 cac agc tgc acc tgc aaa ccg ggc tac gtg ggg aat ggg acc agc tgc       1488
His Ser Cys Thr Cys Lys Pro Gly Tyr Val Gly Asn Gly Thr Ser Cys
                485                 490                 495 aga gcg ttc tgc gaa gag ggc tgc aga tat ggc ggg aca tgc gtg gct       1536
Arg Ala Phe Cys Glu Glu Gly Cys Arg Tyr Gly Gly Thr Cys Val Ala
            500                 505                 510 cct aac aaa tgt gtc tgt cct tct gga ttc aca gga agc cac tgt gag       1584
Pro Asn Lys Cys Val Cys Pro Ser Gly Phe Thr Gly Ser His Cys Glu
            515                 520                 525 aaa gat att gat gaa tgt aca gag gga atc att gag tgc cac aac cat       1632
Lys Asp Ile Asp Glu Cys Thr Glu Gly Ile Ile Glu Cys His Asn His
            530                 535                 540 tcc cgc tgc gtt aac ctg cca ggg tgg tac cac tgt gag tgc aga agc       1680
Ser Arg Cys Val Asn Leu Pro Gly Trp Tyr His Cys Glu Cys Arg Ser
545                 550                 555                 560 ggt ttc cat gac gat ggg acc tat tca ctg tcc ggg gag tcc tgt att       1728
Gly Phe His Asp Asp Gly Thr Tyr Ser Leu Ser Gly Glu Ser Cys Ile
                565                 570                 575
```

```
gac att gat gaa tgt gcc tta aga act cac acc tgt tgg aat gat tct    1776
Asp Ile Asp Glu Cys Ala Leu Arg Thr His Thr Cys Trp Asn Asp Ser
            580                 585                 590 gcc tgc atc aac ttg gca ggg ggc ttc gac tgc ctg tgt ccc tca ggg    1824
Ala Cys Ile Asn Leu Ala Gly Gly Phe Asp Cys Leu Cys Pro Ser Gly
                595                 600                 605 cca tcc tgc tct ggt gac tgc ccc cac gaa gga gga ctg aag cgc aac    1872
Pro Ser Cys Ser Gly Asp Cys Pro His Glu Gly Gly Leu Lys Arg Asn
            610                 615                 620 ggg cag gtg tgg acc ctg aaa gaa gac agg tgt tct gtg tgt tcc tgc    1920
Gly Gln Val Trp Thr Leu Lys Glu Asp Arg Cys Ser Val Cys Ser Cys
625                 630                 635                 640 aag gat ggg aag ata ttc tgc cga cgg aca gct tgt gat tgc cag aat    1968
Lys Asp Gly Lys Ile Phe Cys Arg Arg Thr Ala Cys Asp Cys Gln Asn
                645                 650                 655 cca agc gtt gac ctt ttc tgt tgc cca gag tgt gac acc agg gtc aca    2016
Pro Ser Val Asp Leu Phe Cys Cys Pro Glu Cys Asp Thr Arg Val Thr
            660                 665                 670 agt caa tgt tta gac caa aat gga cac aag ctc tat cga agt gga gac    2064
Ser Gln Cys Leu Asp Gln Asn Gly His Lys Leu Tyr Arg Ser Gly Asp
        675                 680                 685 aat tgg act cac agc tgt cag cag tgc cgg tgt ctg gaa gga gag gta    2112
Asn Trp Thr His Ser Cys Gln Gln Cys Arg Cys Leu Glu Gly Glu Val
690                 695                 700 gat tgc tgg cca ctc act tgc ccc aga ttg agc tgt gag tac aca gcc    2160
Asp Cys Trp Pro Leu Thr Cys Pro Arg Leu Ser Cys Glu Tyr Thr Ala
705                 710                 715                 720 atc ttg gaa ggg gag tgt tgt cca cgc tgt gtc agc gac ccc tgc ctg    2208
Ile Leu Glu Gly Glu Cys Cys Pro Arg Cys Val Ser Asp Pro Cys Leu
                725                 730                 735 gcg gat aac atc gtc tat gac atc aga gaa act tgc ctg gac agc tat    2256
Ala Asp Asn Ile Val Tyr Asp Ile Arg Glu Thr Cys Leu Asp Ser Tyr
            740                 745                 750 gga gtt tca agg ctt agt ggc tca gtg tgg aca ttg gct gga tct ccc    2304
Gly Val Ser Arg Leu Ser Gly Ser Val Trp Thr Leu Ala Gly Ser Pro
        755                 760                 765 tgc acg acc tgc aaa tgc aag aat gga agt gtc tgc tgt tct gtg gat    2352
Cys Thr Thr Cys Lys Cys Lys Asn Gly Ser Val Cys Cys Ser Val Asp
770                 775                 780 ttg gag tgt ctt cat aat aat tga aggatttaaa atggactcat gatcgccaga   2406
Leu Glu Cys Leu His Asn Asn
785                 790 gaaaaatgga caaatgacca tccatgatga tgaaagaaca ggagttggtg tttttttac   2466 cacagacaat taccaaagtc tccgtctgag gaaggtgttt gcaggttgcc ttttggacct   2526
cccactctgc tcattcttgc taacctagtc taggtgacct acagtgcatt tcagtctatg   2586
gttgttaaaa gaagttttcc gtgttgtaaa tcacgtttcc cttaccaggt cattgcaaat   2646
acatttaaat gatttcatgg taaatgttga tgtattttt gggtttattt tgtgtactaa    2706
cataatagag attcagctgc ttttatttat tttttcttg acttttggat caaattcaac    2766
aaataaagtt gcctgttgtg atttt                                          2791

<210> SEQ ID NO 6
<211> LENGTH: 791
<212> TYPE: PRT
<213> ORGANISM: Equus caballus

<400> SEQUENCE: 6

Met Gly Phe Gly Met Asp Pro Asp Leu Gln Met Asp Ile Ile Thr Glu
```

-continued

```
1               5                   10                  15
Leu Asp Leu Val Asn Thr Thr Leu Gly Val Thr Gln Val Ser Gly Leu
                20                  25                  30

His Asn Ala Ser Lys Ala Phe Leu Phe Gln Asp Val Glu Arg Glu Ile
                35                  40                  45

His Ala Ala Pro His Val Ser Glu Lys Leu Ile Gln Leu Phe Arg Asn
 50                  55                  60

Lys Ser Glu Phe Thr Phe Leu Ala Thr Val Gln Gln Lys Pro Ser Thr
 65                  70                  75                  80

Ser Gly Val Ile Leu Ser Ile Arg Glu Leu Glu Asn Ser Tyr Phe Glu
                85                  90                  95

Leu Glu Ser Ser Gly Leu Arg Asp Glu Ile Arg Tyr His Tyr Thr His
                100                 105                 110

Lys Gly Lys Pro Arg Thr Glu Ala Leu Pro Tyr Arg Met Ala Asp Gly
                115                 120                 125

Arg Trp His Lys Val Ala Leu Ser Val Ser Ala Ser His Leu Leu Leu
                130                 135                 140

His Ile Asp Cys Asn Arg Ile Tyr Glu Arg Val Ile Asp Thr Pro Glu
145                 150                 155                 160

Thr Asn Leu Pro Pro Gly Ser Asn Leu Trp Leu Gly Gln Arg Asn Gln
                165                 170                 175

Lys His Gly Leu Phe Lys Gly Ile Ile Gln Asp Gly Lys Ile Ile Phe
                180                 185                 190

Met Pro Asn Gly Tyr Ile Thr Gln Cys Pro Asn Leu Asn Arg Thr Cys
                195                 200                 205

Pro Thr Cys Ser Asp Phe Leu Ser Leu Val Gln Gly Ile Met Asp Leu
                210                 215                 220

Gln Glu Leu Leu Ala Lys Met Thr Ala Lys Leu Asn Tyr Ala Glu Thr
225                 230                 235                 240

Arg Leu Ser Gln Leu Glu Asn Cys His Cys Glu Lys Thr Cys Gln Val
                245                 250                 255

Ser Gly Leu Leu Tyr Arg Asp Gln Asp Ser Trp Val Asp Gly Asp His
                260                 265                 270

Cys Arg Asn Cys Thr Cys Lys Ser Gly Ala Val Glu Cys Arg Arg Met
                275                 280                 285

Ser Cys Pro Pro Leu Asn Cys Ser Pro Asp Ser Leu Pro Val His Val
                290                 295                 300

Ala Gly Gln Cys Cys Lys Val Cys Arg Pro Lys Cys Ile Tyr Gly Gly
305                 310                 315                 320

Lys Val Leu Ala Glu Gly Gln Arg Ile Leu Thr Lys Ser Cys Arg Glu
                325                 330                 335

Cys Arg Gly Gly Val Leu Val Lys Ile Thr Glu Ala Cys Pro Pro Leu
                340                 345                 350

Asn Cys Ser Asp Lys Asp His Ile Leu Pro Glu Asn Gln Cys Cys Ser
                355                 360                 365

Val Cys Arg Gly His Asn Phe Cys Ala Glu Gly Pro Lys Cys Gly Glu
                370                 375                 380

Asn Ser Glu Cys Lys Asn Trp Asn Thr Lys Ala Thr Cys Glu Cys Lys
385                 390                 395                 400

Asn Gly Tyr Ile Ser Val Gln Gly Asp Ser Ala Tyr Cys Glu Asp Ile
                405                 410                 415

Asp Glu Cys Ala Ala Lys Met His Tyr Cys Arg Ala Asn Thr Val Cys
                420                 425                 430
```

```
Val Asn Leu Pro Gly Leu Tyr Arg Cys Asp Cys Val Pro Gly Tyr Ile
        435                 440                 445

Arg Val Asp Asp Phe Ser Cys Thr Glu His Asp Glu Cys Gly Ser Gly
450                 455                 460

Gln His Asn Cys Asp Glu Asn Ala Ile Cys Thr Asn Thr Val Gln Gly
465                 470                 475                 480

His Ser Cys Thr Cys Lys Pro Gly Tyr Val Gly Asn Gly Thr Ser Cys
                485                 490                 495

Arg Ala Phe Cys Glu Glu Gly Cys Arg Tyr Gly Gly Thr Cys Val Ala
                500                 505                 510

Pro Asn Lys Cys Val Cys Pro Ser Gly Phe Thr Gly Ser His Cys Glu
                515                 520                 525

Lys Asp Ile Asp Glu Cys Thr Glu Gly Ile Ile Glu Cys His Asn His
                530                 535                 540

Ser Arg Cys Val Asn Leu Pro Gly Trp Tyr His Cys Glu Cys Arg Ser
545                 550                 555                 560

Gly Phe His Asp Asp Gly Thr Tyr Ser Leu Ser Gly Glu Ser Cys Ile
                565                 570                 575

Asp Ile Asp Glu Cys Ala Leu Arg Thr His Thr Cys Trp Asn Asp Ser
                580                 585                 590

Ala Cys Ile Asn Leu Ala Gly Gly Phe Asp Cys Leu Cys Pro Ser Gly
                595                 600                 605

Pro Ser Cys Ser Gly Asp Cys Pro His Glu Gly Gly Leu Lys Arg Asn
                610                 615                 620

Gly Gln Val Trp Thr Leu Lys Glu Asp Arg Cys Ser Val Cys Ser Cys
625                 630                 635                 640

Lys Asp Gly Lys Ile Phe Cys Arg Arg Thr Ala Cys Asp Cys Gln Asn
                645                 650                 655

Pro Ser Val Asp Leu Phe Cys Cys Pro Glu Cys Asp Thr Arg Val Thr
                660                 665                 670

Ser Gln Cys Leu Asp Gln Asn Gly His Lys Leu Tyr Arg Ser Gly Asp
                675                 680                 685

Asn Trp Thr His Ser Cys Gln Gln Cys Arg Cys Leu Glu Gly Glu Val
                690                 695                 700

Asp Cys Trp Pro Leu Thr Cys Pro Arg Leu Ser Cys Glu Tyr Thr Ala
705                 710                 715                 720

Ile Leu Glu Gly Glu Cys Cys Pro Arg Cys Val Ser Asp Pro Cys Leu
                725                 730                 735

Ala Asp Asn Ile Val Tyr Asp Ile Arg Glu Thr Cys Leu Asp Ser Tyr
                740                 745                 750

Gly Val Ser Arg Leu Ser Gly Ser Val Trp Thr Leu Ala Gly Ser Pro
                755                 760                 765

Cys Thr Thr Cys Lys Cys Lys Asn Gly Ser Val Cys Cys Ser Val Asp
                770                 775                 780

Leu Glu Cys Leu His Asn Asn
785                 790

<210> SEQ ID NO 7
<211> LENGTH: 2285
<212> TYPE: DNA
<213> ORGANISM: Equus caballus
<220> FEATURE:
<221> NAME/KEY: CDS
<222> LOCATION: (1)..(2235)
```

<400> SEQUENCE: 7

```
atg ggc ttt ggg atg gac ccc gac ctt caa atg gat att atc acc gag      48
Met Gly Phe Gly Met Asp Pro Asp Leu Gln Met Asp Ile Ile Thr Glu
 1               5                  10                  15 ctc gac ctc gtg aac acc acc ctt gga gtc act cag gtg tcc gga ctg      96
Leu Asp Leu Val Asn Thr Thr Leu Gly Val Thr Gln Val Ser Gly Leu
                20                  25                  30 cac aat gcc agc aaa gca ttt tta ttt caa gat gta gag aga gag atc     144
His Asn Ala Ser Lys Ala Phe Leu Phe Gln Asp Val Glu Arg Glu Ile
             35                  40                  45 cat gca gcc cca cac gtg agt gag aaa tta att cag ctg ttc cgg aat     192
His Ala Ala Pro His Val Ser Glu Lys Leu Ile Gln Leu Phe Arg Asn
         50                  55                  60 aag agt gaa ttc acc ttt ttg gcc act gtg cag cag aag ccg tca act     240
Lys Ser Glu Phe Thr Phe Leu Ala Thr Val Gln Gln Lys Pro Ser Thr
 65                  70                  75                  80 tca gga gtg ata ctg tcc att cga gaa ctg gaa aac agt tat ttt gaa     288
Ser Gly Val Ile Leu Ser Ile Arg Glu Leu Glu Asn Ser Tyr Phe Glu
                 85                  90                  95 ctg gag agc agt ggc ctg aga gat gag att cga tat cac tac aca cac     336
Leu Glu Ser Ser Gly Leu Arg Asp Glu Ile Arg Tyr His Tyr Thr His
            100                 105                 110 aag ggg aag ccc agg aca gag gca ctt ccc tac cgg atg gcg gac gga     384
Lys Gly Lys Pro Arg Thr Glu Ala Leu Pro Tyr Arg Met Ala Asp Gly
        115                 120                 125 cgg tgg cac aag gtg gcg ctg tca gtt agc gcc tct cat ctc ctg ctc     432
Arg Trp His Lys Val Ala Leu Ser Val Ser Ala Ser His Leu Leu Leu
    130                 135                 140 cac atc gac tgc aac agg att tat gaa cgt gtg ata gac act cct gag     480
His Ile Asp Cys Asn Arg Ile Tyr Glu Arg Val Ile Asp Thr Pro Glu
145                 150                 155                 160 acc aac ctc ccc cca gga agc aat ttg tgg ctg ggt cag cga aac caa     528
Thr Asn Leu Pro Pro Gly Ser Asn Leu Trp Leu Gly Gln Arg Asn Gln
                165                 170                 175 aag cac ggc tta ttc aaa gga atc atc caa gat gga aaa atc atc ttc     576
Lys His Gly Leu Phe Lys Gly Ile Ile Gln Asp Gly Lys Ile Ile Phe
            180                 185                 190 atg ccg aat gga tac ata aca cag tgt ccg aac ctg aat cgc act tgc     624
Met Pro Asn Gly Tyr Ile Thr Gln Cys Pro Asn Leu Asn Arg Thr Cys
        195                 200                 205 cca acg tgc agt gat ttc tta agc ctg gtg caa gga atc atg gat tta     672
Pro Thr Cys Ser Asp Phe Leu Ser Leu Val Gln Gly Ile Met Asp Leu
    210                 215                 220 caa gag ctt ctg gcc aag atg act gcg aaa cta aat tat gca gag aca     720
Gln Glu Leu Leu Ala Lys Met Thr Ala Lys Leu Asn Tyr Ala Glu Thr
225                 230                 235                 240 cga ctt agt caa ttg gaa aac tgc cac tgc gag aag acc tgt caa gtg     768
Arg Leu Ser Gln Leu Glu Asn Cys His Cys Glu Lys Thr Cys Gln Val
                245                 250                 255 agt gga ctg ctc tat aga gac cag gac tcc tgg gtt gat ggc gat cac     816
Ser Gly Leu Leu Tyr Arg Asp Gln Asp Ser Trp Val Asp Gly Asp His
            260                 265                 270 tgt agg aac tgc acg tgc aaa agc ggc gct gtg gaa tgt cgg agg atg     864
Cys Arg Asn Cys Thr Cys Lys Ser Gly Ala Val Glu Cys Arg Arg Met
        275                 280                 285 tct tgt ccc cct ctc aat tgc tcc cca gac tcc ctc cct gtg cac gtt     912
Ser Cys Pro Pro Leu Asn Cys Ser Pro Asp Ser Leu Pro Val His Val
    290                 295                 300 gcc ggc cag tgc tgt aag gtc tgc cga cca aaa tgt atc tac gga ggg     960
```

| | | | | | | | | | | | | | | |
|---|---|---|---|---|---|---|---|---|---|---|---|---|---|---|
| Ala | Gly | Gln | Cys | Cys | Lys | Val | Cys | Arg | Pro | Lys | Cys | Ile | Tyr | Gly |
| 305 | | | | 310 | | | | 315 | | | | | | 320 |

```
aaa gtc ctt gca gaa ggc cag cgg att tta acc aag agc tgt cgg gaa     1008
Lys Val Leu Ala Glu Gly Gln Arg Ile Leu Thr Lys Ser Cys Arg Glu
                325                 330                 335 tgc cga ggt gga gtt tta gtg aaa att aca gaa gcg tgc cct cct ttg     1056
Cys Arg Gly Gly Val Leu Val Lys Ile Thr Glu Ala Cys Pro Pro Leu
            340                 345                 350 aac tgc tca gac aag gat cac att ctc cca gag aat cag tgc tgc agc     1104
Asn Cys Ser Asp Lys Asp His Ile Leu Pro Glu Asn Gln Cys Cys Ser
355                 360                 365 gtc tgc aga ggt cat aac ttt tgt gcg gaa gga cct aaa tgt ggt gaa     1152
Val Cys Arg Gly His Asn Phe Cys Ala Glu Gly Pro Lys Cys Gly Glu
    370                 375                 380 aat tca gag tgc aaa aac tgg aat aca aaa gct act tgc gag tgc aag     1200
Asn Ser Glu Cys Lys Asn Trp Asn Thr Lys Ala Thr Cys Glu Cys Lys
385                 390                 395                 400 aat ggt tat atc tct gtc cag ggg gac tcc gcc tac tgt gaa gat atc     1248
Asn Gly Tyr Ile Ser Val Gln Gly Asp Ser Ala Tyr Cys Glu Asp Ile
            405                 410                 415 gat gag tgt gct gct aag atg cat tac tgt cgt gcc aat act gtg tgt     1296
Asp Glu Cys Ala Ala Lys Met His Tyr Cys Arg Ala Asn Thr Val Cys
        420                 425                 430 gtc aac ctg cct ggg tta tat cgg tgt gac tgt gtc ccg gga tac att     1344
Val Asn Leu Pro Gly Leu Tyr Arg Cys Asp Cys Val Pro Gly Tyr Ile
            435                 440                 445 cgc gtg gat gat ttc tct tgt aca gaa cat gac gaa tgt ggc agc ggg     1392
Arg Val Asp Asp Phe Ser Cys Thr Glu His Asp Glu Cys Gly Ser Gly
    450                 455                 460 cag cac aac tgt gat gag aat gcc atc tgc acc aac act gtc cag gga     1440
Gln His Asn Cys Asp Glu Asn Ala Ile Cys Thr Asn Thr Val Gln Gly
465                 470                 475                 480 cac agc tgc acc tgc aaa ccg ggc tac gtg ggg aat ggg acc agc tgc     1488
His Ser Cys Thr Cys Lys Pro Gly Tyr Val Gly Asn Gly Thr Ser Cys
            485                 490                 495 aga gcg ttc tgc gaa gag ggc tgc aga tat ggc ggg aca tgc gtg gct     1536
Arg Ala Phe Cys Glu Glu Gly Cys Arg Tyr Gly Gly Thr Cys Val Ala
        500                 505                 510 cct aac aaa tgt gtc tgt cct tct gga ttc aca gga agc cac tgt gag     1584
Pro Asn Lys Cys Val Cys Pro Ser Gly Phe Thr Gly Ser His Cys Glu
            515                 520                 525 aaa gac att gat gaa tgt gcc tta aga act cac acc tgt tgg aat gat     1632
Lys Asp Ile Asp Glu Cys Ala Leu Arg Thr His Thr Cys Trp Asn Asp
    530                 535                 540 tct gcc tgc atc aac ttg gca ggg ggc ttc gac tgc ctg tgt ccc tca     1680
Ser Ala Cys Ile Asn Leu Ala Gly Gly Phe Asp Cys Leu Cys Pro Ser
545                 550                 555                 560 ggg cca tcc tgc tct ggt gac tgc ccc cac gaa gga gga ctg aag cgc     1728
Gly Pro Ser Cys Ser Gly Asp Cys Pro His Glu Gly Gly Leu Lys Arg
            565                 570                 575 aac ggg cag gtg tgg acc ctg aaa gaa gac agg tgt tct gtg tgt tcc     1776
Asn Gly Gln Val Trp Thr Leu Lys Glu Asp Arg Cys Ser Val Cys Ser
        580                 585                 590 tgc aag gat ggg aag ata ttc tgc cga cgg aca gct tgt gat tgc cag     1824
Cys Lys Asp Gly Lys Ile Phe Cys Arg Arg Thr Ala Cys Asp Cys Gln
            595                 600                 605 aat cca agc gtt gac ctt ttc tgt tgc cca gag tgt gac acc agg gtc     1872
Asn Pro Ser Val Asp Leu Phe Cys Cys Pro Glu Cys Asp Thr Arg Val
    610                 615                 620
```

-continued

| | | |
|---|---|---|
| aca agt caa tgt tta gac caa aat gga cac aag ctc tat cga agt gga<br>Thr Ser Gln Cys Leu Asp Gln Asn Gly His Lys Leu Tyr Arg Ser Gly<br>625                    630                    635                    640 | 1920 |
| gac aat tgg act cac agc tgt cag cag tgc cgg tgt ctg gaa gga gag<br>Asp Asn Trp Thr His Ser Cys Gln Gln Cys Arg Cys Leu Glu Gly Glu<br>                645                    650                    655 | 1968 |
| gta gat tgc tgg cca ctc act tgc ccc aga ttg agc tgt gag tac aca<br>Val Asp Cys Trp Pro Leu Thr Cys Pro Arg Leu Ser Cys Glu Tyr Thr<br>660                    665                    670 | 2016 |
| gcc atc ttg gaa ggg gag tgt tgt cca cgc tgt gtc agc gac ccc tgc<br>Ala Ile Leu Glu Gly Glu Cys Cys Pro Arg Cys Val Ser Asp Pro Cys<br>675                    680                    685 | 2064 |
| ctg gcg gat aac atc gtc tat gac atc aga gaa act tgc ctg gac agc<br>Leu Ala Asp Asn Ile Val Tyr Asp Ile Arg Glu Thr Cys Leu Asp Ser<br>690                    695                    700 | 2112 |
| tat gga gtt tca agg ctt agt ggc tca gtg tgg aca ttg gct gga tct<br>Tyr Gly Val Ser Arg Leu Ser Gly Ser Val Trp Thr Leu Ala Gly Ser<br>705                    710                    715                    720 | 2160 |
| ccc tgc acg acc tgc aaa tgc aag aat gga agt gtc tgc tgt tct gtg<br>Pro Cys Thr Thr Cys Lys Cys Lys Asn Gly Ser Val Cys Cys Ser Val<br>                725                    730                    735 | 2208 |
| gat ttg gag tgt ctt cat aat aat tga aggatttaaa atggactcat<br>Asp Leu Glu Cys Leu His Asn Asn<br>                740 | 2255 |
| gatcgccaga gaaaaatgga caaatgacca | 2285 |

<210> SEQ ID NO 8
<211> LENGTH: 744
<212> TYPE: PRT
<213> ORGANISM: Equus caballus

<400> SEQUENCE: 8

Met Gly Phe Gly Met Asp Pro Asp Leu Gln Met Asp Ile Ile Thr Glu
1                   5                       10                     15

Leu Asp Leu Val Asn Thr Thr Leu Gly Val Thr Gln Val Ser Gly Leu
                  20                       25                      30

His Asn Ala Ser Lys Ala Phe Leu Phe Gln Asp Val Glu Arg Glu Ile
            35                       40                       45

His Ala Ala Pro His Val Ser Glu Lys Leu Ile Gln Leu Phe Arg Asn
    50                       55                       60

Lys Ser Glu Phe Thr Phe Leu Ala Thr Val Gln Gln Lys Pro Ser Thr
65                    70                       75                    80

Ser Gly Val Ile Leu Ser Ile Arg Glu Leu Glu Asn Ser Tyr Phe Glu
                  85                       90                      95

Leu Glu Ser Ser Gly Leu Arg Asp Glu Ile Arg Tyr His Tyr Thr His
            100                       105                    110

Lys Gly Lys Pro Arg Thr Glu Ala Leu Pro Tyr Arg Met Ala Asp Gly
        115                       120                    125

Arg Trp His Lys Val Ala Leu Ser Val Ser Ala Ser His Leu Leu Leu
130                       135                       140

His Ile Asp Cys Asn Arg Ile Tyr Glu Arg Val Ile Asp Thr Pro Glu
145                   150                       155                    160

Thr Asn Leu Pro Pro Gly Ser Asn Leu Trp Leu Gly Gln Arg Asn Gln
                  165                       170                    175

Lys His Gly Leu Phe Lys Gly Ile Ile Gln Asp Gly Lys Ile Ile Phe
            180                       185                    190

Met Pro Asn Gly Tyr Ile Thr Gln Cys Pro Asn Leu Asn Arg Thr Cys

```
            195                 200                 205
Pro Thr Cys Ser Asp Phe Leu Ser Leu Val Gln Gly Ile Met Asp Leu
210                 215                 220

Gln Glu Leu Leu Ala Lys Met Thr Ala Lys Leu Asn Tyr Ala Glu Thr
225                 230                 235                 240

Arg Leu Ser Gln Leu Glu Asn Cys His Cys Glu Lys Thr Cys Gln Val
                245                 250                 255

Ser Gly Leu Leu Tyr Arg Asp Gln Asp Ser Trp Val Asp Gly Asp His
            260                 265                 270

Cys Arg Asn Cys Thr Cys Lys Ser Gly Ala Val Glu Cys Arg Arg Met
        275                 280                 285

Ser Cys Pro Pro Leu Asn Cys Ser Pro Asp Ser Leu Pro Val His Val
    290                 295                 300

Ala Gly Gln Cys Cys Lys Val Cys Arg Pro Lys Cys Ile Tyr Gly Gly
305                 310                 315                 320

Lys Val Leu Ala Glu Gly Gln Arg Ile Leu Thr Lys Ser Cys Arg Glu
                325                 330                 335

Cys Arg Gly Gly Val Leu Val Lys Ile Thr Glu Ala Cys Pro Pro Leu
            340                 345                 350

Asn Cys Ser Asp Lys Asp His Ile Leu Pro Glu Asn Gln Cys Cys Ser
        355                 360                 365

Val Cys Arg Gly His Asn Phe Cys Ala Glu Gly Pro Lys Cys Gly Glu
    370                 375                 380

Asn Ser Glu Cys Lys Asn Trp Asn Thr Lys Ala Thr Cys Glu Cys Lys
385                 390                 395                 400

Asn Gly Tyr Ile Ser Val Gln Gly Asp Ser Ala Tyr Cys Glu Asp Ile
                405                 410                 415

Asp Glu Cys Ala Ala Lys Met His Tyr Cys Arg Ala Asn Thr Val Cys
            420                 425                 430

Val Asn Leu Pro Gly Leu Tyr Arg Cys Asp Cys Val Pro Gly Tyr Ile
        435                 440                 445

Arg Val Asp Asp Phe Ser Cys Thr Glu His Asp Glu Cys Gly Ser Gly
    450                 455                 460

Gln His Asn Cys Asp Glu Asn Ala Ile Cys Thr Asn Thr Val Gln Gly
465                 470                 475                 480

His Ser Cys Thr Cys Lys Pro Gly Tyr Val Gly Asn Gly Thr Ser Cys
                485                 490                 495

Arg Ala Phe Cys Glu Glu Gly Cys Arg Tyr Gly Gly Thr Cys Val Ala
            500                 505                 510

Pro Asn Lys Cys Val Cys Pro Ser Gly Phe Thr Gly Ser His Cys Glu
        515                 520                 525

Lys Asp Ile Asp Glu Cys Ala Leu Arg Thr His Thr Cys Trp Asn Asp
    530                 535                 540

Ser Ala Cys Ile Asn Leu Ala Gly Gly Phe Asp Cys Leu Cys Pro Ser
545                 550                 555                 560

Gly Pro Ser Cys Ser Gly Asp Cys Pro His Glu Gly Gly Leu Lys Arg
                565                 570                 575

Asn Gly Gln Val Trp Thr Leu Lys Glu Asp Arg Cys Ser Val Cys Ser
            580                 585                 590

Cys Lys Asp Gly Lys Ile Phe Cys Arg Arg Thr Ala Cys Asp Cys Gln
        595                 600                 605

Asn Pro Ser Val Asp Leu Phe Cys Cys Pro Glu Cys Asp Thr Arg Val
    610                 615                 620
```

```
Thr Ser Gln Cys Leu Asp Gln Asn Gly His Lys Leu Tyr Arg Ser Gly
625                 630                 635                 640

Asp Asn Trp Thr His Ser Cys Gln Gln Cys Arg Cys Leu Glu Gly Glu
            645                 650                 655

Val Asp Cys Trp Pro Leu Thr Cys Pro Arg Leu Ser Cys Glu Tyr Thr
            660                 665                 670

Ala Ile Leu Glu Gly Glu Cys Cys Pro Arg Cys Val Ser Asp Pro Cys
            675                 680                 685

Leu Ala Asp Asn Ile Val Tyr Asp Ile Arg Glu Thr Cys Leu Asp Ser
    690                 695                 700

Tyr Gly Val Ser Arg Leu Ser Gly Ser Val Trp Thr Leu Ala Gly Ser
705                 710                 715                 720

Pro Cys Thr Thr Cys Lys Cys Lys Asn Gly Ser Val Cys Cys Ser Val
                725                 730                 735

Asp Leu Glu Cys Leu His Asn Asn
            740
```

<210> SEQ ID NO 9
<211> LENGTH: 2812
<212> TYPE: DNA
<213> ORGANISM: Mus musculus
<220> FEATURE:
<221> NAME/KEY: CDS
<222> LOCATION: (40)..(2472)

<400> SEQUENCE: 9

```
gcgttggtgc gccctgcttg gcggggggcc tccggagcg atg ccg atg gat gtg        54
                                           Met Pro Met Asp Val
                                           1               5 att tta gtt ttg tgg ttc tgt gtg tgc acc gcc agg aca gtg ctg ggc       102
Ile Leu Val Leu Trp Phe Cys Val Cys Thr Ala Arg Thr Val Leu Gly
                10                  15                  20 ttt ggg atg gac cct gac ctt cag atg gac atc atc act gaa ctt gac       150
Phe Gly Met Asp Pro Asp Leu Gln Met Asp Ile Ile Thr Glu Leu Asp
            25                  30                  35 ctt gtg aac acc acc ctg ggc gtc act cag gtg gct gga cta cac aat       198
Leu Val Asn Thr Thr Leu Gly Val Thr Gln Val Ala Gly Leu His Asn
        40                  45                  50 gcc agt aag gca ttt ctg ttt caa gat gta cag aga gag atc cac tca       246
Ala Ser Lys Ala Phe Leu Phe Gln Asp Val Gln Arg Glu Ile His Ser
    55                  60                  65 gcc cct cat gtg agt gag aag ctg atc cag cta ttc cgg aat aag agt       294
Ala Pro His Val Ser Glu Lys Leu Ile Gln Leu Phe Arg Asn Lys Ser
70                  75                  80                  85 gag ttt acc ttt ttg gct aca gtg cag cag aag ccg tcc acc tca ggg       342
Glu Phe Thr Phe Leu Ala Thr Val Gln Gln Lys Pro Ser Thr Ser Gly
                90                  95                 100 gtg ata ctg tcg atc cgg gag ctg gaa cac agc tat ttt gaa ctg gag       390
Val Ile Leu Ser Ile Arg Glu Leu Glu His Ser Tyr Phe Glu Leu Glu
            105                 110                 115 agc agt ggc cca aga gaa gag ata cgc tat cat tac atc cat ggc ggc       438
Ser Ser Gly Pro Arg Glu Glu Ile Arg Tyr His Tyr Ile His Gly Gly
        120                 125                 130 aag ccc agg act gag gcc ctt ccc tac cgc atg gcc gat gga cag tgg       486
Lys Pro Arg Thr Glu Ala Leu Pro Tyr Arg Met Ala Asp Gly Gln Trp
    135                 140                 145 cac aag gtc gcg ctg tct gtg agc gcc tct cac ctc cta ctc cat gtc       534
His Lys Val Ala Leu Ser Val Ser Ala Ser His Leu Leu Leu His Val
150                 155                 160                 165
```

```
gac tgc aat agg att tat gag cgt gtg ata gat cct ccg gag acc aac      582
Asp Cys Asn Arg Ile Tyr Glu Arg Val Ile Asp Pro Pro Glu Thr Asn
            170                 175                 180 ctt cct cca gga agc aat cta tgg ctt ggg caa cgt aat caa aag cat      630
Leu Pro Pro Gly Ser Asn Leu Trp Leu Gly Gln Arg Asn Gln Lys His
                185                 190                 195 ggc ttt ttc aaa gga atc atc caa gat ggc aag atc atc ttc atg ccg      678
Gly Phe Phe Lys Gly Ile Ile Gln Asp Gly Lys Ile Ile Phe Met Pro
            200                 205                 210 aac ggc ttc atc aca cag tgc ccc aac cta aat cgc act tgc cca aca      726
Asn Gly Phe Ile Thr Gln Cys Pro Asn Leu Asn Arg Thr Cys Pro Thr
                215                 220                 225 tgc agt gat ttc ctg agc ctg gtt caa gga ata atg gat ttg caa gag      774
Cys Ser Asp Phe Leu Ser Leu Val Gln Gly Ile Met Asp Leu Gln Glu
230                 235                 240                 245 ctt ttg gcc aag atg act gca aaa ctg aat tat gca gag acg aga ctt      822
Leu Leu Ala Lys Met Thr Ala Lys Leu Asn Tyr Ala Glu Thr Arg Leu
                250                 255                 260 ggt caa ctg gaa aat tgc cac tgt gag aag acc tgc caa gtg agt ggg      870
Gly Gln Leu Glu Asn Cys His Cys Glu Lys Thr Cys Gln Val Ser Gly
            265                 270                 275 ctg ctc tac agg gac caa gac tcc tgg gta gat ggt gac aac tgc agg      918
Leu Leu Tyr Arg Asp Gln Asp Ser Trp Val Asp Gly Asp Asn Cys Arg
            280                 285                 290 aac tgc aca tgc aaa agt ggt gct gtg gag tgc cga agg atg tcc tgt      966
Asn Cys Thr Cys Lys Ser Gly Ala Val Glu Cys Arg Arg Met Ser Cys
            295                 300                 305 ccc cca ctc aac tgt tcc cca gac tca ctt cct gtg cat att tct ggc     1014
Pro Pro Leu Asn Cys Ser Pro Asp Ser Leu Pro Val His Ile Ser Gly
310                 315                 320                 325 caa tgt tgt aaa gtt tgc aga cca aaa tgt atc tat gga gga aaa gtt     1062
Gln Cys Cys Lys Val Cys Arg Pro Lys Cys Ile Tyr Gly Gly Lys Val
                330                 335                 340 ctt gct gag ggc cag cgg att tta acc aag acc tgc cgg gaa tgt cga     1110
Leu Ala Glu Gly Gln Arg Ile Leu Thr Lys Thr Cys Arg Glu Cys Arg
            345                 350                 355 ggt gga gtc ttg gta aaa atc aca gaa gct tgc cct cct ttg aac tgc     1158
Gly Gly Val Leu Val Lys Ile Thr Glu Ala Cys Pro Pro Leu Asn Cys
            360                 365                 370 tca gag aag gat cat att ctt ccg gag aac cag tgc tgc agg gtc tgc     1206
Ser Glu Lys Asp His Ile Leu Pro Glu Asn Gln Cys Cys Arg Val Cys
375                 380                 385 cga ggt cat aac ttc tgt gca gaa gca cct aag tgt gga gaa aac tcg     1254
Arg Gly His Asn Phe Cys Ala Glu Ala Pro Lys Cys Gly Glu Asn Ser
390                 395                 400                 405 gaa tgc aaa aat tgg aat aca aaa gcg act tgt gag tgc aag aat gga     1302
Glu Cys Lys Asn Trp Asn Thr Lys Ala Thr Cys Glu Cys Lys Asn Gly
                410                 415                 420 tac atc tct gtc cag ggc aac tct gca tac tgt gaa gat atc gat gag     1350
Tyr Ile Ser Val Gln Gly Asn Ser Ala Tyr Cys Glu Asp Ile Asp Glu
                425                 430                 435 tgt gca gca aag atg cac tac tgt cat gcc aac acg gtg tgt gtc aac     1398
Cys Ala Ala Lys Met His Tyr Cys His Ala Asn Thr Val Cys Val Asn
                440                 445                 450 ttg ccg ggg tta tat cgc tgt gac tgc atc cca gga tac atc cgt gtg     1446
Leu Pro Gly Leu Tyr Arg Cys Asp Cys Ile Pro Gly Tyr Ile Arg Val
            455                 460                 465 gat gac ttc tct tgt acg gag cat gat gat tgt ggc agc gga caa cac     1494
Asp Asp Phe Ser Cys Thr Glu His Asp Asp Cys Gly Ser Gly Gln His
```

```
                470              475              480              485
       aac tgt gac aaa aat gcc atc tgt acc aac aca gtc cag gga cac agc      1542
       Asn Cys Asp Lys Asn Ala Ile Cys Thr Asn Thr Val Gln Gly His Ser
                   490              495              500 tgt acc tgc cag cca ggc tac gtg gga aat ggt act gtc tgc aaa gca      1590
       Cys Thr Cys Gln Pro Gly Tyr Val Gly Asn Gly Thr Val Cys Lys Ala
                   505              510              515 ttc tgt gaa gag ggt tgc aga tac gga ggt acc tgt gtg gcc cct aac      1638
       Phe Cys Glu Glu Gly Cys Arg Tyr Gly Gly Thr Cys Val Ala Pro Asn
                   520              525              530 aaa tgt gtc tgt cct tct gga ttc aca gga agc cac tgt gag aaa gat      1686
       Lys Cys Val Cys Pro Ser Gly Phe Thr Gly Ser His Cys Glu Lys Asp
                   535              540              545 att gat gaa tgt gca gag gga ttc gtt gag tgc cac aac cac tcc cgc      1734
       Ile Asp Glu Cys Ala Glu Gly Phe Val Glu Cys His Asn His Ser Arg
       550              555              560              565 tgc gtt aac ctt cca ggg tgg tac cac tgt gag tgc aga agc ggt ttc      1782
       Cys Val Asn Leu Pro Gly Trp Tyr His Cys Glu Cys Arg Ser Gly Phe
                   570              575              580 cat gac gat ggg acc tat tca ctg tcc ggg gag tcc tgc att gat att      1830
       His Asp Asp Gly Thr Tyr Ser Leu Ser Gly Glu Ser Cys Ile Asp Ile
                   585              590              595 gat gaa tgt gcc tta aga act cac act tgt tgg aat gac tct gcc tgc      1878
       Asp Glu Cys Ala Leu Arg Thr His Thr Cys Trp Asn Asp Ser Ala Cys
                   600              605              610 atc aac tta gca gga gga ttt gac tgc ctg tgt ccc tct ggg ccc tcc      1926
       Ile Asn Leu Ala Gly Gly Phe Asp Cys Leu Cys Pro Ser Gly Pro Ser
                   615              620              625 tgc tct ggt gac tgt ccc cac gaa ggg ggg ctg aag cat aat ggg cag      1974
       Cys Ser Gly Asp Cys Pro His Glu Gly Gly Leu Lys His Asn Gly Gln
       630              635              640              645 gtg tgg att ctg aga gaa gac agg tgt tca gtc tgt tcc tgt aag gat      2022
       Val Trp Ile Leu Arg Glu Asp Arg Cys Ser Val Cys Ser Cys Lys Asp
                   650              655              660 ggg aag ata ttc tgc cgg cgg aca gct tgt gat tgc cag aat cca aat      2070
       Gly Lys Ile Phe Cys Arg Arg Thr Ala Cys Asp Cys Gln Asn Pro Asn
                   665              670              675 gtt gac ctt ttc tgc tgc cca gag tgt gac acc agg gtc act agc caa      2118
       Val Asp Leu Phe Cys Cys Pro Glu Cys Asp Thr Arg Val Thr Ser Gln
                   680              685              690 tgt tta gat caa agc gga cag aag ctc tat cga agt gga gac aac tgg      2166
       Cys Leu Asp Gln Ser Gly Gln Lys Leu Tyr Arg Ser Gly Asp Asn Trp
                   695              700              705 acc cac agc tgc cag cag tgc cga tgt ctg gaa gga gag gca gac tgc      2214
       Thr His Ser Cys Gln Gln Cys Arg Cys Leu Glu Gly Glu Ala Asp Cys
       710              715              720              725 tgg cct cta gct tgc cct agt ttg agc tgt gaa tac aca gcc atc ttt      2262
       Trp Pro Leu Ala Cys Pro Ser Leu Ser Cys Glu Tyr Thr Ala Ile Phe
                   730              735              740 gaa gga gag tgt tgt ccc cgc tgt gtc agt gac ccc tgc ctg gct gat      2310
       Glu Gly Glu Cys Cys Pro Arg Cys Val Ser Asp Pro Cys Leu Ala Asp
                   745              750              755 aat att gcc tat gac atc aga aaa act tgc ctg gac agc tct ggt att      2358
       Asn Ile Ala Tyr Asp Ile Arg Lys Thr Cys Leu Asp Ser Ser Gly Ile
                   760              765              770 tcg agg ctg agc ggc gca gtg tgg aca atg gct gga tct ccc tgt aca      2406
       Ser Arg Leu Ser Gly Ala Val Trp Thr Met Ala Gly Ser Pro Cys Thr
                   775              780              785 acc tgt caa tgc aag aat ggg aga gtc tgc tgc tct gtg gat ctg gtg      2454
       Thr Cys Gln Cys Lys Asn Gly Arg Val Cys Cys Ser Val Asp Leu Val
```

```
Thr Cys Gln Cys Lys Asn Gly Arg Val Cys Cys Ser Val Asp Leu Val
790                 795                 800                 805 tgt ctt gag aat aac tga agattttaaa tggactcatc acatgagaaa              2502
Cys Leu Glu Asn Asn
                810 atggacaaaa tgaccatcca acctgaggaa gaggaggggc tgatttcttt ttcttttaa     2562 ccacagtcaa ttaccaaagt ctccatcaga ggaaggcgtt tgggttgcct ttaccacttt    2622 gctcatcctt gctgacctag tctagatgcc tgcagtaccg tgtatttcgg tcgatggttg    2682 ttgagtctcc gtgctgtaaa tcacatttcc cttgtcagat catttacaga tacatttaaa    2742 ggattccatg ataaatgtta aagtacccttt tgtttatttt gtgtaccaac ataatagaga   2802 cttggcacca                                                            2812

<210> SEQ ID NO 10
<211> LENGTH: 810
<212> TYPE: PRT
<213> ORGANISM: Mus musculus

<400> SEQUENCE: 10

Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Met Asp Ile
            20                  25                  30

Ile Thr Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
```

```
            275                 280                 285
Gly Asp Asn Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                    325                 330                 335

Tyr Gly Gly Lys Val Leu Ala Glu Gly Gln Arg Ile Leu Thr Lys Thr
                340                 345                 350

Cys Arg Glu Cys Arg Gly Gly Val Leu Val Lys Ile Thr Glu Ala Cys
            355                 360                 365

Pro Pro Leu Asn Cys Ser Glu Lys Asp His Ile Leu Pro Glu Asn Gln
370                 375                 380

Cys Cys Arg Val Cys Arg Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
            420                 425                 430

Glu Asp Ile Asp Glu Cys Ala Ala Lys Met His Tyr Cys His Ala Asn
        435                 440                 445

Thr Val Cys Val Asn Leu Pro Gly Leu Tyr Arg Cys Asp Cys Ile Pro
450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
            500                 505                 510

Thr Val Cys Lys Ala Phe Cys Glu Glu Gly Cys Arg Tyr Gly Gly Thr
        515                 520                 525

Cys Val Ala Pro Asn Lys Cys Val Cys Pro Ser Gly Phe Thr Gly Ser
    530                 535                 540

His Cys Glu Lys Asp Ile Asp Glu Cys Ala Glu Gly Phe Val Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
            580                 585                 590

Ser Cys Ile Asp Ile Asp Glu Cys Ala Leu Arg Thr His Thr Cys Trp
        595                 600                 605

Asn Asp Ser Ala Cys Ile Asn Leu Ala Gly Gly Phe Asp Cys Leu Cys
    610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
            660                 665                 670

Cys Gln Asn Pro Asn Val Asp Leu Phe Cys Cys Pro Glu Cys Asp Thr
        675                 680                 685

Arg Val Thr Ser Gln Cys Leu Asp Gln Ser Gly Gln Lys Leu Tyr Arg
690                 695                 700
```

```
Ser Gly Asp Asn Trp Thr His Ser Cys Gln Gln Cys Arg Cys Leu Glu
705                 710                 715                 720

Gly Glu Ala Asp Cys Trp Pro Leu Ala Cys Pro Ser Leu Ser Cys Glu
            725                 730                 735

Tyr Thr Ala Ile Phe Glu Gly Glu Cys Cys Pro Arg Cys Val Ser Asp
            740                 745                 750

Pro Cys Leu Ala Asp Asn Ile Ala Tyr Asp Ile Arg Lys Thr Cys Leu
        755                 760                 765

Asp Ser Ser Gly Ile Ser Arg Leu Ser Gly Ala Val Trp Thr Met Ala
        770                 775                 780

Gly Ser Pro Cys Thr Thr Cys Gln Cys Lys Asn Gly Arg Val Cys Cys
785                 790                 795                 800

Ser Val Asp Leu Val Cys Leu Glu Asn Asn
                805                 810

<210> SEQ ID NO 11
<211> LENGTH: 2915
<212> TYPE: DNA
<213> ORGANISM: Rattus norvegicus
<220> FEATURE:
<221> NAME/KEY: CDS
<222> LOCATION: (59)..(2491)

<400> SEQUENCE: 11
```

| | |
|---|---:|
| aagcactggt tccttgttag cgttggtgcg ccctgcttgg cggggggttct ccggagcg | 58 |
| atg ccg atg gat gtg att tta gtt ttg tgg ttc tgt gta tgc acc gcc<br>Met Pro Met Asp Val Ile Leu Val Leu Trp Phe Cys Val Cys Thr Ala<br>1               5                   10                  15 | 106 |
| agg aca gtg ttg ggc ttt ggg atg gac cct gac ctt cag ctg gac atc<br>Arg Thr Val Leu Gly Phe Gly Met Asp Pro Asp Leu Gln Leu Asp Ile<br>            20                  25                  30 | 154 |
| atc tca gag ctc gac ctg gtg aac acc acc ctg gga gtc acg cag gtg<br>Ile Ser Glu Leu Asp Leu Val Asn Thr Thr Leu Gly Val Thr Gln Val<br>        35                  40                  45 | 202 |
| gct gga ctg cac aac gcc agt aaa gca ttt cta ttt caa gat gta cag<br>Ala Gly Leu His Asn Ala Ser Lys Ala Phe Leu Phe Gln Asp Val Gln<br>    50                  55                  60 | 250 |
| aga gag atc cat tcg gcc cct cac gtg agt gag aag ctg atc cag cta<br>Arg Glu Ile His Ser Ala Pro His Val Ser Glu Lys Leu Ile Gln Leu<br>65                  70                  75                  80 | 298 |
| ttc cgg aat aag agc gag ttc acc ttt ttg gct aca gtg cag cag aaa<br>Phe Arg Asn Lys Ser Glu Phe Thr Phe Leu Ala Thr Val Gln Gln Lys<br>                85                  90                  95 | 346 |
| cca tcc acc tca ggg gtg ata ctg tcc atc cgg gag ctg gag cac agc<br>Pro Ser Thr Ser Gly Val Ile Leu Ser Ile Arg Glu Leu Glu His Ser<br>            100                 105                 110 | 394 |
| tat ttt gaa ctg gag agc agt ggc cca aga gaa gag ata cgc tac cat<br>Tyr Phe Glu Leu Glu Ser Ser Gly Pro Arg Glu Glu Ile Arg Tyr His<br>        115                 120                 125 | 442 |
| tac ata cat ggt gga aag ccc agg act gag gcc ctt ccc tac cgc atg<br>Tyr Ile His Gly Gly Lys Pro Arg Thr Glu Ala Leu Pro Tyr Arg Met<br>    130                 135                 140 | 490 |
| gca gac gga caa tgg cac aag gtc gcg ctg tca gtg agc gcc tct cac<br>Ala Asp Gly Gln Trp His Lys Val Ala Leu Ser Val Ser Ala Ser His<br>145                 150                 155                 160 | 538 |
| ctc ctg ctc cac atc gac tgc aat agg att tac gag cgt gtg ata gac<br>Leu Leu Leu His Ile Asp Cys Asn Arg Ile Tyr Glu Arg Val Ile Asp<br>                165                 170                 175 | 586 |

-continued

| | |
|---|---|
| cct ccg gag acc aac ctt cct cca gga agc aat ctg tgg ctt ggg caa<br>Pro Pro Glu Thr Asn Leu Pro Pro Gly Ser Asn Leu Trp Leu Gly Gln<br>180 185 190 | 634 |
| cgt aac caa aag cat ggc ttt ttc aaa gga atc atc caa gat ggt aag<br>Arg Asn Gln Lys His Gly Phe Phe Lys Gly Ile Ile Gln Asp Gly Lys<br>195 200 205 | 682 |
| atc atc ttc atg ccg aat ggt ttc atc aca cag tgt ccc aac ctc aat<br>Ile Ile Phe Met Pro Asn Gly Phe Ile Thr Gln Cys Pro Asn Leu Asn<br>210 215 220 | 730 |
| cgc act tgc cca aca tgc agt gac ttc ctg agc ctg gtt caa gga ata<br>Arg Thr Cys Pro Thr Cys Ser Asp Phe Leu Ser Leu Val Gln Gly Ile<br>225 230 235 240 | 778 |
| atg gat ttg caa gag ctt ttg gcc aag atg act gca aaa ctg aat tat<br>Met Asp Leu Gln Glu Leu Leu Ala Lys Met Thr Ala Lys Leu Asn Tyr<br>245 250 255 | 826 |
| gca gag acg aga ctt ggt caa ctg gaa aat tgc cac tgt gag aag acc<br>Ala Glu Thr Arg Leu Gly Gln Leu Glu Asn Cys His Cys Glu Lys Thr<br>260 265 270 | 874 |
| tgc caa gtg agt ggg ctc ctc tac agg gac caa gac tcc tgg gtg gat<br>Cys Gln Val Ser Gly Leu Leu Tyr Arg Asp Gln Asp Ser Trp Val Asp<br>275 280 285 | 922 |
| ggt gac aac tgt ggg aac tgc acg tgc aaa agt ggt gcc gtg gag tgc<br>Gly Asp Asn Cys Gly Asn Cys Thr Cys Lys Ser Gly Ala Val Glu Cys<br>290 295 300 | 970 |
| cgc agg atg tcc tgt ccc ccg ctc aac tgt tcc ccg gac tca ctt cct<br>Arg Arg Met Ser Cys Pro Pro Leu Asn Cys Ser Pro Asp Ser Leu Pro<br>305 310 315 320 | 1018 |
| gtg cac att tcc ggc cag tgt tgt aaa gtt tgc aga cca aaa tgt atc<br>Val His Ile Ser Gly Gln Cys Cys Lys Val Cys Arg Pro Lys Cys Ile<br>325 330 335 | 1066 |
| tat gga gga aaa gtt ctt gct gag ggc cag cgg att tta acc aag acc<br>Tyr Gly Gly Lys Val Leu Ala Glu Gly Gln Arg Ile Leu Thr Lys Thr<br>340 345 350 | 1114 |
| tgc cgg gaa tgt cga ggt gga gtc ttg gta aaa atc aca gaa gct tgc<br>Cys Arg Glu Cys Arg Gly Gly Val Leu Val Lys Ile Thr Glu Ala Cys<br>355 360 365 | 1162 |
| cct cct ttg aac tgc tca gca aag gat cat att ctt cca gag aat cag<br>Pro Pro Leu Asn Cys Ser Ala Lys Asp His Ile Leu Pro Glu Asn Gln<br>370 375 380 | 1210 |
| tgc tgc agg gtc tgc cca ggt cat aac ttc tgt gca gaa gca cct aag<br>Cys Cys Arg Val Cys Pro Gly His Asn Phe Cys Ala Glu Ala Pro Lys<br>385 390 395 400 | 1258 |
| tgc gga gaa aac tcg gaa tgc aaa aat tgg aat aca aaa gca acc tgt<br>Cys Gly Glu Asn Ser Glu Cys Lys Asn Trp Asn Thr Lys Ala Thr Cys<br>405 410 415 | 1306 |
| gag tgc aag aat gga tac atc tct gtc cag ggc aac tct gca tac tgt<br>Glu Cys Lys Asn Gly Tyr Ile Ser Val Gln Gly Asn Ser Ala Tyr Cys<br>420 425 430 | 1354 |
| gaa gat att gat gag tgt gca gct aaa atg cac tat tgt cat gcc aac<br>Glu Asp Ile Asp Glu Cys Ala Ala Lys Met His Tyr Cys His Ala Asn<br>435 440 445 | 1402 |
| acc gtg tgt gtc aac ttg ccg ggg ttg tat cgc tgt gac tgc gtc cca<br>Thr Val Cys Val Asn Leu Pro Gly Leu Tyr Arg Cys Asp Cys Val Pro<br>450 455 460 | 1450 |
| ggg tac atc cgt gtg gat gac ttc tct tgt acg gag cat gat gat tgt<br>Gly Tyr Ile Arg Val Asp Asp Phe Ser Cys Thr Glu His Asp Asp Cys<br>465 470 475 480 | 1498 |
| ggc agc gga caa cac aac tgc gac aaa aat gcc atc tgt acc aac aca<br>Gly Ser Gly Gln His Asn Cys Asp Lys Asn Ala Ile Cys Thr Asn Thr<br>485 490 495 | 1546 |

```
gtc cag gga cac agc tgc acc tgc cag ccg ggt tac gtg gga aat ggc    1594
Val Gln Gly His Ser Cys Thr Cys Gln Pro Gly Tyr Val Gly Asn Gly
            500                 505                 510 acc atc tgc aaa gca ttc tgt gaa gag ggt tgc aga tac gga ggt acc    1642
Thr Ile Cys Lys Ala Phe Cys Glu Glu Gly Cys Arg Tyr Gly Gly Thr
        515                 520                 525 tgt gtg gct cct aac aag tgt gtc tgt cct tct gga ttc acg gga agc    1690
Cys Val Ala Pro Asn Lys Cys Val Cys Pro Ser Gly Phe Thr Gly Ser
530                 535                 540 cac tgt gag aaa gat att gat gaa tgc gca gag gga ttc gtt gaa tgc    1738
His Cys Glu Lys Asp Ile Asp Glu Cys Ala Glu Gly Phe Val Glu Cys
545                 550                 555                 560 cac aac tac tcc cgc tgt gtt aac ctg cca ggg tgg tac cac tgt gag    1786
His Asn Tyr Ser Arg Cys Val Asn Leu Pro Gly Trp Tyr His Cys Glu
                565                 570                 575 tgc aga agc ggt ttc cat gac gat ggg acc tac tca ctg tcc ggg gag    1834
Cys Arg Ser Gly Phe His Asp Asp Gly Thr Tyr Ser Leu Ser Gly Glu
            580                 585                 590 tcc tgc att gat atc gat gaa tgt gcc tta aga act cac act tgt tgg    1882
Ser Cys Ile Asp Ile Asp Glu Cys Ala Leu Arg Thr His Thr Cys Trp
        595                 600                 605 aat gac tct gcc tgc atc aac tta gca gga gga ttt gac tgc ctg tgt    1930
Asn Asp Ser Ala Cys Ile Asn Leu Ala Gly Gly Phe Asp Cys Leu Cys
610                 615                 620 ccc tct ggg ccc tcc tgc tct ggt gac tgt ccc cac gaa gga ggg ctg    1978
Pro Ser Gly Pro Ser Cys Ser Gly Asp Cys Pro His Glu Gly Gly Leu
625                 630                 635                 640 aag cat aat ggg cag gtg tgg att ctg aga gaa gac agg tgt tca gtc    2026
Lys His Asn Gly Gln Val Trp Ile Leu Arg Glu Asp Arg Cys Ser Val
                645                 650                 655 tgt tcc tgc aag gat ggg aag ata ttc tgc cgg cgg aca gct tgt gat    2074
Cys Ser Cys Lys Asp Gly Lys Ile Phe Cys Arg Arg Thr Ala Cys Asp
            660                 665                 670 tgc cag aat cca aat gtt gac ctt ttt tgc tgc cca gag tgc gat acc    2122
Cys Gln Asn Pro Asn Val Asp Leu Phe Cys Cys Pro Glu Cys Asp Thr
        675                 680                 685 agg gtc acc agc caa tgt tta gat caa agt gga cag aag ctc tat cga    2170
Arg Val Thr Ser Gln Cys Leu Asp Gln Ser Gly Gln Lys Leu Tyr Arg
690                 695                 700 agt gga gac aac tgg acc cac agc tgc cag cag tgc cga tgt ctg gaa    2218
Ser Gly Asp Asn Trp Thr His Ser Cys Gln Gln Cys Arg Cys Leu Glu
705                 710                 715                 720 gga gag gca gac tgc tgg cct ctg gct tgc cct agt ttg ggc tgt gaa    2266
Gly Glu Ala Asp Cys Trp Pro Leu Ala Cys Pro Ser Leu Gly Cys Glu
                725                 730                 735 tac aca gcc atg ttt gaa ggg gag tgt tgt ccc cga tgt gtc agt gac    2314
Tyr Thr Ala Met Phe Glu Gly Glu Cys Cys Pro Arg Cys Val Ser Asp
            740                 745                 750 ccc tgc ctg gct ggt aat att gcc tat gac atc aga aaa act tgc ctg    2362
Pro Cys Leu Ala Gly Asn Ile Ala Tyr Asp Ile Arg Lys Thr Cys Leu
        755                 760                 765 gac agc ttt ggt gtt tcg agg ctg agc gga gcc gtg tgg aca atg gct    2410
Asp Ser Phe Gly Val Ser Arg Leu Ser Gly Ala Val Trp Thr Met Ala
770                 775                 780 gga tct cct tgt aca acc tgc aaa tgc aag aat ggg aga gtc tgc tgc    2458
Gly Ser Pro Cys Thr Thr Cys Lys Cys Lys Asn Gly Arg Val Cys Cys
785                 790                 795                 800 tct gtg gat ctg gag tgt att gag aat aac tga agatttaaa tggactcgtc   2511
Ser Val Asp Leu Glu Cys Ile Glu Asn Asn
```

```
                       805                810
acgtgagaaa atgggcaaaa tgatcatccc acctgaggaa gaagaggggc tgatttcttt    2571 ttcttttaa ccacagtcaa ttaccaaagt ctccatctga ggaaggcgtt tggattgcct     2631
ttgccacttt gctcatcctt gctgacctag tctagatgcc tgcagtaccg tgcatttcgg    2691
tcgatggttg ttgagtctca gtgttgtaaa tcgcatttcc ctcgtcagat catttacaga   2751
tacatttaaa ggggttccat gataaatgtt aatgtaactt tgtttatttt tgtgtactga   2811
cataatagag acttggcacc atttatttat ttttcttgat ttttggatca aattctaaaa   2871
ataaagttgc ctgttgcgaa aaaaaaaaaa aaaaaaaaaa aaaa                    2915
```

<210> SEQ ID NO 12
<211> LENGTH: 810
<212> TYPE: PRT
<213> ORGANISM: Rattus norvegicus

<400> SEQUENCE: 12

```
Met Pro Met Asp Val Ile Leu Val Leu Trp Phe Cys Val Cys Thr Ala
1               5                   10                  15

Arg Thr Val Leu Gly Phe Gly Met Asp Pro Asp Leu Gln Leu Asp Ile
            20                  25                  30

Ile Ser Glu Leu Asp Leu Val Asn Thr Thr Leu Gly Val Thr Gln Val
        35                  40                  45

Ala Gly Leu His Asn Ala Ser Lys Ala Phe Leu Phe Gln Asp Val Gln
    50                  55                  60

Arg Glu Ile His Ser Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Pro Arg Glu Ile Arg Tyr His
        115                 120                 125

Tyr Ile His Gly Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
            180                 185                 190

Arg Asn Gln Lys His Gly Phe Phe Lys Gly Ile Ile Gln Asp Gly Lys
        195                 200                 205

Ile Ile Phe Met Pro Asn Gly Phe Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Gly Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp Asn Cys Gly Asn Cys Thr Cys Lys Ser Gly Ala Val Glu Cys
```

```
            290                 295                 300
Arg Arg Met Ser Cys Pro Pro Leu Asn Cys Ser Pro Asp Ser Leu Pro
305                 310                 315                 320

Val His Ile Ser Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Thr
                340                 345                 350

Cys Arg Glu Cys Arg Gly Gly Val Leu Val Lys Ile Thr Glu Ala Cys
                355                 360                 365

Pro Pro Leu Asn Cys Ser Ala Lys Asp His Ile Leu Pro Glu Asn Gln
370                 375                 380

Cys Cys Arg Val Cys Pro Gly His Asn Phe Cys Ala Glu Ala Pro Lys
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asn Ser Ala Tyr Cys
                420                 425                 430

Glu Asp Ile Asp Glu Cys Ala Ala Lys Met His Tyr Cys His Ala Asn
                435                 440                 445

Thr Val Cys Val Asn Leu Pro Gly Leu Tyr Arg Cys Asp Cys Val Pro
450                 455                 460

Gly Tyr Ile Arg Val Asp Asp Phe Ser Cys Thr Glu His Asp Asp Cys
465                 470                 475                 480

Gly Ser Gly Gln His Asn Cys Asp Lys Asn Ala Ile Cys Thr Asn Thr
                485                 490                 495

Val Gln Gly His Ser Cys Thr Cys Gln Pro Gly Tyr Val Gly Asn Gly
                500                 505                 510

Thr Ile Cys Lys Ala Phe Cys Glu Glu Gly Cys Arg Tyr Gly Gly Thr
                515                 520                 525

Cys Val Ala Pro Asn Lys Cys Val Cys Pro Ser Gly Phe Thr Gly Ser
                530                 535                 540

His Cys Glu Lys Asp Ile Asp Glu Cys Ala Glu Gly Phe Val Glu Cys
545                 550                 555                 560

His Asn Tyr Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
                595                 600                 605

Asn Asp Ser Ala Cys Ile Asn Leu Ala Gly Gly Phe Asp Cys Leu Cys
610                 615                 620

Pro Ser Gly Pro Ser Cys Ser Gly Asp Cys Pro His Glu Gly Gly Leu
625                 630                 635                 640

Lys His Asn Gly Gln Val Trp Ile Leu Arg Glu Asp Arg Cys Ser Val
                645                 650                 655

Cys Ser Cys Lys Asp Gly Lys Ile Phe Cys Arg Arg Thr Ala Cys Asp
                660                 665                 670

Cys Gln Asn Pro Asn Val Asp Leu Phe Cys Cys Pro Glu Cys Asp Thr
                675                 680                 685

Arg Val Thr Ser Gln Cys Leu Asp Gln Ser Gly Gln Lys Leu Tyr Arg
                690                 695                 700

Ser Gly Asp Asn Trp Thr His Ser Cys Gln Gln Cys Arg Cys Leu Glu
705                 710                 715                 720
```

Gly Glu Ala Asp Cys Trp Pro Leu Ala Cys Pro Ser Leu Gly Cys Glu
                725                 730                 735

Tyr Thr Ala Met Phe Glu Gly Glu Cys Cys Pro Arg Cys Val Ser Asp
                740                 745                 750

Pro Cys Leu Ala Gly Asn Ile Ala Tyr Asp Ile Arg Lys Thr Cys Leu
            755                 760                 765

Asp Ser Phe Gly Val Ser Arg Leu Ser Gly Ala Val Trp Thr Met Ala
770                 775                 780

Gly Ser Pro Cys Thr Thr Cys Lys Cys Lys Asn Gly Arg Val Cys Cys
785                 790                 795                 800

Ser Val Asp Leu Glu Cys Ile Glu Asn Asn
            805                 810

<210> SEQ ID NO 13
<211> LENGTH: 810
<212> TYPE: PRT
<213> ORGANISM: Felis catus

<400> SEQUENCE: 13

Met Pro Arg Asp Val Ile Leu Val Val Trp Phe Cys Val Cys Thr Ala
1               5                   10                  15

Arg Thr Val Val Gly Phe Gly Thr Asp Pro Asp Leu Gln Val Asp Ile
                20                  25                  30

Ile Ala Glu Leu Asp Leu Val Asn Thr Thr Ala Gly Val Thr Gln Val
            35                  40                  45

Ser Gly Leu His Asn Ala Ser Lys Ala Tyr Leu Phe Gln Glu Thr Glu
        50                  55                  60

Arg Glu Ile His Ala Ala Pro His Val Ser Glu Lys Leu Ile Gln Leu
65                  70                  75                  80

Phe Arg Asn Lys Ser Glu Phe Ser Phe Leu Ala Thr Val Gln Gln Lys
                85                  90                  95

Pro Ser Thr Ser Gly Val Ile Leu Ser Ile Arg Glu Leu Glu His Ser
                100                 105                 110

Tyr Phe Glu Leu Glu Ser Ser Gly Leu Arg Asp Glu Ile Arg Tyr His
            115                 120                 125

Tyr Ile His Asn Gly Lys Pro Arg Thr Glu Ala Leu Pro Tyr Arg Met
        130                 135                 140

Ala Asp Gly Gln Trp His Lys Val Ala Leu Ser Ile Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Val Trp Leu Gly Gln
                180                 185                 190

Arg Asn Gln Lys His Gly Leu Phe Lys Gly Ile Ile Gln Asp Gly Lys
            195                 200                 205

Ile Ile Phe Met Pro Asn Gly Tyr Ile Thr Gln Cys Pro Asn Leu Asn
        210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Asn Gln Leu Glu Asn Cys His Cys Glu Lys Thr
                260                 265                 270

Cys Gln Val Ser Gly Leu Leu Tyr Arg Asp Gln Asp Ser Trp Val Asp

```
              275                 280                 285
Gly Asp His Cys Arg Asn Cys Thr Cys Lys Ser Gly Ala Val Glu Cys
290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                    325                 330                 335

Tyr Gly Gly Lys Val Leu Ala Glu Gly Gln Arg Ile Leu Thr Lys Ser
                340                 345                 350

Cys Arg Glu Cys Arg Gly Gly Val Leu Val Lys Ile Thr Asp Ala Cys
            355                 360                 365

Pro Pro Leu Asn Cys Ser Glu Lys Asp His Ile Leu Pro Glu Asn Gln
370                 375                 380

Cys Cys Ser Val Cys Arg Gly His Asn Phe Cys Ala Glu Gly Pro Thr
385                 390                 395                 400

Cys Gly Glu Asn Ser Glu Cys Lys Asn Trp Asn Thr Lys Ala Thr Cys
                405                 410                 415

Glu Cys Lys Asn Gly Tyr Ile Ser Val Gln Gly Asp Ser Ala Tyr Cys
                420                 425                 430

Glu Asp Ile Asp Glu Cys Ala Ala Lys Met His Tyr Cys His Ala Asn
            435                 440                 445

Thr Val Cys Val Asn Leu Pro Gly Leu Tyr Arg Cys Asp Cys Val Pro
450                 455                 460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
                500                 505                 510

Thr Ile Cys Arg Ala Phe Cys Gln Glu Gly Cys Arg Tyr Gly Gly Thr
            515                 520                 525

Cys Val Ser Pro Asn Lys Cys Val Cys Pro Ser Gly Phe Thr Gly Ser
530                 535                 540

His Cys Glu Lys Asp Ile Asp Glu Cys Thr Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
            595                 600                 605

Asn Asp Ser Ala Cys Ile Asn Leu Ala Gly Gly Phe Asp Cys Leu Cys
610                 615                 620

Pro Ser Gly Pro Ser Cys Ser Gly Asp Cys Pro His Glu Gly Gly Leu
625                 630                 635                 640

Lys Arg Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
                660                 665                 670

Cys Gln Asn Pro Ser Val Asp Leu Phe Cys Cys Pro Glu Cys Asp Thr
            675                 680                 685

Arg Val Thr Ser Gln Cys Leu Asp Gln Asn Gly His Lys Leu Tyr Arg
690                 695                 700
```

```
Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
            725                 730                 735

Tyr Thr Ala Met Leu Glu Gly Glu Cys Cys Pro Arg Cys Val Ser Asp
        740                 745                 750

Pro Cys Leu Ala Asp Asn Ile Ala Tyr Asp Ile Arg Lys Thr Cys Leu
    755                 760                 765

Asp Ser Tyr Gly Ile Ser Arg Leu Ser Gly Ala Val Trp Thr Met Ala
770                 775                 780

Gly Ser Pro Cys Thr Thr Cys Lys Cys Lys Asn Gly Ser Val Cys Cys
785                 790                 795                 800

Ser Val Asp Leu Glu Cys Leu His Asn Asn
            805                 810

<210> SEQ ID NO 14
<211> LENGTH: 763
<212> TYPE: PRT
<213> ORGANISM: Felis catus

<400> SEQUENCE: 14

Met Pro Arg Asp Val Ile Leu Val Val Trp Phe Cys Val Cys Thr Ala
1               5                   10                  15

Arg Thr Val Val Gly Phe Gly Thr Asp Pro Asp Leu Gln Val Asp Ile
            20                  25                  30

Ile Ala Glu Leu Asp Leu Val Asn Thr Thr Ala Gly Val Thr Gln Val
        35                  40                  45

Ser Gly Leu His Asn Ala Ser Lys Ala Tyr Leu Phe Gln Glu Thr Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Ser Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Ile Ser Ala Ser His
145                 150                 155                 160

Leu Leu Leu His Val Asp Cys Asn Arg Ile Tyr Glu Arg Val Ile Asp
                165                 170                 175

Pro Pro Glu Thr Asn Leu Pro Pro Gly Ser Asn Val Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Asn Gln Leu Glu Asn Cys His Cys Glu Lys Thr
```

-continued

```
                260                 265                 270
Cys Gln Val Ser Gly Leu Leu Tyr Arg Asp Gln Asp Ser Trp Val Asp
            275                 280                 285
Gly Asp His Cys Arg Asn Cys Thr Cys Lys Ser Gly Ala Val Glu Cys
        290                 295                 300
Arg Arg Met Ser Cys Pro Pro Leu Asn Cys Ser Pro Asp Ser Leu Pro
305                 310                 315                 320
Val His Ile Ala Gly Gln Cys Cys Lys Val Cys Arg Pro Lys Cys Ile
                325                 330                 335
Tyr Gly Gly Lys Val Leu Ala Glu Gly Gln Arg Ile Leu Thr Lys Ser
            340                 345                 350
Cys Arg Glu Cys Arg Gly Gly Val Leu Val Lys Ile Thr Asp Ala Cys
        355                 360                 365
Pro Pro Leu Asn Cys Ser Glu Lys Asp His Ile Leu Pro Glu Asn Gln
        370                 375                 380
Cys Cys Ser Val Cys Arg Gly His Asn Phe Cys Ala Glu Gly Pro Thr
385                 390                 395                 400
Cys Gly Glu Asn Ser Glu Cys Lys Asn Trp Asn Thr Lys Ala Thr Cys
                405                 410                 415
Glu Cys Lys Asn Gly Tyr Ile Ser Val Gln Gly Asp Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Gln Glu Gly Cys Arg Tyr Gly Gly Thr
        515                 520                 525
Cys Val Ser Pro Asn Lys Cys Val Cys Pro Ser Gly Phe Thr Gly Ser
    530                 535                 540
His Cys Glu Lys Asp Ile Asp Glu Cys Ala Leu Arg Thr His Thr Cys
545                 550                 555                 560
Trp Asn Asp Ser Ala Cys Ile Asn Leu Ala Gly Gly Phe Asp Cys Leu
                565                 570                 575
Cys Pro Ser Gly Pro Ser Cys Ser Gly Asp Cys Pro His Glu Gly Gly
            580                 585                 590
Leu Lys Arg Asn Gly Gln Val Trp Thr Leu Lys Glu Asp Arg Cys Ser
        595                 600                 605
Val Cys Ser Cys Lys Asp Gly Lys Ile Phe Cys Arg Arg Thr Ala Cys
    610                 615                 620
Asp Cys Gln Asn Pro Ser Val Asp Leu Phe Cys Cys Pro Glu Cys Asp
625                 630                 635                 640
Thr Arg Val Thr Ser Gln Cys Leu Asp Gln Asn Gly His Lys Leu Tyr
                645                 650                 655
Arg Ser Gly Asp Asn Trp Thr His Ser Cys Gln Gln Cys Arg Cys Leu
            660                 665                 670
Glu Gly Glu Val Asp Cys Trp Pro Leu Thr Cys Pro Asn Leu Ser Cys
        675                 680                 685
```

Glu Tyr Thr Ala Met Leu Gly Glu Cys Cys Pro Arg Cys Val Ser
            690                 695                 700

Asp Pro Cys Leu Ala Asp Asn Ile Ala Tyr Asp Ile Arg Lys Thr Cys
705                 710                 715                 720

Leu Asp Ser Tyr Gly Ile Ser Arg Leu Ser Gly Ala Val Trp Thr Met
                725                 730                 735

Ala Gly Ser Pro Cys Thr Thr Cys Lys Cys Lys Asn Gly Ser Val Cys
            740                 745                 750

Cys Ser Val Asp Leu Glu Cys Leu His Asn Asn
            755                 760

<210> SEQ ID NO 15
<211> LENGTH: 901
<212> TYPE: PRT
<213> ORGANISM: Canis familiaris

<400> SEQUENCE: 15

Met Thr Ser Thr Ser Phe Leu Leu Trp Leu Gly Cys Val His Asn Thr
1               5                   10                  15

Lys Phe Pro Phe Pro Leu Val Leu Val Thr Arg Ala Ile Val Val Val
                20                  25                  30

Val Val Glu Val Gly Val Gly Ser Pro Gly Val Arg Ile Arg Ser
            35                  40                  45

Thr Gly Cys Asp Ile Leu Leu Leu Tyr Glu Val Leu Glu His Leu Leu
    50                  55                  60

Gly Ile Arg Phe Leu Cys Val Asp Gln Gly Glu Asn Ser Cys His His
65                  70                  75                  80

Gly Gln Cys Ala Cys Arg Leu Gln Val Ile Val Pro Lys Ala Leu Met
                85                  90                  95

Ser Val Phe Glu Ala Lys Thr Ala Val Cys Phe Phe Pro Val Val Gly
                100                 105                 110

Phe Gly Thr Asp Pro Asp Leu Gln Met Asp Ile Ile Thr Glu Leu Asp
            115                 120                 125

Leu Val Asn Ile Ser Leu Gly Val Thr Gln Val Ser Gly Leu His Asn
130                 135                 140

Ala Ser Lys Ala Tyr Val Phe Gln Asp Thr Ala Arg Glu Ile His Ala
145                 150                 155                 160

Ala Pro His Val Ser Glu Lys Leu Ile Gln Leu Phe Arg Asn Lys Ser
                165                 170                 175

Asp Phe Thr Phe Leu Ala Thr Val Gln Gln Lys Pro Ser Thr Ser Gly
            180                 185                 190

Val Ile Leu Ser Ile Arg Glu Leu Glu His Ser Tyr Phe Glu Leu Glu
        195                 200                 205

Ser Ser Gly Leu Arg Asp Glu Ile Arg Tyr His Tyr Met His Asn Gly
    210                 215                 220

Lys Pro Arg Thr Glu Ala Leu Pro Tyr Arg Leu Ala Asp Gly Gln Trp
225                 230                 235                 240

His Lys Val Ala Leu Ser Val Ser Ala Ser His Leu Leu His Ile
                245                 250                 255

Asp Cys Asn Arg Ile Tyr Glu Arg Val Ile Asp Pro Pro Glu Thr Asn
                260                 265                 270

Leu Pro Pro Gly Ser Asn Leu Trp Leu Gly Gln Arg Asn Gln Lys His
            275                 280                 285

Gly Phe Phe Lys Gly Ile Ile Gln Asp Gly Lys Ile Ile Phe Met Pro

```
              290                 295                 300
Asn Gly Tyr Ile Thr Gln Cys Pro Asn Leu Asn Arg Thr Cys Pro Thr
305                 310                 315                 320

Cys Ser Asp Phe Leu Ser Leu Val Gln Gly Ile Met Asp Leu Gln Glu
                325                 330                 335

Leu Leu Ala Lys Met Thr Ala Lys Leu Asn Tyr Ala Glu Thr Arg Leu
                340                 345                 350

Ser Gln Leu Glu Asn Cys His Cys Glu Lys Thr Cys Gln Val Ser Gly
                355                 360                 365

Leu Leu Tyr Arg Asp Gln Asp Ser Trp Val Asp Gly Asp His Cys Arg
                370                 375                 380

Asn Cys Thr Cys Lys Gly Gly Ala Val Glu Cys Arg Arg Met Ser Cys
385                 390                 395                 400

Pro Pro Leu Asn Cys Ser Pro Asp Ser Leu Pro Val His Ile Ala Gly
                405                 410                 415

Gln Cys Cys Lys Val Cys Arg Pro Lys Cys Ile Tyr Gly Gly Arg Val
                420                 425                 430

Leu Ala Glu Gly Gln Arg Ile Leu Thr Lys Ser Cys Arg Glu Cys Arg
                435                 440                 445

Gly Gly Val Leu Val Lys Ile Thr Asp Ala Cys Pro Pro Leu Asn Cys
                450                 455                 460

Ser Glu Lys Asp His Ile Leu Pro Glu Asn Gln Cys Cys Ser Val Cys
465                 470                 475                 480

Arg Gly His Asn Phe Cys Ala Glu Gly Pro Lys Cys Gly Glu Asn Ser
                485                 490                 495

Glu Cys Lys Asn Trp Asn Thr Lys Ala Thr Cys Glu Cys Lys Asn Gly
                500                 505                 510

Tyr Ile Ser Val Gln Gly Asp Ser Ala Tyr Cys Glu Asp Ile Asp Glu
                515                 520                 525

Cys Ala Ala Lys Met His Tyr Cys His Ala Asn Thr Val Cys Val Asn
                530                 535                 540

Leu Pro Gly Leu Tyr Arg Cys Asp Cys Val Pro Gly Tyr Ile Arg Val
545                 550                 555                 560

Asp Asp Phe Ser Cys Thr Glu His Asp Glu Cys Gly Ser Gly Gln His
                565                 570                 575

Asn Cys Asp Glu Asn Ala Ile Cys Thr Asn Thr Val Arg Gly His Ser
                580                 585                 590

Cys Thr Cys Lys Pro Gly Tyr Val Gly Asn Gly Thr Ile Cys Arg Ala
                595                 600                 605

Phe Cys Gln Glu Gly Cys Arg Tyr Gly Gly Ser Cys Val Ser Pro Asn
                610                 615                 620

Lys Cys Val Cys Pro Ser Gly Phe Thr Gly Ser His Cys Glu Lys Asp
625                 630                 635                 640

Ile Asp Glu Cys Thr Glu Gly Ile Ile Glu Cys His Asn His Ser Arg
                645                 650                 655

Cys Val Asn Leu Pro Gly Trp Tyr His Cys Glu Cys Arg Ser Gly Phe
                660                 665                 670

His Asp Asp Gly Thr Tyr Ser Leu Ser Gly Glu Ser Cys Ile Asp Ile
                675                 680                 685

Asp Glu Cys Ala Leu Arg Thr His Thr Cys Trp Asn Asp Ser Ala Cys
                690                 695                 700

Ile Asn Leu Ala Gly Gly Phe Asp Cys Leu Cys Pro Ser Gly Pro Ser
705                 710                 715                 720
```

```
Cys Ser Gly Asp Cys Pro His Glu Gly Gly Leu Lys Arg Asn Gly Gln
            725                 730                 735

Val Trp Thr Leu Lys Glu Asp Arg Cys Ser Val Cys Ser Cys Lys Asp
        740                 745                 750

Gly Lys Ile Leu Cys Arg Arg Thr Ala Cys Asp Cys Gln Asn Pro Ser
            755                 760                 765

Val Asp Leu Phe Cys Cys Pro Glu Cys Asp Thr Arg Val Thr Ser Gln
    770                 775                 780

Cys Leu Asp Gln Asn Gly His Lys Leu Tyr Arg Ser Gly Asp Asn Trp
785                 790                 795                 800

Thr His Ser Cys Gln Gln Cys Arg Cys Leu Glu Gly Glu Val Asp Cys
                805                 810                 815

Trp Pro Leu Thr Cys Pro Asn Leu Ser Cys Glu Tyr Thr Ala Ile Leu
            820                 825                 830

Glu Gly Glu Cys Cys Pro Arg Cys Val Ser Asp Pro Cys Leu Ala Asp
            835                 840                 845

Asn Ile Ala Tyr Asp Ile Arg Lys Thr Cys Leu Asp Ser Tyr Gly Ile
        850                 855                 860

Ser Arg Leu Ser Gly Ser Val Trp Thr Met Ala Gly Ser Pro Cys Thr
865                 870                 875                 880

Thr Cys Lys Cys Lys Asn Gly Ser Val Cys Cys Ser Val Asp Leu Glu
                885                 890                 895

Cys Leu His Asn Asn
            900

<210> SEQ ID NO 16
<211> LENGTH: 810
<212> TYPE: PRT
<213> ORGANISM: Ovis aries

<400> SEQUENCE: 16

Met Pro Arg Gly Val Ile Leu Val Val Cys Phe Cys Val Cys Ala Ala
1               5                   10                  15

Arg Thr Val Val Gly Phe Gly Met Asp Pro Asp Leu Gln Leu Asp Ile
            20                  25                  30

Ile Thr Glu Leu Asp Leu Val Asn Thr Thr Leu Gly Val Thr Gln Val
        35                  40                  45

Ser Gly Leu His Asn Thr Ser Lys Ala Phe Leu Phe Gln Asp Ala Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Thr Phe Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Met His Ser Gly Arg Pro Arg Thr Glu Ala Leu Pro Tyr Arg Leu
    130                 135                 140

Ala Asp Gly Gln Trp His Arg Val Ala Leu Ser Val Ser Ala Ser His
145                 150                 155                 160

Leu Leu Leu His Ile Asp Cys Asn Arg Ile Tyr Glu Arg Val Ile Asp
                165                 170                 175

Pro Pro Glu Thr Asn Leu Pro Pro Gly Ser Asn Leu Trp Leu Gly Gln
```

```
                180                 185                 190
Arg Asn Gln Lys His Gly Leu Phe Lys Gly Ile Ile Gln Asp Gly Lys
            195                 200                 205

Ile Ile Phe Met Pro Asn Gly Tyr Ile Thr Gln Cys Pro Asn Leu Asn
            210                 215                 220

Arg Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
            245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
            275                 280                 285

Gly Asp His Cys Arg Asn Cys Thr Cys Lys Ser Gly Ala Val Glu Cys
            290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
            325                 330                 335

Tyr Gly Gly Lys Val Leu Ala Glu Gly Gln Arg Ile Leu Ser Lys Asn
            340                 345                 350

Cys Gln Glu Cys Arg Gly Gly Val Leu Val Lys Ile Thr Glu Ala Cys
            355                 360                 365

Pro Leu Leu Asn Cys Ser Glu Lys Asp His Ile Leu Pro Glu Asn Gln
            370                 375                 380

Cys Cys Ser Val Cys Arg Gly His Asn Phe Cys Ala Glu Gly Pro Lys
385                 390                 395                 400

Cys Gly Glu Asn Ser Glu Cys Lys Asn Trp Asn Thr Lys Ala Thr Cys
            405                 410                 415

Glu Cys Lys Asn Gly Tyr Ile Ser Val Gln Gly Asp Ser Ala Tyr Cys
            420                 425                 430

Glu Asp Ile Asp Glu Cys Ala Ala Lys Met His Tyr Cys His Ala Asn
            435                 440                 445

Thr Val Cys Val Asn Leu Pro Gly Leu Tyr Arg Cys Asp Cys Val Pro
            450                 455                 460

Gly Tyr Ile Arg Val Asp Asp Phe Ser Cys Thr Glu His Asp Asp Cys
465                 470                 475                 480

Gly Ser Gly Gln His Asn Cys Asp Glu Asn Ala Ile Cys Thr Asn Thr
            485                 490                 495

Val Gln Gly His Ser Cys Thr Cys Lys Pro Gly Tyr Val Gly Asn Gly
            500                 505                 510

Thr Ile Cys Arg Ala Phe Cys Glu Glu Gly Cys Arg Tyr Gly Gly Thr
            515                 520                 525

Cys Met Ala Pro Asn Lys Cys Val Cys Pro Ser Gly Phe Thr Gly Ser
            530                 535                 540

His Cys Glu Lys Asp Ile Asp Glu Cys Ala Glu Gly Ile Ile Glu Cys
545                 550                 555                 560

His Ser His Ser Arg Cys Val Asn Leu Pro Gly Trp Tyr His Cys Glu
            565                 570                 575

Cys Arg Ser Gly Phe His Asp Asp Gly Thr Tyr Ser Leu Ser Gly Glu
            580                 585                 590

Ser Cys Val Asp Ile Asp Glu Cys Ala Leu Arg Thr His Thr Cys Trp
            595                 600                 605
```

-continued

Asn Asp Ser Ala Cys Ile Asn Leu Ala Gly Gly Phe Asp Cys Leu Cys
        610                 615                 620

Pro Ser Gly Pro Ser Cys Ser Gly Asp Cys Pro His Glu Gly Gly Leu
625                 630                 635                 640

Lys Arg Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
                660                 665                 670

Cys Gln Asn Pro Ser Val Asp Leu Phe Cys Cys Pro Glu Cys Asp Thr
        675                 680                 685

Arg Val Thr Ser Gln Cys Leu Asp Gln Asn Gly Asn Lys Leu Tyr Arg
690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Ser Leu Ser Cys Glu
                725                 730                 735

Tyr Thr Thr Ile Leu Glu Gly Glu Cys Cys Pro Arg Cys Val Ser Asp
                740                 745                 750

Pro Cys Leu Ala Asp Asn Ile Ala Tyr Asp Ile Arg Lys Thr Cys Leu
        755                 760                 765

Asp Ser Tyr Gly Leu Ser Arg Leu Ser Gly Ser Val Trp Thr Met Ala
770                 775                 780

Gly Ser Pro Cys Thr Thr Cys Lys Cys Lys Asn Gly Ser Val Cys Cys
785                 790                 795                 800

Ser Val Asp Leu Glu Cys Leu His Asn Asn
                805                 810

<210> SEQ ID NO 17
<211> LENGTH: 610
<212> TYPE: PRT
<213> ORGANISM: Homo sapiens

<400> SEQUENCE: 17

Phe Gly Met Asp Pro Asp Leu Gln Met Asp Ile Val Thr Glu Leu Asp
1               5                   10                  15

Leu Val Asn Thr Thr Leu Gly Val Ala Gln Val Ser Gly Met His Asn
                20                  25                  30

Ala Ser Lys Ala Phe Leu Phe Gln Asp Ile Glu Arg Glu Ile His Ala
            35                  40                  45

Ala Pro His Val Ser Glu Lys Leu Ile Gln Leu Phe Arg Asn Lys Ser
        50                  55                  60

Glu Phe Thr Ile Leu Ala Thr Val Gln Gln Lys Pro Ser Thr Ser Gly
65                  70                  75                  80

Val Ile Leu Ser Ile Arg Glu Leu Glu His Ser Tyr Phe Glu Leu Glu
                85                  90                  95

Ser Ser Gly Leu Arg Asp Glu Ile Arg Tyr His Tyr Ile His Asn Gly
                100                 105                 110

Lys Pro Arg Thr Glu Ala Leu Pro Tyr Arg Met Ala Asp Gly Gln Trp
            115                 120                 125

His Lys Val Ala Leu Ser Val Ser Ala Ser His Leu Leu His Val
        130                 135                 140

Asp Cys Asn Arg Ile Tyr Glu Arg Val Ile Asp Pro Pro Asp Thr Asn
145                 150                 155                 160

Leu Pro Pro Gly Ile Asn Leu Trp Leu Gly Gln Arg Asn Gln Lys His

```
                165                 170                 175
Gly Leu Phe Lys Gly Ile Ile Gln Asp Gly Lys Ile Ile Phe Met Pro
            180                 185                 190

Asn Gly Tyr Ile Thr Gln Cys Pro Asn Leu Asn His Thr Cys Pro Thr
        195                 200                 205

Cys Ser Asp Phe Leu Ser Leu Val Gln Gly Ile Met Asp Leu Gln Glu
    210                 215                 220

Leu Leu Ala Lys Met Thr Ala Lys Leu Asn Tyr Ala Glu Thr Arg Leu
225                 230                 235                 240

Ser Gln Leu Glu Asn Cys His Cys Glu Lys Thr Cys Gln Val Ser Gly
                245                 250                 255

Leu Leu Tyr Arg Asp Gln Asp Ser Trp Val Asp Gly Asp His Cys Arg
            260                 265                 270

Asn Cys Thr Cys Lys Ser Gly Ala Val Glu Cys Arg Arg Met Ser Cys
        275                 280                 285

Pro Pro Leu Asn Cys Ser Pro Asp Ser Leu Pro Val His Ile Ala Gly
    290                 295                 300

Gln Cys Cys Lys Val Cys Arg Pro Lys Cys Ile Tyr Gly Gly Lys Val
305                 310                 315                 320

Leu Ala Glu Gly Gln Arg Ile Leu Thr Lys Ser Cys Arg Glu Cys Arg
                325                 330                 335

Gly Gly Val Leu Val Lys Ile Thr Glu Met Cys Pro Pro Leu Asn Cys
            340                 345                 350

Ser Glu Lys Asp His Ile Leu Pro Glu Asn Gln Cys Cys Arg Val Cys
        355                 360                 365

Arg Gly His Asn Phe Cys Ala Glu Gly Pro Lys Cys Gly Glu Asn Ser
    370                 375                 380

Glu Cys Lys Asn Trp Asn Thr Lys Ala Thr Cys Glu Cys Lys Ser Gly
385                 390                 395                 400

Tyr Ile Ser Val Gln Gly Asp Ser Ala Tyr Cys Glu Asp Ile Asp Glu
                405                 410                 415

Cys Ala Ala Lys Met His Tyr Cys His Ala Asn Thr Val Cys Val Asn
            420                 425                 430

Leu Pro Gly Leu Tyr Arg Cys Asp Cys Val Pro Gly Tyr Ile Arg Val
        435                 440                 445

Asp Asp Phe Ser Cys Thr Glu His Asp Glu Cys Gly Ser Gly Gln His
    450                 455                 460

Asn Cys Asp Glu Asn Ala Ile Cys Thr Asn Thr Val Gln Gly His Ser
465                 470                 475                 480

Cys Thr Cys Lys Pro Gly Tyr Val Gly Asn Gly Thr Ile Cys Arg Ala
                485                 490                 495

Phe Cys Glu Glu Gly Cys Arg Tyr Gly Gly Thr Cys Val Ala Pro Asn
            500                 505                 510

Lys Cys Val Cys Pro Ser Gly Phe Thr Gly Ser His Cys Glu Lys Asp
        515                 520                 525

Ile Asp Glu Cys Ser Glu Gly Ile Ile Glu Cys His Asn His Ser Arg
    530                 535                 540

Cys Val Asn Leu Pro Gly Trp Tyr His Cys Glu Cys Arg Ser Gly Phe
545                 550                 555                 560

His Asp Asp Gly Thr Tyr Ser Leu Ser Gly Glu Ser Cys Ile Asp Ile
                565                 570                 575

Asp Glu Cys Ala Leu Arg Thr His Thr Cys Trp Asn Asp Ser Ala Cys
            580                 585                 590
```

```
Ile Asn Leu Ala Gly Gly Phe Asp Cys Leu Cys Pro Ser Gly Pro Ser
            595                 600                 605

Cys Ser
    610

<210> SEQ ID NO 18
<211> LENGTH: 610
<212> TYPE: PRT
<213> ORGANISM: Equus caballus

<400> SEQUENCE: 18

Phe Gly Met Asp Pro Asp Leu Gln Met Asp Ile Ile Thr Glu Leu Asp
1               5                   10                  15

Leu Val Asn Thr Thr Leu Gly Val Thr Gln Val Ser Gly Leu His Asn
            20                  25                  30

Ala Ser Lys Ala Phe Leu Phe Gln Asp Val Glu Arg Glu Ile His Ala
        35                  40                  45

Ala Pro His Val Ser Glu Lys Leu Ile Gln Leu Phe Arg Asn Lys Ser
    50                  55                  60

Glu Phe Thr Phe Leu Ala Thr Val Gln Gln Lys Pro Ser Thr Ser Gly
65                  70                  75                  80

Val Ile Leu Ser Ile Arg Glu Leu Glu Asn Ser Tyr Phe Glu Leu Glu
                85                  90                  95

Ser Ser Gly Leu Arg Asp Glu Ile Arg Tyr His Tyr Thr His Lys Gly
            100                 105                 110

Lys Pro Arg Thr Glu Ala Leu Pro Tyr Arg Met Ala Asp Gly Arg Trp
        115                 120                 125

His Lys Val Ala Leu Ser Val Ser Ala Ser His Leu Leu His Ile
    130                 135                 140

Asp Cys Asn Arg Ile Tyr Glu Arg Val Ile Asp Thr Pro Glu Thr Asn
145                 150                 155                 160

Leu Pro Pro Gly Ser Asn Leu Trp Leu Gly Gln Arg Asn Gln Lys His
                165                 170                 175

Gly Leu Phe Lys Gly Ile Ile Gln Asp Gly Lys Ile Ile Phe Met Pro
            180                 185                 190

Asn Gly Tyr Ile Thr Gln Cys Pro Asn Leu Asn Arg Thr Cys Pro Thr
        195                 200                 205

Cys Ser Asp Phe Leu Ser Leu Val Gln Gly Ile Met Asp Leu Gln Glu
    210                 215                 220

Leu Leu Ala Lys Met Thr Ala Lys Leu Asn Tyr Ala Glu Thr Arg Leu
225                 230                 235                 240

Ser Gln Leu Glu Asn Cys His Cys Glu Lys Thr Cys Gln Val Ser Gly
                245                 250                 255

Leu Leu Tyr Arg Asp Gln Asp Ser Trp Val Asp Gly Asp His Cys Arg
            260                 265                 270

Asn Cys Thr Cys Lys Ser Gly Ala Val Glu Cys Arg Arg Met Ser Cys
        275                 280                 285

Pro Pro Leu Asn Cys Ser Pro Asp Ser Leu Pro Val His Val Ala Gly
    290                 295                 300

Gln Cys Cys Lys Val Cys Arg Pro Lys Cys Ile Tyr Gly Gly Lys Val
305                 310                 315                 320

Leu Ala Glu Gly Gln Arg Ile Leu Thr Lys Ser Cys Arg Glu Cys Arg
                325                 330                 335

Gly Gly Val Leu Val Lys Ile Thr Glu Ala Cys Pro Pro Leu Asn Cys
```

```
                340               345               350
Ser Asp Lys Asp His Ile Leu Pro Glu Asn Gln Cys Cys Ser Val Cys
        355                 360                 365
Arg Gly His Asn Phe Cys Ala Glu Gly Pro Lys Cys Gly Glu Asn Ser
        370                 375                 380
Glu Cys Lys Asn Trp Asn Thr Lys Ala Thr Cys Glu Cys Lys Asn Gly
385                 390                 395                 400
Tyr Ile Ser Val Gln Gly Asp Ser Ala Tyr Cys Glu Asp Ile Asp Glu
                405                 410                 415
Cys Ala Ala Lys Met His Tyr Cys Arg Ala Asn Thr Val Cys Val Asn
                420                 425                 430
Leu Pro Gly Leu Tyr Arg Cys Asp Cys Val Pro Gly Tyr Ile Arg Val
                435                 440                 445
Asp Asp Phe Ser Cys Thr Glu His Asp Glu Cys Gly Ser Gly Gln His
                450                 455                 460
Asn Cys Asp Glu Asn Ala Ile Cys Thr Asn Thr Val Gln Gly His Ser
465                 470                 475                 480
Cys Thr Cys Lys Pro Gly Tyr Val Gly Asn Gly Thr Ser Cys Arg Ala
                485                 490                 495
Phe Cys Glu Glu Gly Cys Arg Tyr Gly Gly Thr Cys Val Ala Pro Asn
                500                 505                 510
Lys Cys Val Cys Pro Ser Gly Phe Thr Gly Ser His Cys Glu Lys Asp
                515                 520                 525
Ile Asp Glu Cys Thr Glu Gly Ile Ile Glu Cys His Asn His Ser Arg
                530                 535                 540
Cys Val Asn Leu Pro Gly Trp Tyr His Cys Glu Cys Arg Ser Gly Phe
545                 550                 555                 560
His Asp Asp Gly Thr Tyr Ser Leu Ser Gly Glu Ser Cys Ile Asp Ile
                565                 570                 575
Asp Glu Cys Ala Leu Arg Thr His Thr Cys Trp Asn Asp Ser Ala Cys
                580                 585                 590
Ile Asn Leu Ala Gly Gly Phe Asp Cys Leu Cys Pro Ser Gly Pro Ser
                595                 600                 605
Cys Ser
    610

<210> SEQ ID NO 19
<211> LENGTH: 599
<212> TYPE: PRT
<213> ORGANISM: Bos taurus

<400> SEQUENCE: 19

Met Ala Leu Cys Ser Phe Ser Val Val Gly Phe Gly Leu Asp Pro Asp
1               5                   10                  15
Leu Gln Leu Asp Ile Ile Thr Glu Leu Asp Leu Val Asn Thr Thr Leu
                20                  25                  30
Gly Val Thr Gln Val Ser Gly Leu His Asn Thr Ser Lys Ala Phe Leu
            35                  40                  45
Phe Gln Asp Ala Glu Arg Glu Ile His Ala Ala Pro His Val Ser Glu
        50                  55                  60
Lys Leu Ile Gln Leu Phe Arg Asn Lys Ser Glu Phe Thr Phe Leu Ala
65                  70                  75                  80
Thr Val Gln Gln Lys Pro Ser Thr Ser Gly Val Ile Leu Ser Ile Arg
                85                  90                  95
```

```
Glu Leu Glu His Ser Tyr Phe Glu Leu Ser Ser Gly Leu Arg Asp
            100                 105                 110

Glu Ile Arg Tyr His Tyr Val His Ser Gly Arg Pro Arg Thr Glu Ala
        115                 120                 125

Leu Pro Tyr Arg Leu Ala Asp Gly Gln Trp His Arg Val Ala Leu Ser
    130                 135                 140

Val Ser Ala Ser His Leu Leu His Ile Asp Cys Asn Arg Ile Tyr
145                 150                 155                 160

Glu Arg Val Ile Asp Pro Pro Glu Thr Asn Leu Pro Pro Gly Ser Asn
                165                 170                 175

Leu Trp Leu Gly Gln Arg Asn Gln Lys His Gly Leu Phe Lys Gly Ile
            180                 185                 190

Ile Gln Asp Gly Lys Ile Ile Phe Met Pro Asn Gly Tyr Ile Thr Gln
        195                 200                 205

Cys Pro Asn Leu Asn Arg Thr Cys Pro Thr Cys Ser Asp Phe Leu Ser
    210                 215                 220

Leu Val Gln Gly Ile Met Asp Leu Gln Glu Leu Leu Ala Lys Met Thr
225                 230                 235                 240

Ala Lys Leu Asn Tyr Ala Glu Thr Arg Leu Ser Gln Leu Glu Asn Cys
                245                 250                 255

His Cys Glu Lys Thr Cys Gln Val Ser Gly Leu Leu Tyr Arg Asp Gln
            260                 265                 270

Asp Ser Trp Val Asp Gly Asp His Cys Arg Asn Cys Thr Cys Lys Ser
        275                 280                 285

Gly Ala Val Glu Cys Arg Arg Met Ser Cys Pro Pro Leu Asn Cys Ser
    290                 295                 300

Pro Asp Ser Leu Pro Val His Ile Ala Gly Glu Cys Cys Lys Val Cys
305                 310                 315                 320

Arg Pro Lys Cys Ile Tyr Gly Gly Lys Val Leu Ala Glu Gly Gln Arg
                325                 330                 335

Ile Leu Ser Lys Ser Cys Gln Glu Cys Arg Gly Gly Val Leu Val Lys
            340                 345                 350

Ile Thr Glu Ala Cys Pro Leu Leu Asn Cys Ser Glu Lys Asp His Ile
        355                 360                 365

Leu Pro Glu Asn Gln Cys Cys Ser Val Cys Arg Gly His Asn Phe Cys
    370                 375                 380

Ala Glu Gly Pro Lys Cys Gly Glu Asn Ser Glu Cys Lys Asn Trp Asn
385                 390                 395                 400

Thr Lys Ala Thr Cys Glu Cys Lys Asn Gly Tyr Ile Ser Val Gln Gly
                405                 410                 415

Asp Ser Ala Tyr Cys Glu Asp Ile Asp Glu Cys Ala Ala Lys Met His
            420                 425                 430

Tyr Cys His Ala Asn Thr Val Cys Val Asn Leu Pro Gly Leu Tyr Arg
        435                 440                 445

Cys Asp Cys Val Pro Gly Tyr Ile Arg Val Asp Asp Phe Ser Cys Thr
    450                 455                 460

Glu His Asp Asp Cys Gly Ser Gly Gln His Asn Cys Asp Glu Asn Ala
465                 470                 475                 480

Ile Cys Thr Asn Thr Val Gln Gly His Ser Cys Thr Cys Lys Pro Gly
                485                 490                 495

Tyr Val Gly Asn Gly Thr Ile Cys Arg Gly Met Pro Glu Val Gly Pro
            500                 505                 510

Pro Arg Ala Leu Leu Asn Ser Leu Asp Leu Gly Phe Leu Ser Phe Ser
```

-continued

```
            515                 520                 525
Lys Glu Ala Leu Ala Val Gly Met Ile Thr Leu Glu Gly Asn Ile Val
        530                 535                 540

Ala Lys Ser Phe Thr Asp Asp Glu Thr Leu Val Glu Arg Gly Arg Glu
545                 550                 555                 560

Lys Val Ile Ala Leu Leu Phe Ser Trp Leu His Lys Glu Lys Leu Ser
                565                 570                 575

Leu Glu Asn Leu Arg Asp Ile Tyr Cys Lys Ala Asn Ser Leu Val Gly
                580                 585                 590

Leu Asp His Leu Pro Gln Arg
            595
```